US006903128B2

United States Patent
Duplantier et al.

(10) Patent No.: US 6,903,128 B2
(45) Date of Patent: Jun. 7, 2005

(54) NON-PEPTIDYL INHIBITORS OF VLA-4 DEPENDENT CELL BINDING USEFUL IN TREATING INFLAMMATORY, AUTOIMMUNE, AND RESPIRATORY DISEASES

(75) Inventors: Allen J. Duplantier, Ledyard, CT (US); Louis S. Chupak, Old Saybrook, CT (US); Anthony J. Milici, Branford, CT (US); Wan F. Lau, Noank, CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 10/702,539

(22) Filed: Nov. 5, 2003

(65) Prior Publication Data

US 2004/0102496 A1 May 27, 2004

Related U.S. Application Data

(62) Division of application No. 10/170,289, filed on Jun. 12, 2002, now Pat. No. 6,668,527, which is a division of application No. 09/747,246, filed on Dec. 21, 2000, now abandoned.
(60) Provisional application No. 60/173,260, filed on Dec. 28, 1999.

(51) Int. Cl.$^7$ .................. A61K 31/4184; C07D 263/54; C07D 235/04
(52) U.S. Cl. ...................... 514/394; 548/304; 548/215; 548/217
(58) Field of Search .............................. 548/304.4, 215, 548/217; 514/394

(56) References Cited

U.S. PATENT DOCUMENTS 5,294,713 A   3/1994   Sugihara et al. ............. 544/384

(Continued)

FOREIGN PATENT DOCUMENTS

DE   19741873   3/1999   ........... C07K/5/078

(Continued)

OTHER PUBLICATIONS

Hemler, *Ann. Rev. Immunol.*, 8, p. 365, 1990.

(Continued)

*Primary Examiner*—Rita Desai
(74) *Attorney, Agent, or Firm*—Peter C. Richardson; Gregg C. Benson; Robert T. Ronau

(57) ABSTRACT

There is disclosed a genus of non-peptidyl compounds, wherein said compounds are VLA-4 inhibitors useful in treating inflammatory, autoimmune, and respiratory diseases, and wherein said compounds comprise a compound of Formula (1.0.0):

(1.0.0)

and pharmaceutically acceptable salts and other prodrug derivatives thereof, wherein:

A is $(C_1–C_6)$ alkyl, cycloalkyl, aryl, heteroaryl or heterocyclyl optionally substituted with 0 to 3 $R^9$; or is a member selected from the group consisiting of the following radicals: $A^1$-NHC(=O)NH-$A^2$-, $A^1$-NHC(=O)O-$A^2$-, $A^1$-OC(=O)NH-$A^2$-, $A^1$-NHSO$_2$NH-$A^2$-, $A^1$-NHC(=O)-$A^2$-, $A^1$-C(=O)NH-$A^2$-, $A^1$-NHSO$_2$-$A^2$-, $A^1$-SO$_2$NH-$A^2$-, $A^1$-(CH$_2$)$_k$O-$A^2$-, $A^1$-O(CH$_2$)$_r$-$A^2$, $A^1$-(CH$_2$)$_r$-$A^2$-, where $A^1$ and $A^2$ are each independently selected from the group consisting of hydrogen, aryl, $(C_1–C_6)$ alkyl, $(C_2–C_6)$ alkenyl, $(C_2–C_6)$ alkynyl, cycloalkyl, heteroaryl, and heterocyclyl substituted with 0 to 3 $R^9$;

B is a member independently selected from the group consisting of the following:

E is a single bond; —O—; —NR$^{10}$—; —CH=CH—; —CC—; S(=O)$_q$; —CR$^{11}$R$^{12}$NR$^{10}$—; or —CR$^{11}$R$^{12}$—;
X is —O—; —C(=O)—; —S(=O)$_q$—; or —NR$^{10}$—; $X^1$, $X^2$ and $X^3$ are each independently selected from the group consisting of CH, CR$^9$ or N; Y is a single bond; —C(=O)—; —C(=S)—; or —S(=O)$_2$—; R$^7$ is $(C_1–C_6)$ alkyl; (CH$_2$)$_k$OR$^5$; (CH$_2$)$_k$NR$^6$C(=O)R$^5$; (CH$_2$)$_k$NR$^6$C(=O)OR$^5$; (CH$_2$)$_k$NR$^6$SO$_2$R$^5$; (CH$_2$)$_k$NR$^6$R$^5$; F; CF$_3$; OCF$_3$; aryl, substituted with 0 to 3 R$^9$; heterocyclyl, substituted with 0 to 3 R$^9$; heteroaryl, substituted with 0 to 3 R$^9$; cycloalkyl, substituted with 0 to 3 R$^9$; or R$^7$ may be taken together with R$^8$ to form a cycloalkyl or heterocyclyl ring; or R$^7$ may be taken together with R$^{11}$ to form a cycloalkyl or heterocyclyl ring; and R$^8$ is hydrogen; F; $(C_1–C_6)$ alkyl or $(C_1–C_6)$ alkoxy.

14 Claims, No Drawings

U.S. PATENT DOCUMENTS

| | | | | |
|---|---|---|---|---|
| 5,821,231 | A | 10/1998 | Arrhenius et al. | 514/18 |
| 5,869,448 | A | 2/1999 | Arrhenius et al. | 514/11 |
| 5,936,065 | A | 8/1999 | Arrhenius et al. | 530/331 |
| 6,667,331 | B2 | 12/2003 | Duplantier et al. | 514/378 |
| 6,668,527 | B2 | 12/2003 | Duplantier et al. | 54/378 |
| 2002/0049236 | A1 * | 4/2002 | Duplantier et al. | 514/343 |
| 2003/0004196 | A1 * | 1/2003 | Duplantier et al. | 514/365 |

FOREIGN PATENT DOCUMENTS

| | | | |
|---|---|---|---|
| DE | 19821483 | 11/1999 | C07D/233/40 |
| EP | 529858 | 3/1993 | C07D/241/08 |
| EP | 842943 | 5/1998 | C07K/5/023 |
| EP | 842945 | 5/1998 | C07K/5/117 |
| EP | 903353 | 3/1999 | C07K/5/02 |
| EP | 918059 | 5/1999 | C07K/5/097 |
| EP | 842944 | 12/1999 | A01N/43/40 |
| WO | 9200995 | 1/1992 | C07K/7/00 |
| WO | 9515973 | 6/1995 | C07K/5/08 |
| WO | 9600581 | 1/1996 | A61K/38/12 |
| WO | 9601644 | 1/1996 | A61K/38/04 |
| WO | 9606108 | 2/1996 | C07K/5/10 |
| WO | 9620216 | 7/1996 | C07K/14/78 |
| WO | 9622966 | 8/1996 | C07C/237/22 |
| WO | 9640781 | 12/1996 | C07K/14/78 |
| WO | 9702289 | 1/1997 | C07K/14/78 |
| WO | 9703094 | 1/1997 | C07K/14/78 |
| WO | 9749731 | 12/1997 | C07K/14/78 |
| WO | 9804247 | 2/1998 | A61K/31/00 |
| WO | 9804913 | 2/1998 | G01N/33/00 |
| WO | 9842656 | 10/1998 | C07C/229/00 |
| WO | 9853814 | 12/1998 | A61K/31/395 |
| WO | 9853817 | 12/1998 | A61K/31/42 |
| WO | 9853818 | 12/1998 | A61K/31/42 |
| WO | 9854207 | 12/1998 | C07K/5/06 |
| WO | 9858902 | 12/1998 | C07C/233/63 |
| WO | 9906390 | 2/1999 | C07D/311/18 |
| WO | 9906391 | 2/1999 | C07D/311/18 |
| WO | 9906431 | 2/1999 | C07K/5/062 |
| WO | 9906432 | 2/1999 | C07K/5/062 |
| WO | 9906433 | 2/1999 | C07K/5/062 |
| WO | 9906434 | 2/1999 | C07K/5/078 |
| WO | 9906435 | 2/1999 | C07K/5/078 |
| WO | 9906436 | 2/1999 | C07K/5/078 |
| WO | 9906437 | 2/1999 | C07K/5/078 |
| WO | 9910312 | 3/1999 | C07C/233/87 |
| WO | 9910313 | 3/1999 | C07C/237/34 |
| WO | 9920272 | 4/1999 | A61K/31/415 |
| WO | 9923063 | 5/1999 | A61K/31/17 |
| WO | 9924398 | 5/1999 | C07C/273/00 |
| WO | 9925685 | 5/1999 | C07D/211/30 |
| WO | 9926615 | 6/1999 | A61K/31/165 |
| WO | 9926921 | 6/1999 | C07D/207/16 |
| WO | 9926922 | 6/1999 | C07D/207/48 |
| WO | 9926923 | 6/1999 | C07D/211/56 |
| WO | 9933789 | 7/1999 | C07C/275/42 |
| WO | 9935163 | 7/1999 | C07K/5/078 |
| WO | 9936393 | 7/1999 | C07C/233/87 |
| WO | 9937605 | 7/1999 | C07C/275/42 |
| WO | 9937618 | 7/1999 | C07D/213/82 |
| WO | 9943642 | 9/1999 | C07C/235/60 |
| WO | 9947547 | 9/1999 | C07K/5/078 |
| WO | 9948879 | 9/1999 | C07D/277/06 |
| WO | 9952493 | 10/1999 | |
| WO | 9952898 | 10/1999 | C07D/405/00 |
| WO | 9954321 | 10/1999 | C07D/295/182 |
| WO | 9960015 | 11/1999 | C07K/5/02 |
| WO | 9961421 | 12/1999 | C07D/207/16 |
| WO | 9961465 | 12/1999 | C07K/5/078 |
| WO | 9962901 | 12/1999 | C07D/401/12 |
| WO | 9964390 | 12/1999 | C07C/233/87 |
| WO | 9964395 | 12/1999 | C07D/207/04 |
| WO | 9967230 | 12/1999 | C07D/277/06 |
| WO | 0000477 | 1/2000 | C07D/241/08 |
| WO | 0001690 | 1/2000 | C07D/401/12 |
| WO | 0002903 | 1/2000 | C07K/5/02 |
| WO | 0005223 | 2/2000 | C07D/263/00 |
| WO | 0005224 | 2/2000 | C07D/263/00 |
| WO | 0015612 | 3/2000 | C07D/209/12 |
| WO | 0018759 | 4/2000 | C07D/401/12 |
| WO | 0018760 | 4/2000 | C07D/401/12 |
| WO | 0020396 | 4/2000 | C07D/213/81 |
| WO | 0032575 | 6/2000 | C07D/213/79 |
| WO | 0035855 | 6/2000 | C07C/225/20 |
| WO | 0037444 | 6/2000 | C07D/211/58 |
| WO | 0043354 | 7/2000 | C07C/231/00 |
| WO | 0043369 | 7/2000 | C07D/233/66 |
| WO | 0043371 | 7/2000 | C07D/235/30 |
| WO | 0043372 | 7/2000 | C07D/239/42 |

OTHER PUBLICATIONS

Walsh et al., *Clin. and Exp. Allergy*, 25, p. 1128, 1995.
Huhtala et al., *J. Cell Biol.*, 129, p. 867, 1995.
Ruegg et al., *J. Cell Biol.*, 117, p. 179, 1992.
Wayner et al., *J. Cell Biol.*, 105, p. 1873, 1987.
Kramer et al., *J. Biol. Chem.*, 264, p. 4684, 1989.
Gehlsen et al., *Science*, 241, p. 1228, 1988.
Chisholm et al., *Eur. J. Immunol.*, 23, p. 682, 1993.
Lobb et al., *J. Clin, Invest.*, 94, p. 1722, 1994.
Richards et al., *Am. J. Respir. Cell Mol. Biol.*, 15, p. 172, 1996.
Soilu–Hänninen et al., *J. Neuroimmunol.*, 72, p. 95, 1997.
Sagara et al., *Int. Arch. Allergy Immunol.*, 112, p. 287, 1997.
Fryer et al., *J. Clin. Invest.*, 99, pp. 2036, 1997.
Ferguson et al., *Proc. Natl. Acad. Sci.*, 88, p. 8072, 1991.
Henderson et al., *J. of Clin. Invest.*, 100, p. 3083, 1997.
Wahl et al., *J. Clin. Invest.*, 94, p. 655, 1994.
Molossi et al., *J. Clin. Invest.*, 95, p. 2601, 1995.
Abraham et al., *Am. J. Respir. Crit. Care Med.*, 156, p. 696, 1997.
Jackson et al., *J. Med. Chem.*, 40, p. 3359, 1997.
Bernardi et al., *J. Cell Biol.*, 105, p. 489, 1987.
Humphries et al., *J. Biol. Chem.*, 262, p. 6886, 1987.
Garcia–Pardo et al., *J. Immunol.*, 144, p. 3361, 1990.
Komoriya et al., *J. Biol. Chem.*, 266, p. 15075, 1991.
Wayner et al., *J. Cell Biol.*, 116, p. 489, 1992.
Nowlin et al., *J. Biol. Chem.*, 268, p. 20352, 1993.
Turner et al., *Inflammation Research*, 45, p. 239, 1996.

* cited by examiner

NON-PEPTIDYL INHIBITORS OF VLA-4 DEPENDENT CELL BINDING USEFUL IN TREATING INFLAMMATORY, AUTOIMMUNE, AND RESPIRATORY DISEASES

REFERENCE TO CO-PENDING APPLICATIONS

This application is a division of U.S. application Ser. No. 10/170,289, filed Jun. 12, 2002 now U.S. Pat. No. 6,668,527, which is a division of U.S. application Ser. No. 09/747,246, filed Dec. 21 2000 now abandoned, which claims the benefit of U.S. Provisional Application No. 60/173,260, filed Dec. 28, 1999.

The present invention relates to compounds which are non-peptidyl in structure and active as potent inhibitors of the binding of very late antigen-4 (VLA-4; $\alpha_4\beta_1$; CD49d/CD29) to proteins such as vascular cell adhesion molecule-1 (VCAM-1), the HepII/IIICS domain (CS-1 region) of fibronectin and osteopontin. As such they are useful in the inhibition of cell adhesion and consequent or associated pathogenic processes subsequently mediated by VLA-4. The compounds and pharmaceutical compositions of this invention may be used in the treatment of many inflammatory, autoimmune and respiratory diseases, especially asthma.

BACKGROUND OF THE INVENTION

One of the most fundamental processes necessary for normal host defence is the regulated trafficking of leukocytes out of the vasculature. This system is designed to allow normal recirculation of leukocytes, yet because it enables the rapid extravasation of leukocytes at sites of injury it is one of the central pathogenic mechanisms of inflammatory, respiratory and autoimmune diseases in mammals. Cell adhesion is a key factor in this process, and it is particularly relevant to the present invention regarding the cell/cell and cell/matrix binding of hematopoietic cells containing VLA-4.

VLA-4 is a member of a superfamily of cell surface macromolecular receptors called integrins, which are non-covalent heterodimeric complexes consisting of an $\alpha$ subunit and a $\beta$ subunit (Hemler, *Ann. Rev. Immunol.*, 8, p. 365, 1990). Eighteen different $\alpha$ subunits have been identified and labeled $\alpha_1$–$\alpha_{10}$, $\alpha_L$, $\alpha_M$, $\alpha_X$, $\alpha_D$, $\alpha_{LRI}$, $\alpha_{IIB}$, $\alpha_V$ and $\alpha_E$; while eight different $\beta$ subunits have been identified and labeled $\beta_1$–$\beta_8$. Each integrin molecule can be categorized into a subfamily based on the type of its $\alpha$ and $\beta$ subunits.

The $\alpha_4\beta_1$ integrin, VLA-4, is an integrin constitutively expressed by all leukocytes (e.g., monocytes, lymphocytes, basophils, eosinophils, mast cells and macrophages) except polymorphonuclear leukocytes. The binding of this integrin to one of its ligands has a number of known cell adhesion and activation functions (Hemler, *Ann. Rev. Immunol.*, 8, p. 365, 1990; Walsh et al., *Clin. and Exp. Allergy*, 25, p. 1128, 1995; Huhtala et al., *J. Cell Biol.*, 129, p. 867, 1995). In particular, it is a receptor for the cytokine-inducible endothelial cell surface protein known as vascular cell adhesion molecule-1 (VCAM-1), for the alternatively spliced forms of the extracellular matrix protein fibronectin (FN) containing the CS-1 domain (Ruegg et al., *J. Cell Biol.*, 177, p. 179, 1991; Wayner et al., *J. Cell Biol.*, 105, p. 1873, 1987; Kramer et al., *J. Biol. Chem.*, 264, p. 4684, 1989; Gehlsen et al., *Science*, 24, p. 1228, 1988) and for the extracellular matrix protein osteopontin (Bayless, K. I. et al., *J. Cell Science*, 111, p. 1165–1174, 1998). The importance of VLA-4 cell adhesion interactions has been established by the use of specific monoclonal antibody (mAb) antagonists of the $\alpha$ subunit of VLA-4, which have demonstrated that inhibitors of VLA-4 dependent cell adhesion prevent or inhibit numerous inflammatory, respiratory and autoimmune pathological conditions (Chisholm et al., *Eur. J. Immunol.*, 23, p. 682, 1993; Lobb et al., *J. Clin. Invest.*, 94, p. 1722, 1994; Richards et al., *Am. J. Respir. Cell Mol. Biol.*, 15, p. 172, 1996; Soiluhanninen et al., *J. Neuroimmunol.*, 72, p. 95, 1997; Sagara et al., *Int. Arch. Allergy Immunol.*, 112, p. 287, 1997; Fryer et al., *J. Clin. Invest.*, 99, p. 2036, 1997). In addition, confirmation that this pathological processes can be inhibited with agents other than antibodies has been observed in animal models following treatment with a synthetic CS-1 peptide or a small molecule peptide inhibitor of VLA-4 (Ferguson et al., *Proc. Natl. Acad. Sci.*, 88, p. 8072, 1991; Wahl et al., *J. Clin. Invest.*, 94, p. 655, 1994; Molossi et al., *J. Clin. Invest.*, 95, p. 2601, 1995; Abraham et al., *Am. J. Respir. Crit. Care Med.*, 156, p. 696, 1997; Jackson et al., *J. Med. Chem.*, 40, p. 3359, 1997).

DESCRIPTION OF THE STATE OF THE ART

The investigation of mAb and peptide VLA-4 antagonists in the art has already been noted above. In defining the binding site for $\alpha_4\beta_1$ it has been observed that lymphoid cells can bind to two different sites on fibronectin (Bernardi et al., *J. Cell Biol.*, 105, p. 489, 1987). One component of this cell binding activity has previously been identified as the tripeptide Arg-Gly-Asp (RGD) that binds to the integrin $\alpha_5\beta_1$ (VLA5). Subsequently, the minimum amino acid sequence required to bind and antagonize the activity of VLA-4 on leukocytes to the alternatively spliced site in fibronectin was determined (Humphries et al., *J. Biol. Chem.*, 266, p. 6886, 1987; Garcia-Pardo et al., *J. Immunol.*, 144, p. 3361, 1990; Komoriya et al., *J. Biol. Chem.*, 266, p. 15075, 1991). It has been discovered that the VLA-4 binding domain in the CS-1 region of fibronectin (FN) comprises the octapeptide: Glu-Ile-Leu-Asp-Val-Pro-Ser-Thr, as well as two overlapping pentapeptides: Glu-Ile-Leu-Asp-Val and Leu-Asp-Val-Pro-Ser. All of these peptides inhibit FN-dependent cell adhesion, leading to the early conclusion that the minimal amino acid sequence required for inhibition would be Leu-Asp-Val (LDV). In fact the LDV minimal inhibitory sequence has been observed to be equally effective as the full length CS-1 fragment in binding the activated form of VLA-4 (Wayner et al., *J. Cell Biol.*, 116, p. 489, 1992).

Various integrins are believed to bind to extracellular matrix proteins at an Arg-Gly Asp (RGD) recognition site. RGD based cyclic peptides have been made that are said to be able to inhibit both $\alpha_4\beta_1$ and $\alpha_5\beta_1$ binding to FN (Nowlin et al., *J. Biol. Chem.*, 268, p. 20352, 1993; PCT/US91/04862) even though the primary recognition on FN for $\alpha_4\beta_1$ is LDV. The cyclic peptide may be represented by Formula (0.0.1):

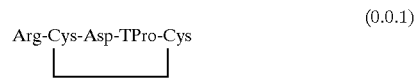
(0.0.1)

where TPro denotes 4-thioproline.

Other peptidyl inhibitors of VLA-4 are those referred to in Arrhenius et al., "CS-1 Peptidomimetics," WO 95/15973, which is assigned to the Cytel Corporation and is related to the two US patents noted below. A representative compound of the type described is the peptide of Formula (0.0.2):

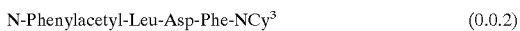
(0.0.2)

wherein NCy³ is selected from, inter alia, morpholinamido; thiomorpholinamido; 4-(thiadioxo)piperidinamido; and D-2-(carboxamide)-pyrrolidinamido; piperidinamido; and substituted piperidinamido.

WO 95/15973 . . . U.S. Pat. No. 5,821,231 . . . U.S. Pat. No. 5,936,065 . . . Cytel Corporation Further work by Arrhenius et al. involving cyclic CS-1 peptidomimetics is described in WO 96/06108 assigned to the Cytel Corporation, which is related to the US patent noted below.

WO 96/06108 . . . U.S. Pat. No. 5,869,448 . . . Cytel Corporation

The Arrhenius group has also discovered non-peptidal inhibitors of VLA-4 dependent cell binding as described in He et al. WO 98/42656. The inhibitors therein described are of the general Formula (0.0.3):

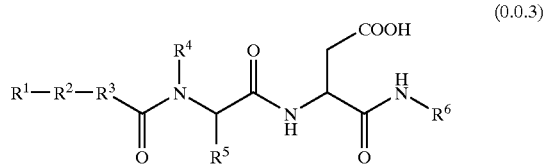

(0.0.3)

A typical inhibitor is that represented by Formula (0.0.4):

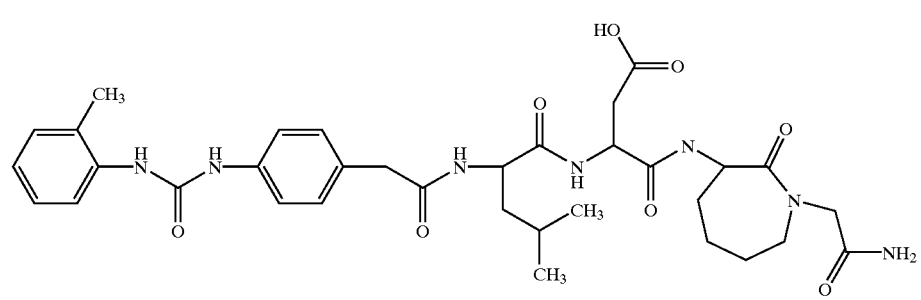

(0.0.4)

WO 98/42656 . . . Cytel Corporation

The Leu-Asp-Val tripeptide has been used as the core of a group of inhibitors of VLA-4 dependent cell adhesion described in Adams et al. WO 96/22966, which is assigned to Biogen, Inc. These inhibitors may be represented by Formula (0.0.5):

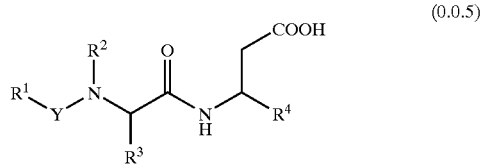

(0.0.5)

where $R^1$ may be 4-(N'-(2-methylphenyl)urea) phenylmethyl; Y may be C=O; $R^2$ may be H; $R^3$ may be iso-butyl; and $R^{14}$ may be 1,3-benzodioxol-5-yl. An example of a typical inhibitor of this type is that of Formula (0.0.6):

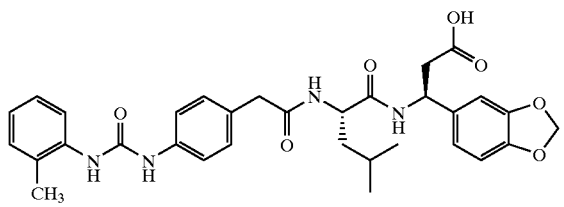

(0.0.6)

WO 96/22966 . . . Biogen, Inc.

The Adams group has also discovered semi-peptidic cell adhesion inhibitors for the treatment of inflammation and autoimmune disease, described in Lin et al., WO 97/03094. These inhibitors may be represented by Formula (0.0.7):

$$Z-(Y^1)-(Y^2)-(Y^3)_n-X \qquad (0.0.7)$$

where Z may be 4-(N'-(2-methylphenyl)urea)phenylacetyl; $(Y^1)-(Y^2)-(Y^3)_n$ represents a series of amino acids forming a peptide chain; and X may be OH. A typical inhibitor of this type is shown in Formula (0.0.8):

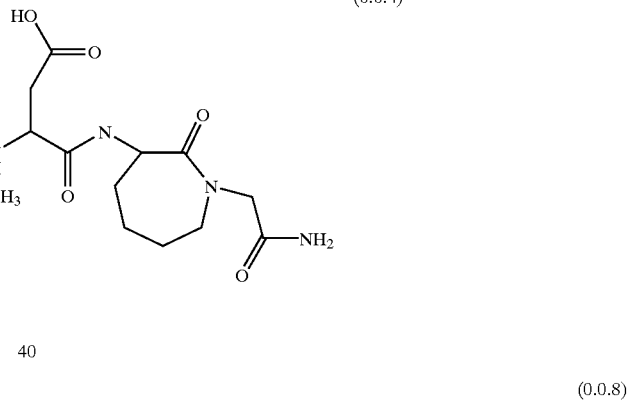

(0.0.8)

WO 97/03094 . . . Biogen, Inc.

The Adams group has also asserted, in Zheng et al., WO 98/04247, the discovery that existing IIb/IIIa integrin inhibitory compounds may be converted into VLA-4 inhibitory compounds, and that IIb/IIIa inhibitory compounds can be made by combining a unique VLA-4 integrin scaffold with a IIb/IIIa specificity determinant. These cell adhesion inhibitors may b viewed as comprising a compound of the formula: A-B, where A comprises a VLA-4 specificity determinant which does not impart significant IIb/IIIa integrin inhibitory activity, and B is an integrin scaffold derived from a IIb/IIIa inhibitor. A three dimensional pharmacophore model of a compound having VLA-4 inhibitory acitivity is also described. Representative of the inhibitors thus derived are the compounds of Formulas (0.0.9) and (0.0.10):

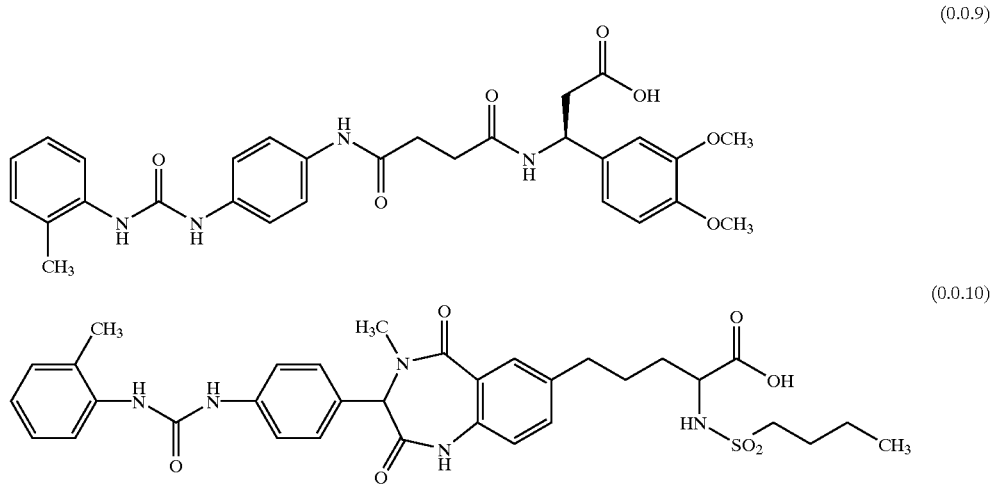

(0.0.9)

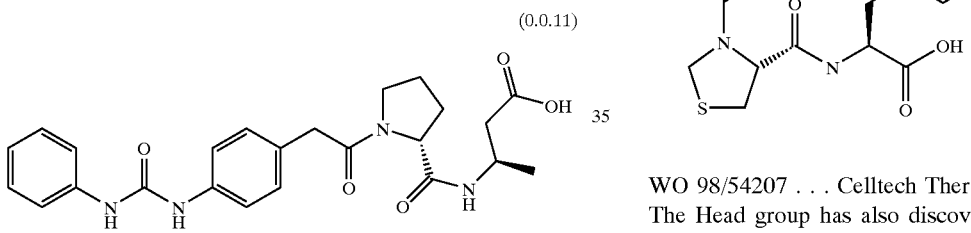

(0.0.10)

WO 98/04247 . . . Biogen, Inc.

See also Singh et al., WO 98/04913, which refers to a three dimensional pharmacophore model of a compound having VLA-4 inhibitory activity, comprising features defined by a table of tolerances and three dimensional coordinates x, y, and z. The following compound, representative of those referred to, may be represented by Formula (0.0.11):

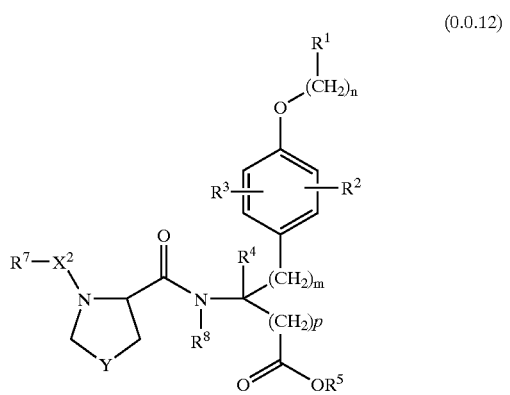

(0.0.11)

WO 98/04913 . . . Biogen, Inc.

Another type of VLA-4 dependent cell adhesion inhibitor is that described in Head et al., "Anti-inflammatory Tyrosine Derivatives", WO 98/54207, which may be represented by general Formula (0.0.12):

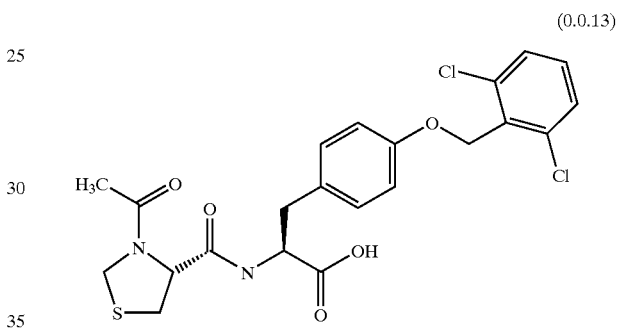

(0.0.12)

where $R^1$ is an optionally substituted alkyl or aromatic group; $X^2$ is —C(=O)—; —C(=O)O—; —C(=O)NH—; or —S(=O)$_2$—; and $R^7$ is an optionally substitutued alkyl or aryl group. A compound typical of this type of inhibitor may be represented by Formula (0.0.13):

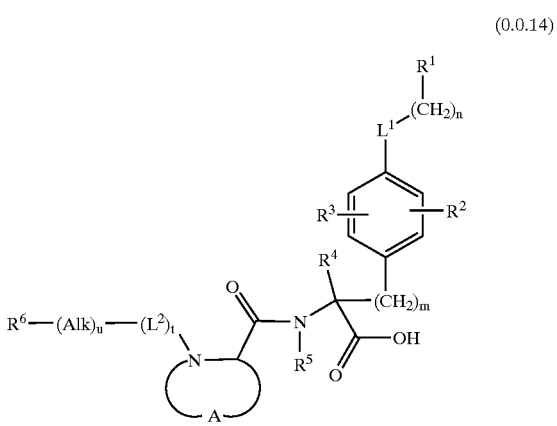

(0.0.13)

WO 98/54207 . . . Celltech Therapeutics Ltd.

The Head group has also discovered a related group of VLA-4 dependent cell adhesion inhibitors, described in Head et al., "Phenylalanine Derivatives Useful As Pharmaceutical Agents," WO 99/37618, which are of the general Formula (0.0.14):

(0.0.14)

where $L^1$ is a linker atom or group; A is a chain —[C(R$^7$)(R$^8$)]$_p$—Y—[C(R$^9$)(R$^{10}$)]$_q$—; and $L^2$ is a linker group selected from —C(=O)—; —C(=O)O—; —C(=S)—; —S(=O)$_2$, or —C(=O)N(R$^{11}$)—. An example of this type of inhibitor is that of a compound of Formula (0.0.15):

(0.0.15)

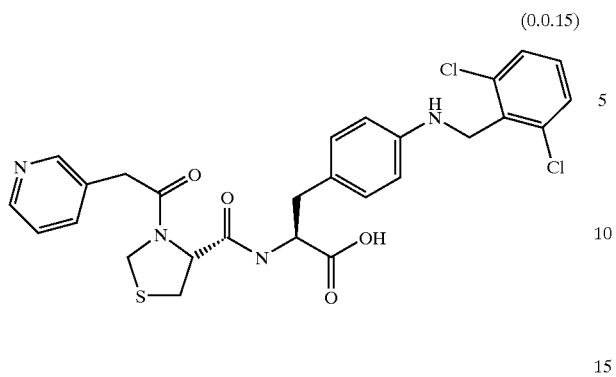

WO 99/35163 . . . Celltech Therapeutics, Ltd.

Another closely related group of VLA-4 inhibitors discovered by the Head group is described in Head et al., "Novel Phenylalanine Derivatives Useful as Integrin Antagonists," WO 99/37618, which is characterized by general Formula (0.0.16):

(0.0.16)

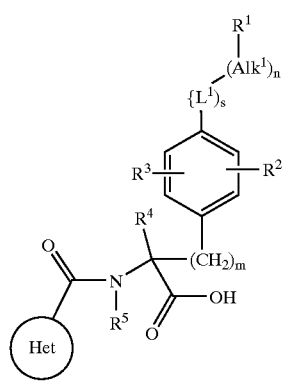

A representative example of these inhibitory compounds is that of Formula (0.0.17):

(0.0.17)

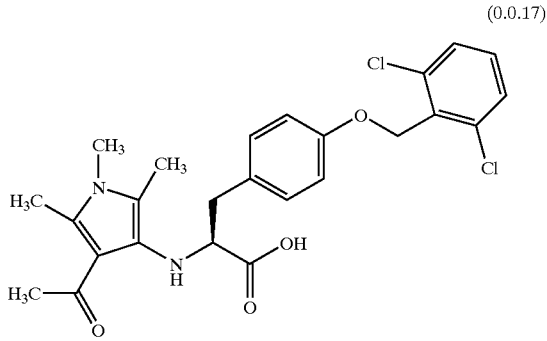

WO 99/37618 . . . Celltech Therapeutics, Ltd.

A still further related group of compounds discovered by the Head group to be inhibitors of VLA-4 dependent cell adhesion is described in Head et al., "Phenylalanine Derivatives As Inhibitors of Alpha4 Integrins," WO 99/43642, and may be characterized by general Formula (0.0.18):

(0.0.18)

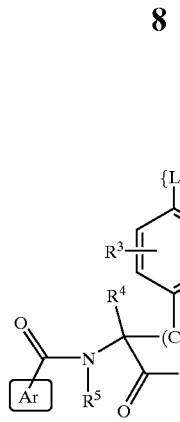

Inhibitors of the type described are illustrated in Formula (0.0.19):

(0.0.19)

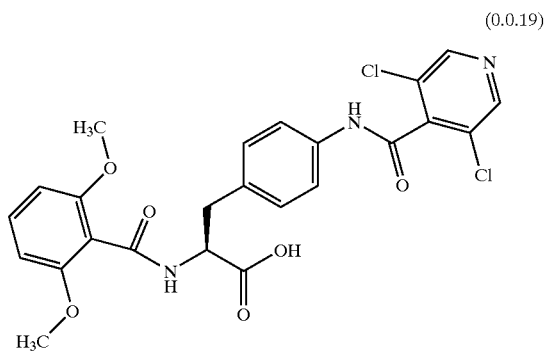

WO 99/43642 . . . Celltech Therapeutics, Ltd.

Early work in the discovery of inhibitors of VLA-4 dependent cell adhesion has also been done by Pleiss and Thorsett and their co-workers, e.g., as described in Thorsett et al., "Inhibitors of Leukocyte Adhesion," WO 96/01544 assigned to Athena Neurosciences, Inc. These inhibitors comprise inhibitors that block cellular adhesion mediated by VLA-4 and they are used to treat a number of inflammatory diseases, especially inflammatory brain disorders.

Non-peptide, i.e., small molecule inhibitors of VLA-4 have also been discovered by the Pleiss and Thorsett group, e.g., as described in Thorselt, "Carbamoyloxy Compounds Which Inhibit Leukocyte Adhesion Mediated by VLA-4," WO 99/06390 assigned to Athena Neurosciences, Inc. Inhibitors of this type may be represented by general Formula (0.0.20):

(0.0.20)

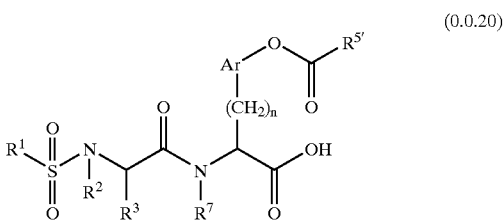

where $R^1$ is alkyl, aryl, cycloalkyl, heterocyclic, or heteroaryl, all of which are optionally substituted; $R^2$ is defined similarly to $R^1$ and may be combined with it and the —S(=O)$_2$-moiety to form an optionally substituted heterocyclic group; $R^3$ is defined similarly to $R^1$ and is optionally taken together with the nitrogen atom bound to $R^2$ and the carbon atom bound to $R^3$ to form an optionally substituted heterocyclic group; $R^7$ is —H or alkyl; Ar is optionally substituted aryl or heteroaryl; and $R^{5'}$ is —O-Z-$NR^8R^{8'}$ or —O-Z-$R^{12}$ where Z is —C(=O) or —S(=O)$_2$, $R^8$ and $R^{8'}$ are —H, or optionally substituted alkyl, cycloalkyl or hetercyclic, or $R^8$ and $R^{8'}$ may be joined to form an optionally substituted heterocycle, and $R^{12}$ is optionally substituted heterocycle.

A representative example of the above-described VLA-4 inhibitors is the compound of Formula (0.0.21):

(0.0.21)

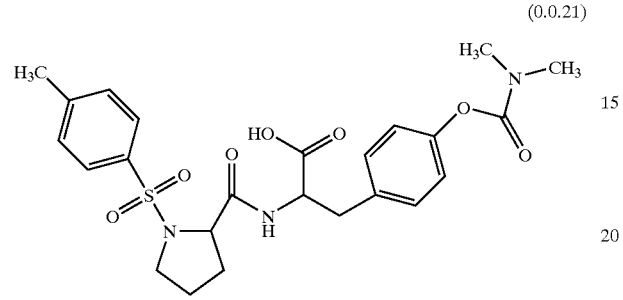

WO 99/06390 . . . Athena Neurosciences, Inc.

In Yednock and Pleiss "Alpha-9 Integrin Antagonists and Anti-inflammatory Compositions thereof," WO 99/06391 assigned to Athena Neurosciences, Inc., there is described the use of the inhibitory compounds of above-mentioned WO 99/06390 in methods of treating disorders that involve binding of α-9 integrin, particularly adhesion macrophages or neutrophils. Disorders said to be susceptible to treatment include airway hyper-responsiveness and occlusion that occur in conjunction with chronic asthma, smooth muscle cell proliferation in atherosclerosis, vascular occlusion following angioplasty, fibrosis and glomerular scarring as a result of renal disease, aortic stenosis, hypertrophy of synovial membranes in rheumatoid arthritis, and inflammation and scarring that occur with the progression of ulcerative colitis, and Crohn's disease.

The Thorsett and Pleiss group has discovered a group of inhibitors of VLA-4 which is described in Thorsett et al. "Substituted Phenylalanine Type Compounds Which Inhibit Leukocyte Adhesion Mediated by VLA-4," WO 99/06431 assigned to Athena Neurosciences, Inc. and American Home Products Corporation, which may be represented by general Formula (0.0.22):

(0.0.22)

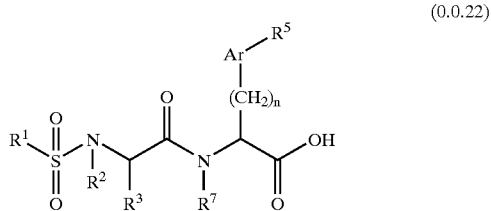

where $R^1$, $R^2$, $R^3$, $R^7$, and Ar have substantially the same meaning as described above with respect to WO 99/06390; and $R^5$ is an optionally substituted member selected from the group consisting of —NHC(=O)R; alkoxyaryl; aryl; heteroaryl; —NRR'; alkoxy-NRR'; alkenyl; alkynyl; aryloxy; heteroaryloxy; alkoxy-heterocyclic; O-heterocyclic; tetrazolyl; —NRS(=O)$_2$-alkyl; alkenylsulfonylamino; alkynylsulfonylamino; alkoxy; amidine; —C(=O)NRR'; —NRC(=O)R'; —S(=O)$_2$-aryl; S(=O)$_2$-heteroaryl; —NRC(=O)NRR'; —NRC(=O)OR'; aminocarbonyl-(N-formylheterocyclyl); and alkyl-C(=O)NH-heterocyclyl.

A compound which illustrates the type of VLA-4 inhibitors disclosed is that of Formula (0.0.23):

(0.0.23)

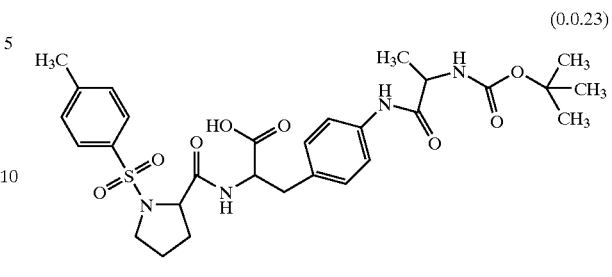

WO 99/06431 . . . Athena Neurosciences, Inc.

A related group of inhibitory compounds which has also been discovered by the Thorsett and Pleiss group is described in Thorsett et al., "Dipeptide and Related Compounds Which Inhibit Leukocyte Adhesion Mediated by VLA-4," WO 99/06432 assigned to Athena Neurosciences, Inc. and American Home Products Corporation. Inhibitory compounds of this type are characterized by general Formula (0.0.24):

(0.0.24)

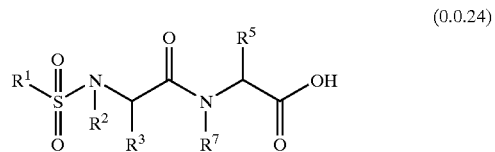

where $R^1$, $R^2$, $R^3$, and $R^7$ have substantially the same meaning as described above with respect to WO 99/06390 and WO 99/06431; and $R^5$ is -ALK-X or =CH—Y where X and Y are defined to mean a wide variety of groups, all of which are optionally substituted.

An example of this type of VLA-4 inhibitor is the compound of Formula (0.0.25):

(0.0.25)

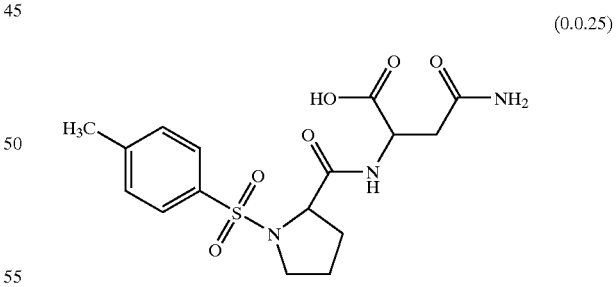

WO 99/06432 . . . Athena Neurosciences, Inc.

A further related group of VLA-4 inhibitory compounds which has also been discovered by the Thorsett and Pleiss group is described in Dappen et al., "Compounds Which Inhibit Leukocyte Adhesion Mediated by VLA-4," WO 99/06433 assigned to Athena Neurosciences, Inc. and American Home Products Corporation. Inhibitory compounds of this type are characterized by general Formula (0.0.26):

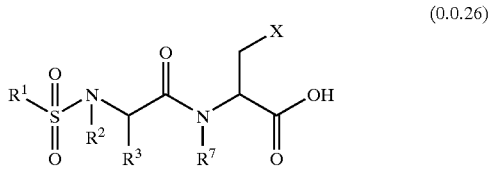

(0.0.26)

where $R^1$, $R^2$, $R^3$, and $R^7$ have substantially the same meaning as described above with respect to WO 99/06390, WO 99/06431, and WO 99/06432; and X is —H; —OH; acylamino; —C(=O)OH; and optionally substituted alkyl; alkoxy; aryl; aryloxy; aryloxyaryl; carboxy-alkyl; carboxy-cycloalkyl; carboxy-aryl; carboxy-heteroaryl; carboxy-heterocyclic; and cycloalkyl.

The type of VLA-4 inhibitor described in the paragraph immediately above may be represented by the compound of Formula (0.0.27):

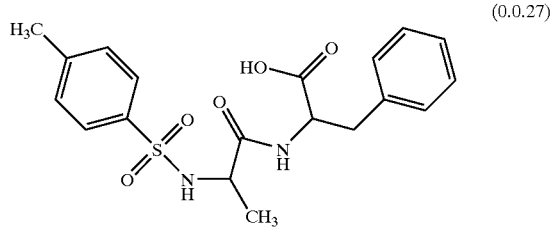

(0.0.27)

WO 99/06433 . . . Athena Neurosciences, Inc.

A still further group of VLA-4 inhibitory compounds which has been discovered by the Thorsett and Pleiss group is described in Ashwell et al., "4-Amino-Phenylalanin Type Compounds Which Inhibit Leukocyte Adhesion Mediated by VLA-4," WO 99/06434 assigned to Athena Neurosciences, Inc. and American Home Products Corporation. Inhibitory compounds of this type are characterized by general Formula (0.0.28):

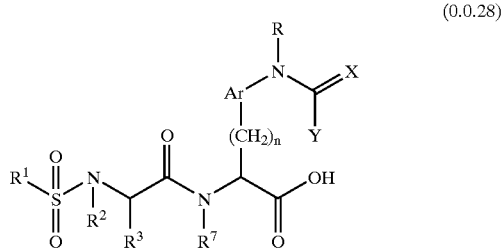

(0.0.28)

where $R^1$, $R^2$, $R^3$, and $R^7$ have substantially the same meaning as described above with respect to WO 99/06390, WO 99/06431, WO 99/06432, and WO 99/06433; and R is —H, alkyl, or aryl; X is O, S, or NR; and Y is NRR' or heterocycle, all of which are optionally substituted by a wide variety of groups.

This further type of VLA-4 inhibitor may be illustrated by the compound of Formula (0.0.29):

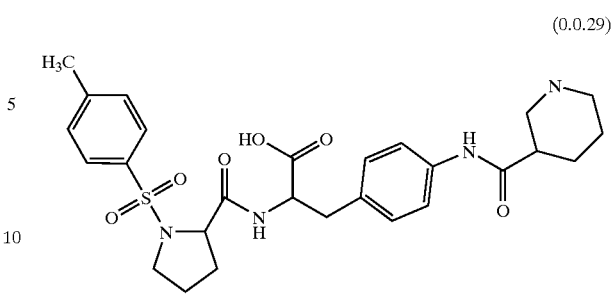

(0.0.29)

WO 99/06434 . . . Athena Neurosciences, Inc.

Another group of VLA-4 inhibitors structurally related to those groups of VLA-4 inhibitors described above, which has been discovered by the Thorsett and Pleiss group is described in Thorsett et al., "Dipeptide Compounds Which Inhibit Leukocyte Adhesion Mediated by VLA-4," WO 99/06435 assigned to Athena Neurosciences, Inc. and American Home Products Corporation. Inhibitory compounds of this type are characterized by general Formula (0.0.30):

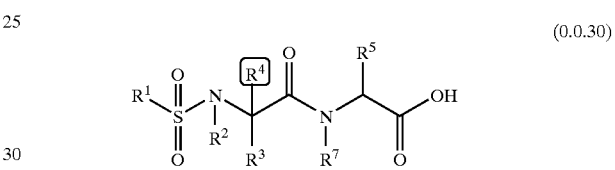

(0.0.30)

where $R^1$, $R^2$, $R^3$, and $R^7$ have substantially the same meaning as described above with respect to WO 99/06390, WO 99/06431, WO 99/06432, WO 99/06433, and WO 99/06434; $R^5$ has substantially the same meaning as described above with respect to WO 99/06432; and $R^4$ is —H; and optionally substituted alkyl; cycloalkyl; aryl; heteroaryl; heterocyclic; and $R^1$ and $R^2$ may be taken together, or $R^2$ and $R^3$ may be taken together, or $R^3$ and $R^4$ may be taken together to form cycloalkyl or heterocyclic groups.

This type of VLA-4 inhibitor may be illustrated by the compound of Formula (0.0.31):

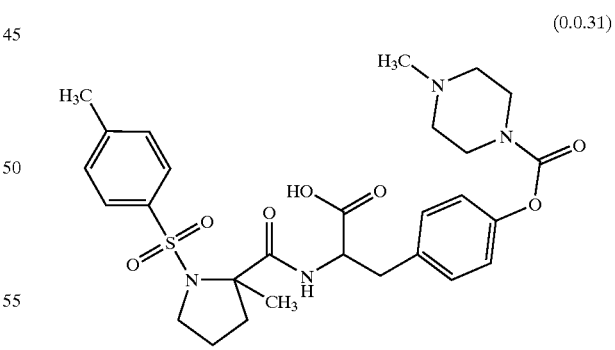

(0.0.31)

WO 99/06435 . . . Athena Neurosciences, Inc.

A still further group of structurally related inhibitors of VLA-4 dependent cell adhesion which has been discovered by the Thorsett and Pleiss group is described in Thorsett et al., "Benzyl Compounds Which Inhibit Leukocyte Adhesion Mediated by VLA-4," WO 99/06436 assigned to Athena Neurosciences, Inc. and American Home Products Corporation. Inhibitory compounds of this type are characterized by general Formula (0.0.32):

(0.0.32)

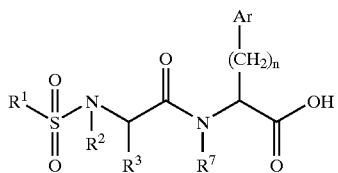

where R¹, R², R³, and R⁷ have substantially the same meaning-as described above with respect to WO 99/06390, WO 99/06431, WO 99/06432, WO 99/06433, and WO 99/06434; and Ar is aryl or heteroaryl. This type of VLA-4 inhibitor may be illustrated by the compound of Formula (0.0.33):

(0.0.33)

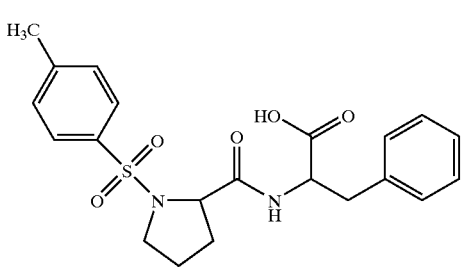

WO 99/06436 . . . Athena Neurosciences, Inc.

There is a further description of compounds related structurally to those described above in WO 99/06390, WO 99/06431, WO 99/06432, WO 99/06433, WO 99/06434, WO 99/06435, and WO 99/06436, but distinguished from them by means of extensive provisos, that is set out in Thorsett et al., "Sulfonylated Dipeptide Compounds Which Inhibit Leukocyte Adhesion Mediated by VLA-4," WO 99/06437. Three such inhibitory compounds are those of Formulas (0.0.34) through (0.0.36):

(0.0.34)

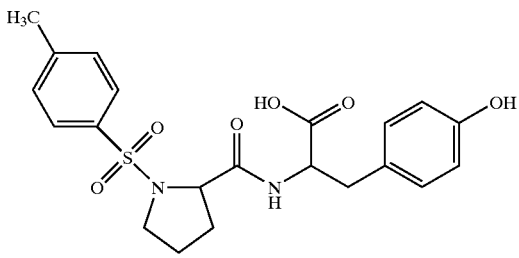

(0.0.35)

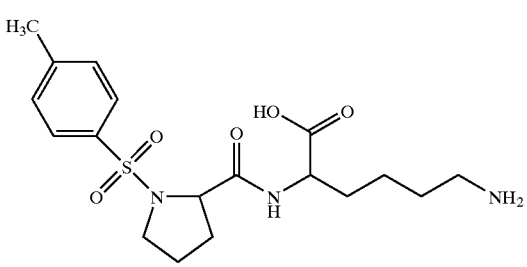

(0.0.36)

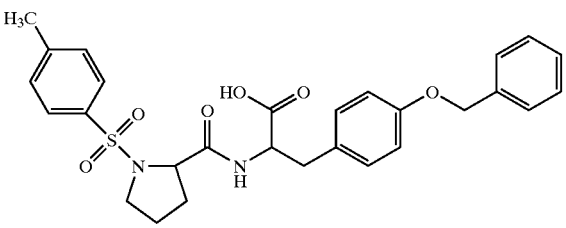

WO 99/06437 . . . Athena Neurosciences, Inc.

The Stilz and Wehner group has discovered a different class of compounds which possess inhibitory activity with regard to VLA-4 mediated cell adhesion. These inhibitory compounds are described, e.g., in Stilz et al., "5-Ring Heterocycles As Inhibitors of Leukocyte Adhesion and As VLA-4 Antagonists," EP 842 943 assigned to Hoechst AG., which may be characterized by general Formula (0.0.37):

(0.0.37)

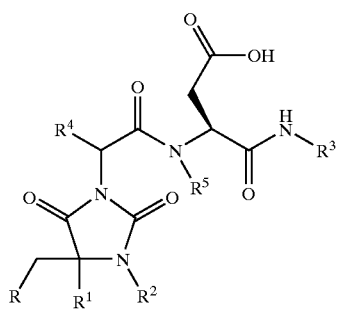

where R is 4-amido-phenyl, 4-guanidino-phenyl, 4-aminomethyl-phenyl, 3-amino-propyl, or 3-guanidino-propyl; R¹ is methyl or benzyl; R² is —H, methyl, ethyl, optionally substituted benzyl, or naphthylmethyl; R³ is a mono-, di-, or tri-peptide; R⁴ is —H, methyl, or butyl; and R⁵ is —H, alkyl, cycloalkyl, or optionally substituted aryl. A representative compound falling within the scope of the above-described class of VLA-4 inhibitors is that of Formula (0.0.38):

(0.0.38)

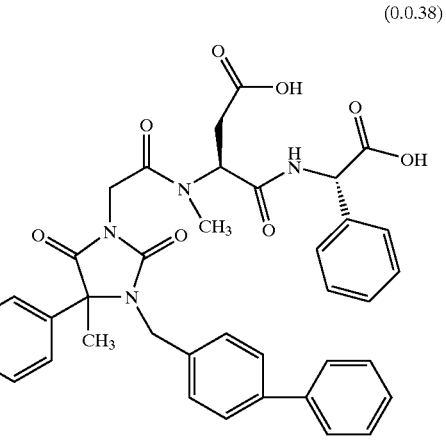

EP 842 943. Hoechst AG.

The Stilz and Wehner group has also discovered inhibitory compounds which are structurally close to those in above-described EP 842 943, and which are described in Stilz et al., "Heterocycles As Inhibitors of Leukocyte Adhesion and As Antagonists of VLA-4," EP 842 944. These compounds may be characterized by general Formula (0.0.39):

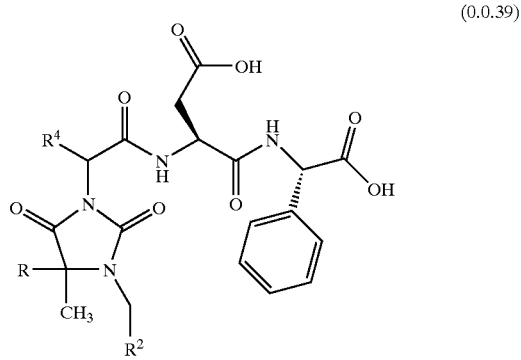

where $R^4$ is methyl or 4-$R^3$-phenyl where $R^3$ is 4,5-dihydroimidazol-2-yl or —C(=O)NH$_2$; $R^2$ is optionally substituted phenyl, pyridyl, or naphthyl; and $R^4$ is —H, ethyl, n-butyl, or isobutyl. A representative example of this type of inhibitory compound is that of Formula (0.0.40):

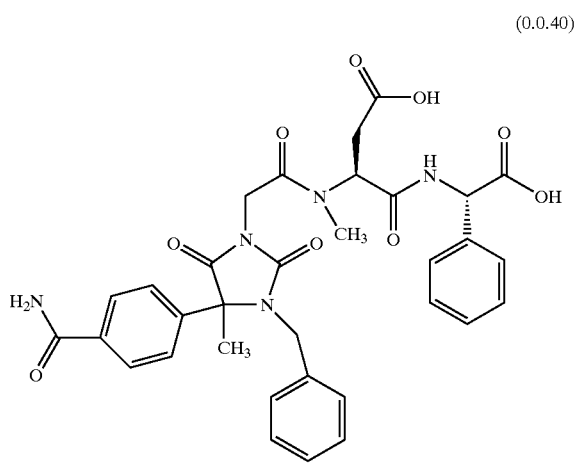

EP 842 944. Hoechst AG.

Further inhibitory compounds structurally close to those in above-described EP 842 944 are described in Stilz et al., EP 842 945, which may be characterized by general Formula (0.0.41):

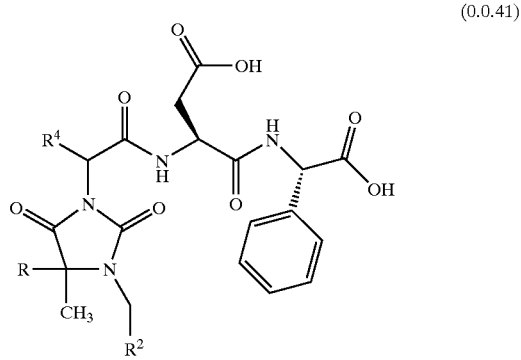

where R is 4-$R^2$-phenyl where $R^2$ is —CN, —NO$_2$, optionally substituted —NH$_2$C(=O)NH, or —NH$_2$C(=O)NHCH$_2$; and $R^2$ is optionally substituted phenyl. A representative example of this type of inhibitory compound is that of Formula (0.0.42):

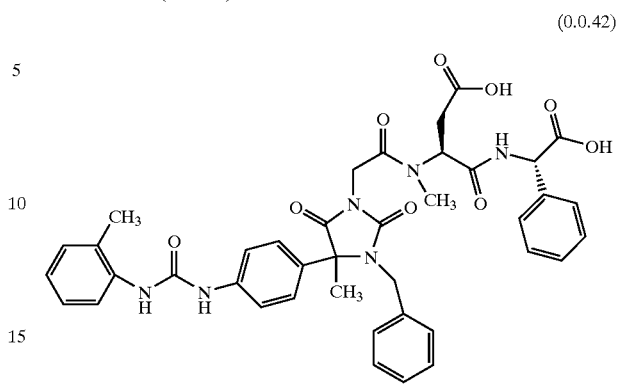

EP 842 945. Hoechst AG.

The Stilz and Wehner group has also further discovered inhibitors of VLA-4 dependent cell adhesion which are described in Wehner et al., "Imidazolidine Derivatives with VLA-4 Antagonist Activity Useful for the Treatment of Diseases Mediated by Leukocyte Adhesion," EP 903 353 assigned to Hoechst Marion Roussel Deutschland GmBH. Compounds of this type are characterized by general Formula (0.0.43):

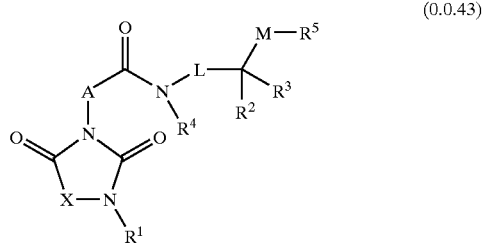

where A is optionally substituted alkylene, alkenylene, phenylene, -phenyl-alkylene, or alkylene-phenyl-; L and M are a bond or —CH$_2$—; X is optionally substituted —CH($R^7$)— or —C(=CHR$^7$)— where $R^7$ is optionally substituted alkyl, phenyl, furyl, thienyl, pyrrolyl, indazolyl, or pyridinyl; $R^1$ is —H, cycloalkyl, optionally substituted alkyl, aryl, heterocyclyl; —C(=O)$R^6$, or —SO$_2$R where $R^6$ is —H, cycloalkyl, optionally substituted alkyl, aryl, or heterocyclyl; $R^2$ is —NH$_2$, —C(=O)NH$_2$, or —C(=O)OH; $R^3$ is —H, alkyl, optionally substituted aryl, or heterocyclyl; and $R^5$ is —C(=O)OH, tetrazolyl, —SO$_3$H, or —SO$_2$NH$_2$.

A typical VLA-4 inhibitor falling within the above-described class of compounds is illustrated by Formula (0.0.44):

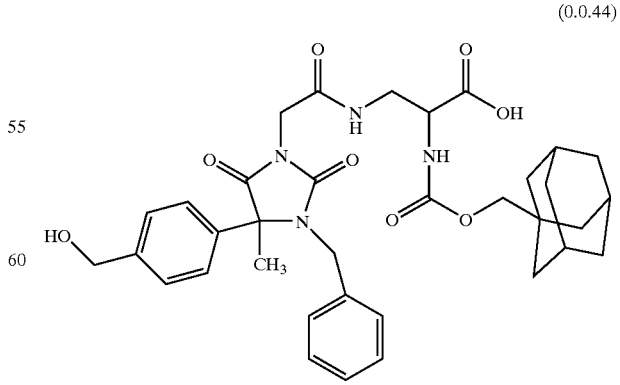

EP 903 353. Hoechst Marion Roussel Deutschland GmBH

Another group of inhibitory compounds closely related in structure to those above-described has been discovered by the Stilz and Wehner group and is described in Wehner et al., "Substituted Imidazoline Derivatives with VLA-4 Antagonist Activity," EP 918 059. Said group may be illustrated by general Formula (0.0.45):

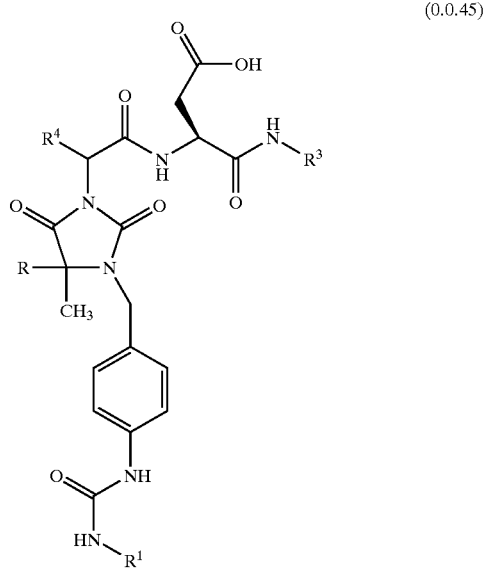

(0.0.45)

where R is methyl or phenyl; $R^1$ is tert-butyl, propyl, iso-propyl, benzyl, cyclohexyl, or optionally substituted phenyl; $R^3$ is adamantyl, —CH(CH$_3$)CH$_2$C(=O)OH, optionally substituted —CH(phenyl)CH$_2$C(=O)OH or —CH(phenyl)C(=O)OH; and $R^4$ is —H or iso-butyl. An example of a compound which illustrates this class of VLA-4 inhibitors is that of Formula (0.0.46):

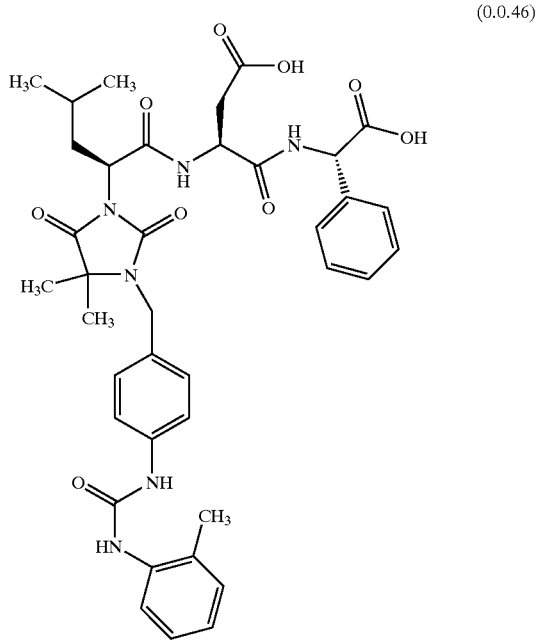

(0.0.46)

EP 918 059. Hoechst Marion Roussel Deutschland GmBH

Yet another class of VLA-4 inhibitors has been discovered by the Chen group, e.g., as described in Chen et al., "Novel N-Aroylphenylalanine Derivatives As Integrin Antagonists," WO 99/10312 assigned to F. Hoffmann-La Roche AG. This class of inhibitors may be illustrated by general Formulas (0.0.47) and (0.0.48):

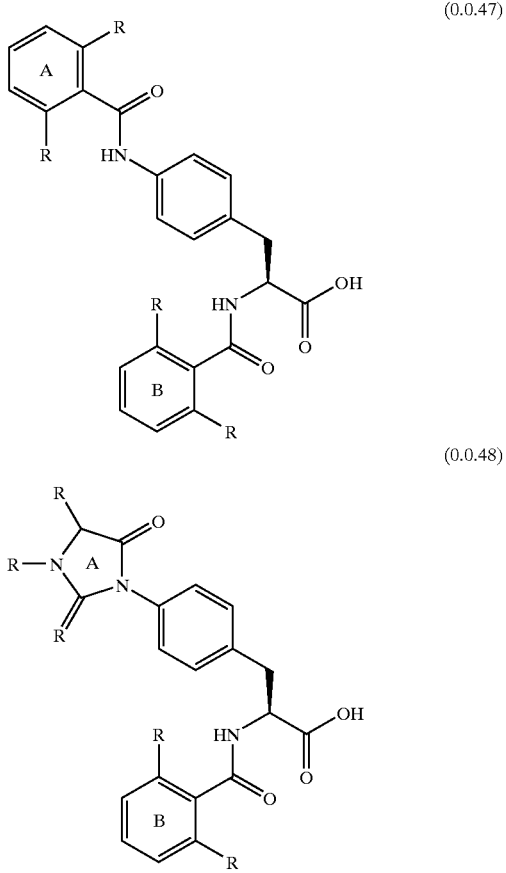

(0.0.47)

(0.0.48)

where there are two sub-classes of compounds based on different A rings as shown above. Further, the A and B rings may be replaced with various heterocycles, although an ortho-substituted B ring is preferred. A representative example of a compound falling within this class of inhibitors is that of Formula (0.0.49):

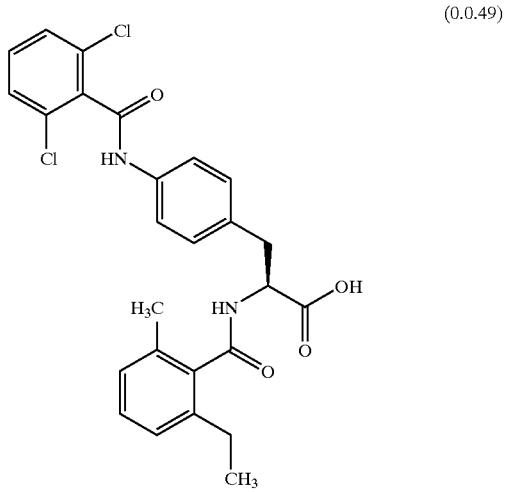

(0.0.49)

WO 99/10312 . . . F. Hoffmann-La Roche AG.

A closely related group of inhibitors discovered by the Chen group is described in Chen et al., WO 99/10313 assigned to F. Hoffmann-La Roche AG., which may be illustrated by general Formulas (0.0.50) and (0.0.51):

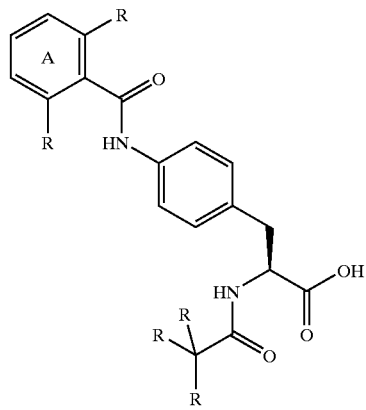

(0.0.50)

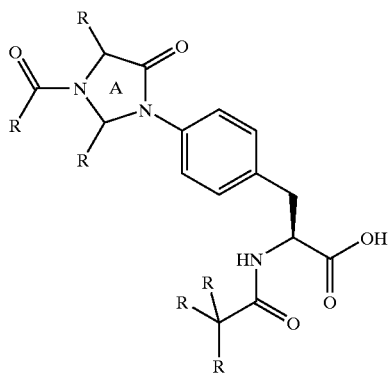

(0.0.51)

where there are two sub-classes of compounds as described above in the case of those of Formulas (0.0.47) and (0.0.48). Further, the three R groups attached to the amide linker combine to form a quaternary center. A typical compound representative of the VLA-4 inhibitors in this class is that of Formula (0.0.52):

(0.0.52)

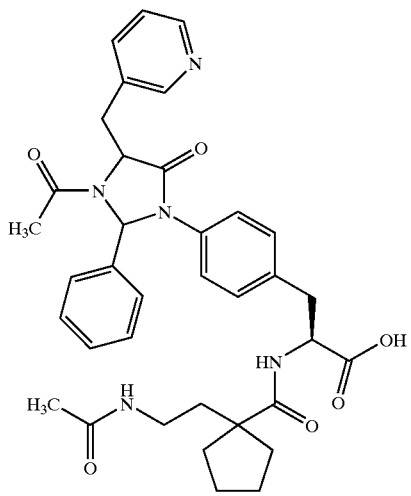

WO 99/10313 . . . F. Hoffmann-La Roche AG.

A still further class of inhibitors of VLA-4 dependent cell adhesion is that discovered by Hagmann and his co-workers, e.g., as described in Durette and Hagmann, "Heterocyclic Amide Compounds As Cell Adhesion Inhibitors," WO 98/53814 which is assigned to Merck & Co., Inc. This class of compounds may be illustrated by general Formula (0.0.53):

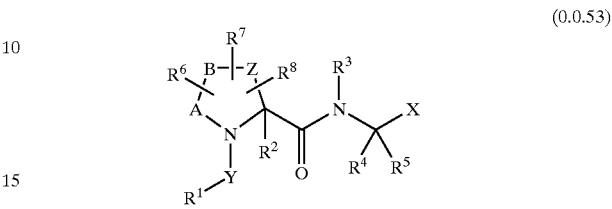

(0.0.53)

where X is —C(=O)OH or acid isostere; Y is —C(=O) or —S(=O)$_2$; $R^1$ through $R^8$ are selected from a wide variety of well known substituents; and A, B, and Z are selected so as to afford heterocycles of different types and ring sizes. An example of an inhibitory compound which is representative of this class is that of Formula (0.0.54):

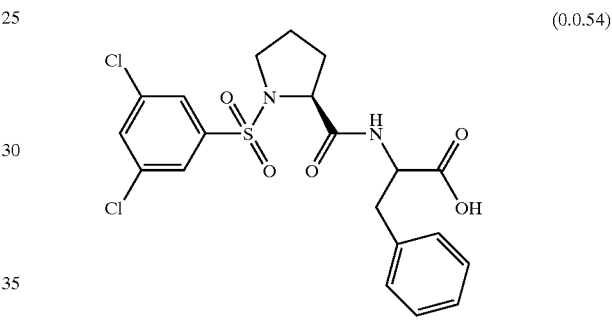

(0.0.54)

WO 98/53814 . . . Merck & Co., Inc.

Another class of structurally related inhibitory compounds discovered by the Hagmann group is described in Durette et al., "Biarylalkanoic Acids As Cell Adhesion Inhibitors," WO 98/53817 assigned to Merck & Co., Inc., which may be illustrated by general Formulas (0.0.55) and (0.0.56):

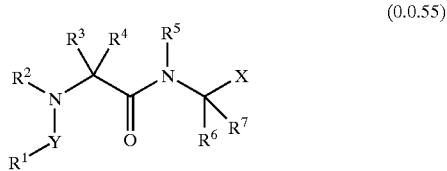

(0.0.55)

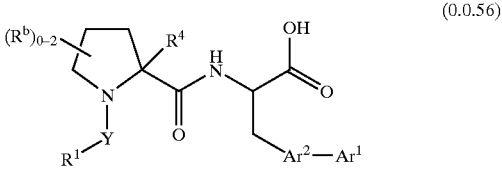

(0.0.56)

where X, Y, and $R^1$ through $R^7$ have substantially the same meaning as defined above for Formula (0.0.53), except that $R^2$ and $R^3$ may be taken together with the atoms to which they are attached to form a ring of 4 to 7 members containing 0–2 additional heteroatoms selected from O, S, and N; and $R^b$ is optionally substituted alkyl, alkenyl, alkynyl, arylalkyl, or heteroarylalkyl. A representative example of a compound falling within the scope of this class of VLA-4 inhibitors is that of Formula (0.0.57):

(0.0.57)

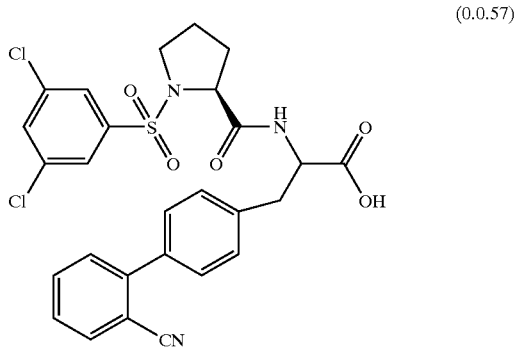

WO 98/53817 . . . Merck & Co., Inc.

A further class of inhibitory compounds discovered by the Hagmann group and closely related in structure to those described immediately above, is disclosed in Durette et al., "Sulfonamides As Cell Adhesion Inhibitors," WO 98/53818 assigned to Merck & Co., Inc. These compounds may be illustrated by general Formulas (0.0.57) and (0.0.58):

(0.0.57)

(0.0.58)

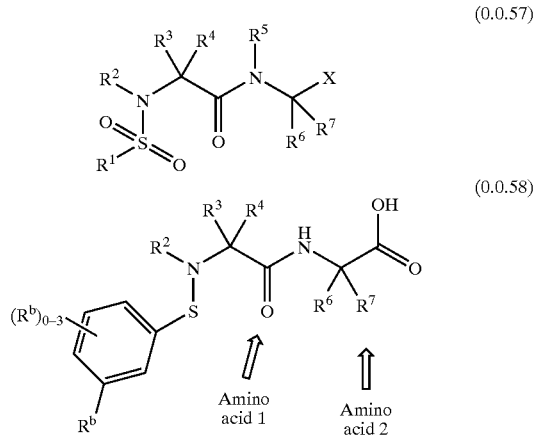

where $R^b$ and $R^1$ through $R^7$ have the same meaning as defined above for Formulas (0.0.55) and (0.0.56). A representative inhibitory compound falling within the above-described class is that of Formula (0.0.59):

(0.0.59)

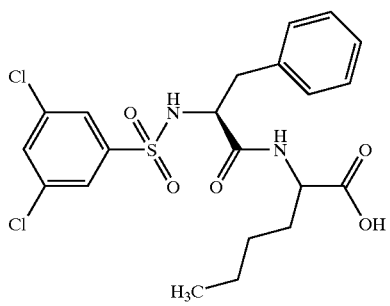

WO 98/53818 . . . Merck & Co., Inc.

A still further class of VLA-4 inhibitory compounds related in structure to those described above has been discovered by the Hagmann group and is disclosed in Delaszlo, "Azapeptide Acids As Cell Adhesion Inhibitors," WO 99/20272. This class of inhibitors may be illustrated by general Formula (0.0.60):

(0.0.60)

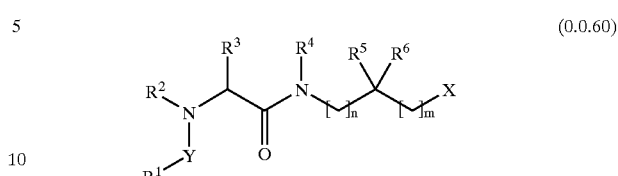

where m and n are 0 to 2; and X, Y, and $R^1$ through $R^6$ have the same meaning as defined above for Formulas (0.0.55) and (0.0.56). Representative inhibitory compounds falling within the above-described class are those of Formulas (0.0.61) and (0.0.62):

(0.0.61)

(0.0.62)

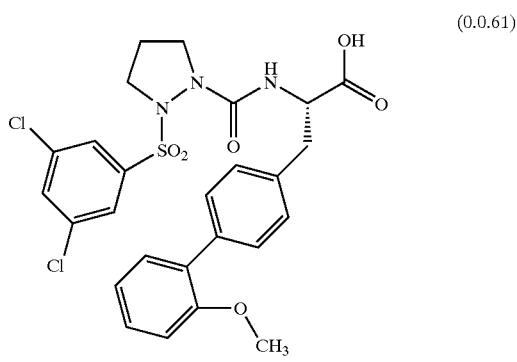

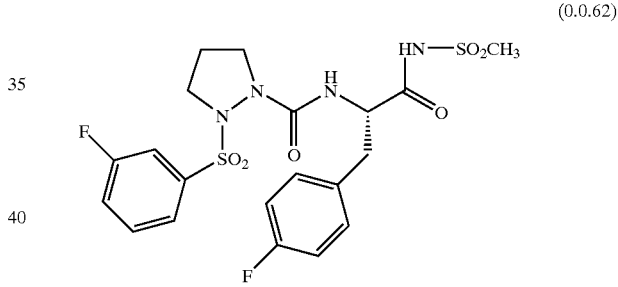

WO 99/20272 . . . Merck & Co., Inc.

Another class of VLA-4 dependent cell adhesion inhibitors discovered by the Hagmann group is described in Delaszlo and Hagmann, "4-Substituted-4-Piperidine Carboxamide Derivatives Useful in the Treatment of Asthma, Inflammation and Multiple Sclerosis." WO 99/25685 assigned to Merck & Co., Inc. Compounds of this class may be illustrated by general Formula (0.0.63):

(0.0.63)

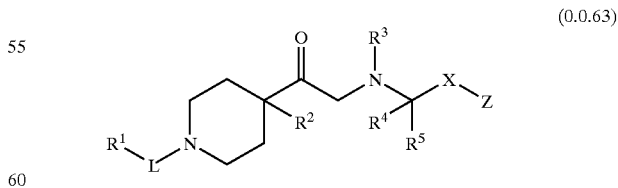

where X is a bond or substituted carbon atom; Z is —C(=O)OH or acid isostere; L is —C(=O)—, —S(=O)$_2$—; and $R^1$ through $R^5$ have the substantially the same meaning as defined above for Formulas (0.0.55) and (0.0.56). A typical VLA-4 inhibitory compound in this class is that of Formula (0.0.64):

(0.0.64)

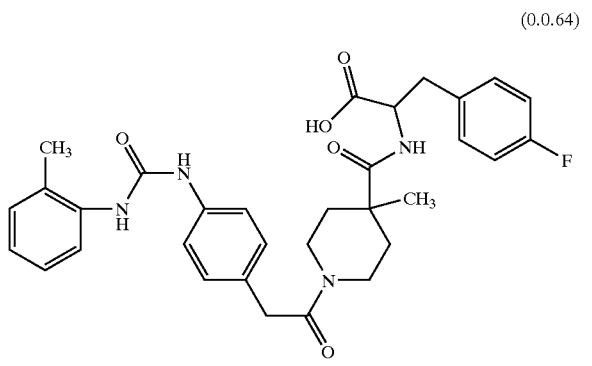

(0.0.67)

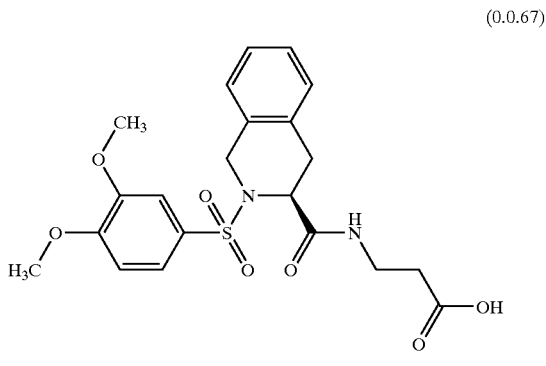

WO 99/25685 . . . Merck & Co., Inc.

Another class of VLA-4 inhibitors closely related in structure to those described above is disclosed in Chang et al., "Cyclic Amino Acids As Cell Adhesion Inhibitors," WO 99/26615 assigned to Merck & Co., Inc. Inhibitory compounds of this class are illustrated by general Formula (0.0.65):

(0.0.68)

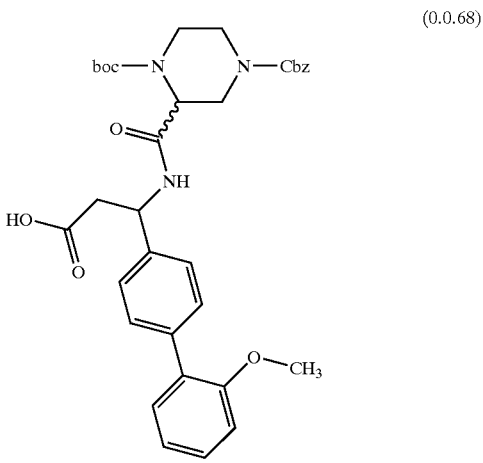

(0.0.65)

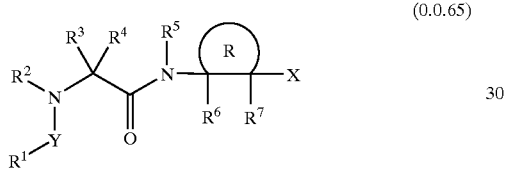

where R indicates the ring size, and X, Y, and $R^1$ through $R^7$ have the same meaning as defined above for Formulas (0.0.55) and (0.0.56). A representative example of an inhibitory compound within this class is that of Formula (0.0.66):

WO 99/26921 . . . Merck & Co., Inc.

A further class of VLA-4 dependent cell adhesion inhibitors related in structure to those described above has been discovered by the Hagmann group and is disclosed in Chang et al., "Substituted Pyrrole Derivates As Cell Adhesion Inhibitors," WO 99/26922 assigned to Merck & Co., Inc. This class of inhibitors is illustrated by general Formula (0.0.69):

(0.0.66)

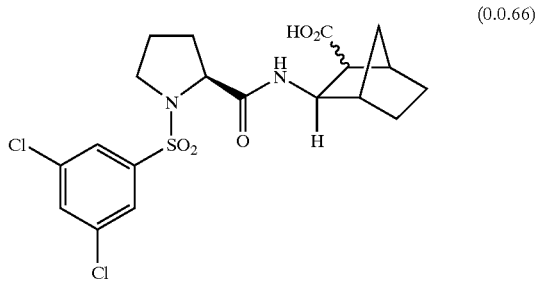

(0.0.69)

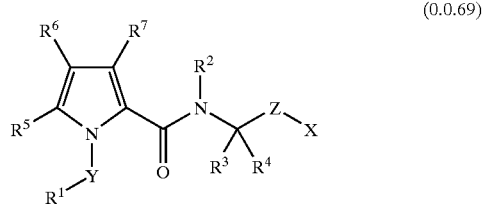

WO 99/26615 . . . Merck & Co., Inc.

A class of VLA-4 dependent cell adhesion inhibitors has been discovered which differs from those disclosed in WO 98/53814 described above only with respect to th terminal amino acid, which is a β-amino acid. Accordingly, reference may be made to general Formula (0.0.53) above. These β-amino acids are disclosed in Durette et al., "Substituted β-Alanine Derivatives As Cell Adhesion Inhibitors," WO 99/26921 assigned to Merck & Co., Inc. Typical inhibitors of this type are illustrated in Formulas (0.0.67) and (0.0.68):

where Y and $R^1$ through $R^7$ have the same meaning as defined above for Formulas (0.0.55) and (0.0.56), and X and Z have the same meaning as defined above for Formula (0.0.63), except that the meanings are reversed because —X-Z- in (0.0.63) has been changed to -Z-X— in (0.0.69). An example of inhibitory compounds falling within this class is illustrated by Formula (0.0.70):

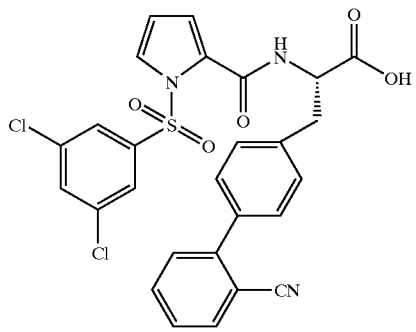

(0.0.70)

WO 99/26922 . . . Merck & Co., Inc.

Another class of VLA-4 inhibitory compounds discovered by the Hagmann group and closely related to those above is that described in Delaszlo and Hagmann, "Para-Aminomethylaryl Carboxamide Derivatives," WO 99/26923 assigned to Merck & Co., Inc., and which may be represent by general Formula (0.0.71):

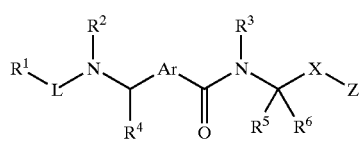

(0.0.71)

where L, X, Z, and $R^1$ through $R^6$ have substantially the same meaning as defined above under Formulas (0.0.55) and (0.0.56). Ar is a 1,4 substituted aryl or heteroaryl moiety. A typical compound falling within the scope of this class of VLA-4 inhibitors is illustrated as Formula (0.0.72):

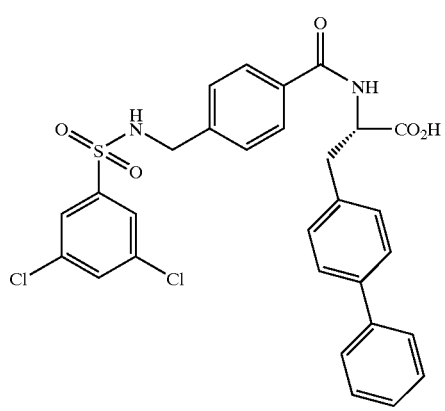

(0.0.72)

WO 99/26923 . . . Merck & Co., Inc.

A different group has discovered a new class of VLA-4 antagonists which is described in Wattanasin and Von Matt, "VLA-4 Antagonists," WO 99/37605 assigned to Novartis. The inhibitory compounds in this new class may be represented by general Formula (0.0.73):

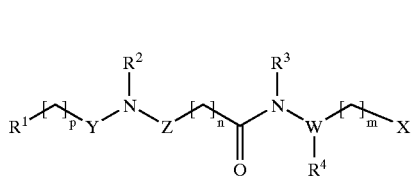

(0.0.73)

where Y is —C(=O)—, —S(=O)$_2$—, or —P(=O)$_2$—; Z is —(CH$_2$)$_n$—, —CHR—, or —NR—; W is —CH— or —N—; X is —C(=O)OH or acid isostere; and $R^1$ through $R^4$ are a wide variety of common substituents. A representative example of a VLA-4 inhibitor from this class is illustrated by Formula (0.0.74):

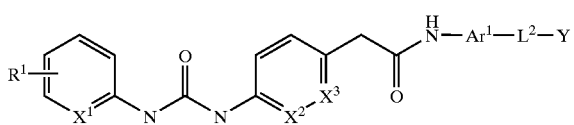

(0.0.74)

WO 99/37605 . . . Novartis

Another different group has discovered a further new class of compounds which inhibit VLA-4 dependent cell adhesion, which is described in Astles et al., "Substituted Anilides and Their Use in the Treatment of Various Disease States including Inflammation, arthritis, and atherosclerosis," WO 99/23063 assigned to Rhone-Poulenc Rorer Ltd. This class of VLA-4 inhibitors may be represented by general Formula (0.0.75):

(0.0.75)

where $X^1$, $X^2$, and $X^3$ are —N— or —CR—; $Ar^1$ is aryl or heteroaryl; $L^2$ is an optionally substituted alkylene linkage; Y is carboxy, an acid bioisostere, or —C(=O)NRR; and $R^1$ is —H, halo, —OH, lower alkyl or lower alkoxy. A representative example of an inhibitory compound which fits into this class is illustrated by Formula (0.0.76):

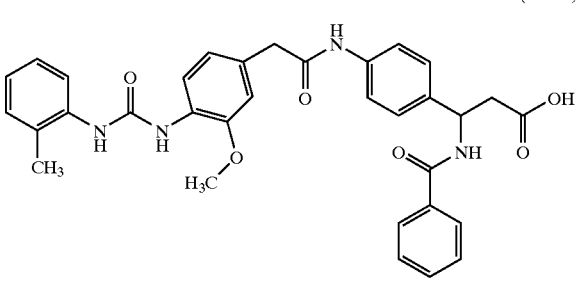

(0.0.76)

WO 99/23063 . . . Rhone-Poulenc Rorer Ltd.

Another class of VLA-4 inhibitors which is closely related in structure to those described immediately above is described in Artles et al. "Biaryl β-Alanine Derivatives Useful As VLA-4 Antagonists," WO 99/33789 assigned to Rhone-Poulenc Rorer Ltd. Members of this class of inhibitors may be represented by general Formula (0.0.77):

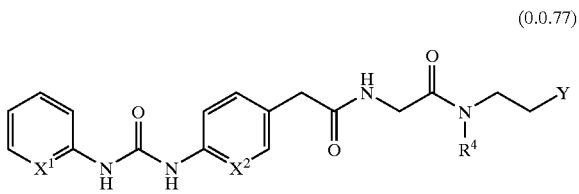

(0.0.77)

where $X^1$, $X^2$, and Y have the same meaning as defined above under Formula (0.0.75). $R^4$ is aryl or heteroaryl or is optionally substituted alkyl, alkenyl or alkynyl. A representative example of an inhibitory compound within this class is illustrated by Formula (0.0.78):

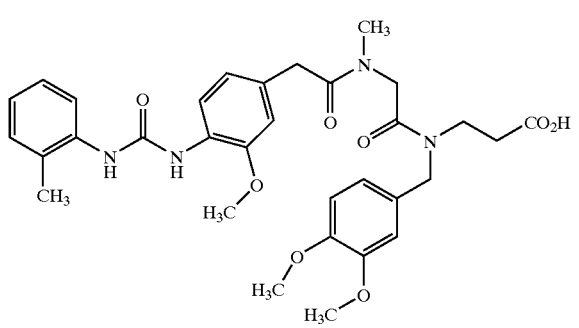

(0.0.78)

WO 99/33789 . . . Rhone-Poulenc Rorer Ltd.

A further different group has also discovered a new class of VLA-4 dependent cell adhesion inhibitors, which is described in Lobl et al. "Cyclic Peptide Inhibitors of $\beta_1$ and $\beta_2$ Integrin-Mediated Adhesion," WO 96/40781 assigned to Tanabe Seiyaku Co., Ltd. The inhibitors are cyclic peptides which contain a free acid.

WO 96/40781 . . . Tanabe Seiyaku Co., Ltd.

Another class of VLA-4 inhibitors discovered by the same group is described in Lobl et al. "Inhibitors of $\alpha_1\beta_4$ Mediated Cell Adhesion," WO 98/58902 assigned to Tanabe Seiyaku Co., Ltd. and Pharmacia & Upjohn Company. Members of this further class of VLA-4 inhibitors may be represented by general Formula (0.0.79):

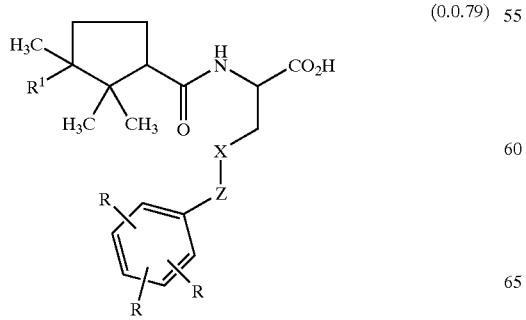

(0.0.79)

where $R^1$ is acid or amide; X is phenyl; and Z is amide or methylene ether. A representative example of an inhibitory compound from this class is that of Formula (0.0.80):

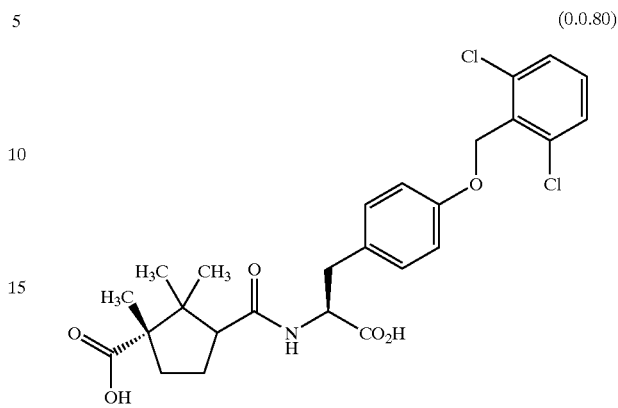

(0.0.80)

WO 98/58902 . . . Tanabe Seiyaku Co., Ltd.

Another class of VLA-4 inhibitors discovered by the same group is described in Sircar et al. "Inhibitors of α4 Mediated Cell Adhesion," WO 99/36393 assigned to Tanabe Seiyaku Co., Ltd. Members of this class of VLA-4 inhibitors may be characterized by general Formula (0.0.81):

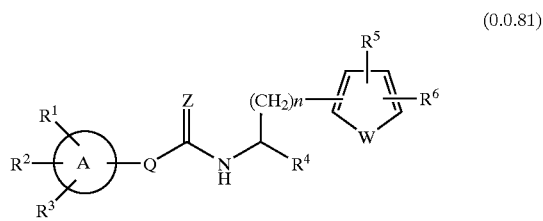

(0.0.81)

where $R^1$ through $R^6$, except $R^4$, are selected from a wide variety of common substituent groups; $R^4$ is acid, acid isostere, or amide; A is aryl or heteroaryl; Q is a bond, —C(=O)—, or substituted alkylene; n is 0 to 2; and W is —O—, —S—, —CH=CH—, or —N=CH—. A representative member of this class of VLA-4 inhibitors is illustrated by Formula (0.0.82):

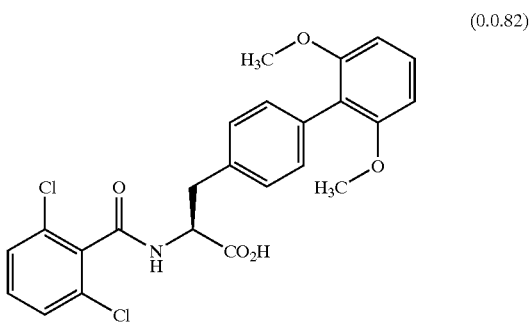

(0.0.82)

WO 99/36393 . . . Tanabe Seiyaku Co., Ltd.

A still further different group has also discovered a new class of VLA-4 dependent cell adhesion inhibitors, which is described in Kogan et al. "Process to Inhibit Binding of the Integrin alpha 4 beta 1 to VCAM-1 or Fibronectin," WO 96/00581 assigned to Texas Biotechnology Corporation. This class of VLA-4 antagonists comprises cyclic peptides of from 5 to 13 residues modeled after a portion of the CS1 peptide, that also contain a free acid.

WO 96/00581 . . . Texas Biotechnology Corporation

A yet still further different group has also discovered a new class of VLA-4 antagonists, which is described in Dutta, "Fibronectin Adhesion Inhibitors," WO 96/20216 assigned to Zeneca Limited. This class of VLA-4 antagonists comprises cyclic peptides that contain a free acid.

WO 96/00581 . . . Zeneca Limited

A related class of VLA-4 antagonists discovered by the same group is described in Dutta, "Cyclic Tetrapeptide Dimers Useful As Fibronectin Inhibitors," WO 97/02289 assigned to Zeneca Limited. This class of VLA-4 antagonists comprises cyclic dimeric peptides in which a peptide 1 and peptide 2 independently representing a tetrapeptide, are juxtaposed in parallel or antiparallel orientation by means of two linking moieties L1 and L2.

WO 97/02289 . . . Zeneca Limited

Another related class of VLA-4 antagonists discovered by the same group is described in Dutta, "Cyclic Octapeptide Derivatives That Are Integrin Antagonists," WO 97/49731 assigned to Zeneca Limited. This class of VLA-4 antagonists comprises a variety of cyclic octapeptides containing a free acid.

WO 97/49731 . . . Zeneca Limited

The same group has also discovered a non-peptidal class of VLA-4 antagonists which is described in Brittain and Johnstone, "Chemical Compounds," WO 99/24398 assigned to Zeneca Limited. Members of this class may be represented by general Formula (0.0.83):

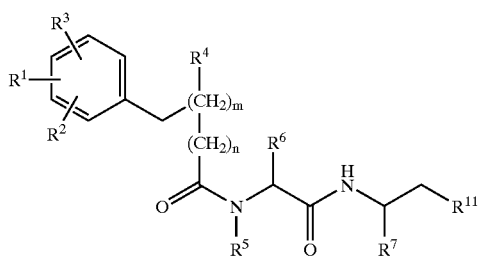

(0.0.83)

where Y is —O—, —S—, or —S(=O)$_2$—; R$^1$ is urea; R$^{11}$ is acid or acid isostere; and m is 0 or 1 and when m is 0 then n is 1 to 4, and when m is 1 then n is 0. A representative member of this class of VLA-4 antagonists is illustrated by Formula (0.0.84):

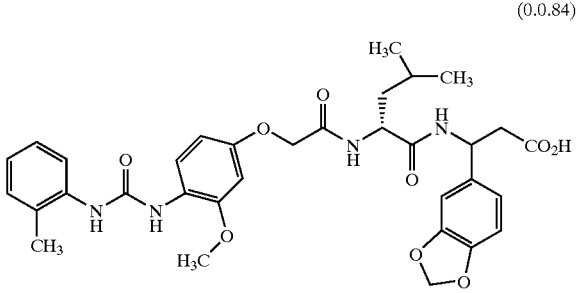

(0.0.84)

WO 99/24398 . . . Zeneca Limited

None of the references discussed above discloses or suggests the compounds of th present invention.

Despite the above-described advances in the art with regard to inhibitors of VLA-4 mediated cell adhesion, the artisan will quickly recognize that the peptidyl inhibitors are prone to poor absorption, poor solubility and are subject to metabolism in vivo (both systemically and locally when administered directly into the lung) diminishing their opportunity to appreciably affect the course of an inflammatory, respiratory or autoimmune disease.

Those of the above-described VLA-4 antagonists that are non-peptidal, i.e., that may be regarded as small molecules, are thereby able to avoid the liabilities of peptidal agents as discussed above. However, the small molecule VLA-4 antagonists known in the art, as described in detail above, have not yet been established to possess sufficiently high levels of the desired potency with low levels of acceptable side effects, together with adequately workable pharmacokinetic and adsorption profiles, such as would enable such compounds to become suitable therapeutic agents for use in treating the diseases and conditions discussed herein. Accordingly, there still exists in the art a need for non-peptidyl or semi-peptidyl therapeutic agents which can effectively treat or prevent such pathological conditions.

SUMMARY OF THE INVENTION

The present invention is concerned with compositions which inhibit VLA-4 dependent cell adhesion in a mammal. The present invention thus relates to a compound of Formula (1.0.0):

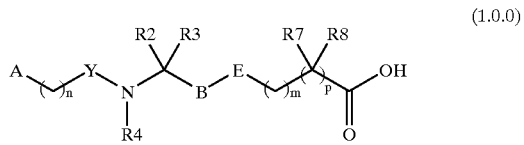

(1.0.0)

and pharmaceutically acceptable salts and other prodrug derivatives thereof, wherein:

A is (C$_1$–C$_6$) alkyl, cycloalkyl, aryl, heteroaryl or heterocyclyl as defined herein; where said alkyl, cycloalkyl, aryl, heteroaryl or heterocyclyl is optionally substituted with 0 to 3 R$^9$; or is a member selected from the group consisting of the following radicals: A$^1$-NHC(=O)NH-A$^2$-, A$^1$-NHC(=O)O-A$^2$-, A$^1$-OC(=O)NH-A$^2$-, A$^1$-NHSO$_2$NH-A$^2$-, A$^1$-NHC(=O)-A$^2$-, A$^1$-C(=O)NH-A$^2$-, A$^1$-NHSO$_2$-A$^2$-, A$^1$-SO$_2$NH-A$^2$-, A$^1$-(CH$_2$)$_r$O-A$^2$-, A$^1$-O(CH$_2$)$_r$-A$^2$-, A-(CH$_2$)$_r$-A$^2$-, where A$^1$ and A$^2$ are each independently selected from the group consisting of hydrogen, aryl, (C$_1$–C$_6$) alkyl, (C$_2$–C$_6$) alkenyl, (C$_2$–C$_6$) alkynyl, cycloalkyl, heteroaryl, and heterocyclyl; where said aryl, alkyl, cycloalkyl, heteroaryl, or heterocyclyl group is substituted with 0 to 3 R$^9$;

B is a member independently selected from the group consisting of the following:

(1.1.0)

(1.1.1)

(1.1.2)

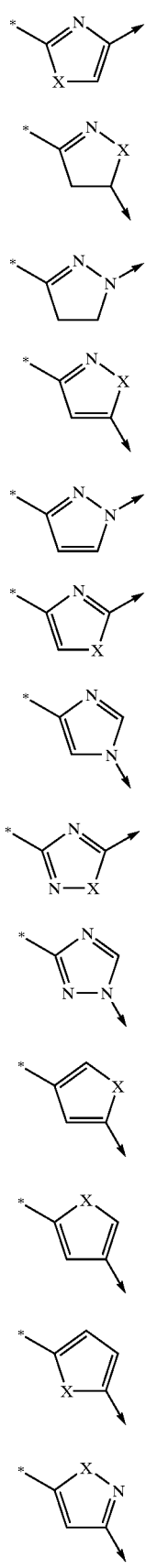
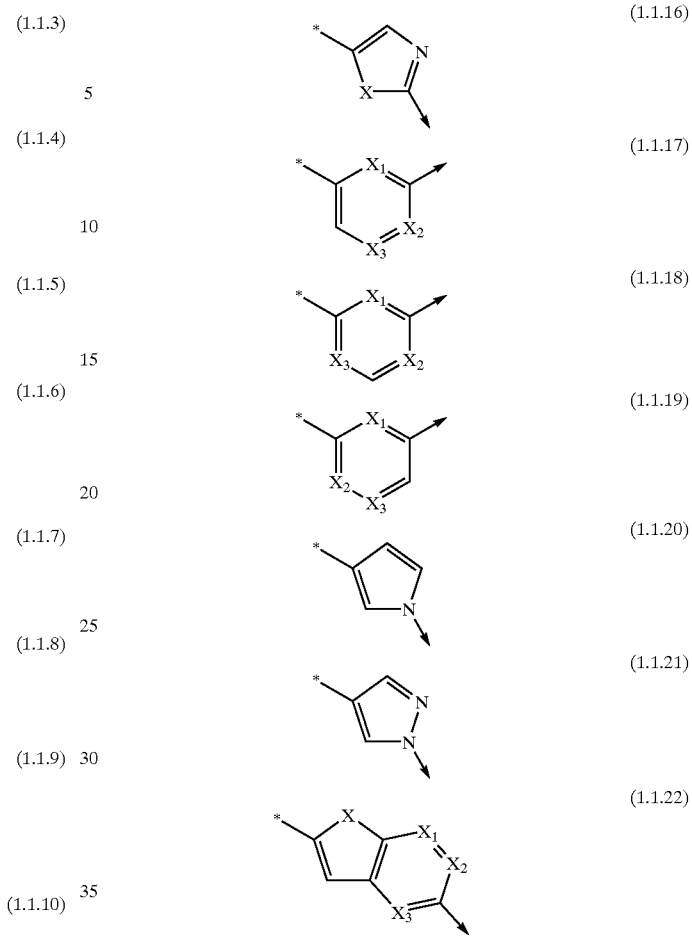

where the symbol "*" indicates the point of attachment of the moiety represented by each partial Formula (1.1.0) through (1.1.22) to the moiety "$CR^2R^3$" in Formula (1.0.0); and the symbol "Π" indicates the point of attachment of the moiety represented by each partial Formula (1.1.0) through (1.1.22) to the moiety "E" in Formula (1.0.0); Each of Formula (1.1.0) through (1.1.22), with the exception of formulas (1.1.10) and (1.1.22), may be optionally substituted with $R^9$;

E is a single bond; —O—; —$NR^{10}$—; —CH=CH—; —CC—; S(=O)$_q$; —$CR^{11}R^{12}NR^{10}$—; or —$CR^{11}R^{12}$—;

X is —O—; —C(=O)—; —S(=O)$_q$—; or —$NR^{10}$—;

$X^1$, $X^2$ and $X^3$ are each independently selected from the group consisting of CH, $CR^9$ or N;

Y is a single bond; —C(=O)—; —C(=S)—; or —S(=O)$_2$—;

k is an integer independently selected from 0, 1 and 2;

m is an integer independently selected from 0 and 1;

n is an integer independently selected from 0, 1 and 2;

p is an integer independently selected from 0 and 1, provided that p must be selected as 1 where B is selected as partial formula (1.1.0) through (1.1.11);

q is an integer independently selected from 0, 1 and 2;

r is an integer independently selected from 0, 1 and 2;

$R^2$ and $R^3$ are each independently selected from the group consisting of hydrogen; ($C_1$–$C_6$) alkyl substituted with 0 to 3 $R^{13}$; ($C_2$–$C_6$) alkenyl substituted with 0 to 3 $R^{13}$; a ($C_3$–$C_{14}$) carbocyclic ring system substituted with 0 to 3 $R^3$; a heterocyclyl ring as defined herein, substituted with 0 to 3 $R^{13}$; ($C_1$–$C_6$) alkyl-$OR^5$ substituted with 0 to 3 $R^{13}$;

(C₁–C₆) alkyl-SR⁵ substituted with 0 to 3 R¹³; (C₁–C₆) alkyl-SO₂R⁵ substituted with 0 to 3 R¹³; a heteroaryl ring as defined herein, substituted with 0 to 3 R¹³; an aryl ring as defined herein, substituted with 0 to 3 R¹³;

provided that

R² and R³ are each defined as above; or they are taken together as defined below; or one of them is taken together with R⁴ as defined below, in which case the other has the meaning of hydrogen or methyl;

R² and R³ are taken together to form either a cycloalkyl or heterocyclyl ring substituted with 0 to 3 R¹³; or R² or R³ is taken together with R⁴ and the carbon and nitrogen atoms to which they are respectively attached to form a heteroaryl or heterocyclyl group as defined herein, substituted with 0 to 3 R¹³;

R⁴ is hydrogen; or (C₁–C₆) alkyl optionally substituted with R¹³; or R⁴ may be taken together with either R² or R³ to form a carbocyclic or heterocyclic ring;

R⁵ and R⁶ are independently hydrogen; (C₁–C₆) alkyl; (C₂–C₆) alkenyl; (C₂–C₆) alkynyl; CF₃; aryl; cycloalkyl; heteroaryl; or heterocyclyl;

R⁷ is (C₁–C₆) alkyl; (CH₂)ₖOR⁵; (CH₂)ₖNR⁶C(=O)R⁵; (CH₂)ₖNR⁶C(=O)OR⁵; (CH₂)ₖNR⁶SO₂R⁵; (CH₂)ₖNR⁶R⁵; F; CF₃; OCF₃; aryl, substituted with 0 to 3 R⁹; heterocyclyl, substituted with 0 to 3 R⁹; heteroaryl, substituted with 0 to 3 R⁹; cycloalkyl, substituted with 0 to 3 R⁹; or R⁷ may be taken together with R⁸ to form a cycloalkyl or heterocyclyl ring; or R⁷ may be taken together with R¹¹ to form a cycloalkyl or heterocyclyl ring;

R⁸ is hydrogen; F; (C₁–C₆) alkyl or (C₁–C₆) alkoxy;

R⁹ is halogen; (C₁–C₆) alkyl; (C₁–C₆) alkoxy; (C₃–C₆) cycloalkyl; (C₃–C₆) cycloalkoxy; cyano; (CH₂)ₖOH; C(=O)R⁵; (CH₂)ₖC(O)NR⁵R⁶; (CH₂)ₖNR⁵R⁶; (CH₂)ₖNR⁵SO₂R⁶; CF₃; OCF₃; SO₂NR⁵R⁶; (CH₂)ₘC(=O)OR⁵; when R⁵ is attached to a saturated carbon atom R⁹ may be =O or =S; when R⁹ is attached to a sulphur atom R⁹ may be =O;

R¹⁰ is hydrogen; C(=O)R⁵; C(=O)OR⁵; (C₁–C₆) alkyl; aryl; heterocyclyl; heteroaryl; cycloalkyl; or SO₂R⁵;

R¹¹ and R¹² are independently hydrogen; (C₁–C₆) alkyl; hydroxy; cyano; (C₁–C₆) alkoxy; NR⁶C(=O)R⁵; NR⁶SO₂R⁵; NR⁶R⁵; CF₃; F; aryl; heterocyclyl; heteroaryl; cycloalkyl; cycloalkoxy; or R¹¹ may be taken together with R¹² to form a cycloalkyl or heterocyclyl ring;

R¹³ is independently selected from the group consisting of halogen; CF₃; (C₁–C₆) alkyl; aryl; heteroaryl; heterocyclyl; hydroxy; cyano; (C₁–C₆) alkoxy; (C₃–C₆) cycloalkyl; (C₃–C₆) cycloalkoxy; (C₂–C₆) alkynyl; (C₂–C₆) alkenyl; —NR⁶R⁵; —C(=O)NR⁵R⁶; SO₂R⁵; C(=O)R⁵; NR⁵SO₂R⁶; NR⁵C(=O)R⁶; C(=O)NR⁵SO₂R⁶; NR⁵C(=O)OR⁶; and SO₂NR⁶R⁵.

The present invention is also concerned with pharmaceutical compositions comprising one or more of the compounds of the present invention as described above together with a pharmaceutically acceptable carrier for said compound(s), wherein the amount of said compound(s) present is effective for preventing, inhibiting, suppressing or reducing cell adhesion and consequent or associated pathogenic processes subsequently mediated by VLA-4. The present invention is further concerned with pharmaceutical compositions which in addition to containing a compound of the present invention, additionally comprise one or more therapeutic agents selected from the group consisting essentially of anti-inflammatory corticosteroids, nonsteroidal anti-inflammatory agents, bronchodilators, anti-asthmatic agents, and immunosuppressant agents.

The present invention is still further concerned with a method of treating or preventing an inflammatory, autoimmune or respiratory diseases by inhibiting cell adhesion and consequent or associated pathogenic processes subsequently mediated by VLA-4, comprising administering to a mammal in need of such treatment a therapeutically effective amount of a pharmaceutical composition of the present invention. The pharmaceutical compositions of the present invention may be used in the treatment of many inflammatory, autoimmune and respiratory diseases, including but not limited to asthma, multiple sclerosis, rheumatoid arthritis, osteoarthritis, inflammatory bowel disease, psoriasis, host rejection following organ transplantation, atherosclerosis, and other diseases mediated by or associated with VLA-4.

DETAILED DESCRIPTION OF THE INVENTION

The present invention relates to compounds which inhibit cell adhesion and subsequent pathogenic processes mediated by VLA-4. These compounds, which are thus useful in the treatment of many inflammatory, autoimmune amd respiratory diseases, may be illustrated by Formula (1.0.0):

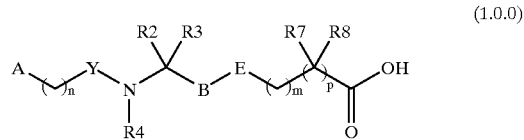

(1.0.0)

For compounds of Formula (1.0.0), the terminal group identified as A has the meaning alkyl, cycloalkyl, aryl, heteroaryl or heterocyclyl substituted with 0 to 3 R⁹; or is a member selected from the group consisiting of the following radicals: A¹-NHC(=O)NH-A²-, A¹-NHC(=O)O-A²-, A¹-OC(=O)NH-A²-, A¹-NHSO₂NH-A²-, A¹-NHC(=O)-A²-, A¹-C(=O)NH-A²-, A¹-NHSO₂-A²-, A¹-SO₂NH-A²-, A¹-(CH₂)ᵣO-A²-, A¹-O(CH₂)ᵣ-A²-, A¹-(CH₂)ᵣ-A²-, where A¹ and A² is each independently selected from the group consisting of hydrogen, aryl, alkyl, alkenyl, alkynyl, cycloalkyl, heteroaryl, and heterocyclyl; where said aryl, alkyl, alkenyl, cycloalkyl, heteroaryl, or heterocyclyl group is substituted with 0 to 3 R⁹.

The term "alkyl" as used with reference to "A", as well as in other contexts throughout the instant specification, and whether used alone or in combination, refers to a straight-chain or branched chain alkyl radical containing the indicated number of carbon atoms, usually from 1 to 6 but often from 1 to 4, carbon atoms. Examples of such radicals include, but are not limited to, methyl, ethyl, n-propyl, iso-propyl, n-butyl, iso-butyl, sec-butyl, tert-butyl, pentyl, iso-amyl, and hexyl.

The term "cycloalkyl" as used with reference to "A", as well as in other contexts throughout the instant specification, and whether used alone or in combination, refers to a cyclic alkyl radical containing from 3 to 6 carbon atoms. Examples of such cycloalkyl radicals include, but are not limited to, cyclopropyl, cyclobutyl, cyclopentyl, and cyclohexyl.

The term "aryl" as used with reference to "A", as well as in other contexts throughout the instant specification, is intended to refer to a carbocyclic aromatic group which is a member selected from the group consisting essentially of phenyl, naphthyl, indenyl, indanyl, and fluorenyl. It is preferred, however, that where "A" is "aryl", that it is phenyl.

The term "heteroaryl" as used with reference to "A", as well as in other contexts throughout the instant specification, is intended to refer to a heterocyclic aromatic group which is a member selected from the group consisting essentially of furyl, thienyl, pyrrolyl, oxazolyl, isoxazolyl, thiazolyl, isothiazolyl, imidazolyl, imidazolinyl, pyrazolyl, pyrazolinyl, oxadiazolyl, thiadiazolyl, triazolyl, pyridyl, pyrazinyl, pyridazinyl, pyrimidinyl, triazinyl, pyranyl, parathiazinyl, indolyl, isoindolyl, 3H-indolyl, indolinyl, benzo[b]furanyl, 2,3-dihydrobenzofuranyl, benzo[b]thiophenyl, 1H-indazolyl, benzimidazolyl, benzthiazolyl, purinyl, quinolinyl, isoquinolinyl, 4H-quinolizinyl, cinnolinyl, phthalazinyl, quinazolinyl, quinoxalinyl, 1,8-naphthyridinyl, pteridinyl, carbazolyl, acridinyl, phenazinyl, phenothiazinyl, phenoxazinyl, and pyrazolo[1,5-c]triazinyl.

It is preferred, however, that where "A" is "heteroaryl" that it is furyl, thienyl, pyrrolyl, oxazolyl, isoxazolyl, thiazolyl, imidazolyl, pyridyl, pyrimidinyl, indolyl, benzo [b]furanyl, benzimidazolyl, or quinolinyl. More preferably, "A" is pyridyl.

The terms "heterocylic" and "heterocyclyl" as used with reference to "A", as well as in other contexts throughout the instant specification, are both intended to refer to a nonaromatic 3- to 10-membered carbocyclic ring in which at least one of the carbon atoms of the ring has been replaced by a heteroatom selected from N, O or S. Preferably two, and more preferably one heteroatom is present, except that in the case of nitrogen, as many as four N heteroatoms may be present. The heterocyclyl group may comprise one or two fused rings, and further may include an aryl-fused ring. In a prefered meaning, "heterocyclyl" refers to a member selected from the group consisting essentially of oxiranyl, pyrrolidinyl, pyrazolidinyl, imidazolidinyl, tetrazolidinyl, piperidinyl, piperazinyl, morpholinyl, thiomorpholinyl, and benzodioxolane, especially 1,3-benzodioxol-5-yl.

It is preferred, however, that where "A" is "heterocyclyl" that it is pyrrolidinyl, piperidinyl, piperazinyl, or morpholinyl.

Where "A" is defined as a moiety selected from the above-defined alkyl, cycloalkyl, aryl, heteroaryl, or heterocyclyl groups, said moiety may be substituted with 0 to 3 $R^9$. The choice of "0" merely denotes that there are no substituents, substitution being optional. Where substitution occurs, preferably there are two substituents, and more preferably there is only one substituent.

Where a substituent $R^9$ is used, it will be independently selected from the group consisting essentially of halogen; $(C_1–C_6)$ alkyl; $(C_1–C_6)$ alkoxy; $(C_3–C_6)$ cycloalkyl; $(C_3–C_6)$ cycloalkoxy; cyano; hydroxy; $C(=O)R^5$; $C(O)NR^6$; $NR^5R^6$; $NR^5SO_2R^6$; $CF_3$; $OCF_3$; $SO_2NR^5R^6$; $C(=O)OR^5$; when $R^9$ is attached to a saturated carbon atom $R^9$ may be $=O$ or $=S$; when $R^9$ is attached to a sulphur atom $R^9$ may be $=O$; where $R^5$ and $R^6$ are as further defined herein. Preferably, however, there is a single substituent and it is F, Cl, OH, methyl, methoxy, cyclohexyl, acetyl, cyclopropyloxy, or $F_3C—$.

The term "alkoxy" as used with reference to the substituents "$R^9$" on the group "A", as well as in other contexts throughout the instant specification, and whether used alone or in combination, refers to an alkyl ether radical, wherein the term "alkyl" is as defined above. Examples of suitable alkyl ether radicals include, but are not limited to, methoxy, ethoxy, n-propoxy, iso-propoxy, n-butoxy, isobutoxy, sec-butoxy, and tert-butoxy.

The term "cycloalkoxy" as used with reference to the substituents "$R^9$" on the group "A", as well as in other contexts throughout the instant specification, and whether used alone or in combination, refers to an cycloalkyl ether radical, wherein the term "cycloalkyl" is as defined above. Examples of suitable cycloalkoxy radicals include, but are not limited to, cyclopropyloxy, cyclobutyloxy, cyclopentyloxy, and cyclohexyloxy.

A preferred meaning of "A" is that of a divalent radical which is a member selected from the group consisting of the following radicals: A1-NHC(=O)NH-A2-, A1-NHC(=O)O-A2-, A1-OC(=O)NH-A2-, A1-NHSO2NH-A2-, A1-NHC(=O)-A2-, A1-C(=O)NH-A2-, A1-NHSO2-A2-, A1-SO2NH-A2-, A1-(CH2)rO-A2-, A1-O(CH2)r-A2-, A1-(CH2)r-A2-, where $A^1$ and $A^2$ is each independently selected from the group consisting of hydrogen, aryl, $(C_1–C_6)$ alkyl, cycloalkyl, heteroaryl, and heterocyclyl; where said aryl, alkyl, cycloalkyl, heteroaryl, or heterocyclyl group is substituted with 0 to 3 $R^9$. The alkyl, cycloalkyl, aryl, heteroaryl or heterocyclyl group which is bonded to one or both sides of the ureido radical is selected in accordance with the definitions set out above, as are the 0 to 3 substituents $R^9$. It is preferred that an aryl group be covalently bonded to the both sides of the ureido radical, and it is further preferred that this aryl group be phenyl. It is most preferred that said phenyl group have a single substituent which is preferably F, Cl, methyl, methoxy, or $F_3C—$. Examples of th preferred meanings of "A" are shown in partial Formulas (4.0.0) though (4.0.11):

(4.0.0)

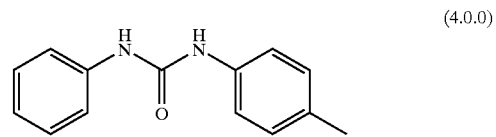

(4.0.1)

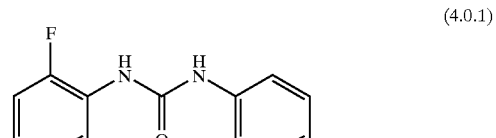

(4.0.2)

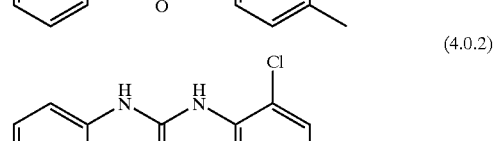

(4.0.3)

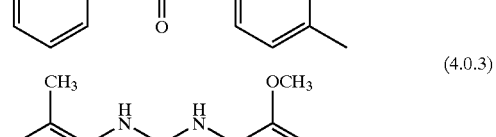

(4.0.4)

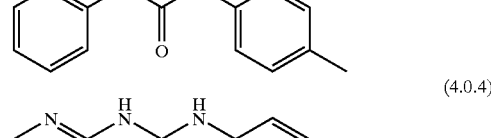

(4.0.5)

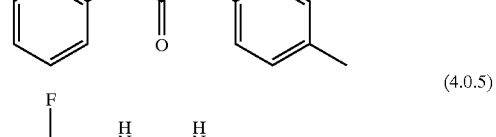

(4.0.6)

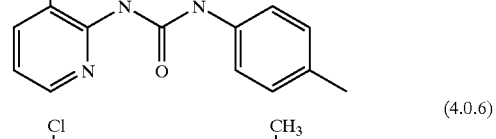

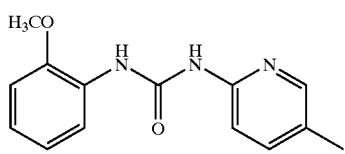
(4.0.7)

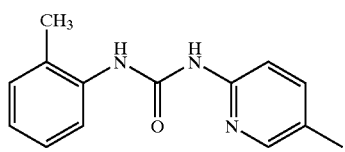
(4.0.8)

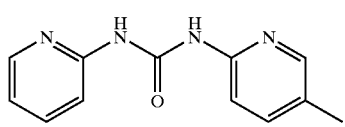
(4.0.9)

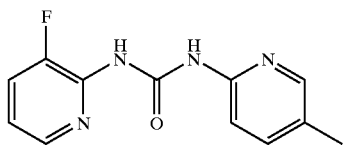
(4.0.10)

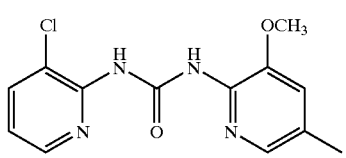
(4.0.11)

The component of the compounds of Formula (1.0.0) which is immediately adjacent to the "A" component, is a single bond, or a methylene or ethylene bridging element where n=0, 1 or 2, respectively. It is preferred that n=1 and that there be a methylene bridge. Accordingly, within the context of the above-stated preferences for the meaning of the "A" component, and adding the methylene bridge, the following most preferred termini which include the component "A", may be represented by the following partial Formulas (4.1.0)

| | | |
|---|---|---|
| 4-hydroxyphenyl- | 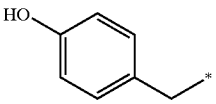 | (4.1.0) |
| 3-methoxy-4-(N'-phenylurea)-phenylmethyl- | 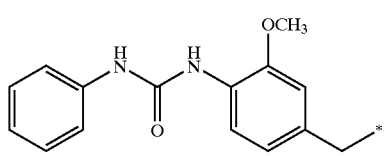 | (4.1.1) |
| 4-(N'-phenylurea)-phenylmethyl- | 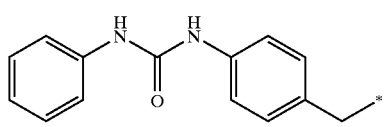 | (4.1.2) |
| 4-[N'-(2-methylphenyl)-urea]-phenylmethyl- | 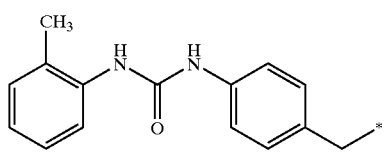 | (4.1.3) |
| 4-[N'-(2-methoxyphenyl)-urea]-phenylmethyl- | 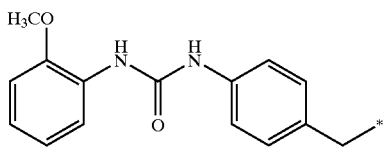 | (4.1.4) |
| 3-methoxy-4-[N'-(2-methylphenyl)-urea]-phenylmethyl- | 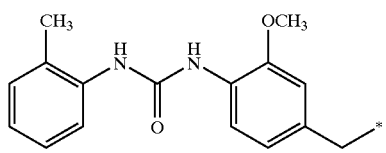 | (4.1.5) |

| | -continued | |
|---|---|---|
| 4-[N'-(2-pyridyl)-urea]-phenylmethyl- | 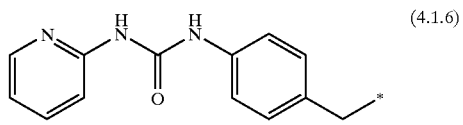 | (4.1.6) |
| 6-methoxy-5-[N'-(2-methylphenyl)-urea]-2-pyridylmethyl- | 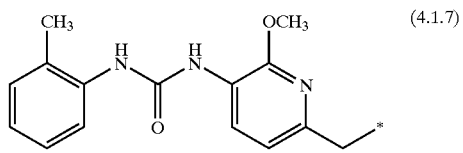 | (4.1.7) |
| 4-[N'-(3-methyl-2-pyridyl)-urea]-phenylmethyl- | 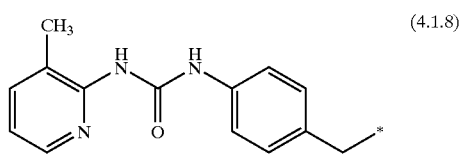 | (4.1.8) |
| 3-methoxy-4-[N'-(3-methyl-2-pyridyl)-urea]-phenylmethyl- | 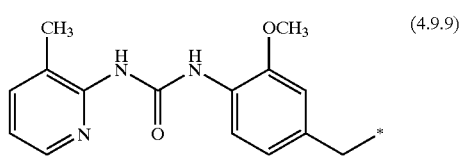 | (4.9.9) |
| 3-methoxy-4-[N'-(2-pyridyl)-urea]-phenylmethyl- | 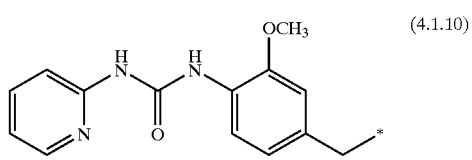 | (4.1.10) |
| 4-[N'-(2-pyridyl)-urea]-phenylmethyl- | 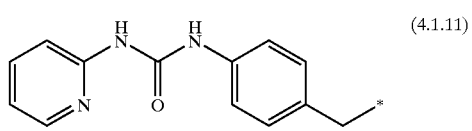 | (4.1.11) |
| 4-[N'-(2-fluorophenyl)-urea]-phenylmethyl- | 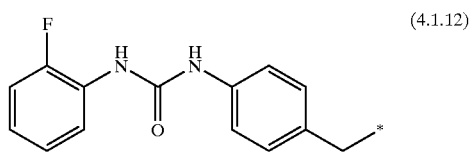 | (4.1.12) |
| 4-[N'-(2-chlorophenyl)-urea]-phenylmethyl- | 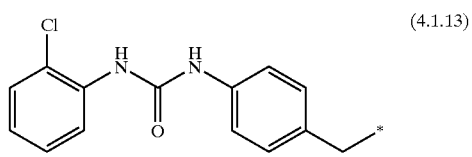 | (4.1.13) |
| 4-[N'-(2-chlorophenyl)-urea]-3-methoxyphenylmethyl- | 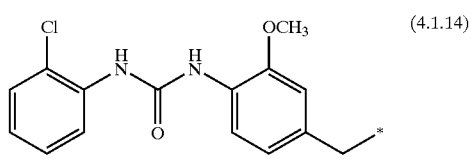 | (4.1.14) |
| 4-[N'-(4-iso-propylphenyl)-urea]-phenylmethyl- | 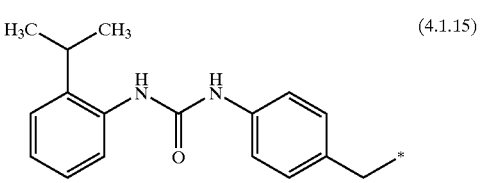 | (4.1.15) |

| | | |
|---|---|---|
| 6-methoxy-5-[N'-(o-toluyl)-urea]-2-pyridylmethyl- | 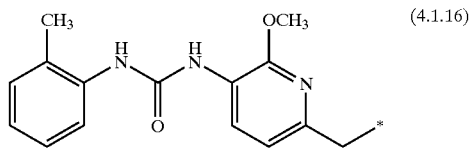 | (4.1.16) |
| 4-[N'-(3-cyclopentyl-2-pyridyl)-urea]-phenylmethyl- | 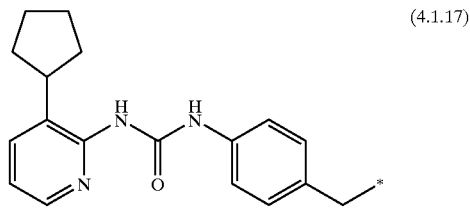 | (4.1.17) |
| 4-[N'-(2-cyclopentyl)-urea]-phenylmethyl- | 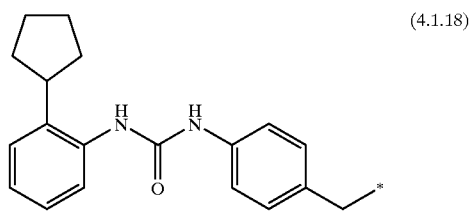 | (4.1.18) |
| 4-[N'-(3-cyclopropyloxy-2-pyridyl)-urea]-phenylmethyl- | 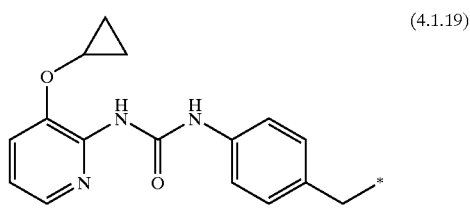 | (4.1.19) |
| 4-[N'-(o-toluyl)-urea]-pyrid-5-ylmethyl- | 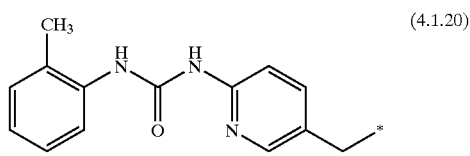 | (4.1.20) |
| 4-[3-(4-methyl-pyridin-3-yl)-ureido]-phenylmethyl- | 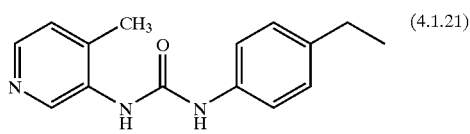 | (4.1.21) |
| 4-[3-(2,6-dichloro-phenyl)-ureido]-phenylmethyl- | 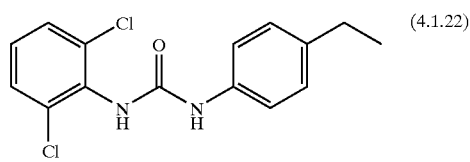 | (4.1.22) |
| 4-[3-(2,6-dimethyl-phenyl)-ureido]-phenylmethyl- | 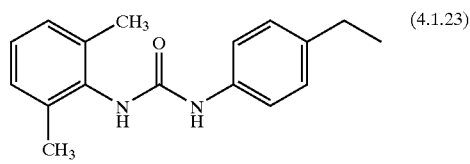 | (4.1.23) |

It will be further noted partial structural formulas that the preferred methylene bridge is also preferably attached to the N,N'-diphenylureido group in a para relationship to the point of attachment of the divalent ureido group to the phenyl group involved.

The "Y" component of Formula (1.0.0) may be —C(=O)—; —C(=S)—; or —S(=O)$_2$—. Overall, however, it is most preferred that "Y" be a carbonyl moiety, i.e., that "Y" is the moiety —C(=O)—.

The next component of the compounds of Formula (1.0.0) is —NR$^4$CR$^2$R$^3$—. In this component R$^2$ and R$^3$ are each independently selected from the group consisting of hydrogen; (C$_1$–C$_6$) alkyl substituted with 0 to 3 R$^{13}$; (C$_2$–C$_6$) alkenyl substituted with 0 to 3 R$^{13}$; a (C$_3$–C$_{14}$) carbocyclic ring system substituted with 0 to 3 R$^3$; a heterocyclyl ring as defined herein, substituted with 0 to 3 R$^{13}$; (C$_1$–C$_6$) alkyl-OR$^5$ substituted with 0 to 3 R$^{13}$; (C$_1$–C$_6$) alkyl-SR$^5$ substituted with 0 to 3 R$^{13}$; (C$_1$–C$_6$) alkyl-SR$_2$R$^5$ substituted with 0 to 3 R$^{13}$; a heteroaryl ring as defined herein, substituted with 0 to 3 R$^{13}$; and an aryl ring as defined herein, substituted with 0 to 3 R$^{13}$. R$^2$ and R$^3$ may also be taken together in accordance with an optional definition of R$^2$ and R$^3$, in which case they form a cycloalkyl or heterocyclyl ring substituted with 0 to 3 R$^{13}$. For example, where R$^2$ and R$^3$ are taken together to form a spirocyclic cyclopropyl, cyclobutyl, or cyclopentyl group, the resulting compounds of the present invention will include moieties such as those of partial Formulas (1.2.0) through (1.2.2):

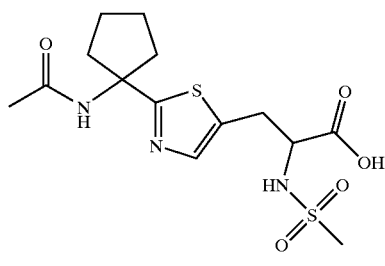
(1.2.0)

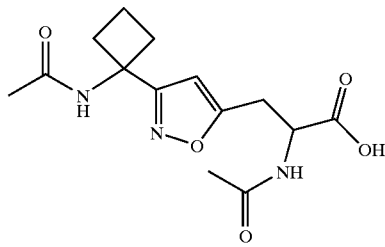
(1.2.1)

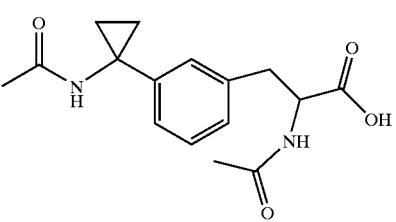
(1.2.2)

Another preferred sub-group of compounds of the present invention is that formed when either R$^2$ or R$^3$ is taken together with R$^4$ and the carbon and nitrogen atoms to which they are respectively attached to form a heteroaryl or heterocyclyl group as defined herein. Said heteroaryl or heterocyclyl group may, in turn, be substituted with 0 to 3 R$^{13}$. In accordance with the above-mentioned proviso, when either R$^2$ or R$^3$ is taken together with R$^4$, the other must be hydrogen or methyl. The sub-group may be represented by partial Formula (1.3.0) as follows:

(1.3.0)

where the symbol "*" indicates the point of attachment of the moiety represented by partial Formula (1.3.0) to the moiety "Y" in Formula (1.0.0); and the symbol "Π" indicates the point of attachment of the moiety represented by partial Formula (1.3.0) to "B" in Formula (1.0.0), defined by partial Formulas (1.1.0) through (1.1.22). The substituent "R$^{2/3}$" indicates the presence of either the R$^2$ substituent or the R$^3$ substituent. They both may not be present, since one or the other has already been selected to be taken together with R$^4$ to form th heteroaryl or heterocyclyl group of partial Formula (1.3.0), represented as follows:

It will be understood that whether R$^2$ or R$^3$ is present, it will have the meaning of hydrogen, alkyl or methyl.

Accordingly, this sub-group of the group "—NR$^4$CR$^2$R$^3$B—" represented by partial Formula (1.3.0) includes, but is not limited to, the embodiments which are represented by partial Formulas (1.3.1) through (1.3.20):

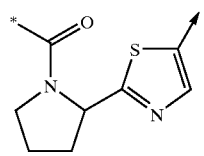
(1.3.1)

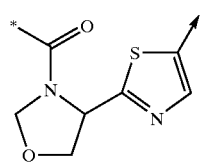
(1.3.2)

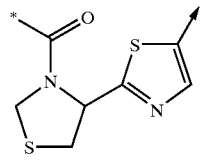
(1.3.3)

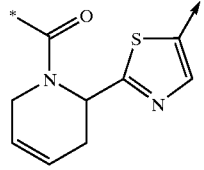
(1.3.4)

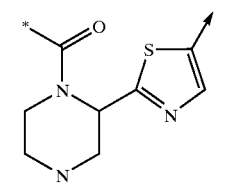
(1.3.5)

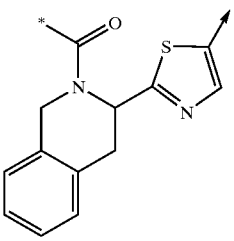
(1.3.6)

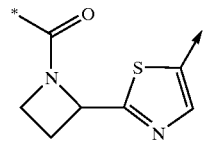
(1.3.7)

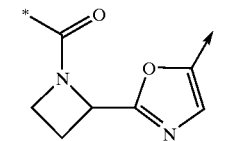
(1.3.8)

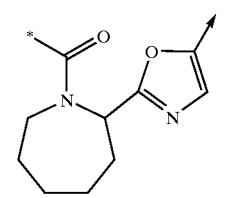
(1.3.9)

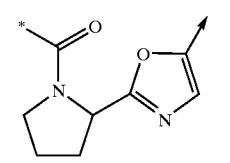
(1.3.10)

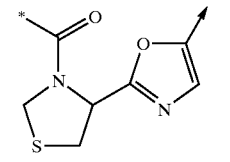
(1.3.11)

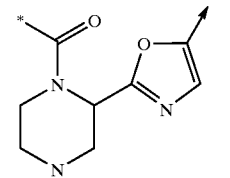
(1.3.12)

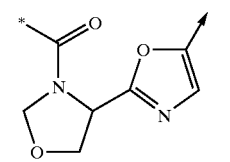
(1.3.13)

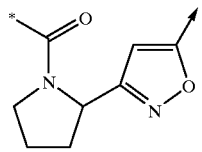
(1.3.14)

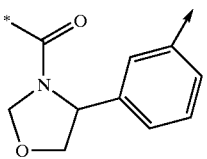
(1.3.15)

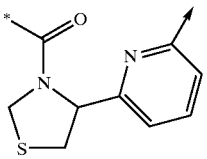
(1.3.16)

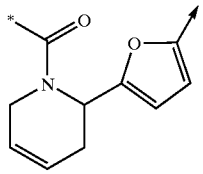
(1.3.17)

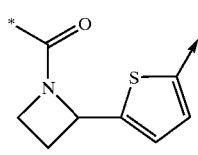
(1.3.18)

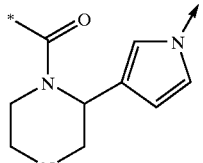
(1.3.19)

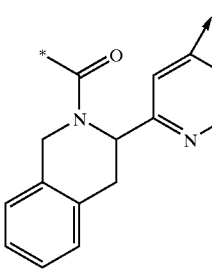
(1.3.20)

where the symbol "*" indicates the point of attachment of the moiety represented by each partial Formula (1.3.1) through (1.3.20) to the moiety "Y" in Formula (1.0.0); and the symbol "↑" indicates the point of attachment of the moiety represented by each partial Formula (1.3.1) through (1.3.20) to the moiety "E" in Formula (1.0.0).

With reference to the optional substituent $R^{13}$ which may be present on the $R^2$ and $R^3$ substituents of the B component, $R^{13}$ is absent when "0" is selected. It is preferred that $R^{13}$ either be absent or be present as a single substituent selected from halogen; $CF_3$; ($C_1$–$C_6$) alkyl; aryl; heteroaryl; heterocyclyl; hydroxy; cyano; ($C_1$–$C_6$) alkoxy; ($C_3$–$C_{14}$) carbocyclic ring system; ($C_3$–$C_6$) cycloalkoxy; ($C_2$–$C_6$) alkynyl; ($C_2$–$C_6$) alkenyl; —$NR^6R^5$; —C(=O)$NR^5R^6$; $SO_2R^5$; C(=O)$R^5$; $NR^5SO_2R^6$; $NR^5C$(=O)$R^6$; C(=O)$NR^5SO_2R^6$;

NR⁵C(=O)OR⁶; and SO₂NR⁵. With reference to the optional substituent R³, but also with reference to the remainder of the instant specification, the term "alkynyl" alone or in combination, refers to a straight-chain or branched-chain alkynyl radical containing from 2 to 6, preferably 2 to 4 carbon atoms. Examples of such radicals include, but are not limited to, ethynyl(acetylenyl), propynyl, propargyl, butynyl, hexynyl, decynyl and the like.

With reference to the definition of R¹³, the term "alkenyl" alone or in combination, refers to a straight-chain or branched-chain alkenyl radical containing from 2 to 6, preferably 2 to 4 carbon atoms. Examples of such radicals include, but are not limited to, ethenyl, E- and Z-propenyl, iso-propenyl, E- and Z-butenyl, E- and Z-isobutenyl, and E- and Z-pentenyl.

The term "(C₃–C₁₄)carbocyclic ring system" as used with reference to R² and R³, as well as in other contexts throughout the instant specification, used alone or in combination, is intended to refer to cycloalkyl and cycloalkenyl groups consisting of one, two or three fused rings containing a total of from three to fourteen carbon atoms. The term "cycloalkyl" in turn, means a cyclic alkyl radical containing from 3 to 8, preferably from 3 to 6, carbon atoms. Examples of such cycloalkyl radicals include, but are not limited to, cyclopropyl, cyclobutyl, cyclopentyl, cyclohexyl and the like. The term "cycloalkenyl" on the other hand, refers to a cyclic carbocycle containing from 4 to 8, preferably 5 or 6, carbon atoms and one or more double bonds. Examples of such cycloalkenyl radicals include, but are not limited to, cyclopentenyl, cyclohexenyl, and cyclopentadienyl.

Where two or three fused rings are present, one of the rings may be a cycloalkyl ring system while the other one or two rings may be cycloalkenyl ring systems.

It is preferred that when one of R² and R³ is hydrogen that the other be selected from the group consisting essentially of hydrogen, methyl, ethyl, propyl, butyl, and iso-butyl; hydroxymethyl, methoxymethyl; allyl, propenyl, E- and Z-iso-butenyl, and E- and Z-pentenyl; cyclopropylmethyl, cyclopentylmethyl and cyclohexylmethyl; cyclohexenylmethyl, benzyl, benzyloxymethyl and phenoxymethyl; 2-(methylthio)ethyl; 3-(hydroxypropylthio)methyl; 2-(methylsulfonyl)ethyl; 4-(acetylamino)butyl; 4-(methylsulfonylamino)butyl; and 4-ethoxycarbonylamino)butyl.

The next component, the "B" group of the compounds of Formula (1.0.0) is one of th more important portions of the molecule and is a key element in providing the unexpectedly good biological properties possess d by the compounds of the pr sent invention. The "B" group comprises a member selected from the group consisting of partial Formulas (1.1.0) through (1.1.22):

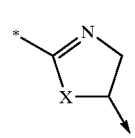

(1.1.0)

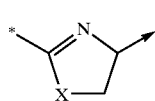

(1.1.1)

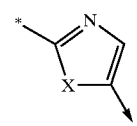

(1.1.2)

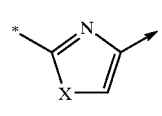

(1.1.3)

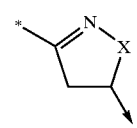

(1.1.4)

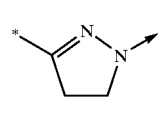

(1.1.5)

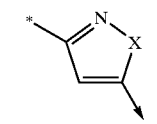

(1.1.6)

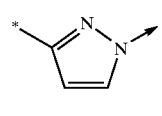

(1.1.7)

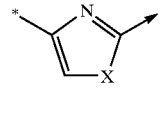

(1.1.8)

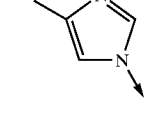

(1.1.9)

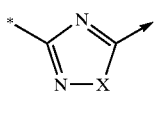

(1.1.10)

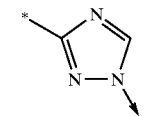

(1.1.11)

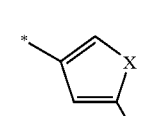

(1.1.12)

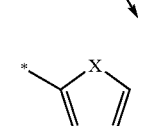

(1.1.13)

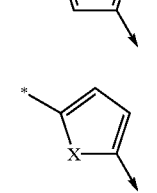

(1.1.14)

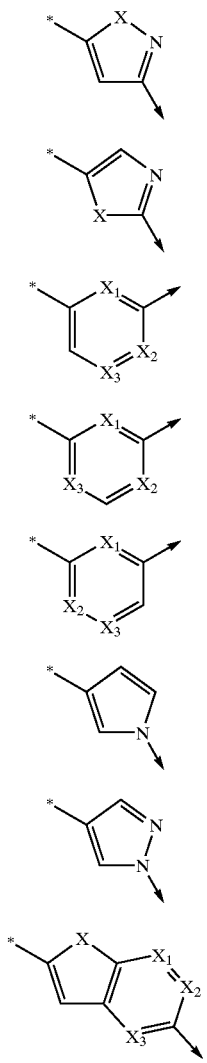

(1.1.15)

(1.1.16)

(1.1.17)

(1.1.18)

(1.1.19)

(1.1.20)

(1.1.21)

(1.1.22)

where the symbol "*" indicates the point of attachment of the moiety represented by each partial Formula (1.1.0) through (1.1.22) to the moiety "CR²R³" in Formula (1.0.0); and the symbol "Π" indicates the point of attachment of the moiety represented by each partial Formula (1.1.0) through (1.1.22) to the moiety "E" in Formula (1.0.0).

All of the above partial Formulas (1.1.0) through (1.1.22) inclusive are illustrated as fragments in the manner above-described, wherein the points of attachment at either end of a particular fragment are indicated by the symbols "*" and "Π".

In the above partial formulas defining the B component of the compounds of Formula (1.0.0), the moiety "X" may be oxygen; sulfur (q=0) and sulfur to which two oxygen atoms is attached (q=2), i.e., sulfonyl; or NH (R¹⁰=hydrogen) or nitrogen which is substituted (R¹⁰=(C₁–C₆)alkyl; (C₃–C₆) cycloalkyl; heterocyclyl; heteroaryl; or aryl). It is preferred, however, that "X" be simply oxygen, sulfur or NH.

Attached to component B in the compounds of Formula (1.0.0) are the remaining structural elements which may be represented by partial Formula (1.4.0):

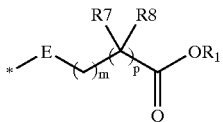

(1.4.0)

It will be noted first that the moiety represented by partial Formula (1.4.0) is directly attached to component B in the overall compound of Formula (1.0.0). E is a single bond; oxygen; —NR¹⁰—; —CH=CH—; or —CR¹¹R¹²—.

Where a substituent R¹⁰ is used, it will be independently selected from the group consisting essentially of hydrogen, C(=O)R⁵; (C₁–C₆) alkyl; aryl; heterocyclyl; heteroaryl; cycloalkyl; or SO₂R⁵.

Where substituents R¹¹ and R¹² are used, they will be independently selected from the group consisting essentially of hydrogen; (C₁–C₆) alkyl; hydroxy; (C₁–C₆) alkoxy; NR⁶COR⁵; NR⁶SO₂R⁵; NR⁶R⁵; CF₃; F; aryl; heterocyclyl; heteroaryl; cycloalkyl; and cycloalkoxy. R¹¹ may be taken together with R¹² to form a cycloalkyl or heterocyclyl ring. R⁵ and R⁶ are independently hydrogen; (C₁–C₆) alkyl; CF₃; aryl; cycloalkyl; heteroaryl; or heterocyclyl.

The groups (C₁–C₆)alkyl, (C₁–C₆)alkoxy, aryl, heterocyclyl, heteroaryl, cycloalkyl and cycloalkoxy have already been defined in detail above. Within the meaning of these groups it is preferred that R¹¹ and R¹² be independently selected from the group consisting of methyl, ethyl, propyl, butyl, iso-butyl, methoxy, cyclopropoxy, cyclopropyl, phenyl, morpholinyl, piperidinyl and pyridyl.

In the portions of the compounds of the present invention represented by partial Formula (1.4.0) above, the moiety E is followed by an optional methylene bridge: (—CH₂—)ₘ where m is an integer independently selected from 0 and 1.

The next component of Formula (1.0.0) is represented by "—(CR⁷R⁸)ₚ—" in which "p" is selected from the integers 0 and 1, provided that "p" must be selected as 1 where "B" is selected as partial formula (1.1.0) through (1.1.11).

The substituent R⁷ is selected from the group consisting of (C₁–C₆) alkyl; hydroxy; (C₁–C₆) alkoxy; NHC(=O)R⁵; NHSO₂R⁵; NR⁶R⁵; F; CF₃; OCF₃; aryl; heterocyclyl; heteroaryl; cycloalkyl; or R⁷ may be taken together with R⁸ to form a cycloalkyl or heterocyclyl ring. The substituent R⁸ is selected from hydrogen; F; (C₁–C₆) alkyl or (C₁–C₆) alkoxy.

The final component of Formula (1.0.0) is the "—C(=O)OR¹" group wherein R¹ is hydrogen.

The compontent represented by partial Formula (1.4.0) includes, but is not limited to, the embodiments which are represented by partial Formulas (1.4.1) through (1.4.20):

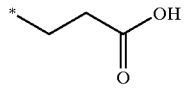

(1.4.1)

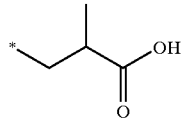

(1.4.2)

-continued (1.4.3) 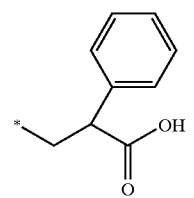

(1.4.4) 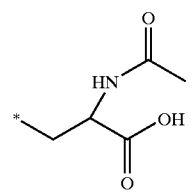

(1.4.5) 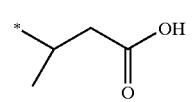

(1.4.6) 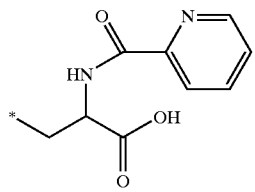

(1.4.7) 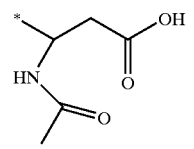

(1.4.8) 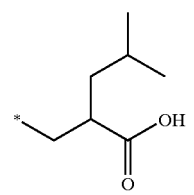

(1.4.9) 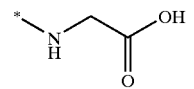

(1.4.10) 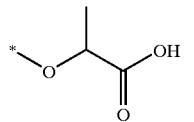

(1.4.11) 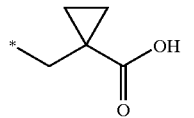

(1.4.12) 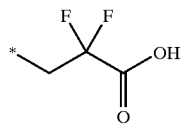

-continued (1.4.13) 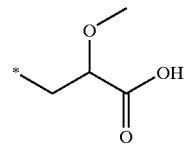

(1.4.14) 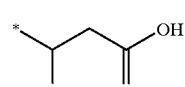

(1.4.15) 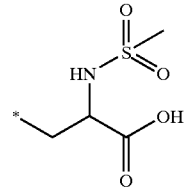

(1.4.16) 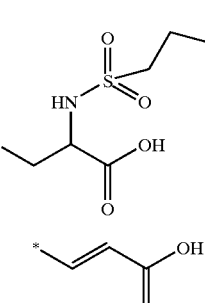

(1.4.17) 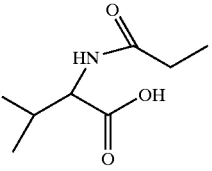

(1.4.18) 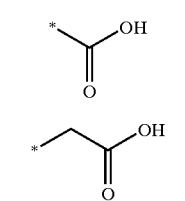

(1.4.19) 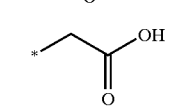

(1.4.20) 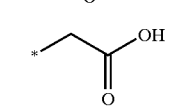

Included within the scope of the present invention are the pharmaceutically acceptable derivatives of the compounds of Formula (1.0.0). The expression "pharmaceutically acceptable derivative" as used in the instant specification denotes any pharmaceutically acceptable salt of a compound of Formula (1.0.0). Further included within the scope of the present invention is any other compound which, upon administration to a patient, is capable of directly or indirectly providing a compound of Formula (1.0.0). Such compounds are recognized as prodrugs, and a number of established procedures are available for preparing such prodrug forms of the compounds of Formula (1.0.0).

The term "patient" as used above and throughout the instant specification, refers to mammals, including humans. And where the term "cell" is used it refers to mammalian cells, including human cells, unless otherwise specified.

Further included within the scope of the present invention are metabolites or residues of the compounds of Formula (1.0.0) which possess biological activity such that they are able to inhibit cell adhesion and consequent or associated pathogenic processes subsequently mediated by VLA-4. Once synthesized, the inhibitory activities and VLA-4 specificities of the compounds of Formula (1.0.0) according to this invention may be determined using in vitro and in vivo assays which are described in detail further below.

The desirable biological activity of the compounds of Formula (1.0.0) may also be improved by appending thereto appropriate functionalities which will function to enhance existing biological properties of the compound, improve the selectivity of th compound for the existing biological activities, or add to the existing biological activities further desirable biological activities. Such modifications are known in the art and include those which increase biological penetration into a given biological system, e.g., blood, the lymphatic system, and central nervous system; increase oral availability; increase solubility to allow administration by injection; alter metabolism; and alter the rate of excretion of the compound of Formula (1.0.0).

In view of the above definitions and others throughout the instant specification, other chemical and biological terms used herein can be easily understood by those of skill in the art. The defined terms may be used alone or in any combination thereof. The preferred and more preferred chain lengths of the radicals which have been specified herein apply to all such combinations.

Further pursuant to the descriptions above of certain preferred subgeneric and more preferred subgeneric definitions of the compounds of Formula (1.0.0), there follows an enumeration of preferred and more preferred species in order to provide a further illustration of the present invention.

Compounds which include the moiety of partial Formula (1.1.0):
3-[2-(1-{2-[3-Methoxy-4-(3-o-tolyl-ureido)-phenyl]-acetylamino}-3-methyl-butyl)-4,5-dihydro-oxazol-5-yl]-2-methyl-propionic acid
2-Acetylamino-3-[2-(1-{2-[3-methoxy-4-(3-o-tolyl-ureido)-phenyl]-acetylamino}-3-methyl-butyl)-4,5-dihydro-oxazol-5-yl]-propionic acid
2-Methanesulfonylamino-3-[2-(1-{2-[3-methoxy-4-(3-o-tolyl-ureido)-phenyl]-acetylamino}-3-methyl-butyl)-4,5-dihydro-oxazol-5-yl]-propionic acid
2,2-Difluoro-3-{2-[1-(methyl-{[6-(3-o-tolyl-ureido)-pyridin-3-yl]-acetyl}-amino)-ethyl]-4,5-dihydro-oxazol-5-yl}-propionic acid
2,2-Dimethyl-3-[2-(1-{[6-(3-phenyl-ureido)-pyridin-3-yl]-acetyl}-pyrrolidin-2-yl)-4,5-dihydro-oxazol-5-yl]-propionic acid
2-Allyloxycarbonylamino-3-{2-[({[3-methoxy-4-(3-o-tolyl-ureido)-phenyl]-acetyl}-methyl-amino)-methyl]-4,5-dihydro-oxazol-5-yl}-propionic acid
2-(Butane-1-sulfonylamino)-3-(2{[methyl-({4-[3-(3-methyl-pyridin-2-yl)-ureido]-piperidin-1-yl}-acetyl)-amino]-methyl}-4,5-dihydro-oxazol-5-yl)-propionic acid
2-Methyl-3-[2-(1-{[4-(2-methyl-benzyloxy)-phenyl]-acetyl}-pyrrolidin-2-yl)-4,5-dihydro-oxazol-5-yl]-propionic acid
2-Formylamino-3-{2-[1-(biphenyl-4-yl-acetyl)-pyrrolidin-2-yl]-4,5-dihydro-thiazol-5-yl}-propionic acid
2-Methyl-3-(2-{1-[(4-o-tolyloxy-phenyl)-acetyl]-pyrrolidin-2-yl}-4,5-dihydro-oxazol-5-yl)-propionic acid
2-Benzenesulfonylamino-3-(2-{1-[(4-phenoxymethyl-phenyl)-acetyl]-pyrrolidin-2-yl}-4,5-dihydro-oxazol-5-yl)-propionic acid
2-Benzenesulfonylamino-3-[2-(1-{[3-methoxy-4-(3-o-tolyl-ureido)-phenyl]-acetyl}-pyrrolidin-2-yl)-4,5-dihydro-oxazol-5-yl]-propionic acid
2-Methanesulfonylamino-3-[2-(3-methyl-1-{[5-(3-o-tolyl-ureido)-pyridin-2-yl]-acetyl}-pyrrolidin-2-yl)-4,5-dihydro-oxazol-5-yl]-propionic acid
2-Acetylamino-3-{2-[({[3-methoxy-4-(3-o-tolyl-ureido)-phenyl]-acetyl}-methyl-amino)-methyl]-4-methyl-4,5-dihydro-oxazol-5-yl}-propionic acid
2-Acetylamino-3-{2-[({[3-methoxy-4-(3-o-tolyl-ureido)-pheny]-acetyl}-methyl-amino)-methyl]-4,5-dihydro-thiazol-5-yl}-propionic acid
3-Acetylamino-3-{2-[({[3-methoxy-4-(3-o-tolyl-ureido)-phenyl]-acetyl}-methyl-amino)-methyl]-4,5-dihydro-3H-imidazol-4-yl}-propionic acid
2-(2,6-Dichloro-benzoylamino)-3-{2-[({[3-methoxy-4-(3-o-tolyl-ureido)-phenyl]-acetyt}-methyl-amino)-methyl]-4,5-dihydro-oxazol-5-yl}-propionic acid Compounds which include the moiety of partial Formula (1.1.1):
3-[2-(1-{2-[3-Methoxy-4-(3-o-tolyl-ureido)-phenyl]-acetylamino}-3-methyl-butyl)-4,5-dihydro-oxazol-4-yl]-2-methyl-propionic acid
2-Acetylamino-3-[2-(1-{2-[3-methoxy-4-(3-o-tolyl-ureido)-phenyl]-acetylamino}-3-methyl-butyl)-4,5-dihydro-oxazol-4-yl]-propionic acid
2-Methanesulfonylamino-3-[2-(1-{2-[3-methoxy-4-(3-o-tolyl-ureido)-phenyl]-acetytamino}-3-methyl-butyl)-4,5-dihydro-oxazol-4-yl]-propionic acid
2,2-Difluoro-3-{2-[1-(methyl-{[6-(3-o-tolyl-ureido)-pyridin-3-yl]-acetyl}-amino)-ethyl]-4,5-dihydro-oxazol-4-yl}-propionic acid
2,2-Dimethyl-3-[2-(1-{[6-(3-phenyl-ureido)-pyridin-3-yl]-acetyl}-pyrrolidin-2-yl)-4,5-dihydro-oxazol-4-yl]-propionic acid
2-Allyloxycarbonylamino-3-{2-[({[3-methoxy-4-(3-o-tolyl-ureido)-phenyl]-acetyl}-methyl-amino)-methyl]-4,5-dihydro-oxazol-4-yl}-propionic acid
2-(Butane-1-sulfonylamino)-3-(2-{[methyl-({4-[3-(3-methyl-pyridin-2-yl)-ureido]-piperidin-1-yl}-acetyl)-amino]-methyl}-4,5-dihydro-oxazol-4-yl)-propionic acid
2-Methyl-3-[2-(1-{[4-(2-methyl-benzyloxy)-phenyl]-acetyl}-pyrrolidin-2-yl)-4,5-dihydro-oxazol-4-yl]-propionic acid
2-Acetylamino-3-{2-[1-(biphenyl-4-yl-acetyl)-pyrrolidin-2-yl]-4,5-dihydro-thiazol-4-yl}-propionic acid
2-Methyl-3-(2-{1-[(4-o-tolyloxy-phenyl)-acetyl]-pyrrolidin-2-yl}-4,5-dihydro-oxazol-4-yl)-propionic acid
2-Benzenesulfonylamino-3-(2-{1-[(4-phenoxymethyl-phenyl)-acetyl]-pyrrolidin-2-yl}-4,5-dihydro-oxazol-4-yl)-propionic acid
2-Benzenesulfonylamino-3-[2-(1-{[3-methoxy-4-(3-o-tolyl-ureido)-phenyl]-acetyl}-pyrrolidin-2-yl)-4,5-dihydro-oxazol-4-yl]-propionic acid
2-Methanesulfonylamino-3-[2-(3-methyl-1-{[5-(3-o-tolyl-ureido)-pyridin-2-yl]-acetyl}-pyrrolidin-2-yl)-4,5-dihydro-oxazol-4-yl]-propionic acid
2-Acetylamino-3-{2-[({[3-methoxy-4-(3-o-tolyl-ureido)-pheny]-acetyl}-methyl-amino)-methyl]-5-methyl-4,5-dihydro-oxazol-4-yl}-propionic acid
2-Acetylamino-3-{2-[({[3-methoxy-4-(3-o-tolyl-ureido)-phenyl]-acetyl}-methyl-amino)-methyl]-4,5-dihydro-thiazol-4-yl}-propionic acid
2-(2,6-Dichloro-benzoylamino)-3-{2-[({[3-methoxy-4-(3-o-tolyl-ureido)-phenyl]-acetyl}-methyl-amino)-methyl]-4,5-dihydro-oxazol-4-yl}-propionic acid Compounds which include the moiety of partial Formula (1.1.2):
3-[2-(1-{2-[3-Methoxy-4-(3-o-tolyl-ureido)-phenyl]-acetylamino}-3-methyl-butyl)-oxazol-5-yl]-2-methyl-propionic acid 2-Acetylamino-3-[2-(1-{2-[3-methoxy-4-(3-o-tolyl-ureido)-phenyl]-acetylamino}-3-methyl-butyl)-oxazol-5-yl]-propionic acid 2-Methanesulfonylamino-3-[2-(1-{2-[3-methoxy-4-(3-o-tolyl-ureido)-phenyl]-acetylamino}-3-methyl-butyl)-oxazol-5-yl]-propionic acid 2,2-Difluoro-3-{2-[1-(methyl-{[6-(3-o-tolyl-ureido)-pyridin-3-yl]-acetyl}-amino)-ethyl]-oxazol-5-yl}-propionic acid 2,2-Dimethyl-3-[2-(1-{[6-(3-phenyl-ureido)-pyridin-3-yl]-acetyl}-pyrrolidin-2-yl-oxazol-5-yl]-propionic acid 2-Allyloxycarbonylamino-3-{2-[({[3-methoxy-4-(3-O-tolyl-ureido)-phenyl]-acetyl}-methyl-amino)-methyl]-oxazol-5-yl}-propionic acid 2-(Butane-1-sulfonylamino)-3-(2-{[methyl-({4-[3-(3-methyl-pyridin-2-yl)-ureido]-piperidin-1-yl}-acetyl)-amino]-methyl}-oxazol-5-yl)-Propionic acid 2-Methyl-3-[2-(1-{[4-(2-methyl-benzyloxy)-phenyl]-acetyl}-pyrrolidin-2-yl)-oxazol-5-yl]-propionic acid 2-Acetylamino-3-{2-[1-(biphenyl-4-yl-acetyl)-pyrrolidin-2-yl]-thiazol-5-yl}-Propionic acid 2-Methyl-3-(2-{1-[(4-o-tolyloxy-phenyl)-acetyl]-pyrrolidin-2-yl}-oxazol-5-yl)-propionic acid 2-Benzenesulfonylamino-3-(2-{1-[(4-phenoxymethyl-phenyl)-acetyl]-pyrrolidin-2-yl}-oxazol-5-yl)-propionic acid 2-Benzenesulfonylamino-3-[2-(1-{[3-methoxy-4-(3-o-tolyl-ureido)-phenyl]-acetyl}-pyrrolidin-2-yl)-oxazol-5-yl]-propionic acid 2-Methanesulfonylamino-3-[2-(3-methyl-1-{[5-(3-o-tolyl-ureido)-pyridin-2-yl]-acetyl}-pyrrolidin-2-yl)-oxazol-5-yl]-propionic acid 2-Acetylamino-3-{2-[({[3-methoxy-4-(3-O-tolyl-ureido)-phenyl]-acetyl}-methyl-amino)-methyl]-4-methyl-oxazol-5-yl}-propionic acid 2-Acetylamino-3-{2-[({[3-methoxy-4-(3-o-tolyl-ureido)-phenyl]-acetyl}-methyl-amino)-methyl]-thiazol-5-yl}-propionic acid 3-Acetylamino-3-{2-[({[3-methoxy-4-(3-o-tolyl-ureido)-phenyl]-acetyl}-methyl-amino)-methyl]-3H-imidazol-4-yl}-propionic acid 2-(2,6-Dichloro-benzoylamino)-3-{2-[({[3-methoxy-4-(3-o-tolyl-ureido)-phenyl]-acetyl}-methyl-amino)-methyl]-oxazol-5-yl}-propionic acid Compounds which include the moiety of partial Formula (1.1.3):

3-[2-(1-{2-[3-Methoxy-4-(3-o-tolyl-ureido)-phenyl]-acetylamino}-3-methyl-butyl)-oxazol-4-yl]-2-methyl-propionic acid 2-Acetylamino-3-[2-(1-{2-[3-methoxy-4-(3-o-tolyl-ureido)-phenyl]-acetylamino}-3-methyl-butyl)-oxazol-4-yl]-propionic acid 2-Methanesulfonylamino-3-[2-(1-{2-[3-methoxy-4-(3-o-tolyl-ureido)-phenyl]-acetylamino}-3-methyl-butyl)-oxazol-4-yl]-propionic acid 2,2-Difluoro-3-{2-[1-(methyl-{[6-(3-o-tolyl-ureido)-pyridin-3-yl]-acetyl}-amino)-ethyl]-oxazol-4-yl}-propionic acid 2,2-Dimethyl-3-[2-(1-{[6-(3-phenyl-ureido)-pyridin-3-yl]-acetyl}-pyrrolidin-2-yl)-oxazol-4-yl]-propionic acid 2-Allyloxycarbonylamino-3-{2-[({[3-methoxy-4-(3-o-tolyl-ureido)-phenyl]-acetyl}-methyl-amino)-methyl]-oxazol-4-yl}-propionic acid 2-(Butane-1-sulfonylamino)-3-(2-{[methyl-({4-[3-(3-methyl-pyridin-2-yl)-ureido]-piperidin-1-yl}-acetyl)-amino]-methyl}-oxazol-4-yl)-propionic acid 2-Methyl-3-[2-(1-{[4-(2-methyl-benzyloxy)-phenyl]-acetyl}-pyrrolidin-2-yl)-oxazol-4-yl]-propionic acid 2-Formylamino-3-{2-[1-(biphenyl-4-yl-acetyl)-pyrrolidin-2-yl]-thiazol-4-yl}-propionic acid 2-Methyl-3-(2-{1-[(4-o-tolyloxy-phenyl)-acetyl]-pyrrolidin-2-yl}-oxazol-4-yl)-propionic acid 2-Benzenesulfonylamino-3-(2-{1-[(4-phenoxymethyl-phenyl)-acetyl]-pyrrolidin-2-yl}-oxazol-4-yl)-propionic acid 2-Benzenesulfonylamino-3-[2-(1-{[3-methoxy-4-(3-o-tolyl-ureido)-phenyl]-acetyl}-pyrrolidin-2-yl)-oxazol-4-yl]-propionic acid 2-Methanesulfonylamino-3-[2-(3-methyl-1-{[5-(3-o-tolyl-ureido)-pyridin-2-yl]-acetyl}-pyrrolidin-2-yl)-oxazol-4-yl]-propionic acid 2-Acetylamino-3-{2-[({[3-methoxy-4-(3-o-tolyl-ureido)-phenyl]-acetyl}-methyl-amino)-methyl]-5-methyl-oxazol-4-yl}-propionic acid 2-Acetylamino-3-{2-[({[3-methoxy-4-(3-o-tolyl-ureido)-phenyl]-acetyl}-methyl-amino)-methyl]-thiazol-4-yl}-propionic acid 2-(2,6-Dichloro-benzoylamino)-3-{2-[({[3-methoxy-4-(3-o-tolyl-ureido)-phenyl]-acetyl}-methyl-amino)-methyl]-oxazol-4-yl}-propionic acid Compounds which include the moiety of partial Formula (1.1.4):

3-[3-(1-{2-[3-Methoxy-4-(3-o-tolyl-ureido)-phenyl]-acetylamino}-3-methyl-butyl)-4,5-dihydro-isooxazol-5-yl]-2-methyl-propionic acid 2-Acetylamino-3-[3-(1-{2-[3-methoxy-4-(3-o-tolyl-ureido)-phenyl]-acetylamino}-3-methyl-butyl)-4,5-dihydro-isoxazol-5-yl]-propionic acid 2-Methanesulfonylamino-3-[3-(1-{2-[3-methoxy-4-(3-o-tolyl-ureido)-phenyl]-acetylamino}-3-methyl-butyl)-4,5-dihydro-isoxazol-5-yl]-propionic acid 2,2-Difluoro-3-{3-[1-(methyl-{[6-(3-o-tolyl-ureido)-pyridin-3-yl]-acetyl}-amino)-ethyl]-4,5-dihydro-isoxazol-5-yl}-propionic acid 2,2-Dimethyl-3-[3-(1-{[6-(3-phenyl-ureido)-pyridin-3-yl]-acetyl}-pyrrolidin-2-yl)-4,5-dihydro-isoxazol-5-yl]-propionic acid 2-Allyloxycarbonylamino-3-{3-[({[3-methoxy-4-(3-o-tolyl-ureido)-phenyl]-acetyl}-methyl-amino)-methyl]-4,5-dihydro-isoxazol-5-yl}-propionic acid 2-(Butane-1-sulfonylamino)-3-(3-{[methyl-({4-[3-(3-methyl-pyridin-2-yl)-ureido]-piperidin-1-yl}-acetyl)-amino]-methyl}-4,5-dihydro-isoxazol-5-yl)-propionic acid 2-Methyl-3-[3-(1-{[4-(2-methyl-benzyloxy)-phenyl]-acetyl}-pyrrolidin-2-yl)-4,5-dihydro-isoxazol-5-yl]-propionic acid 2-Formylamino-3-{3-[1-(biphenyl-4-yl-acetyl)-pyrrolidin-2-yl]-4,5-dihydro-isothiazol-5-yl}-propionic acid 2-Methyl-3-(3-{1-[(4-o-tolyloxy-phenyl)-acetyl]-pyrrolidin-2-yl}-4,5-dihydro-isoxazol-5-yl)-propionic acid 2-Benzenesulfonylamino-3-(3-{1-[(4-phenoxymethyl-phenyl)-acetyl]-pyrrolidin-2-yl}-4,5-dihydro-isoxazol-5-yl)-propionic acid 2-Benzenesulfonylamino-3-[3-(1-{[3-methoxy-4-(3-o-tolyl-ureido)-phenyl]-acetyl}-pyrrolidin-2-yl)-4,5-dihydro-isoxazol-5-yl]-propionic acid 2-Methanesulfonylamino-3-[3-(3-methyl-1-{[5-(3-o-tolyl-ureido)-pyridin-2-yl]-acetyl}-pyrrolidin-2-yl)-4,5-dihydro-isoxazol-5-yl]-propionic acid 2-Acetylamino-3-{3-[({[3-methoxy-4-(3-o-tolyl-ureido)-phenyl]-acetyl}-methyl-amino)-methyl]-4-methyl-4,5-dihydro-isoxazol-5-yl}-propionic acid 2-Acetylamino-3-{3-[({[3-methoxy-4-(3-o-tolyl-ureido)-phenyl]-acetyl}-methyl-amino)-methyl]-4,5-dihydro-isothiazol-5-yl}-propionic acid 3-Acetylamino-3-{5-[({[3-methoxy-4-(3-o-tolyl-ureido)-phenyl]-acetyl}-methyl-amino)-methyl]-3,4-dihydro-2H-pyrazol-3-yl}-propionic acid 2-(2,6-Dichloro-benzoylamino)-3-{3-[({[3-methoxy-4-(3-o-tolyl-ureido)-phenyl]-acetyl}-methyl-amino)-methyl]-4,5-dihydro-isoxazol-5-yl}-propionic acid Compounds which include the moiety of partial Formula (1.1.5):

3-[3-(1-{2-[3-Methoxy-4-(3-o-tolyl-ureido)-phenyl]-acetylamino}-3-methyl-butyl)-4,5-dihydro-pyrazol-1-yl]-2-methyl-propionic acid 2-Acetylamino-3-[3-(1-{2-[3-methoxy-4-(3-o-tolyl-ureido)-phenyl]-acetylamino}-3-methyl-butyl)-4,5-dihydro-pyrazol-1-yl]-propionic acid 2-Methanesulfonylamino-3-[3-(1-{2-[3-methoxy-4-(3-o-tolyl-ureido)-phenyl]-acetylamino}-3-methyl-butyl)-4,5-dihydro-pyrazol-1-yl]-propionic acid 2,2-Difluoro-3-{3-[1-(methyl-{[6-(3-o-tolyl-ureido)-pyridin-3-yl]-acetyl}-amino)-ethyl]-4,5-dihydro-pyrazol-1-yl}-propionic acid 2,2-Dimethyl-3-[3-(1-{[6-(3-phenyl-ureido)-pyridin-3-yl]-acetyf}-pyrrolidin-2-yl)-4,5-dihydro-pyrazol-1-yl]-propionic acid 2-(Butane-1-sulfonylamino)-3-(3-{[methyl-({4-[3-(3-methyl-pyridin-2-yl)-ureido]-piperidin-1-yl}-acetyl)-amino]-methyl}-4,5-dihydro-pyrazol-1-yl)-propionic acid 2-Methyl-3-[3-(1-{[4-(2-methyl-benzyloxy)-phenyl]-acetyl}-pyrrolidin-2-yl)-4,5-dihydro-pyrazol-1-yl]-propionic acid 2-Acetylamino-3-{3-[1-(biphenyl-4-yl-acetyl)-pyrrolidin-2-yl]-4,5-dihydro-pyrazol-1-yl}-propionic acid 2-Methyl-3-(3-{1-[(4-o-tolyloxy-phenyl)-acetyl]-pyrrolidin-2-yl}-4,5-dihydro-pyrazol-1-yl)-propionic acid 2-Benzenesulfonylamino-3-(3-{1-[(4-phenoxymethyl-phenyl)-acetyl]-pyrrolidin-2-yl}-4,5-dihydro-pyrazol-1-yl)-propionic acid 2-Benzenesulfonylamino-3-[3-(1-{[3-methoxy-4-(3-o-tolyl-ureido)-phenyl]-acetyl}-pyrrolidin-2-yl)-4,5-dihydro-pyrazol-1-yl]-propionic acid 2-Methanesulfonylamino-3-[3-(3-methyl-1-{[5-(3-o-tolyl-ureido)-pyridin-2-yl]-acetyl}-pyrrolidin-2-yl)-4,5-dihydro-pyrazol-1-yl]-propionic acid 2-Acetylamino-3-{3-[({[3-methoxy-4-(3-o-tolyl-ureido)-phenyl]-acetyl}-methyl-amino)-methyl]-5-methyl-4,5-dihydro-pyrazol-1-yl}-propionic acid 2-Formylamino-3-{3-[({[3-methoxy-4-(3-o-tolyl-ureido)-phenyl]-acetyl}-methyl-amino)-methyl]-4,5-dihydro-pyrazol-1-yl}-propionic acid 2-(2,6-Dichloro-benzoylamino)-3-{3-[({[3-methoxy-4-(3-O-tolyl-ureido)-phenyl]-acetyl}-methyl-amino)-methyl]-4,5-dihydro-pyrazol-1-yl}-propionic acid Compounds which include the moiety of partial Formula (1.1.6):

3-[3-(1-{2-[3-Methoxy-4-(3-o-tolyl-ureido)-phenyl]-acetylamino}-3-methyl-butyl-isooxazol-5-yl]-2-methyl-propionic acid 2-Acetylamino-3-[3-(1-{2-[3-methoxy-4-(3-o-tolyl-ureido)-phenyl]-acetylamino}-3-methyl-butyl)-isoxazol-5-yl]-propionic acid 2-Methanesulfonylamino-3-[3-(1-{2-[3-methoxy-4-(3-o-tolyl-ureido)-phenyl]-acetylamino}-3-methyl-butyl)-isoxazol-5-yl]-propionic acid 2,2-Difluoro-3-{3-[1-(methyl-{[6-(3-o-tolyl-ureido)-pyridin-3-yl]-acetyl}-amino)-ethyl]-isoxazol-5-yl}-propionic acid 2,2-Dimethyl-3-[3-(1-{[6-(3-phenyl-ureido)-pyridin-3-yl]-acetyl}-pyrrolidin-2-yl)-isoxazol-5-yl]-propionic acid 2-Allyloxycarbonylamino-3-{3-[({[3-methoxy-4-(3-o-tolyl-ureido)-phenyl]-acetyl}-methyl-amino)-methyl]-isoxazol-5-yl}-propionic acid 2-(Butane-1-sulfonylamino)-3-(3-{[methyl-({4-[3-(3-methyl-pyridin-2-yl)-ureido]-piperidin-1-yl}-acetyl)-amino]-methyl}-isoxazol-5-yl)-propionic acid 2-Methyl-3-[3-(1-{[4-(2-methyl-benzyloxy)-phenyl]-acetyl}-pyrrolidin-2-yl)-isoxazol-5-yl]-propionic acid 2-Acetylamino-3-{3-[1-(biphenyl-4-yl-acetyl)-pyrrolidin-2-yl]-isothiazol-5-yl}-propionic acid 2-Methyl-3-(3-{1-[(4-o-tolyloxy-phenyl)-acetyl]-pyrrolidin-2-yl}-isoxazol-5-yl)-propionic acid 2-Benzenesulfonylamino-3-(3-{1-[(4-phenoxymethyl-phenyl)-acetyl]-pyrrolidin-2-yl}-isoxazol-5-yl)-propionic acid 2-Benzenesulfonylamino-3-[3-(1-{[3-methoxy-4-(3-o-tolyl-ureido)-phenyl]-acetyl}-pyrrolidin-2-yl)-isoxazol-5-yl]-propionic acid 2-Methanesulfonylamino-3-[3-(3-methyl-1-{[5-(3-o-tolyl-ureido)-pyridin-2-yl]-acetyl}-pyrrolidin-2-yl)-isoxazol-5-yl]-propionic acid 2-Formylamino-3-{3-[({[3-methoxy-4-(3-o-tolyl-ureido)-phenyl]-acetyl}-methyl-amino)-methyl]-4-methyl-isoxazol-5-yl}-propionic acid 2-Acetylamino-3-{3-[({[3-methoxy-4-(3-o-tolyl-ureido)-phenyl]-acetyl}-methyl-amino)-methyl]-isothiazol-5-yl}-propionic acid 3-Acetylamino-3-{5-[({[3-methoxy-4-(3-o-tolyl-ureido)-phenyl]-acetyl}-methyl-amino)-methyl]-2H-pyrazol-3-yl}-propionic acid 2-(2,6-Dichloro-benzoylamino)-3-{3-[({[3-methoxy-4-(3-o-tolyl-ureido)-phenyl]-acetyl}-methyl-amino)-methyl]-isoxazol-5-yl}-propionic acid Compounds which include the moiety of partial Formula (1.1.7):

3-[3-(1-{2-[3-Methoxy-4-(3-o-tolyl-ureido)-phenyl]-acetylamino}-3-methyl-butyl)-pyrazol-1-yl]-2-methyl-propionic acid 2-Acetylamino-3-[3-(1-{2-[3-methoxy-4-(3-o-tolyl-ureido)-phenyl]-acetylamino}-3-methyl-butyl)-pyrazol-1-yl]-propionic acid 2-Methanesulfonylamino-3-[3-(1-{2-[3-methoxy-4-(3-o-tolyl-ureido)-phenyl]-acetylamino}-3-methyl-butyl)-pyrazol-1-yl]-propionic acid 2,2-Difluoro-3-{3-[1-(methyl-{[6-(3-o-tolyl-ureido)-pyridin-3-yl]-acetyl}-amino)-ethyl]-pyrazol-1-yl}-propionic acid 2,2-Dimethyl-3-[3-(1-{[6-(3-phenyl-ureido)-pyridin-3-yl]-acetyl}-pyrrolidin-2-yl)-pyrazol-1-yl]-propionic acid 2-(Butane-1-sulfonylamino)-3-(3-{[methyl-({4-[3-(3-methyl-pyridin-2-yl)-ureido]-piperidin-1-yl}-acetyl)-amino]-methyl}-pyrazol-1-yl)-propionic acid 2-Methyl-3-[3-(1-{[4-(2-methyl-benzyloxy)-phenyl]-acetyl}-pyrrolidin-2-yl)-pyrazol-1-yl]-propionic acid 2-Formylamino-3-{3-[1-(biphenyl-4-yl-acetyl)-pyrrolidin-2-yl]-pyrazol-1-yl}-propionic acid 2-Methyl-3-(3-{1-[(4-o-tolyloxy-phenyl)-acetyl]-pyrrolidin-2-yl}-pyrazol-1-yl)-propionic acid 2-Benzenesulfonylamino-3-(3-{1-[(4-phenoxymethyl-phenyl)-acetyl]-pyrrolidin-2-yl}-pyrazol-1-yl)-propionic acid 2-Benzenesulfonylamino-3-[3-(1-{[3-methoxy-4-(3-o-tolyl-ureido)-phenyl]-acetyl}-pyrrolidin-2-yl)-pyrazol-1-yl]-propionic acid 2-Methanesulfonylamino-3-[3-(3-methyl-1-{[5-(3-o-tolyl-ureido)-pyridin-2-yl]-acetyl}-pyrrolidin-2-yl)-pyrazol-1-yl]-propionic acid 2-Acetylamino-3-{3-[({[3-methoxy-4-(3-o-tolyl-ureido)-phenyl]-acetyl}-methyl-amino)-methyl]-5-methyl-pyrazol-1-yl}-propionic acid
2-Acetylamino-3-{3-[({[3-methoxy-4-(3-o-tolyl-ureido)-phenyl]-acetyl}-methyl-amino)-methyl]-pyrazol-1-yl}-propionic acid
2-(2,6-Dichloro-benzoylamino)-3-{3-[({[3-methoxy-4-(3-o-tolyl-ureido)-phenyl]-acetyl}-methyl-amino)-methyl]-pyrazol-1-yl}-propionic acid Compounds which include the moiety of partial Formula (1.1.8):

3-[4-(1-{2-[3-Methoxy-4-(3-o-tolyl-ureido)-phenyl]-acetylamino}-3-methyl-butyl)-oxazol-2-yl]-2-methyl-propionic acid
2-Acetylamino-3-[4-(1-{2-[3-methoxy-4-(3-o-tolyl-ureido)-phenyl]-acetylamino}-3-methyl-butyl)-oxazol-2-yl]-propionic acid
2-Methanesulfonylamino-3-[4-(1-{2-[3-methoxy-4-(3-o-tolyl-ureido)-phenyl]-acetylamino}-3-methyl-butyl)-oxazol-2-yl]-propionic acid
2,2-Difluoro-3-{4-[1-(methyl-{[6-(3-o-tolyl-ureido)-pyridin-3-yl]-acetyl}-amino)-ethyl]-oxazol-2-yl}-propionic acid
2,2-Dimethyl-3-[4-(1-{[6-(3-phenyl-ureido)-pyridin-3-yl]-acetyl}-pyrrolidin-2-yl)-oxazol-2-yl]-propionic acid
2-Allyloxycarbonylamino-3-{4-[({[3-methoxy-4-(3-o-tolyl-ureido)-phenyl]-acetyl}-methyl-amino)-methyl]-oxazol-2-yl}-propionic acid
2-(Butane-1-sulfonylamino)-3-(4-{[methyl-({4-[3-(3-methyl-pyridin-2-yl)-ureido]-piperidin-1-yl}-acetyl)-amino]-methyl}-oxazol-2-yl-propionic acid
2-Methyl-3-[4-(1-{[4-(2-methyl-benzyloxy)-phenyl]-acetyl}-pyrrolidin-2-yl)-oxazol-2-yl]-propionic acid
2-Formylamino-3-{4-[1-(biphenyl-4-yl-acetyl)-pyrrolidin-2-yl]-thiazol-2-yl}-propionic acid
2-Methyl-3-(4-{1-[(4-o-tolyloxy-phenyl)-acetyl]-pyrrolidin-2-yl}-oxazol-2-yl)-propionic acid
2-Benzenesulfonylamino-3-(4-{1-[(4-phenoxymethyl-phenyl)-acetyl]-pyrrolidin-2-yl}-oxazol-2-yl)-propionic acid
2-Benzenesulfonylamino-3-[4-(1-{[3-methoxy-4-(3-o-tolyl-ureido)-phenyl]-acetyl}-pyrrolidin-2-yl)-oxazol-2-yl]-propionic acid
2-Methanesulfonylamino-3-[4-(3-methyl-1-{[5-(3-o-tolyl-ureido)-pyridin-2-yl]-acetyl}-pyrrolidin-2-yl)-oxazol-2-yl]-propionic acid
2-Acetylamino-3-{4-[({[3-methoxy-4-(3-o-tolyl-ureido)-phenyl]-acetyl}-methyl-amino)-methyl]-5-methyl-oxazol-2-yl}-propionic acid
2-Acetylamino-3-{4-[({[3-methoxy-4-(3-o-tolyl-ureido)-phenyl]-acetyl}-methyl-amino)-methyl]-thiazol-2-yl}-propionic acid
2-(2,6-Dichloro-benzoylamino)-3-{4-[({[3-methoxy-4-(3-o-tolyl-ureido)-phenyl]-acetyl}-methyl-amino)-methyl]-oxazol-2-yl}-propionic acid
2-Acetylamino-3-{4-[({[3-methoxy-4-(3-o-tolyl-ureido)-phenyl]-acetyl}-methyl-amino)-methyl]-1H-imidazol-2-yl}-propionic acid Compounds which include the moiety of partial Formula (1.1.9):

3-[4-(1-{2-[3-Methoxy-4-(3-o-tolyl-ureido)-phenyl]-acetylamino}-3-methyl-butyl)-imidazol-1-yl]-2-methyl-propionic acid
2-Acetylamino-3-[4-(1-{2-[3-methoxy-4-(3-o-tolyl-ureido)-phenyl]-acetytamino}-3-methyl-butyl)-imidazol-1-yl]-propionic acid
2-Methanesulfonylamino-3-[4-(1-{2-[3-methoxy-4-(3-o-tolyl-ureido)-phenyl]-acetylamino}-3-methyl-butyl)-imidazol-1-yl]-propionic acid
2,2-Difluoro-3-{4-[1-(methyl-{[6-(3-o-tolyl-ureido)-pyridin-3-yl]-acetyl}-amino)-ethyl]-imidazol-1-yl}-propionic acid
2,2-Dimethyl-3-[4-(1-{[6-(3-phenyl-ureido)-pyridin-3-yl]-acetyl}-pyrrolidin-2-yl)-imidazol-1-yl]-propionic acid
2-(Butane-1-sulfonylamino)-3-(4-{[methyl-({4-[3-(3-methyl-pyridin-2-yl)-ureido]-piperidin-1-yl}-acetyl)-amino]-methyl}-imidazol-1-yl)-propionic acid
2-Methyl-3-[4-(1-{[4-(2-methyl-benzyloxy)-phenyl]-acetyl}-pyrrolidin-2-yl)-imidazol-1-yl]-propionic acid
2-Formylamino-3-{4-[1-(biphenyl-4-yl-acetyl)-pyrrolidin-2-yl]-imidazol-1-yl}-propionic acid
2-Methyl-3-(4-{1-[(4-o-tolyloxy-phenyl)-acetyl]-pyrrolidin-2-yl}-imidazol-1-yl)-propionic acid
2-Benzenesulfonylamino-3-(4-{1-[(4-phenoxymethyl-phenyl)-acetyl]-pyrrolidin-2-yl}-imidazol-1-yl)-propionic acid
2-Benzenesulfonylamino-3-[4-(1-{[3-methoxy-4-(3-o-tolyl-ureido)-phenyl]-acetyl}-pyrrolidin-2-yl)-imidazol-1-yl]-propionic acid
2-Methanesulfonylamino-3-[4-(3-methyl-1-{[5-(3-o-tolyl-ureido)-pyridin-2-yl]-acetyl}-pyrrolidin-2-yl)-imidazol-1-yl]-propionic acid
2-Acetylamino-3-{4-[({[3-methoxy-4-(3-o-tolyl-ureido)-phenyl]-acetyl}-methyl-amino)-methyl]-5-methyl-imidazol-1-yl}-propionic acid
2-Acetylamino-3-{4-[({[3-methoxy-4-(3-o-tolyl-ureido)-phenyl]-acetyl}-methyl-amino)-methyl]-imidazol-1-yl}-propionic acid
2-(2,6-Dichloro-benzoylamino)-3-{4-[({[3-methoxy-4-(3-o-tolyl-ureido)-phenyl]-acetyl}-methyl-amino)-methyl]-imidazol-1-yl}-propionic acid Compounds which include the moiety of partial Formula (1.1.10):

3-[3-(1-{2-[3-Methoxy-4-(3-o-tolyl-ureido)-phenyl]-acetylamino}-3-methyl-butyl)-[1,2,4]oxadiazol-5-yl]-2-methyl-propionic acid
2-Acetylamino-3-[3-(1-{2-[3-methoxy-4-(3-o-tolyl-ureido)-phenyl]-acetylamino}-3-methyl-butyl)-[1,2,4]oxadiazol-5-yl]-propionic acid
2-Methanesulfonylamino-3-[3-(1-{2-[3-methoxy-4-(3-o-tolyl-ureido)-phenyl]-acetylamino}-3-methyl-butyl)-[1,2,4]oxadiazol-5-yl]-propionic acid
2,2-Difluoro-3-{3-[1-(methyl-{[6-(3-o-tolyl-ureido)-pyridin-3-yl]-acetyl}-amino)-ethyl]-[1,2,4]oxadiazol-5-yl}-propionic acid
2,2-Dimethyl-3-[3-(1-{[6-(3-phenyl-ureido)-pyridin-3-yl]-acetyl}-pyrrolidin-2-yl)-[1,2,4]oxadiazol-5-yl]-propionic acid
2-Allyloxycarbonylamino-3-{3-[({[3-methoxy-4-(3-o-tolyl-ureido)-phenyl]-acetyl}-methyl-amino)-methyl]-[1,2,4]oxadiazol-5-yl}-propionic acid
2-(Butane-1-sulfonylamino)-3-(3-{[methyl-({4-[3-(3-methyl-pyridin-2-yl)-ureido]-piperidin-1-yl}-acetyl)-amino]-methyl}-[1,2,4]oxadiazol-5-yl)-propionic acid
2-Methyl-3-[3-(1-{[4-(2-methyl-benzyloxy)-phenyl]-acetyl}-pyrrolidin-2-yl)-[1,2,4]oxadiazol-5-yl]-propionic acid
2-Formylamino-3-{3-[1-(biphenyl-4-yl-acetyl)-pyrrolidin-2-yl]-[1,2,4]thiadiazol-5-yl}-propionic acid
2-Methyl-3-(3-{1-[(4-o-tolyloxy-phenyl)-acetyl]-pyrrolidin-2-yl}-[1,2,4]oxadiazol-5-yl)-propionic acid
2-Benzenesulfonylamino-3-(3-{1-[(4-phenoxymethyl-phenyl)-acetyl]-pyrrolidin-2-yl}-[1,2,4]oxadiazol-5-yl)-propionic acid
2-Benzenesulfonylamino-3-[3-(1-{[3-methoxy-4-(3-o-tolyl-ureido)-phenyl]-acetyt}-pyrrolidin-2-yl)-[1,2,4]oxadiazol-5-yl]-propionic acid 2-Methanesulfonylamino-3-[3-(3-methyl-1-{[5-(3-o-tolyl-ureido)-pyridin-2-yl]-acetyl}-pyrrolidin-2-yl)-[1,2,4]oxadiazol-5-yl]-propionic acid
2-Acetylamino-3-{3-[({[3-methoxy-4-(3-o-tolyl-ureido)-phenyl]-acetyl}-methyl-amino)-methyl]-[1,2,4]oxadiazol-5-yl}-propionic acid
2-Formylamino-3-{3-[({[3-methoxy-4-(3-o-tolyl-ureido)-phenyl]-acetyl}-methyl-amino)-methyl]-[1,2,4]thiadiazol-5-yl}-propionic acid
3-Acetylamino-3-{5-[({[3-methoxy-4-(3-o-tolyl-ureido)-phenyl]-acetyl}-methyl-amino)-methyl]-2H-[1,2,4]triazol-3-yl}-propionic acid
2-(2,6-Dichloro-benzoylamino)-3-{3-[({[3-methoxy-4-(3-o-tolyl-ureido)-phenyl]-acetyl}-methyl-amino)-methyl]-[1,2,4]oxadiazol-5-yl}-propionic acid Compounds which include the moiety of partial Formula (1.1.11):

3-[3-(1-{2-[3-Methoxy-4-(3-o-tolyl-ureido)-phenyl]-acetylamino}-3-methyl-butyl)-[1,2,4]triazol-1-yl]-2-methyl-propionic acid
2-Acetylamino-3-[3-(1-{2-[3-methoxy-4-(3-o-tolyl-ureido)-phenyl]-acetylamino}-3-methyl-butyl)-[1,2,4]triazol-1-yl]-propionic acid
2-Methanesulfonylamino-3-[3-(1-{2-[3-methoxy-4-(3-o-tolyl-ureido)-phenyl]-acetylamino}-3-methyl-butyl)-[1,2,4]triazol-1-yl]-propionic acid
2,2-Difluoro-3-{3-[1-(methyl-{[6-(3-o-tolyl-ureido)-pyridin-3-yl]-acetyl}-amino)-ethyl]-[1,2,4]triazol-1-yl}-propionic acid
2,2-Dimethyl-3-[3-(1-{[6-(3-phenyl-ureido)-pyridin-3-yl]-acetyl}-pyrrolidin-2-yl)-[1,2,4]triazol-1-yl]-propionic acid
2-Allyloxycarbonylamino-3-{3-[({[3-methoxy-4-(3-o-tolyl-ureido)-phenyl]-acetyl}-methyl-amino)-methyl]-[1,2,4]triazol-1-yl}-propionic acid
2-(Butane-1-sulfonylamino)-3-(3-{[methyl-({4-[3-(3-methyl-pyridin-2-yl)-ureido]-piperidin-1-yl}-acetyl)-amino]-methyl}-[1,2,4]triazol-1-yl)-propionic acid
2-Methyl-3-[3-(1-{[4-(2-methyl-benzyloxy)-phenyl]-acetyl}-pyrrolidin-2-yl)-[1,2,4]triazol-1-yl]-propionic acid
2-Acetylamino-3-{3-[1-(biphenyl-4-yl-acetyl)-pyrrolidin-2-yl]-[1,2,4]triazol-1-yl}-propionic acid
2-Methyl-3-(3-{1-[(4-o-tolyloxy-phenyl)-acetyl]-pyrrolidin-2-yl}-[1,2,4]triazol-1-yl)-propionic acid
2-Benzenesulfonylamino-3-(3-{1-[(4-phenoxymethyl-phenyl)-acetyl]-pyrrolidin-2-yl}-[1,2,4]triazol-1-yl)-propionic acid
2-Benzenesulfonylamino-3-[3-(1-{[3-methoxy-4-(3-o-tolyl-ureido)-phenyl]-acetyl}-pyrrolidin-2-yl)-[1,2,4]triazol-1-yl]-propionic acid
2-Methanesulfonylamino-3-[3-(3-methyl-1-{[5-(3-o-tolyl-ureido)-pyridin-2-yl]-acetyl}-pyrrolidin-2-yl)-[1,2,4]triazol-1-yl]-propionic acid
2-Acetylamino-3-{3-[({[3-methoxy-4-(3-o-tolyl-ureido)-phenyl]-acetyl}-methyl-amino)-methyl]-4-methyl-[1,2,4]triazol-1-yl}-propionic acid
2-Acetylamino-3-{3-[({[3-methoxy-4-(3-o-tolyl-ureido)-phenyl]-acetyl}-methyl-amino)-methyl]-[1,2,4]triazol-1-yl}-propionic acid
2-(2,6-Dichloro-benzoylamino)-3-{3-[({[3-methoxy-4-(3-o-tolyl-ureido)-phenyl]-acetyl}-methyl-amino)-methyl]-[1,2,4]triazol-1-yl}-propionic acid Compounds which include the moiety of partial Formula (1.1.12):

3-[4-(1-{2-[3-Methoxy-4-(3-o-tolyl-ureido)-phenyl]-acetylamino}-3-methyl-butyl)-thiophen-2-yl]-2-methyl-propionic acid
2-Acetylamino-3-[4-(1-{2-[3-methoxy-4-(3-o-tolyl-ureido)-phenyl]-acetytamino}-3-methyl-butyl)-furan-2-yl]-propionic acid
2-Methanesulfonylamino-3-[4-(1-{2-[3-methoxy-4-(3-o-tolyl-ureido)-phenyl]-acetytamino}-3-methyl-butyl)-thiophen-2-yl]-propionic acid
2,2-Difluoro-3-{4-[1-(methyl-{[6-(3-o-tolyl-ureido)-pyridin-3-yl]-acetyl}-amino)-ethyl]-1H-pyrrol-2-yl}-propionic acid
2,2-Dimethyl-3-[4-(1-{[6-(3-phenyl-ureido)-pyridin-3-yl]-acetyl}-pyrrolidin-2-yl)-thiophen-2-yl]-propionic acid
2-(Butane-1-sulfonylamino)-3-(4-{[methyl-({4-[3-(3-methyl-pyridin-2-yl)-ureido]-piperidin-1-yl}-acetyl)-amino]-methyl}-furan-2-yl)-propionic acid
2-Methyl-3-[4-(1-{[4-(2-methyl-benzyloxy)-phenyl]-acetyl}-pyrrolidin-2-yl)-1H-pyrrol-2-yl]-propionic acid
2-Formylamino-3-{4-[1-(biphenyl-4-yl-acetyl)-pyrrolidin-2-yl]-thiophen-2-yl}-propionic acid
2-Methyl-3-(4-{1-[(4-o-tolyloxy-phenyl)-acetyl]-pyrrolidin-2-yl}-1H-pyrrol-2-yl)-propionic acid
2-Benzenesulfonylamino-3-(4-{1-[(4-phenoxymethyl-phenyl)-acetyl]-pyrrolidin-2-yl}-furan-2-yl)-propionic acid
2-Benzenesulfonylamino-3-[4-(1-{[3-methoxy-4-(3-o-tolyl-ureido)-phenyl]-acetyl}-pyrrolidin-2-yl)-thiophen-2-yl]-propionic acid
2-Methanesulfonylamino-3-[4-(3-methyl-1-{[5-(3-o-tolyl-ureido)-pyridin-2-yl]-acetyl}-pyrrolidin-2-yl)-1H-pyrrol-2-yl]-propionic acid
2-Acetylamino-3-{4-[({[3-methoxy-4-(3-o-tolyl-ureido)-phenyl]-acetyl}-methyl-amino)-methyl]-5-methyl-1H-pyrrol-2-yl}-propionic acid
2-Acetylamino-3-{4-[({[3-methoxy-4-(3-o-tolyl-ureido)-phenyl]-acetyl}-methyl-amino)-methyl]-thiophen-2-yl}-propionic acid
2-(2,6-Dichloro-benzoylamino)-3-{4-[({[3-methoxy-4-(3-o-tolyl-ureido)-phenyl]-acetyl}-methyl-amino)-methyl]-furan-2-yl}-propionic acid Compounds which include the moiety of partial Formula (1.1.13):

3-[5-(1-{2-[3-Methoxy-4-(3-o-tolyl-ureido)-phenyl]-acetylamino}-3-methyl-butyl)-thiophen-3-yl]-2-methyl-propionic acid
2-Acetylamino-3-[5-(1-{2-[3-methoxy-4-(3-o-tolyl-ureido)-phenyl]-acetylamino}-3-methyl-butyl)-furan-3-yl]-propionic acid
2-Methanesulfonylamino-3-[5-(1-{2-[3-methoxy-4-(3-o-tolyl-ureido)-phenyl]-acetylamino}-3-methyl-butyl)-thiophen-3-yl]-propionic acid
2,2-Difluoro-3-{5-[1-(methyl-{[6-(3-o-tolyl-ureido)-pyridin-3-yl]-acetyl}-amino)-ethyl]-1H-pyrrol-3-yl}-propionic acid
2,2-Dimethyl-3-[5-(1-{[6-(3-phenyl-ureido)-pyridin-3-yl]-acetyl}-pyrrolidin-2-yl)-thiophen-3-yl]-propionic acid
2-(Butane-1-sulfonylamino)-3-(5-{[methyl-({4-[3-(3-methyl-pyridin-2-yl)-ureido]-piperidin-1-yl}-acetyl)-amino]-methyl}-furan-3-yl)-propionic acid
2-Methyl-3-[5-(1-{[4-(2-methyl-benzyloxy)-phenyl]-acetyl}-pyrrolidin-2-yl)-1H-pyrrol-3-yl]-propionic acid
2-Formylamino-3-{5-[1-(biphenyl-4-yl-acetyl)-pyrrolidin-2-yl]-thiophen-3-yl}-propionic acid
2-Methyl-3-(5-{1-[(4-o-tolyloxy-phenyl)-acetyl]-pyrrolidin-2-yl}-1H-pyrrol-3-yl)-propionic acid
2-Benzenesulfonylamino-3-(5-{1-[(4-phenoxymethyl-phenyl)-acetyl]-pyrrolidin-2-yl}-furan-3-yl)-propionic acid
2-Benzenesulfonylamino-3-[5-(1-{[3-methoxy-4-(3-o-tolyl-ureido)-phenyl]-acetyl}-pyrrolidin-2-yl)-thiophen-3-yl]-propionic acid 2-Methanesulfonylamino-3-[5-(3-methyl-1-{[5-(3-o-tolyl-ureido)-pyridin-2-yl]-acetyl}-pyrrolidin-2-yl)-1H-pyrrol-3-yl]-propionic acid
2-Acetylamino-3-{5-[({[3-methoxy-4-(3-o-tolyl-ureido)-phenyl]-acetyl}-methyl-amino)-methyl]-2-methyl-1H-pyrrol-3-yl}-propionic acid
2-Acetylamino-3-{5-[({[3-methoxy-4-(3-o-tolyl-ureido)-phenyl]-acetyl}-methyl-amino)methyl]-thiophen-3-yl}-propionic acid
2-(2,6-Dichloro-benzoylamino)-3-{5-[({[3-methoxy-4-(3-o-tolyl-ureido)-phenyl]-acetyl}-methyl-amino)-methyl]-furan-3-yl}-propionic acid
Compounds which include the moiety of partial Formula (1.1.14):
3-[5-(1-{2-[3-Methoxy-4-(3-o-tolyl-ureido)-phenyl]-acetylamino}-3-methyl-butyl)-thiophen-2-yl]-2-methyl-propionic acid
2-Acetylamino-3-[5-(1-{2-[3-methoxy-4-(3-o-tolyl-ureido)-phenyl]-acetylamino}-3-methyl-butyl)-furan-2-yl]-propionic acid
2-Methanesulfonylamino-3-[5-(1-{2-[3-methoxy-4-(3-o-tolyl-ureido)-phenyl]-acetylamino}-3-methyl-butyl)-thiophen-2-yl]-propionic acid
2,2-Difluoro-3-{5-[1-(methyl-{[6-(3-o-tolyl-ureido)-pyridin-3-yl]-acetyl}-amino)-ethyl]-1H-pyrrol-2-yl}-propionic acid
2,2-Dimethyl-3-[5-(1-{[6-(3-phenyl-ureido)-pyridin-3-yl]-acetyl}-pyrrolidin-2-yl)-thiophen-2-yl]-propionic acid
2-(Butane-1-sulfonylamino)-3-(5-{[methyl-({4-[3-(3-methyl-pyridin-2-yl)-ureido]-piperidin-1-yl}-acetyl)-amino]-methyl}-furan-2-yl)-propionic acid
2-Methyl-3-[5-(1-{[4-(2-methyl-benzyloxy)-phenyl]-acetyl}-pyrrolidin-2-yl)-1H-pyrrol-2-yl]-propionic acid
2-Formylamino-3-{5-[1-(biphenyl-4-yl-acetyl)-pyrrolidin-2-yl]-thiophen-2-yl}-propionic acid
2-Methyl-3-(5-{1-[(4-o-tolyloxy-phenyl)-acetyl]-pyrrolidin-2-yl}-1H-pyrrol-2-yl)-propionic acid
2-Benzenesulfonylamino-3-(5-{1-[(4-phenoxymethyl-phenyl)-acetyl]-pyrrolidin-2-yl}-furan-2-yl)-propionic acid
2-Benzenesulfonylamino-3-[5-(1-{[3-methoxy-4-(3-o-tolyl-ureido)-phenyl]-acetyl}-pyrrolidin-2-yl)-thiophen-2-yl]-propionic acid
2-Methanesulfonylamino-3-[5-(3-methyl-1-{[5-(3-o-tolyl-ureido)-pyridin-2-yl]-acetyl}-pyrrolidin-2-yl)-1H-pyrrol-2-yl]-propionic acid
2-Acetylamino-3-{5-[({[3-methoxy-4-(3-o-tolyl-ureido)-phenyl]-acetyl}-methyl-amino)-methyl]-2-methyl-1H-pyrrol-2-yl}-propionic acid
2-Acetylamino-3-{5-[({[3-methoxy-4-(3-o-tolyl-ureido)-phenyl]-acetyl}-methyl-amino)-methyl]-thiophen-2-yl}-propionic acid
2-(2,6-Dichloro-benzoylamino)-3-{5-[({[3-methoxy-4-(3-o-tolyl-ureido)-phenyl]-acetyl}-methyl-amino)-methyl]-furan-2-yl}-propionic acid
Compounds which include the moiety of partial Formula (1.1.15):
3-[5-(1-{2-[3-Methoxy-4-(3-o-tolyl-ureido)-phenyl]-acetylamino}-3-methyl-butyl)-isooxazol-3-yl]-2-methyl-propionic acid
2-Acetylamino-3-[5-(1-{2-[3-methoxy-4-(3-o-tolyl-ureido)-phenyl]-acetylamino}-3-methyl-butyl)-isoxazol-3-yl]-propionic acid
2-Methanesulfonylamino-3-[5-(1-{2-[3-methoxy-4-(3-o-tolyl-ureido)-phenyl]-acetylamino}-3-methyl-butyl)-isoxazol-3-yl]-propionic acid
2,2-Difluoro-3-{5-[1-(methyl-{[6-(3-o-tolyl-ureido)-pyridin-3-yl]-acetyl}-amino)-ethyl]-isoxazol-3-yl}-propionic acid
2,2-Dimethyl-3-[5-(1-{[6-(3-phenyl-ureido)-pyridin-3-yl]-acetyl}-pyrrolidin-2-yl)-isoxazol-3-yl]-propionic acid
2-Allyloxycarbonylamino-3-{5-[({[3-methoxy-4-(3-o-tolyl-ureido)-phenyl]-acetyl}-methyl-amino)-methyl]-isoxazol-3-yl}-propionic acid
2-(Butane-1-sulfonylamino)-3-(5-{[methyl-({4-[3-(3-methyl-pyridin-2-yl)-ureido]-piperidin-1-yl}-acetyl)-amino]-methyl}-isoxazol-3-yl)-propionic acid
2-Methyl-3-[5-(1-{[4-(2-methyl-benzyloxy)-phenyl]-acetyl}-pyrrolidin-2-yl)-isoxazol-3-yl]-propionic acid
2-Acetylamino-3-{5-[1-(biphenyl-4-yl-acetyl)-pyrrolidin-2-yl]-isothiazol-3-yl}-propionic acid
2-Methyl-3-(5-{1-[(4-o-tolyloxy-phenyl)-acetyl]-pyrrolidin-2-yl}-isoxazol-3-yl)-propionic acid
2-Benzenesulfonylamino-3-(5-{1-[(4-phenoxymethyl-phenyl)-acetyl]-pyrrolidin-2-yl}-isoxazol-3-yl)-propionic acid
2-Benzenesulfonylamino-3-[5-(1-{[3-methoxy-4-(3-o-tolyl-ureido)-phenyl]-acetyl}-pyrrolidin-2-yl)-isoxazol-3-yl]-propionic acid
2-Methanesulfonylamino-3-[5-(3-methyl-1-{[5-(3-o-tolyl-ureido)-pyridin-2-yl]-acetyl}pyrrolidin-2-yl)-isoxazol-3-yl]-propionic acid
2-Formylamino-3-{5-[({[3-methoxy-4-(3-o-tolyl-ureido)-phenyl]-acetyl}-methyl-amino)-methyl]-4-methyl-isoxazol-3-yl}-propionic acid
2-Acetylamino-3-{5-[({[3-methoxy-4-(3-o-tolyl-ureido)-phenyl]-acetyl}-methyl-amino)-methyl]-isothiazol-3-yl}-propionic acid
3-Acetylamino-3-{3-[({[3-methoxy-4-(3-o-tolyl-ureido)-phenyl]-acetyl}-methyl-amino)-methyl]-2H-pyrazol-5-yl}-propionic acid
2-(2,6-Dichloro-benzoylamino)-3-{5-[({[3-methoxy-4-(3-o-tolyl-ureido)-phenyl]-acetyl}-methyl-amino)-methyl]-isoxazol-3-yl}-propionic acid
Compounds which include the moiety of partial Formula (1.1.16):
3-[5-(1-{2-[3-Methoxy-4-(3-o-tolyl-ureido)-phenyl]-acetylamino}-3-methyl-butyl)-oxazol-2-yl]-2-methyl-propionic acid
2-Acetylamino-3-[5-(1-{2-[3-methoxy-4-(3-o-tolyl-ureido)-phenyl]-acetylamino}-3-methyl-butyl)-oxazol-2-yl]-propionic acid
2-Methanesulfonylamino-3-[5-(1-{2-[3-methoxy-4-(3-o-tolyl-ureido)-phenyl]-acetylamino}-3-methyl-butyl)-oxazol-2-yl]-propionic acid
2,2-Difluoro-3-{5-[1-(methyl-{[6-(3-o-tolyl-ureido)-pyridin-3-yl]-acetyl}-amino)-ethyl]-oxazol-2-yl}-propionic acid
2,2-Dimethyl-3-[5-(1-{[6-(3-phenyl-ureido)-pyridin-3-yl]-acetyl}-pyrrolidin-2-yl)-oxazol-2-yl]-propionic acid
2-Allyloxycarbonylamino-3-{5-[({[3-methoxy-4-(3-o-tolyl-ureido)-phenyl]-acetyl}-methyl-amino)-methyl]-oxazol-2-yl}-propionic acid
2-(Butane-1-sulfonylamino)-3-(5-{[methyl-({4-[3-(3-methyl-pyridin-2-yl)-ureido]-piperidin-1-yl}-acetyl)-amino]-methyl}-oxazol-2-yl)-propionic acid
2-Methyl-3-[5-(1-{[4-(2-methyl-benzyloxy)-phenyl]-acetyl}-pyrrolidin-2-yl)-oxazol-2-yl]-propionic acid
2-Formylamino-3-{5-[1-(biphenyl-4-yl-acetyl)-pyrrolidin-2-yl]-thiazol-2-yl}-propionic acid
2-Methyl-3-(5-{1-[(4-o-tolyloxy-phenyl)-acetyl]-pyrrolidin-2-yl}-oxazol-2-yl)-propionic acid
2-Benzenesulfonylamino-3-(5-{1-[(4-phenoxymethyl-phenyl)-acetyl]-pyrrolidin-2-yl}-oxazol-2-yl)-propionic acid
2-Benzenesulfonylamino-3-[5-(1-{[3-methoxy-4-(3-o-tolyl-ureido)-phenyl]-acetyl}-pyrrolidin-2-yl)-oxazol-2-yl]-propionic acid 2-Methanesulfonylamino-3-[5-(3-methyl-1-{[5-(3-o-tolyl-ureido)-pyridin-2-yl]-acetyl}-pyrrolidin-2-yl)-oxazol-2-yl]-propionic acid 2-Acetylamino-3-{5-[({[3-methoxy-4-(3-o-tolyl-ureido)-phenyl]-acetyl}-methyl-amino)-methyl]-5-methyl-oxazol-2-yl}-propionic acid 2-Acetylamino-3-{5-[({[3-methoxy-4-(3-o-tolyl-ureido)-phenyl]-acetyi}-methyl-amino)-methyl]-thiazol-2-yl}-propionic acid 2-(2,6-Dichloro-benzoylamino)-3-{5-[({[3-methoxy-4-(3-o-tolyl-ureido)-phenyl]-acetyl}-methyl-amino)-methyl]-oxazol-2-yl}-propionic acid 2-Acetylamino 3-[5-({2-[4-(3-o-tolyl-ureido)-phenyl]-acetylamino}-methyl)-1H-imidazol-2-yl]-propionic acid Compounds which include the moiety of partial Formulas (1.1.17), (1.1.18) and (1.1.19):

2-Acetylamino-3-{3-[({[3-methoxy-4-(3-o-tolyl-ureido)-phenyl]-acetyl}-methyl-amino)-methyl]-phenyl}-propionic acid 2-Formylamino-3-{6-[1-({3-methoxy-4-[3-(3-methyl-pyridin-2-yl)-ureido]-phenyl}-acetyl)-pyrrolidin-2-yl]-pyridin-2-yl}-propionic acid 3-{4-[1-({3-Ethyl-4-[3-(3-methyl-pyridin-2-yl)-ureido]-phenyl}-acetyl)-pyrrolidin-2-yl]-pyrimidin-2-yl}-propionic acid 2-Acetylamino-3-[3-(1-{[3-methoxy-4-(3-o-tolyl-ureido)-phenyl]-acetyl}-pyrrolidin-2-yl)-phenyl]-propionic acid 2-Acetylamino-3-[3-({2-[3-methoxy-4-(3-o-tolyl-ureido)-phenyl]-acetylamino}-methyl)-phenyl]-propionic acid 2-{2-[({[3-Methoxy-4-(3-o-tolyl-ureido)-phenyl]-acetyl}-methyl-amino)-methyl]-pyridin-4-ylmethyl}-4-methyl-pentanoic acid 3-{2-[(Methyl-{[4-(3-o-tolyl-ureido)-phenyl]-acetyl}-amino)-methyl]-pyridin-4-yl}-propionic acid 2-Methanesulfonylamino-3-{4-[({[3-methoxy-4-(3-o-tolyl-ureido)-phenyl]-acetyl}-methyl-amino)-methyl]-[1,3,5]triazin-2-yl}-propionic acid 1-[4-(1-{[6-(3-Pyridin-2-yl-ureido)-pyridin-3-yl]-acetyl}-pyrrolidin-2-yl)-pyridin-2-ylmethyl]-cyclopropanecarboxylic acid 3-[3-(1-{[6-(3-Pyridin-2-yl-ureido)-pyridin-3-yl]-acetyl}-pyrrolidin-2-yl)-phenyl]-butyric acid 2-(Butane-1-sulfonylamino)-3-{3-[({[3-methoxy-4-(3-o-tolyl-ureido)-phenyl]-acetyt}-methyl-amino)-methyl]-phenyl}-propionic acid 2-Benzenesulfonylamino-3-[3-({[(2-methoxy-2-methyl-biphenyl-4-yl)-acetyl]-methyl-amino}-methyl)-phenyl]-propionic acid Compounds which include the moiety of partial Formula (1.1.20):

3-[4-(1-{2-[3-Methoxy-4-(3-o-tolyl-ureido)-phenyl]-acetylamino}-3-methyl-butyl)-pyrrol-1-yl]-2-methyl-propionic acid 2-Acetylamino-3-[4-(1-{2-[3-methoxy-4-(3-o-tolyl-ureido)-phenyl]-acetylamino}-3-methyl-butyl)-pyrrol-1-yl]-propionic acid 2-Methanesulfonylamino-3-[4-(1-{2-[3-methoxy-4-(3-o-tolyl-ureido)-phenyl]-acetytamino}-3-methyl-butyl)-pyrrol-1-yl]-propionic acid 2,2-Difluoro-3-{4-[1-(methyl-{[6-(3-o-tolyl-ureido)-pyridin-3-yl]-acetyl}-amino)-ethyl]-pyrrol-1-yl}-propionic acid 2,2-Dimethyl-3-[4-(1-{[6-(3-phenyl-ureido)-pyridin-3-yl]-acetyl}-pyrrolidin-2-yl)-pyrrol-1-yl]-propionic acid 2-(Butane-1-sulfonylamino)-3-(4-{[methyl-({4-[3-(3-methyl-pyridin-2-yl)-ureido]-piperidin-1-yl}-acetyl)-amina]-methyl}-pyrrol-1-yl)-propionic acid 2-Methyl-3-[4-(1-{[4-(2-methyl-benzyloxy)-phenyl]-acetyl}-pyrrolidin-2-yl)-pyrrol-1-yl]-propionic acid 2-Formylamino-3-{4-[1-(biphenyl-4-yl-acetyl)-pyrrolidin-2-yl]-pyrrol-1-yl}-propionic acid 2-Methyl-3-(4-{1-[(4-o-tolyloxy-phenyl)-acetyl]-pyrrolidin-2-yl}-pyrrol-1-yl)-propionic acid 2-Benzenesulfonylamino-3-(4-{1-[(4-phenoxymethyl-phenyl)-acetyl]-pyrrolidin-2-yl}-pyrrol-1-yl)-propionic acid 2-Benzenesulfonylamino-3-[4-(1-{[3-methoxy-4-(3-o-tolyl-ureido)-phenyl]-acetyl}-pyrrolidin-2-yl)-pyrrol-1-yl]-propionic acid 2-Methanesulfonylamino-3-[4-(3-methyl-1-{[5-(3-o-tolyl-ureido)-pyridin-2-yl]-acetyl}-pyrrolidin-2-yl)-pyrrol-1-yl]-propionic acid 2-Acetylamino-3-{4-[({[3-methoxy-4-(3-o-tolyl-ureido)-phenyl]-acetyl}-methyl-amino)-methyl]-5-methyl-pyrrol-1-yl}-propionic acid 2-Acetylamino-3-{4-[({[3-methoxy-4-(3-o-tolyl-ureido)-phenyl]-acetyl}-methyl-amino)-methyl]-pyrrol-1-yl}-propionic acid 2-(2,6-Dichloro-benzoyl amino)-3-{4-[({[3-methoxy-4-(3-o-tolyl-ureido)-phenyl]-acetyl}-methyl-amino)-methyl]-pyrrol-1-yl}-propionic acid Compounds which include the moiety of partial Formula (1.1.21):

3-[4-(1-{2-[3-Methoxy-4-(3-o-tolyl-ureido)-phenyl]-acetylamino}-3-methyl-butyl)-pyrazol-1-yl]-2-methyl-propionic acid 2-Acetylamino-3-[4-(1-{2-[3-methoxy-4-(3-o-tolyl-ureido)-phenyl]-acetylamino}-3-methyl-butyl)-pyrazol-1-yl]-propionic acid 2-Methanesulfonylamino-3-[4-(1-{2-[3-methoxy-4-(3-o-tolyl-ureido)-phenyl]-acetylamino}-3-methyl-butyl)-pyrazol-1-yl]-propionic acid 2,2-Difluoro-3-{4-[1-(methyl-{[6-(3-o-tolyl-ureido)-pyridin-3-yl]-acetyl}-amino)-ethyl]-pyrazol-1-yl}-propionic acid 2,2-Dimethyl-3-[4-({[6-(3-phenyl-ureido)-pyridin-3-yl]-acetyl}-pyrrolidin-2-yl)-pyrazol-1-yl]-propionic acid 2-(Butane-1-sulfonylamino)-3-(4-{[methyl-({4-[3-(3-methyl-pyridin-2-yl)-ureido]-piperidin-1-yl}-acetyl)-amino]-methyl}-pyrazol-1-yl)-propionic acid 2-Methyl-3-[4-(1-{[4-(2-methyl-benzyloxy)-phenyl]-acetyl}-pyrrolidin-2-yl)-pyrazol-1-yl]-propionic acid 2-Formylamino-3-{4-[1-(biphenyl-4-yl-acetyl)-pyrrolidin-2-yl]-pyrazol-1-yl}-propionic acid 2-Methyl-3-(4-{1-[(4-o-tolyloxy-phenyl)-acetyl]-pyrrolidin-2-yl}-pyrazol-1-yl)-propionic acid 2-Benzenesulfonylamino-3-(4-{1-[(4-phenoxymethyl-phenyl)-acetyl]-pyrrolidin-2-yl}-pyrazol-1-yl)-propionic acid 2-Benzenesulfonylamino-3-[4-(1-{[3-methoxy-4-(3-o-tolyl-ureido)-phenyl]-acetyl}-pyrrolidin-2-yl)-pyrazol-1-yl]-propionic acid 2-Methanesulfonylamino-3-[4-(3-methyl-1-{[5-(3-o-tolyl-ureido)-pyridin-2-yl]-acetyl}-pyrrolidin-2-yl)-pyrazol-1-yl]-propionic acid 2-Acetylamino-3-{4-[({[3-methoxy-4-(3-o-tolyl-ureido)-phenyl]-acetyl}-methyl-amino)-methyl]-5-methyl-pyrazol-1-yl}-propionic acid 2-Acetylamino-3-{4-[({[3-methoxy-4-(3-o-tolyl-ureido)-phenyl]-acetyl}-methyl-amino)-methyl]-pyrazol-1-yl}-propionic acid 2-(2,6-Dichloro-benzoylamino)-3-{4-[({[3-methoxy-4-(3-o-tolyl-ureido)-phenyl]-acetyl}-methyl-amino)-methyl]-pyrazol-1-yl}-propionic acid Compounds which include the moiety of partial Formula (1.1.22):
2-[({[3-Methoxy-4-(3-o-tolyl-ureido)-phenyl]-acetyl}-methyl-amino)-methyl]-benzooxazole-6-carboxylic acid
2-[1-(2-{3-Methoxy-4-[3-(3-methyl-pyridin-2-yl)-ureido]-phenyl}-acetylamino)-3-methyl-butyl]-3H-benzoimidazole-5-carboxlylic acid
2-(1-{[4-(3-Pyridin-2-yl-ureido)-phenyl]-acetyl}-pyrrolidin-2-yl)-1H-imidazo[4,5-c]pyridine-6-carboxylic acid
2-(1-{[3-Ethoxy-4-(3-pyridin-2-yl-ureido)-phenyl]-acetyl}-pyrrolidin-2-yl)-benzothiazole-6-carboxylic acid
2-[({[3-Methoxy-4-(3-o-tolyl-ureido)-phenyl]-acetyl}-methyl-amino)-methyl]-benzothiazole-6-carboxylic acid
2-({[(4-Benzyloxy-phenyl)-acetyl]-methyl-amino}-methyl)-oxazolo[5,4-b]pyridine-5-carboxylic acid
3-Methyl-2-{1-[(4-phenoxy-phenyl)-acetyl]-pyrrolidin-2-yl}-3H-benzoimidazole-5-carboxylic acid The above-described compounds of the present invention may be utilized in the form of acids, esters, or other chemical classes of compounds to which the compounds described belong. It is also within the scope of the present invention to utilize those compounds in the form of pharmaceutically acceptable salts derived from various organic and inorganic acids and bases in accordance with procedures well known in the art. Such well-known pharmaceutically acceptable salts include, but are not limited to acetate, adipate, alginate, aspartate, benzoate, benzenesulfonate, besylate, bisulfate, butyrate, citrate, camphorate, camphorsulfonate, cyclopentanepropionate, digluconate, dodecysulfate, ethanesulfonate, fumarate, glucoheptanoate, gluconate, glycerophosphate, hemisuccinate, hemisulfate, heptanoate, hexanoate, hippurate, hydrochloride, hydrobromide, hydroiodide, 2-hydroxyethanesulfonate, isethionate, lactate, lactobionate, maleate, mandelate, methanesulfonate, 2-naphthalenesulfonate, nicotinate, nitrate, oxalate, oleate, pamoate, pectinate, persulfate, 3-phenylpropionate, phosphonate, picrate, pivalate, propionate, salicylate, sodium phosphate, stearate, succinate, sulfate, sulfosalicylate, tartrate, thiocyanate, thiomalate, tosylate, and undecanoate.

Base salts of the compounds of the present invention include, but are not limited to ammonium salts; alkali metal salts such as sodium and potassium; alkaline earth metal salts such as calcium and magnesium; salts with organic bases such as dicyclohexylamine, meglumine, N-methyl-D-glucamine, tris-(hydroxymethyl)-methylamine (tromethamine), and salts with amino acids such as arginine, lysine, etc. Compounds of the present invention which comprise basic nitrogen-containing groups may be quaternized with such agents as $(C_1-C_4)$alkyl halides, e.g., methyl, ethyl, iso-propyl and tert-butyl chlorides, bromides and iodides; di$(C_1-C_4)$ alkyl sulfate, e.g., dimethyl, diethyl and diamyl sulfates; $(C_{10}-C_{18})$ alkyl halides, e.g., decyl, dodecyl, lauryl, myristyl and and stearyl chlorides, bromides and iodides; and aryl-$(C_1-C_4)$ alkyl halides, e.g., benzyl chloride and phenethyl bromide. Such salts permit the preparation of both water-soluble and oil-soluble compounds of the present invention.

Among the above-recited pharmaceutical salts those which are preferred include, but are not limited to acetate, mesylate, citrate, fumarate, gluconate, hemisuccinate, hippurate, hydrochloride, hydrobromide, isothionate, mandelate, meglumine, nitrate, oleate, phosphonate, pivalate, sodium phosphate, stearate, sulfate, sulfosalicylate, tartrate, thiomalate, tosylate, and trimethylamine.

Multiple salts forms are included within the scope of the present invention where a compound of the present invention contains more than one group capable of forming such pharmaceutically acceptable salts. Examples of typical multiple salt forms include, but are not limited to bitartrate, diacetate, difumarate, dimeglumine, diphosphate, disodium, and trihydrochloride.

The pharmaceutical compositions of the present invention comprise any one or more of the above-described inhibitory compounds of the present invention, or a pharmaceutically acceptable salt thereof as also above-described, together with a pharmaceutically acceptable carrier in accordance with the properties and expected performance of such carriers which are well-known in the pertinent art.

The term "carrier" as used herein includes acceptable diluents, excipient, adjuvants and vehicles. Pharmaceutically acceptable carriers that may be used in the pharmaceutical compositions of this invention include but are not limited to, ion exchange compositions; alumina; aluminum stearate; lecithin; serum proteins, e.g., human serum albumin; phosphates; glycine; sorbic acid; potassium sorbate; partial glyceride mixtures of saturated vegetable fatty acids; water; salts or electrolytes, e.g., prolamine sulfate, disodium hydrogen phosphate, potassium hydrogen phosphate, sodium chloride, and zinc salts; colloidal silica; magnesium trisilicate; polyvinyl pyrrolidone; cellulose-based substances; e.g., sodium carboxymethylcellulose; polyethylene glycol; polyacrylates; waxes; polyethylenepolyoxypropylene-block polymers; and wool fat.

More particularly, the diluents, excipient, adjuvants and vehicles used in the pharmaceutical compositions of the present invention comprise members selected from the groups consisting essentially of the following: acidifying and alkalizing agents added to obtain a desired or predetermined pH comprise acidifying agents, e.g., acetic acid, glacial acetic acid, malic acid, and propionic acid, and alkalizing agents, e.g., edetol, potassium carbonate, potassium hydroxide, sodium borate, sodium carbonate, and sodium hydroxide; aerosol propellants required where the pharmaceutical composition is to be delivered as an aerosol under significant pressure, e.g., acceptable halogenated hydrocarbons; nitrogen; or a volatile hydrocarbon such as butane, propane, isobutane or mixtures thereof; antimicrobial agents including antibacterial, antifungal and antiprotozoal agents added where the pharmaceutical composition is topically applied, e.g., antimicrobial agents such as benzyl alcohol, chlorobutanol, phenylethyl alcohol, phenylmercuric acetate, potassium sorbate, and sorbic acid, and antifungal agents such as benzoic acid, butylparaben, ethylparaben, methylparaben, propylparaben, and sodium benzoate; antimicrobial preservatives added to the pharmaceutical compositions in order to protect them against the growth of potentially harmful microorganisms, e.g., alkyl esters of p-hydroxybenzoic acid, propionate salts, phenoxyethanol, methylparaben sodium, propylparaben sodium, sodium dehydroacetate, benzalkonium chloride, benzethonium chloride, and benzyl alcohol; antioxidants added to protect all of the ingredients of the pharmaceutical composition from damage or degradation by oxidizing agents present in the composition itself or the use environment, e.g., anoxomer, ascorbyl palmitate, butylated hydroxyanisole, butylated hydroxytoluene, hypophosphorous acid, potassium metabisulfite, propyl octyl and dodecyl gallate, sodium metabisulfite, sulfur dioxide, and tocopherols; buffering agents used to maintain a desired pH of a composition once established, e.g., calcium acetate, potassium metaphosphate, potassium phosphate monobasic, and tartaric acid; and chelating agents used to help maintain the ionic strength of the pharmaceutical composition and bind to and effectively remove destructive compounds and metals, e.g., edetate dipotassium, edetate disodium, and edetic acid.

Dermatologically active agents are added to the pharmaceutical compositions of the present invention to be applied topically, e.g., wound healing agents such as peptide derivatives, yeast, panthenol, hexylresorcinol, phenol, tetracycline hydrochloride, lamin and kinetin, glucocorticosteroids for treating inflammation, e.g., hydrocortisone, dexamethasone, betamethasone, triamcinolone, fluocinolone and methylprednisolone, retinoids for treating acne, psoriasis, cutaneous aging, and skin cancer, e.g., retinol, tretinoin, isotretinoin, etretinate, acitretin, and arotinoid, immunosuppressive agents for treating inflammation, e.g., dapsone and sulfasalazine; mild antibacterial agents, e.g., resorcinol, salicylic acid, benzoyl peroxide, erythromycinbenzoyl peroxide, erythromycin, clindamycin, and mupirocin, antifungal agents, e.g., griseofulvin, azoles such as miconazole, econazole, itraconazole, fluconazole, and ketoconazole, and allylamines such as naftifine and terfinafine, antiviral agents, e.g., acyclovir, famciclovir, and valacyclovir, antihistamines, e.g., diphenhydramine, terfenadine, astemizole, loratadine, cetirizine, acrivastine, and temelastine, topical anesthetics, e.g., benzocaine, lidocaine, dibucaine, and pramoxine hydrochloride, topical analgesics, e.g., methyl salicylate, camphor, menthol, and resorcinol; topical antiseptics for preventing infection, e.g., benzalkonium chloride and povidone-iodine; vitamins and derivatives thereof such as tocopherol, tocopherol acetate, retinoic acid and retinol.

Further examples of diluents, excipient, adjuvants and vehicles used in the pharmaceutical compositions of the present invention comprise members selected from the groups consisting essentially of the following: dispersing and suspending agents, e.g., poligeenan, povidone, and silicon dioxide; emollients, e.g., hydrocarbon oils and waxes, triglyceride esters, acetylated monoglycerides, methyl and other alkyl esters of $C_{10}$–$C_{20}$ fatty acids, $C_{10}$–$C_{20}$ fatty acids, $C_{10}$–$C_{20}$ fatty alcohols, lanolin and derivatives, polyhydric alcohol esters such as polyethylene glycol (200–600), polyoxyethylene sorbitan fatty acid esters, wax esters, phospholipids, and sterols; emulsifying agents used for preparing oil-in-water emulsions; excipients, e.g., laurocapram and polyethylene glycol monomethyl ether; humectants, e.g., sorbitol, glycerin and hyaluronic acid; ointment bases, e.g., petrolatum, polyethylene glycol, lanolin, and poloxamer; penetration enhancers, e.g., dimethyl isosorbide, diethyl-glycol-monoethylether, 1-dodecylazacycloheptan-2-one, and dimethylsulfoxide (DMSO); preservatives, e.g., benzalkonium chloride, benzethonium chloride, alkyl esters of p-hydroxybenzoic acid, hydantoin derivatives, cetylpyridinium chloride, propylparaben, quaternary ammonium compounds such as potassium benzoate, and thimerosal; sequestering agents comprising cyclodextrins; solvents, e.g., acetone, alcohol, amylene hydrate, butyl alcohol, corn oil, cottonseed oil, ethyl acetate, glycerin, hexylene glycol, isopropyl alcohol, isostearyl alcohol, methyl alcohol, methylene chloride, mineral oil, peanut oil, phosphoric acid, polyethylene glycol, polyoxypropylene 15 stearyl ether, propylene glycol, propylene glycol diacetate, sesame oil, and purified water; stabilizers, e.g., calcium saccharate and thymol; surfactants, e.g., lapyrium chloride; laureth 4, i.e., α-dodecyl-ω-hydroxy-poly(oxy-1,2-ethanediyl) or polyethylene glycol monododecyl ether.

According to this invention, the pharmaceutical compositions may be in the form of a sterile injectable preparation, for example a sterile injectable aqueous or oleaginous suspension. This suspension may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as do natural pharmaceutically-acceptable oils, such as olive oil or castor oil, especially in their polyoxyethylated versions. These oil solutions or suspensions may also contain a long-chain alcohol diluent or dispersant, such as Rh, HClX or similar alcohol.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added. Alternatively, the pharmaceutical compositions of this invention may be administered in the form of suppositories for rectal administration. These can be prepared by mixing the agent with a suitable non-irritating excipient which is solid at room temperature but liquid at the rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation, as described above, or in a suitable enema formulation. Topically active transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate, cetyl esters wax, cetearyl alcohol, 2-octyldodecanol, benzyl alcohol and water.

For ophthalmic use, the pharmaceutical compositions may be formulated as micronized suspension in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation through the use of a nebulizer, a dry powder inhaler or a metered dose inhaler. Such compositions are prepared according to techniques well-known in the art of pharmaceutical formulation and may be prepared as solutions in saline, employing benzyl alcohol or other suitable preservatives, absorption promoters to enhance bioavailability, hydrofluorocarbons, and/or other conventional solubilizing or dispersing agents.

The amount of active ingredient that may be combined with the carrier materials to produce a single dosage form will vary depending upon the host treated, and the particular mode of administration. It should be understood, however, that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredient may also depend upon the therapeutic or prophylactic agent, if any, with which the ingredient is co-administered.

The dosage and dose rate of the compounds of this invention effective for preventing, inhibiting, suppressing or reducing cell adhesion and consequent or associated pathogenic processes subsequently mediated by VLA-4 will depend on a variety of factors, such as th nature of the inhibitor, the size of the patient, the goal of the treatment, the nature of the pathology to be treated, the specific pharmaceutical composition used, and the observations and conclusions of the treating physician.

For example, where the dosage form is oral, e.g., a tablet or capsule, suitable dosage levels of the compounds of Formula (1.0.0) will be between about 1.0 µg and about 10.0 mg/kg body weight per day, preferably between about 5.0 µg and about 5.0 mg/kg body weight per day, more preferably between about 10.0 µg and about 1.0 mg/kg of body weight per day, and most preferably between about 20.0 µg and about 0.5 mg/kg of body weight per day of the active ingredient.

Where the dosage form is topically administered to the bronchia and lungs, e.g., by means of a powder inhaler or nebulizer, suitable dosage levels of the compounds of Formula (1.0.0) will be between about 0.1 µg and about 1.0 mg/kg body weight per day, preferably between about 0.5 µg and about 0.5 mg/kg body weight per day, more preferably between about 1.0 µg and about 0.1 mg/kg of body weight per day, and most preferably between about 2.0 µg and about 0.05 mg/kg of body weight per day of the active ingredient.

Using representative body weights of 10 kg and 100 kg in order to illustrate the range of daily topical dosages which might be used as described above, suitable dosage levels of the compounds of Formula (1.0.0) will be between about 1.0–10.0 µg and 10.0–100.0 mg per day, preferably between about 5.0–50.0 g and 5.0–50.0 mg per day, more preferably between about 10.0–100.0 µg and 1.0–10.0 mg per day, and most perferably between about 20.0–200.0 µg and about 0.5–5.0 mg per day of the active ingredient comprising a compound of Formula (1.0.0). These ranges of dosage amounts represent total dosage amounts of the active ingredient per day for a given patient. The number of times per day that a dose is administered will depend upon such pharmacological and pharmacokinetic factors as the half-life of the active ingredient, which reflects its rate of catabolism and clearance, as well as the minimal and optimal blood plasma or other body fluid levels of said active ingredient attained in the patient which are required for therapeutic efficacy Numerous other factors must also be considered in deciding upon the number of doses per day and the amount of active ingredient per dose which will be administered. Not the least important of such other factors is the individual respsonse of the patient being treated. Thus, for example, where the active ingredient is used to treat or prevent asthma, and is administered topically via aerosol inhalation into the lungs, from one to four doses consisting of acuations of a dispensing device, i.e., "puffs" of an inhaler, will be administered each day, each dose containing from about 50.0 µg to about 10.0 mg of active ingredient.

Included within the scope of the present invention are embodiments comprising compositions which contain, in addition to a compound of the present invention as active ingredient, additional therapeutic agent active ingredients selected from the group consisting essentially of anti-inflammatory corticosteroids; bronchodilators; antiasthmatics; non-steroidal anti-inflammatories; immunosuppressants; immunostimulants; antimetabolites; antipsoriatics and antidiabetics. Specific compounds within each of these classes may be selected from those listed under the appropriate headings in *Comprehensive Medicinal Chemistry*, Pergamon Press, Oxford, England, pp. 970–986 (1990); and *Goodman and Gilman's The Pharmacological Basis of Therapeutics*, 9th ed., Hardman, J. G. and Limbird, L. E., eds., McGraw-Hill, 1996, the disclosure of which are incorporated herein by reference in their entireties. Especially preferred active ingredients to be included for use in combination with the compounds of Formula (1.0.0) are anti-inflammatory compounds such as theophylline, sulfasalazine and aminosalicylates; immunosuppressants such as cyclosporin, FK-506, and rapamycin; antimetabolites such as cyclophosphamide and methotrexate; and immunomodulators such as the interferons.

Still further embodiments of the present invention relate to a method of treating or preventing an inflammatory, autoimmune or respiratory disease by inhibiting cell adhesion and consequent or associated pathogenic processes subsequently mediated by VLA-4. As already mentioned, VLA-4-associated cell adhesion plays a central role in a variety of inflammatory, immune and autoimmune diseases. Thus, inhibition of cell adhesion by the compounds of this invention may be utilized in methods of treating or preventing inflammatory, immune and autoimmune diseases. Preferably the diseases to be treated with the methods of this invention are selected from asthma, arthritis, psoriasis, transplantation rejection, multiple sclerosis, diabetes and inflammatory bowel disease.

The above-described methods of treatment of the present invention may employ the compounds of Formula (1.0.0) in the form of monotherapy, but said methods may also be used in the form of multiple therapy in which one or more compounds of Formula (1.0.0) are coadministered in combiination with a known anti-inflammatory, immunomodulating, immunostimulating or immunosuppressive agent. The terms "coadministered" or "coadministration" as used herein are intended to mean therapeutic utilization of one or more compounds of Formula (1.0.0) in combination with one or more additional therapeutic agents, including but not limited to, administration of the combination of therapeutic active agents in a single dosage form or in multiple dosage forms representing the same or different routes of administration, said multiple dosage forms being administered at substantially the same time or at different times.

Subsequent to synthesis of any of the above-recited preferred species of the present invention or any other compounds falling within the scope of the present invention, the biological activities relating to the VLA-4 specificities of said compounds may be determined using one or more of the numerous in vitro and in vivo assays which have been described heretofore in the technical literature pertinent to the art. For example, some of the now very-well established assay methods and models concern measurement of VLA-4 activity by determining the concentration of a test candidate inhibitor required to block the binding of VLA-4-expressing cells to fibronectin- or CS-1 coated plates. In this assay microtiter wells are coated with either fibronectin (containing the CS-1 sequence), CS-1 peptide or soluble VCAM-1. Once the wells are coated, varying concentrations of the test compound are then added together with appropriately labelled, VLA-4-expressing cells. Alternatively, the test compound may be added first and allowed to incubate with the coated wells prior to the addition of the cells. The cells are allowed to incubate in the wells for at least 30 minutes. Following incubation, the wells are emptied and washed. Inhibition of binding is measured by quantitating the fluorescence or radioactivity bound to the plate for each of the various concentrations of test compound, as well as for controls containing no test compound. However, the assay just described is less preferred than other assays mentioned further below in determining the VLA-4 activity of the compounds of Formula (1.0.0).

VLA-4-expressing cells that may be utilized in this assay include Ramos cells, Jurkat cells, A375 melanoma cells, as well as human peripheral blood lymphocytes (PBL). The cells used in this assay may be fluorescently or radioactively labelled.

In order to assess the VLA-4 inhibitory specificity of test compounds, assays for other major groups of integrins, i.e., $\beta_2$ and $\beta_3$, as well as other $\beta_1$ integrins, such as VLA-5, VLA-6 and $\alpha_4\beta_7$ may be performed. These assays may be similar to the adhesion inhibition and direct binding assays described above, substituting the appropriate integrin-expressing cell and corresponding ligand. For example, polymorphonuclear cells (PMNs) express $\beta_2$ integrins on their surface and bind to ICAM; while $\beta_3$ integrins are involved in platelet aggregation and inhibition may be measured in a standard platelet aggregation assay. VLA-5 binds specifically to Arg-Gly-Asp sequences, while VLA-6 binds to laminin. Further, $\alpha_4\beta_7$ is a recently discovered homologue of VLA-4, which also binds fibronectin and VCAM as well as MAdCAM-1. Specificity with respect to $\alpha_4\beta_7$ is determined in a binding assay that utilizes CS-1, VCAM or MAdCAM-1 and a cell line that expresses $\alpha_4\beta_7$, but not VLA-4, such as RPMI-8866 cells.

Once VLA-4-specific inhibitors are identified, they may be further characterized in in vivo assays. One such assay tests the inhibition of allergen induced airway hyperresponsiveness and cell influx, such as described by Henderson et al., "Blockade of CD49d ($\alpha_4$ integrin) on intrapulmonary but not circulating leukocytes inhibits airway inflammation and hyperresponsiveness in a mouse model of asthma", *J. Clin. Invest*, 100(12), pp. 3083–92 (1997). In this assay, mice are sensitized by ip exposure to an irritant, such as ovalbumin. Following a recovery period, the mice are challenged by aerosol exposure to the allergen. Before aerosol exposure, the mice are given various doses of the VLA-4 inhibitor by intratracheal injection. In vivo inhibition of cell adhesion associated inflammation is assessed by measuring the number of cells and cytokines in the bronchial alveolar lavage fluid. In this manner, one may identify those inhibitors of this invention which are best suited for inhibiting inflammation.

Another in vivo assay that may be employed is the primate asthma assay. This assay is performed essentially as described in Turner, C. R., et al., "Characterization of a primate model of asthma using anti-allergy/anti-asthma agents", *Inflammation Research*, 45(5), pp. 239–45 (1996), the disclosure of which is incorporated herein by reference in its entirety. This assay measures inhibition of Ascaris antigen-induced late phase airway responses and airway hyperresponsiveness in allergic primates following administration of anti-allergy/anti-asthma agents.

The compounds of the present invention may be formulated into pharmaceutical compositions that may be administered orally, parenterally, by inhalation (metered dose inhaler, dry powder inhaler or nebulizer), topically, rectally, nasally, intraocularly, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

The compounds of Formula (1.0.0) may be prepared in accordance with well-known procedures for carrying out the synthesis of organic compounds which are non-peptidyl or semi-peptidyl in nature. A number of different procedures are available which are fully disclosed in the technical literature and with which the skilled artisan will be familiar. Th description which follows of several such synthesis schemes is merely representative and not intended to be in any way limiting. A number of abbreviations are used in said description in order to conserve space. Although these abbreviations are also well known to the artisan, they are set out immediately below for clarity and convenience:

| | |
|---|---|
| BOP | benzotriazol-1-yloxy-tris(dimethylamino)phosphonium hexafluorophosphate |
| DAST | diethylaminosulfur trifluoride |
| DIEA | diisopropylethyl amine |
| DMF | Dimethylformamide |
| EDCI | 1-(3-dimethylaminopropyl)-3-ethylcarbodiimide hydrochloride |
| HOBT | 1-hydroxybenzotriazole |
| THF | tetrahydrofuran |

Synthesis Scheme 1 step A

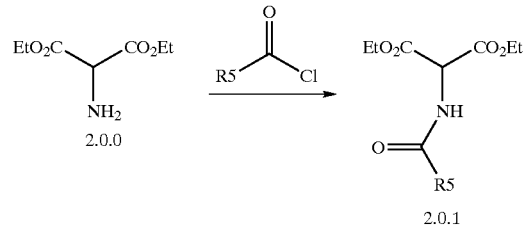

The synthesis of compounds of the Formula 1.0.0 in which the "B" component is an isoxazole ring and the "Y" component is —SO$_2$— is illustrated in Scheme 1, steps A through G. In Scheme 1, step A, the starting material, diethyl amino malonate, is commercially available, e.g., from Aldrich Chemical Company, Milwaukee, Wis. 53233. The amide product (2.0.1), where R$^5$ is hydrogen, methyl or phenyl, is also commercially available. Other amides, where R$^5$ is alkyl, aryl, heterocyclyl or heteroaryl are made readily available by the reaction of the appropriate acid chloride with the amine (2.0.0) using the conditions that are well described in the literature (e.g. March, J. "Advanced Organic Chemistry", 3rd edition, 1985). Under similar conditions, the amine (2.0.0) may be converted to its corresponding sulfonamide by the reaction of 2.0.0 with an alkyl or aryl sulfonyl chloride. The carbamate product (2.0.1), where $R^5$ is alkoxy or aryloxy is prepared from amine 2.0.0 in accordance with procedures described by Paik, Yi Hyon; Dowd, Paul; *J. Org. Chem.* 1986, 51(15), 2910–2913; and Kawai, Masao; Nyfeler, Rolf; Berman, Judd M.; Goodman, Murray; *J. Med. Chem.,* 1982 25(4), 397–402.

Synthesis Scheme 1 Step B

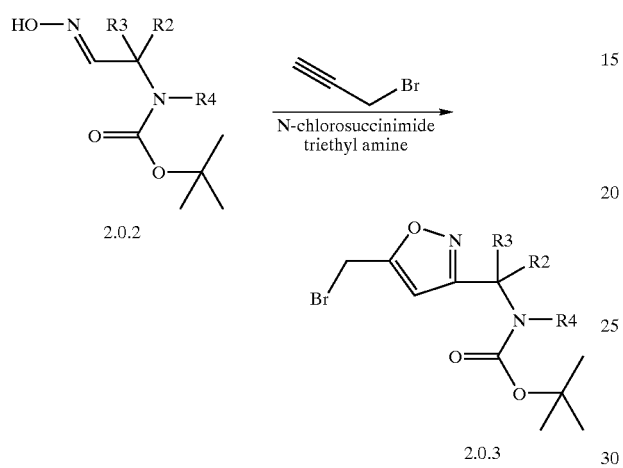

2.0.2

2.0.3

In Scheme 1, Step B, the intermediate 2.0.3 is prepared from the oxime 2.0.2. Oxime 2.0.2 is prepared from its corresponding aldehyde by procedures well known to those skilled in the art (e.g. Chung, Yong Jun; Ryu, Eun Jung; Keum, Gyochang; Kim, Byeang Hyean; *Bioorg. Med. Chem.;* 1996, 4(2) 209–226; and Kim, Byeang Hyean; Chung, Yong Jun; Keum, Gyochang; Kim, Jaheon; Kim, Kimoon; *Tetrahedron Left.;* 1992, 33(45); 6811–6814). Oxime 2.0.2 is converted to the isoxazole 2.0.3 by oxidation with a suitable oxidant such as sodium hypochlorite, tert-butyl hypochlorite, or N-chlorosuccinimide in a suitable solvent such as THF, chloroform or methylene chloride; and reacting the resulting nitrile N-oxide in situ with propargyl bromide. This [2+3] cycloaddition reaction is well known in the literature as a method for preparing the isoxazole ring structure. See, e.g., *Synthesis,* 508–9, 1982.

Synthesis Scheme 1 Step C

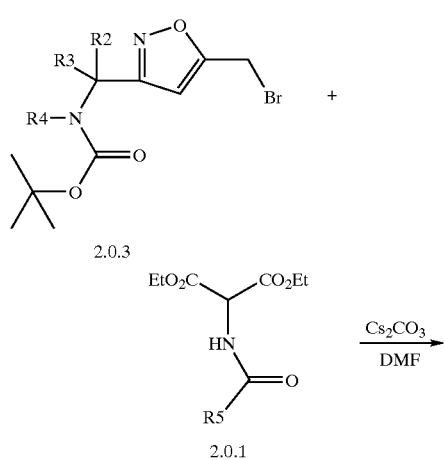

2.0.3

2.0.1

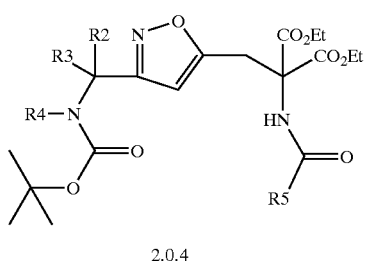

2.0.4

In Scheme 1, Step C, the bromide intermediate 2.0.3 is converted to the isoxazole containing component 2.0.4. The bromide 2.0.3 is reacted with an optionally substituted malonate (2.0.1) in a suitable solvent such as DMF, DMSO or methylene chloride, in the presence of a base such as triethylamine or cesium carbonate. DMF is the preferred solvent and cesium carbonate is the preferred base. The reaction is performed at a temperature between 0 and 30° C. for a period of 1 to 16 hours. The reaction of bromide 2.0.3 with malonate 2.0.1 in Scheme 1, step C, is not limited to 2-amino malonates, but can be expanded to include malonates of the formula [EtOC(=O)CHR$^7$C(=O)OEt], where $R^7$ is defined above in the definition of Formula 1.0.0.

Synthesis Scheme 1 Step D

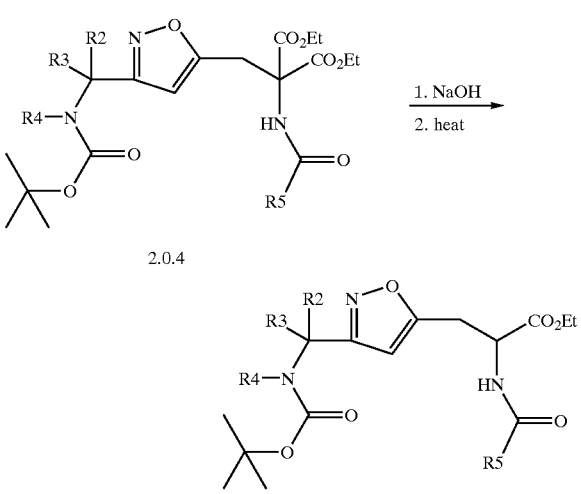

2.0.4

2.0.5

The synthesis of the mono ester intermediate 2.0.5 is illustrated in Scheme 1, Step D. The diethyl malonate 2.0.4 is converted to its half-ester intermediate by reaction with one equivalent of a suitable base such as aqueous sodium hydroxide or lithium hydroxide in a solvent such as THF, methanol, tert-butanol or dioxane. The use of aqueous sodium hydroxide in dioxane is preferred. The reaction is conducted at a temperature between 0 and 50° C. for a time period of between 1 and 16 hours. Three hours at ambient temperature is preferred. This half-ester intermediate is subsequently transformed to mono ester 2.0.5 in situ by heating it in a suitable solvent such as benzene, toluene or dioxane at a temperature between 0 and 200° C. for a time period of between 1 and 16 hours. Heating at 125° C. for 3 hours in dioxane is preferred.

Synthesis Scheme 1 Step E

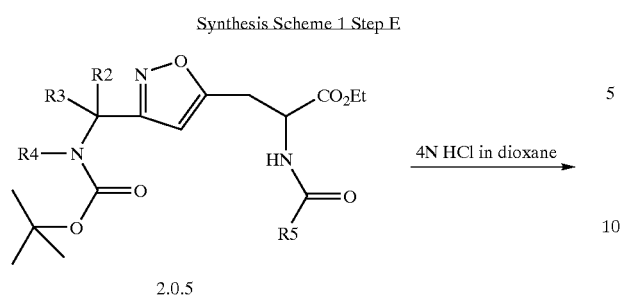

2.0.5

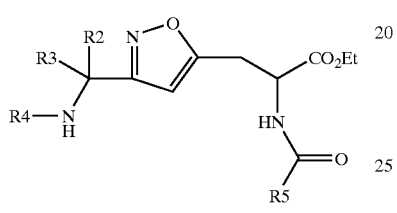

2.0.6

The synthesis of the amine intermediate 2.0.6 is illustrated in Scheme 1, Step E. The tert-butyloxycarbamate intermediate 2.0.5 is reacted with an acid such as neat trifluoroacetic acid, or a solution hydrochloric acid in a suitable non-aqueous solvent such as dioxane. The reaction is conducted at a temperature between 0 and 50° C. for a time period of between 1 and 16 hours. Hydrochloric acid in dioxane at ambient temperature for 1 hour is the preferred conditions. It will be recognized by those skilled in the art that the tert-butyloxycarbonyl group serves as a protecting group for the amine and that other suitable protecting groups can be employed. It will be further recognized that methods for removal of these protecting groups must be compatible with all the functionality present in $R^5$. These methods are well-known in the technical literature of the relevant art. For example, see Greene, T. W., Wuts, P. G. M. *Protective Group in Organic Synthesis*; John Wiley & Sons: New York, 1991.

Synthesis Scheme 1 step F

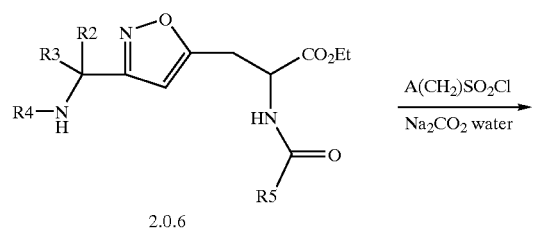

2.0.6

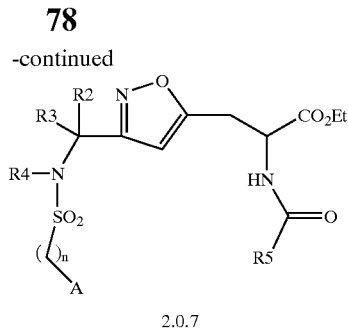

2.0.7

The synthesis of the sulfonamide intermediate 2.0.7 is described in scheme 1 step F. The amine 2.0.6 is reacted with a sulfonyl chloride [A(CH$_2$)$_n$—SO$_2$Cl, where "A" and "n" are defined above in the definition of formula 1.0.0] in a solvent such as dichloromethane, water, or pyridine with or without a base such as sodium carbonate or diisopropylethylamine. The reaction is conducted at a temperature between 0 and 50° C. for a period of between 1 and 16 hours. The preferred conditions are sodium carbonate in water at ambient temperature for 16 hours.

Synthesis Scheme 1 step G

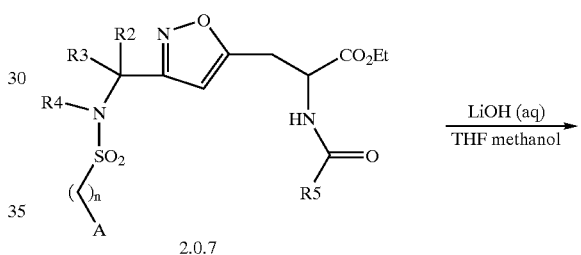

2.0.7

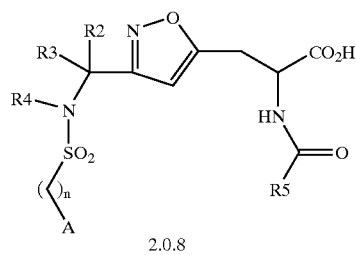

2.0.8

The carboxylic acid product is prepared from ester intermediate 2.0.7 as illustrated in scheme 1, step G. The ester intermediate 2.0.7 is reacted with a suitable aqueous base, such as lithium hydroxide, potassium hydroxide or sodium hydroxide in a solvent such as tert-butanol, methanol, and/or THF. The reaction is conducted at a temperature between 0 and 50° C. for a time period between 0.5 and 24 hours. Aqueous lithium hydroxide in a mixture of THF and methanol at ambient temperature for 1 hour are the preferred conditions.

The above-described synthesis is broadly applicable to the compounds of Formula (1.0.0). In order to make said synthesis even more clear, there is set out below Synthesis Scheme 1-α, Steps A through G with reference to a particular compound of the present invention:

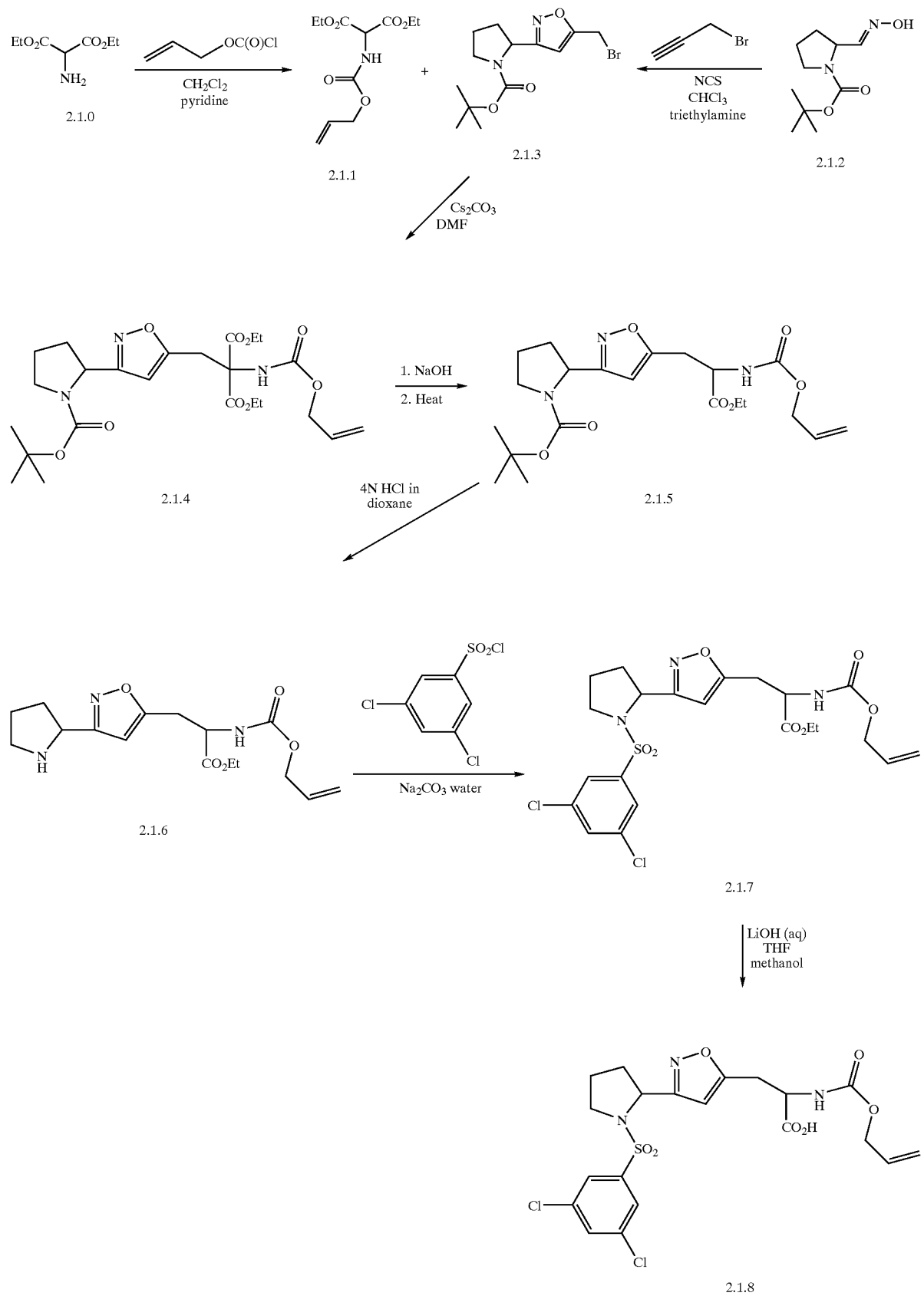
Synthesis Scheme 1-α

The following schematic synthesis diagram illustrates a generalized preparation process for the compounds of Formula 1.0.0 in which the "Y" component is C=O:

Synthesis Scheme 2-Step A

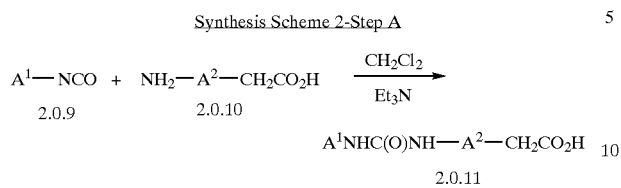

The starting material $A^1$-NCO is an isocyanate in which "$A^1$" has the same definition as the A component of Formula (1.0.0) regarding the aryl, heteroaryl and heterocyclyl moieties substituted with 0 to 3 $R^9$. Isocyanate starting materials for making component A, such as phenyl isocyanate, o-tolyl isocyanate, 2-fluorophenyl isocyanate and 2-chlorophenyl isocyanate are commercially available, e.g., from Aldrich Chemical Company, Milwaukee, Wis. 53233. Alternatively, isocyanate starting materials can be readily prepared from their corresponding amines using the methods described in the literature (e.g. March, J. "Advanced Organic Chemistry", $3^{rd}$ edition, 1985). Pyridyl analogues of the above phenyl isocyanates can be used to prepare the corresponding compounds of Formula (1.0.0) where the A component contains a pyridyl group.

One of the above-described isocyantes is reacted with an amine of formula 2.0.10. The addition of amines to isocyanates is a well-known reaction which provides substituted ureas in a facile manner. The reaction can be carried out in a solvent such as methylene chloride with triethylamine at slightly elevated temperatures. The disubstituted urea (2.0.11) prepared as in the above-indicated reaction scheme, which forms the reactant eventually resulting in component A of the compounds of Formula (1.0.0), is next reacted with an amine of the formula "—$NR^4CR^2R^3$—B", in which "B" is defined as one of the partial Formulas (1.1.0)–(1.1.22).

Synthesis Scheme 2-Step B

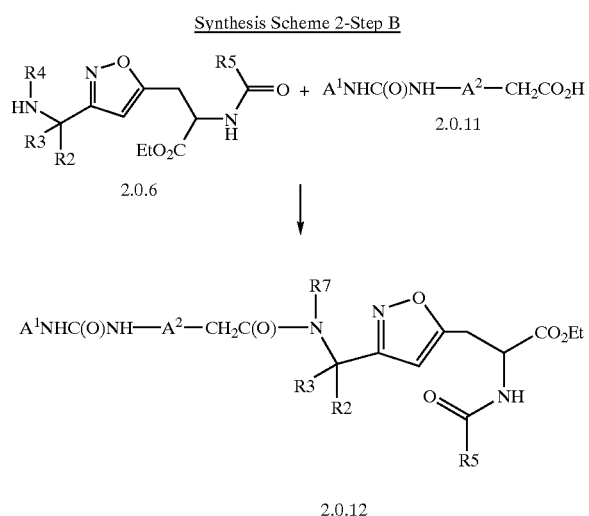

The reaction between the component A forming reactant (2.0.11) and the amine 2.0.6 will be recognized by the artisan as one involving the acylation of an amine by a carboxylic acid which can be made to proceed in good yield at room temperature or slightly above by the use of coupling agents such as 1-(3-dimethylaminopropyl)-3-ethylcarbodiimide hydrochloride (EDCl) and 1-hydroxybenzotriazole (HOBT); dicyclohexylcarbodiimide (DCCl); N,N'-carbonyldiimidazole; N,N,N',N'-tetramethyl(succinimido) uronium tetrafluoroborate; and benzotriazol-1-yloxy-tris (dimethylamino)phosphonium hexafluorophosphate (BOP). The amine component (2.0.6) is available as described in Scheme 1. This reaction may be illustrated in the above schematic synthesis diagram which provides a generalized preparation process for the compounds of Formulas (1.0.0).

To prepare the final product of Formula (1.0.0) in the form of the acid, an additional step is required, as is shown in the following reaction scheme:

Synthesis Scheme 2-Step C

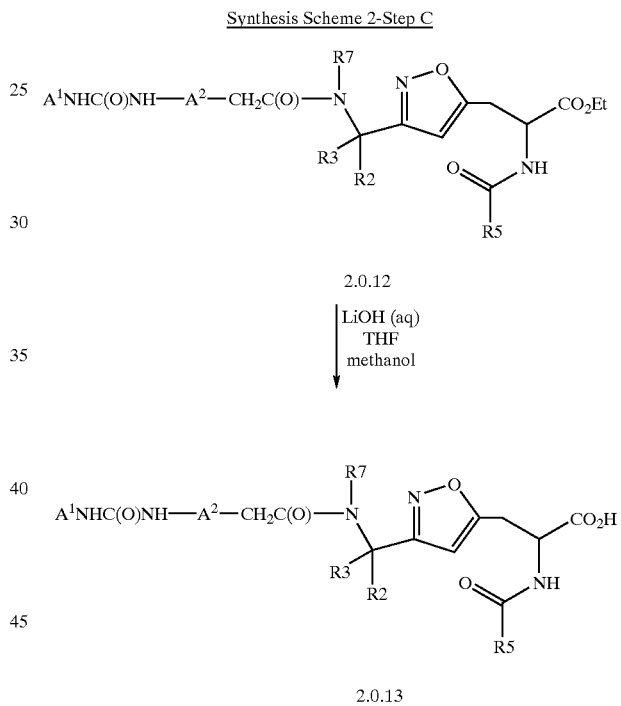

The final acid product (2.0.13) is prepared from ester 2.0.12 as illustrated in the above scheme. The intermediate is reacted with a suitable aqueous hydroxide base, such as lithium hydroxide, potassium hydroxide or sodium hydroxide in a solvent system comprised of tert-butanol, methanol or THF and methanol. The reaction is conducted at a temperature between 0 and 50° C. for 0.5 to 16 hours. Lithium hydroxide in THF, methanol, and water at ambient temperature for 1 hour are the preferred conditions.

The above-described synthesis is broadly applicable to the compounds of Formula (1.0.0). In order to make said synthesis even more clear, there is set out below Synthesis Scheme 2-α, Steps A through C with reference to a particular compound of the present invention:

Synthesis Scheme 2-α
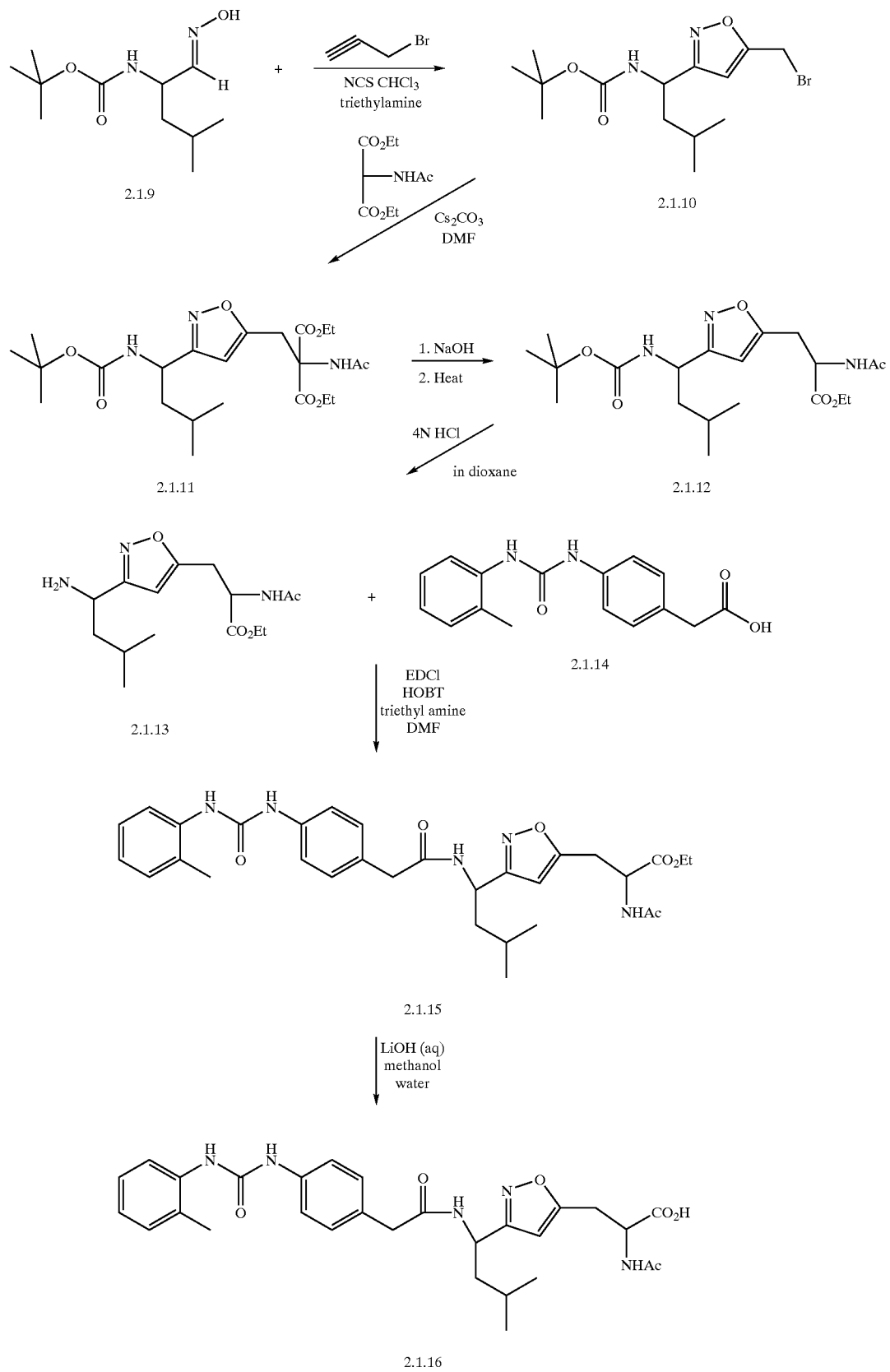

An alternative synthesis of compounds of the Formula (1.0.0) is illustrated in Synthesis Scheme 3, steps A through C. The synthesis of the amine intermediate 2.0.14 is illustrated in scheme 3, step A. Tert-butyloxycarbamate intermediate 2.0.4 is reacted with an acid such as neat trifluoroacetic acid, or a solution hydrochloric acid in a suitable non-aqueous solvent such as dioxane. The reaction is conducted at a temperature between 0 and 50° C. for a time period of between 1 and 16 hours. Hydrochloric acid in dioxane at ambient temperature for 1 hour are the preferred conditions. It will be recognized by those skilled in the art that the tert-butyloxycarbonyl group serves as a protecting group for the amine and that other suitable protecting groups can be employed. It will be further recognized that methods for removal of these protecting groups must be compatible with all of the functionality present in $R^5$. These methods are well-known in the technical literature of the relevant art. For example, see Greene, T. W., Wuts, P. G. M. *Protective Group in Organic Synthesis*; John Wiley & Sons: New York, 1991.

Synthesis Scheme 3 Step A

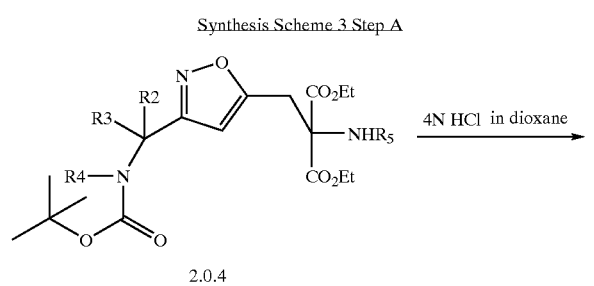

2.0.4

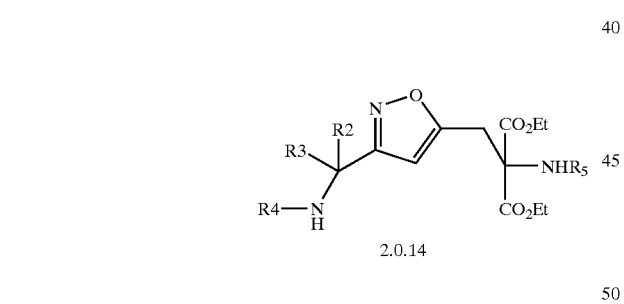

2.0.14

Synthesis Scheme 3 Step B

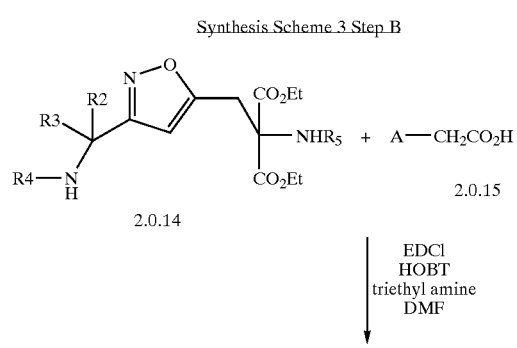

2.0.14

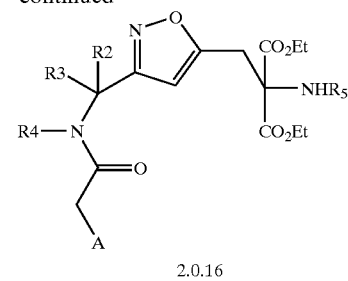

2.0.16

In scheme 3, step B, the amine 2.0.14 is reacted with acid 2.0.15 under the same conditions as synthesis Scheme 2, step B.

To prepare the final product of Formula (1.0.0) in the form of the acid, an additional step is required, as is shown in the following reaction scheme:

Synthesis Scheme 3 Step C

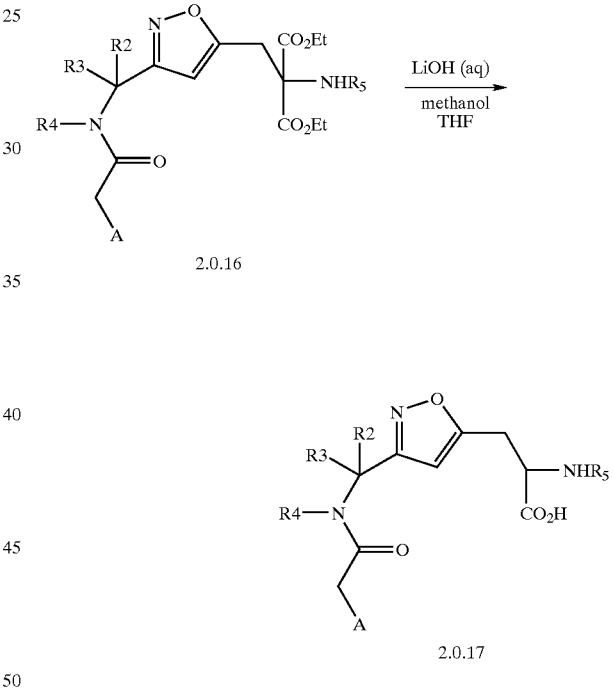

The final acid product (2.0.17) is prepared from ester 2.0.16 as illustrated in the above scheme. The intermediate is reacted with a suitable aqueous hydroxide base, such as lithium hydroxide, potassium hydroxide or sodium hydroxide in a solvent system comprised of tert-butanol, methanol or THF and methanol. The reaction is conducted at a temperature between 0 and 50° C. for 0.5 to 16 hours. Lithium hydroxide in THF, methanol, and water at ambient temperature for 1 hour are the preferred conditions.

The above-described synthesis is broadly applicable to the compounds of Formula (1.0.0). In order to make said synthesis even more clear, there is set out below Synthesis Scheme 3-α, Steps A through C with reference to a particular compound of the present invention:

Synthesis Scheme 3-α

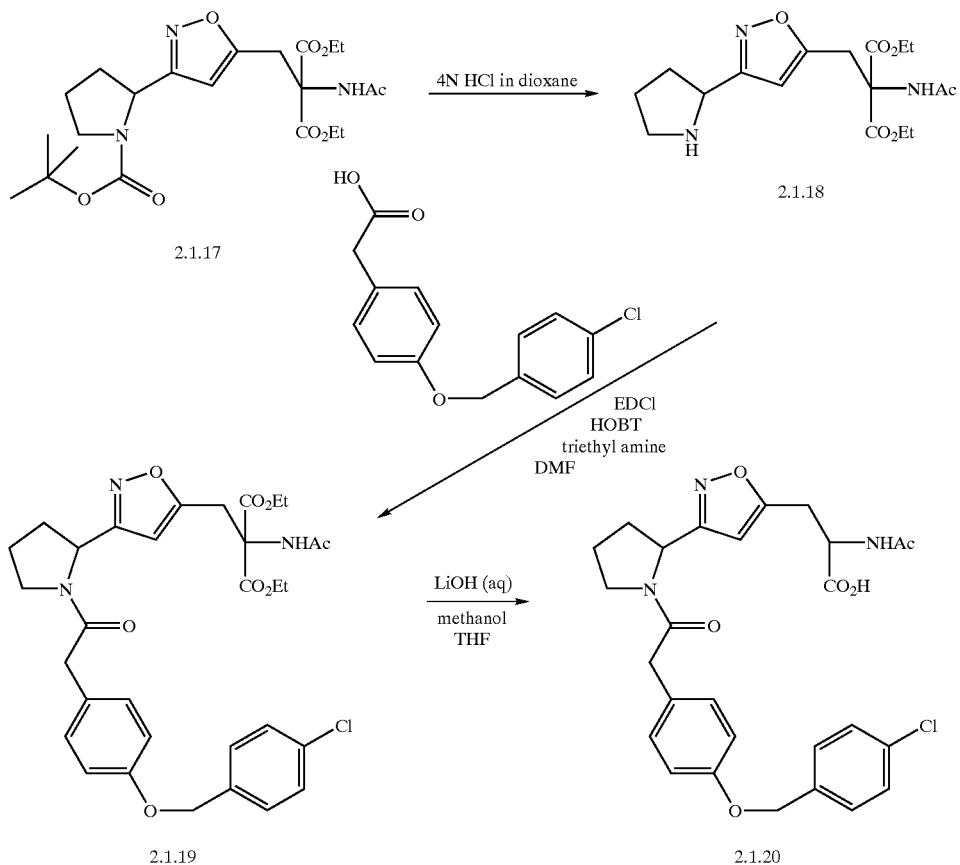

An alternative mode for the synthesis of compounds of the Formula (1.0.0) is illustrated in Synthesis Scheme 4, Steps A through D.

Synthesis Scheme 4-Step A

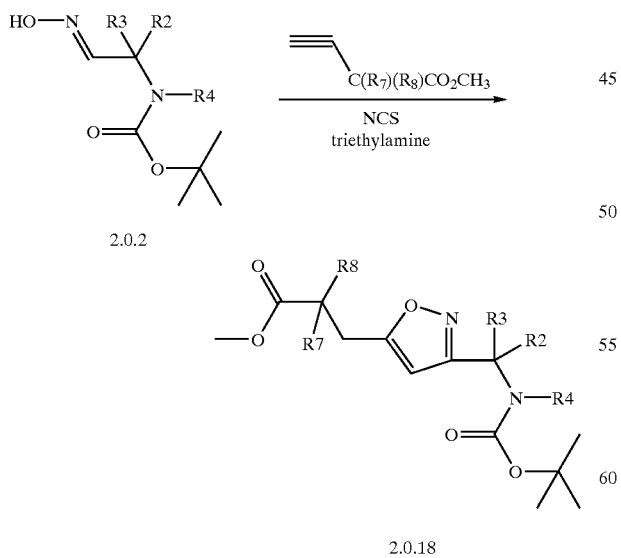

In Scheme 4, Step A, the oxime 2.0.2 is converted to the isoxazole 2.0.18 by oxidation with a suitable oxidant such as sodium hypochlorite, tert-butyl hypochlorite, or N-chlorosuccinimide in a suitable solvent such as THF, chloroform or methylene chloride; and reacting the resulting nitrile N-oxide in situ with a 2,2-disubstituted methyl pent-4-ynoate. This [2+3] cycloaddition reaction is well known in the literature as a method for preparing the isoxazole ring structure. See, e.g., *Synthesis*, 508–9,1982.

Synthesis Scheme 4 Step B

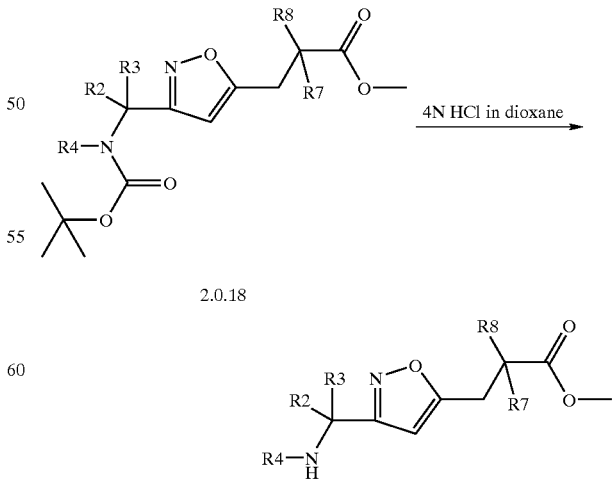

The synthesis of the amine intermediate 2.0.19 is illustrated in the above reaction scheme using the same conditions as Scheme 3, step A. The starting material is the tert-butyloxycarbamate intermediate 2.0.18.

Synthesis Scheme 4 Step C

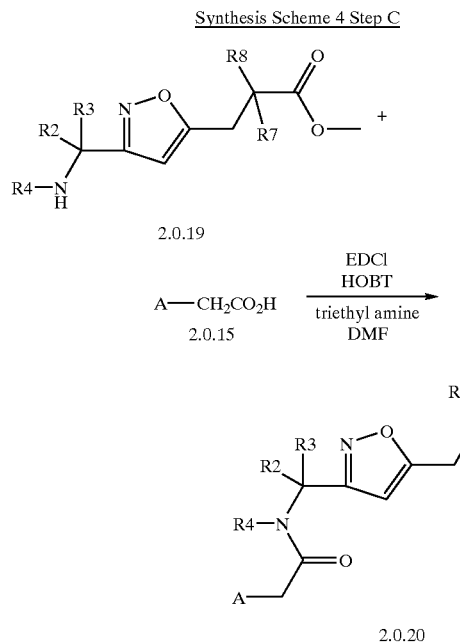

2.0.19

A—CH$_2$CO$_2$H
2.0.15

EDCl
HOBT
triethyl amine
DMF 2.0.20

In scheme 4, step C, the amine 2.0.19 is reacted with acid 2.0.15 under the same conditions as synthesis Scheme 2, step B. This reaction may be illustrated in the above schematic synthesis diagram which provides a generalized preparation process for the compounds of Formulas (1.0.0).

To prepare the final product of Formula (1.0.0) in the form of the acid, an additional step is required, as is shown in the following reaction scheme:

Synthesis Scheme 4 Step D

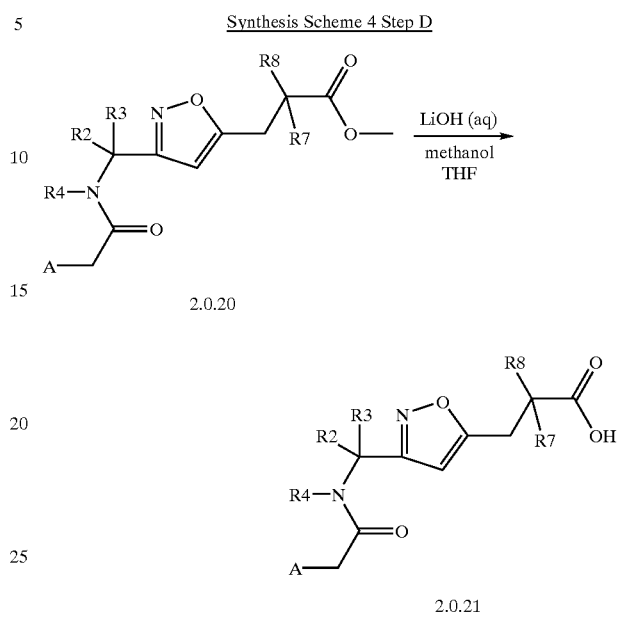

2.0.20

LiOH (aq)
methanol
THF 2.0.21

The final acid product 2.0.21 was prepared from ester 2.0.20 as illustrated in the above scheme using the method of Scheme 3, step C.

The above-described synthesis is broadly applicable to the compounds of Formula (1.0.0). In order to make said synthesis even more clear, there is set out below Synthesis Scheme 4-α, Steps A through C with reference to a particular compound of the present invention:

Synthesis Scheme 4-α

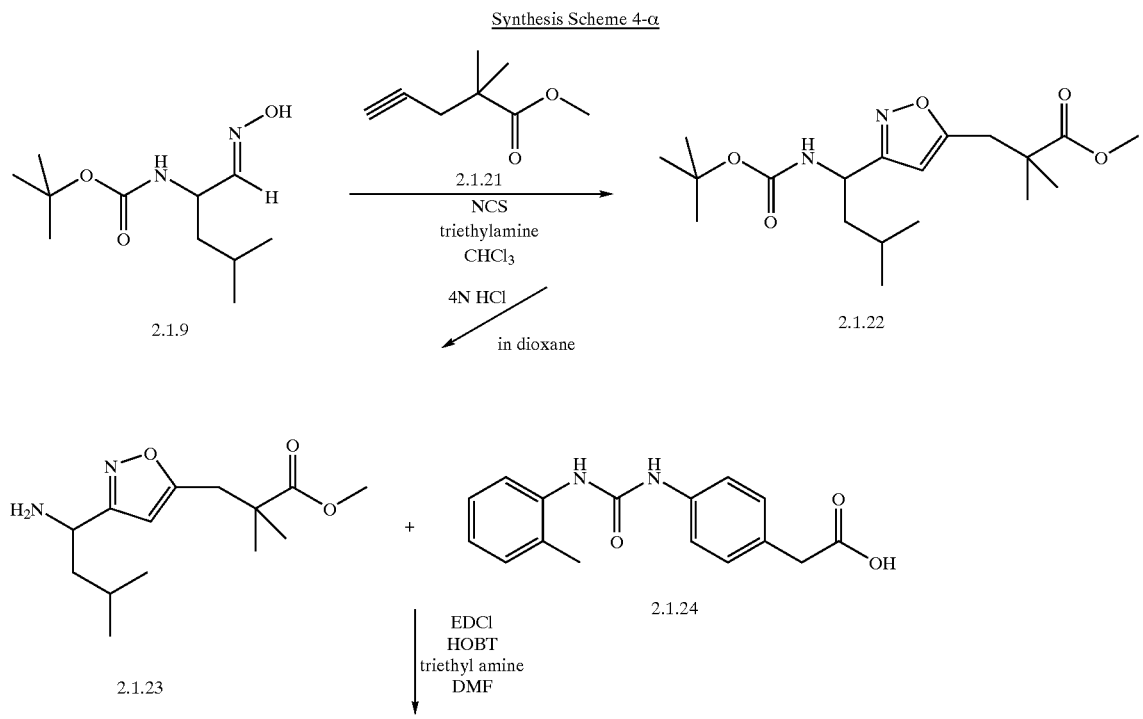

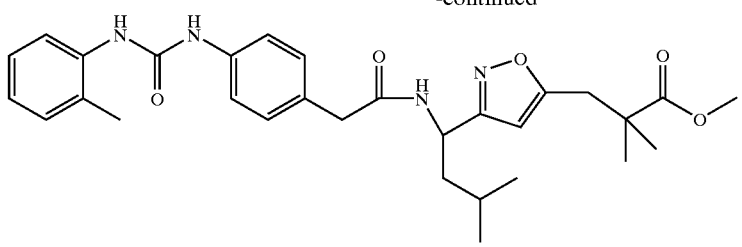

2.1.25

LiOH (aq)
methanol
THF

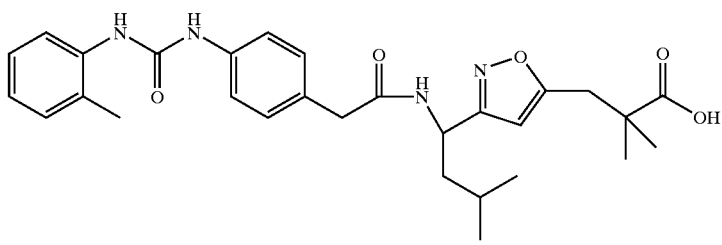

2.1.26

An alternative mode for the synthesis of compounds of the Formula (1.0.0) is illustrated in Synthesis Scheme 5 Steps A through D.

Synthesis Scheme 5 Step A

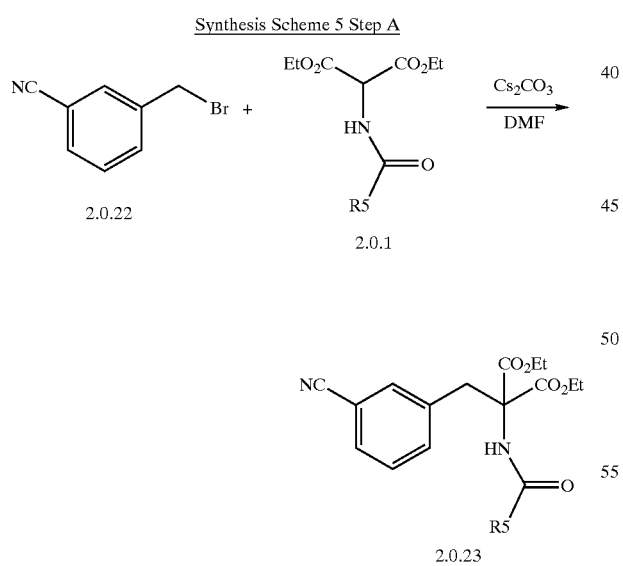

The bromide 2.0.22 is available commercially from, for example, from Aldrich Chemical Company, Milwaukee, Wis. 53233. Bromide 2.0.22 is converted into the desired diester containing component 2.0.23, as shown in the above scheme. The bromide is reacted with an amino malonate under the conditions described in scheme 1, step C.

Synthesis Scheme 5 Step B

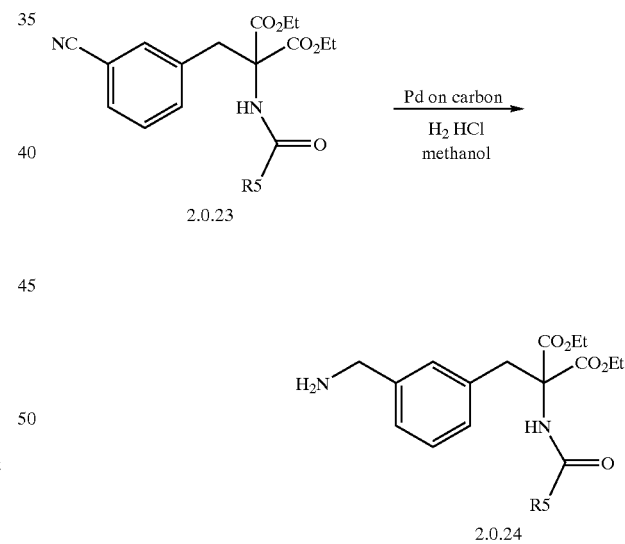

The nitrile 2.0.23 is converted to the desired amine 2.0.24 as illustrated in the above reaction scheme. The nitrile 2.0.23 is reduced to the corresponding amine 2.0.24 by hydrogenation as described in the literature (e.g. March, J. "Advanced Organic Chemistry", $3^{rd}$ edition, 1985).

The above-described synthesis is broadly applicable to the compounds of Formula (1.0.0). In order to make said synthesis even more clear, there is set out below Synthesis Scheme 5-α:

Synthesis Scheme 5-α
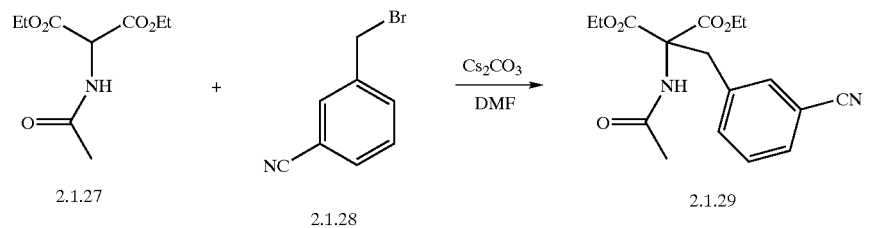
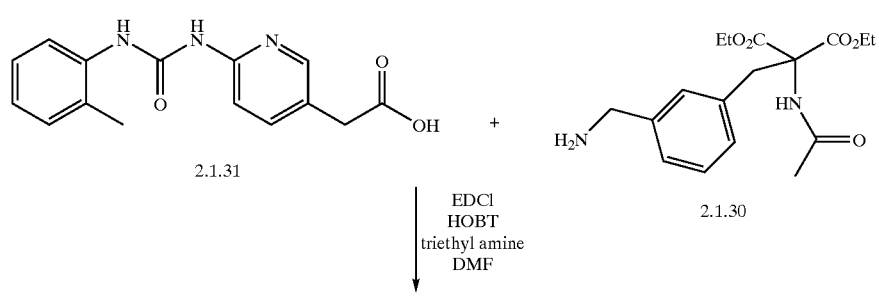
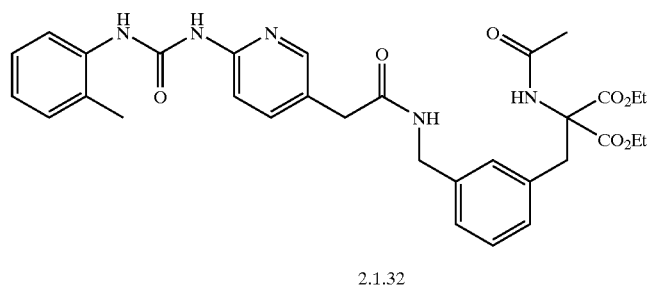
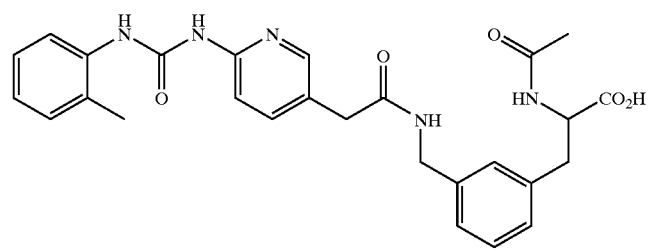
The synthesis of bicyclic compounds of the Formula (1.0.0) is illustrated in Synthesis Scheme 6 Steps A through D. Starting materials are acids and amines available from commercial sources, eg., Aldrich Chemical Company, Milwaukee, Wis. 53233.

Synthesis Scheme 6 Step A

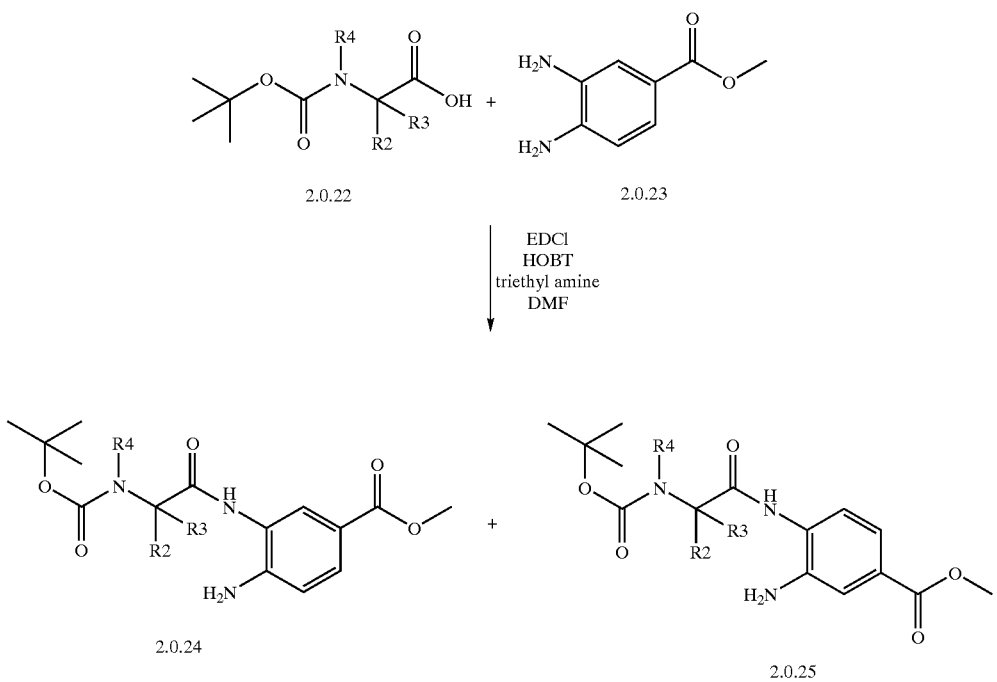

The reaction illustrated in the above scheme will be recognized by the artisan as one involving the acylation of an amine 2.0.22 by a carboxylic acid 2.0.23 which can be made to proceed in good yield at room temperature or slightly above by the use of coupling agents such as 1-(3-dimethylaminopropyl)-3-ethylcarbodiimide hydrochloride (EDCl) and 1-hydroxybenzotriazole (HOBT); dicyclohexylcarbodiimide (DCCl); N,N'-carbonyldiimidazole; $POCl_3$; $TiCl_4$; $SO_2ClF$; $Ti(OBu)_4$; $P_2I_4$; $Bu_3N$; benzotriazol-1-yl diethyl phosphate; N,N,N',N'-tetramethyl(succinimido) uronium tetrafluoroborate; and preferably di-iso-propylethyl amine (DIEA) and benzotriazol-1-yloxy-tris (dimethylamino)phosphonium hexafluorophosphate (BOP).

Synthesis Scheme 6 Step B

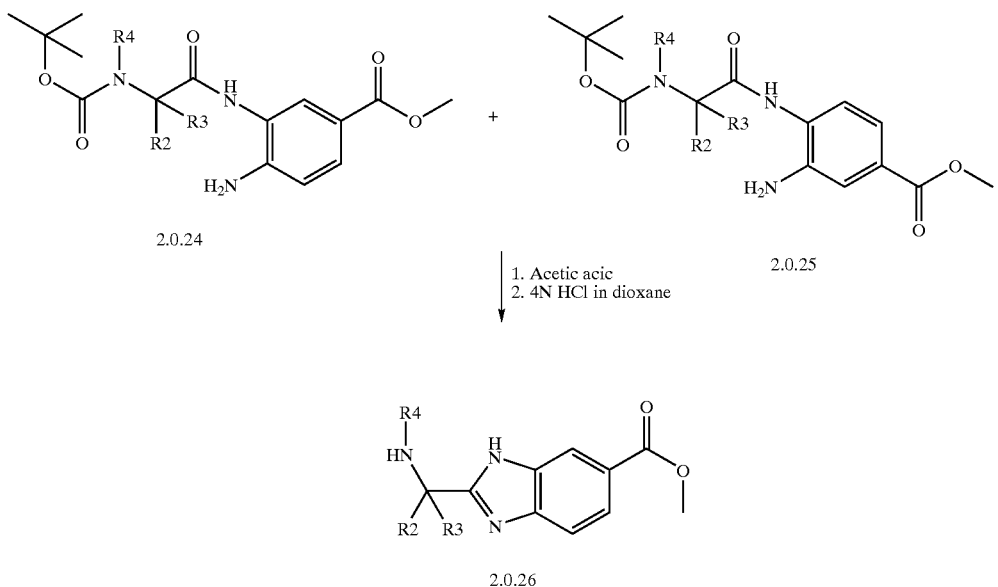

The synthesis of the amine intermediate 2.0.26 is illustrated in the above reaction scheme. The starting material is a mixture of the tert-butyloxycarbamate intermediates 2.0.24 and 2.0.25. Intermediates 2.0.24 and 2.0.25 are reacted with an acid such as hydrochloric acid or acetic acid with or without a suitable solvent such as dioxane. The reaction is conducted at a temperature between 0 and 100° C. for 1 to 16 hours. Acetic acid in the absence of additional solvent at 80° for 1.5 hours is preferred. It will be recognized by those skilled in the art that these conditions accomplish both the cyclization to form the desired bicyclic ring system and removal of the tert-butyloxycarbonyl group. It will also be recognized by those skilled in the art that the tert-butyloxycarbonyl group serves as a protecting group for the amine and that other suitable protecting groups can be employed. It will be further recognized that methods for removal of these protecting groups must be compatible with all the functionality present in intermediate 2.0.26. These methods are well-known in th technical literature of the relevant art. For example, see Greene, T. W., Wuts, P. G. M. *Protective Group in Organic Synthesis*; John Wiley & Sons: New York, 1991.

The above-described synthesis is broadly applicable: to the compounds of Formula (1.0.0). In order to make said synthesis even more clear, there is set out below Synthesis Scheme 6-α, with reference to a particular compound of the present invention:

Synthesis Scheme 6-α

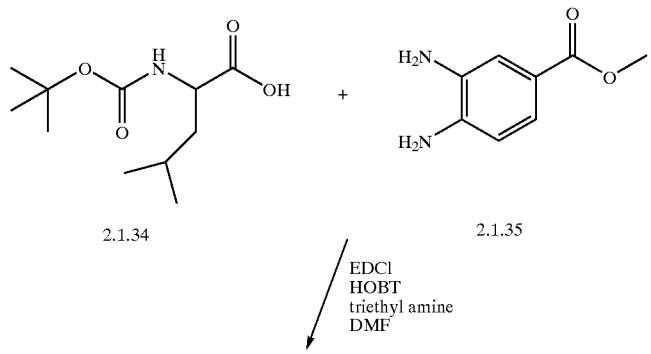

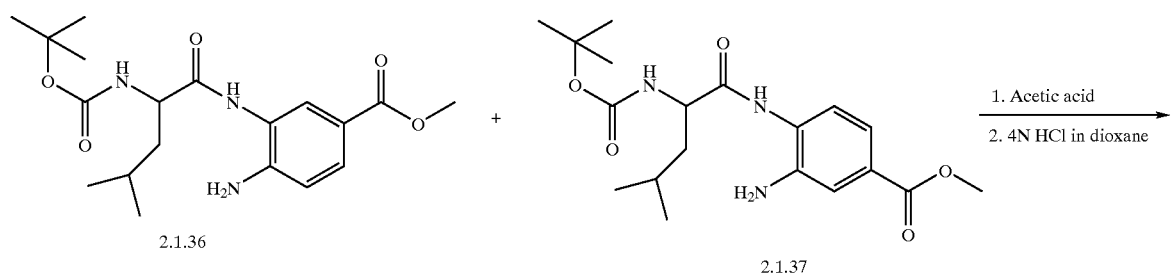

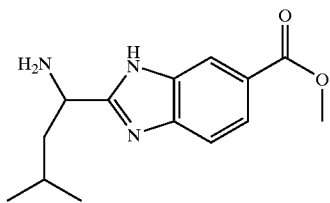

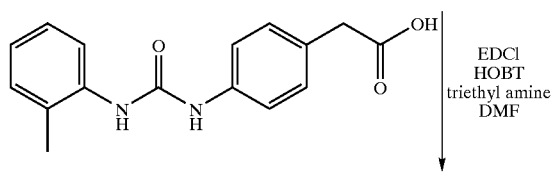

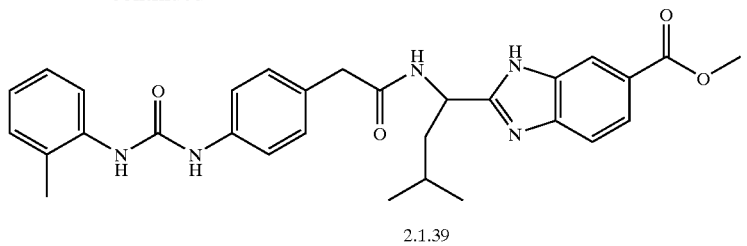

2.1.39

LiOH (aq)
methanol
THF

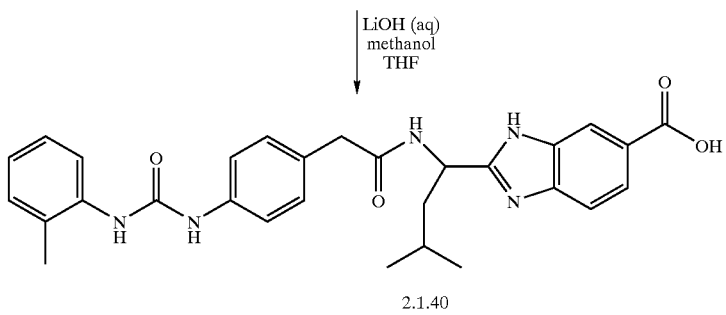

2.1.40

An alternative mode for the synthesis of compounds of the Formula (1.0.0) is illustrated in Synthesis Scheme 7 Steps A through C. These steps describe an alternative route to the B component used in the coupling reaction as decribes in Synthesis Scheme 2 Step B.

Synthesis Scheme 7 Step A

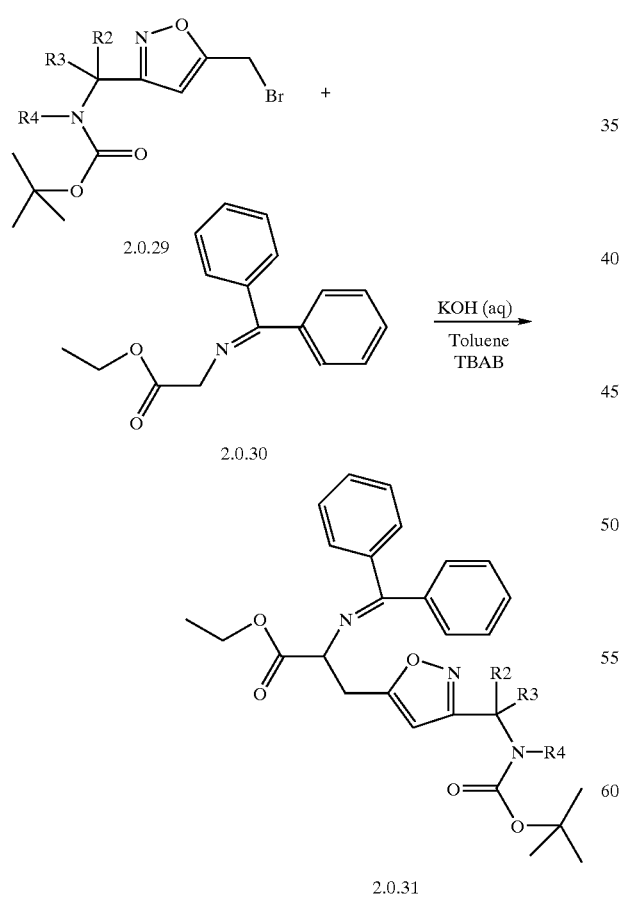

The preparation of bromide intermediate 2.0.29 was described in Synthesis Scheme 1 Step A. The intermediate bromide 2.0.29 was reacted with the commercially available imine 2.0.30 in a suitable solvent such as toluene, methylene chloride or DMF with a base such as cesium carbonate, cesium hydroxide or potassium hydroxide in the presence of an additive such as tertabutyl ammonium bromide, tetrabutyl ammonium chloride, or tetraphenylammonium bromide. The reaction was performed at a temperature between −78 and 50° C. for a period of 1 to 16 hours. The reaction of the bromide intermediate 2.0.29 with the imine 2.0.30 in toluene at ambient temperature in the presence of tetrabutylammonium bromide for 1 hour was preferred.

Synthesis Scheme 7 Step B

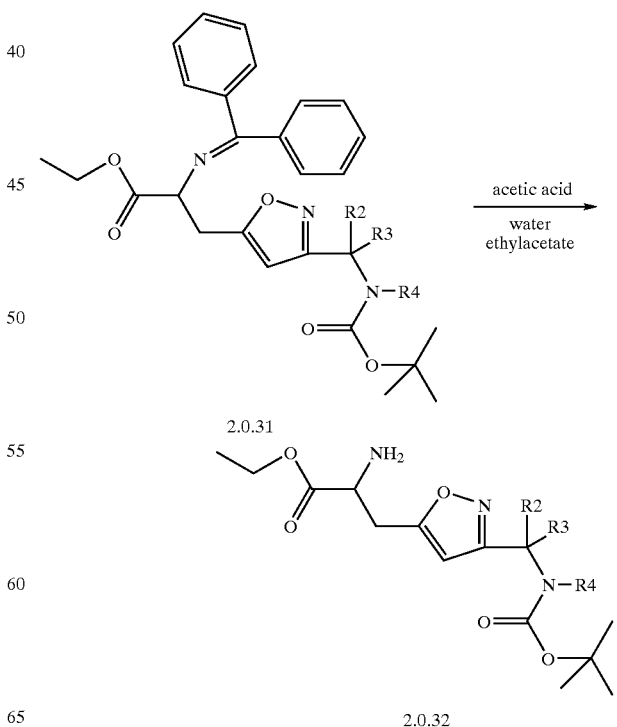

The synthesis of the amine intermediate 2.0.32 is illustrated in the above reaction scheme. The imine intermediate 2.0.31 can be transformed to the amine 2.0.32 by a variety of methods well known to those skilled in the art and desribed in the literature. For examples, Wolfe, John P.; Ahman, Jens; Sadighi, Joseph P.; Singer, Robert A.; Buchwald, Stephen L.; *Tetrahedron Lett.;* 1997, 38(36); 6367–6370; and Corey, E. J.; Xu, Feng; Noe, Mark C.; *J. Am. Chem, Soc.,* 1997, 119, 12414–12415. In the preferred method, intermediate imine 2.0.31 is treated with a mixture of ethyl acetate and hydrochloric acid for three hours at ambient temperature.

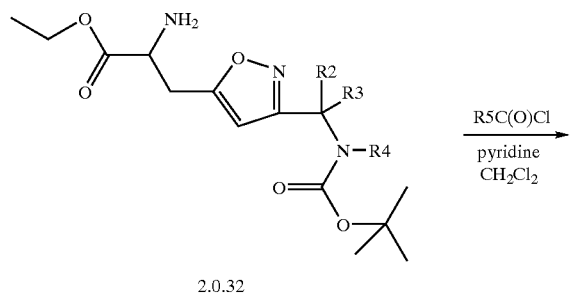

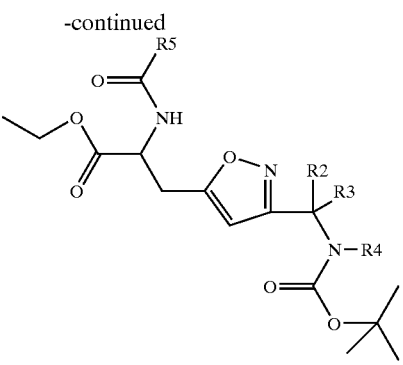

The synthesis of the amide intermediate 2.0.33 is illustrated in the above reaction scheme. The amine with or without a solvent, such as dicloromethane, chloroform, benzene, water or pyridine is reacted with an acid anhydride or acid chloride with or without the addition of a base such as sodium carbonate, pyridine or diisopropyl ethyl amine. The reaction is performed between 0 and 50° C. for a period of 1 to 16 hours. The preferred conditions employ dichloromethane and pyridine at ambient temperature for 16 hours.

The above-described synthesis is broadly applicable to the compounds of Formula (1.0.0). In order to make said synthesis even more clear, there is set out below Synthesis Scheme 7-α:

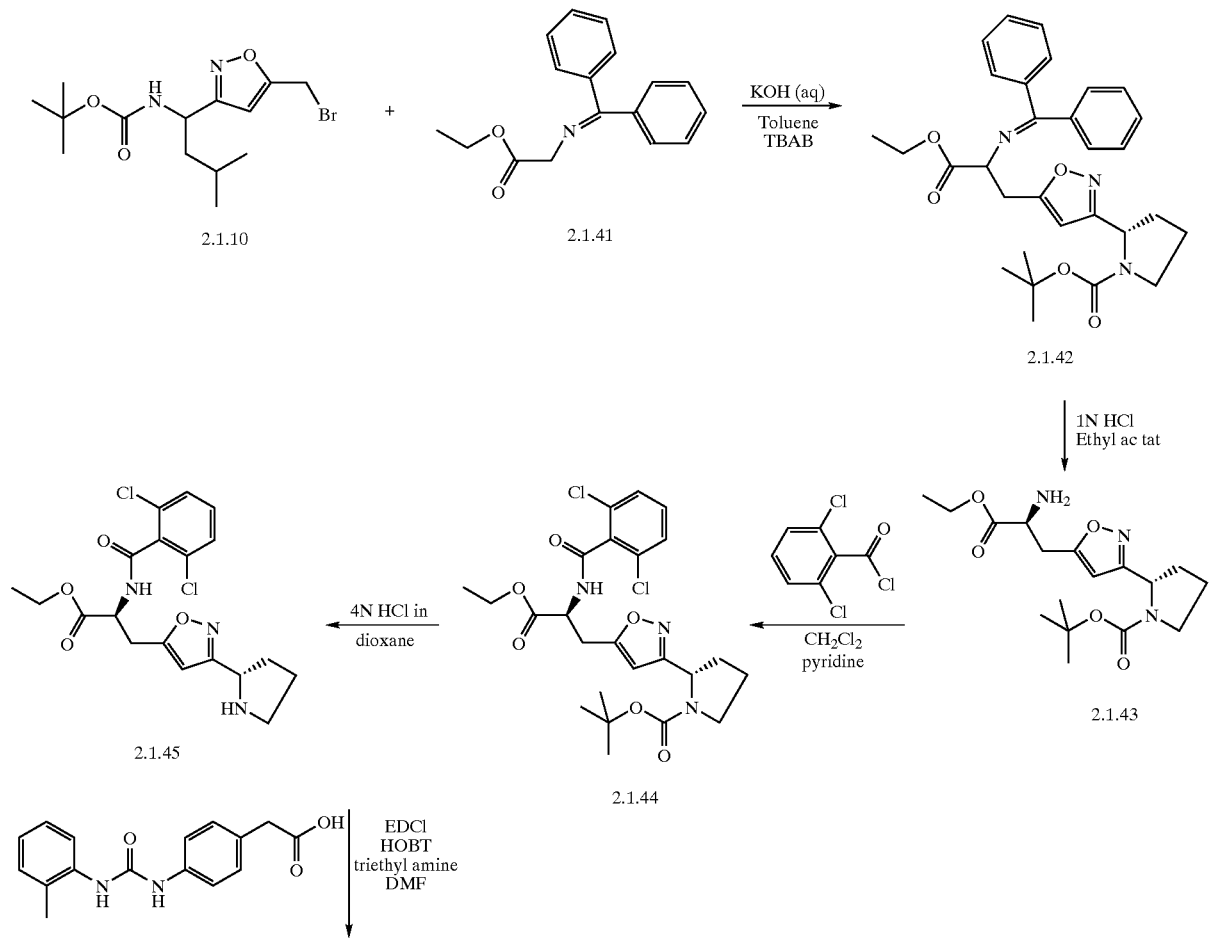

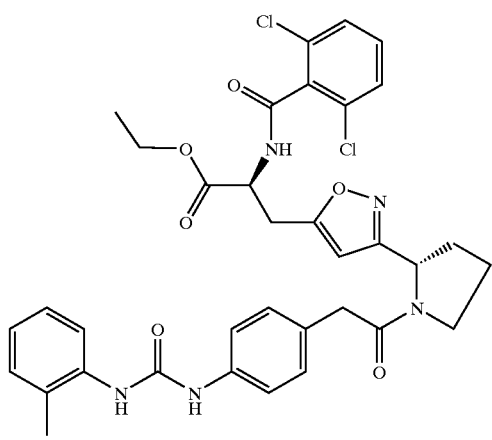

2.1.46

→ LiOH (aq) methanol THF

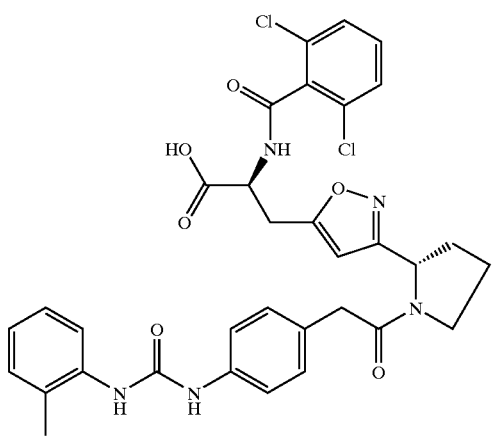

2.1.47

EXEMPLIFICATION OF PREFERRED EMBODIMENTS

The examples which follow further illustrate the compounds, compositions and methods of treatment of the present invention, but are not intended to thereby limit the scope of the present invention. A number abbreviations are used in the following examples in order to conserve space. Although these abbreviations are well known to the artisan, they are set out immediately below for clarity and convenience of the reader:

| | |
|---|---|
| BOP | benzotriazol-1-yloxy-tris(dimethylamino) phosphonium hexafluorophosphate |
| DAST | diethylaminosulfur trifluoride |
| DIEA | diisopropylethyl amine |
| DMF | dimethylformamide |
| EDCl | 1-(3-dimethylaminopropyl)-3-ethylcarbodiimide hydrochloride |
| HOBT | 1-hydroxybenzotriazole |
| THF | tetrahydrofuran |

EXAMPLE 1

A. 2-Allyloxycarbonylamino-3-{3-[1-(3,5-dichloro-benzenesulfonyl)-pyrrolidin-2-yl]-isoxazol-5-yl}-propionic acid

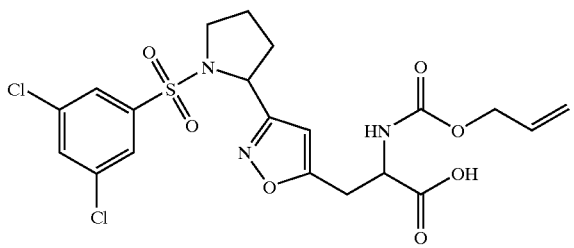

A tetrahydrofuran (1.0 mL) and methanol (0.5 mL) solution of 2-allyloxycarbonylamino-3-{3-[1-(3,5-dichloro-benzenesulfonyl)-pyrrolidin-2-yl]-isoxazol-5-yl}-propionic acid ethyl ester (59 mg, 0.108 mmol) was stirred with 2M aqueous lithium hydroxide (0.5 mL) at room temperature for 40 minutes. The reaction was acidified to pH 1 with 1M hydrochloric acid and extracted twice with ethyl acetate. The combined extracts were dried over magnesium sulfate and concentrated in vacuo to give the title compound as a white solid (51 mg, 91%). MS (Cl) m/z 518 (M+1).

B. 2-Allyloxycarbonylamino-3-{3-[1-(3,5-dichloro-benzenesulfonyl)-pyrrolidin-2-yl]-isoxazol-5-yl}-propionic acid ethyl ester

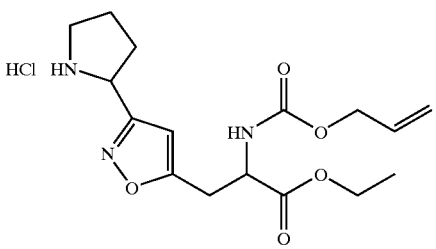

2-Allyloxycarbonylamino-3-(3-pyrrolidin-2-yl-isoxazol-5-yl)-propionic acid ethyl ester hydrochloride (110 mg, 0.294 mmol) and sodium carbonate (93.5 mg, 0.882 mmol) were dissolved in water (1.5 mL) and 3,5-dichlorobenzenesulfonylchloride (86.7 mg, 0.353 mmol) was added. This mixture was stirred overnight. The reaction was extracted twice with dichloromethane. The combined organic portion was washed with brine, dried over magnesium sulfate and concentrated in vacuo to yield the title compound (59 mg, 37%). MS (Cl) m/z 545.7 (M+1)

C. 2-Allyloxycarbonylamino-3-(3-pyrrolidin-2-yl-isoxazol-5-yl)-propionic acid ethyl ester hydrochloride 2-[5-(2-Allyloxycarbonylamino-2-ethoxycarbonyl-ethyl)-isoxazol-3-yl]-pyrrolidine-1-carboxylic acid tert-butyl ester (3.44 g, 7.86 mmol) was dissolved in 4M hydrochloric acid in dioxane (10 mL) and stirred at room temperature for 2 hours. The reaction was then concentrated in vacuo and co-evaporated with dichloromethane to give the desired product as a brown waxy solid. MS (Cl) m/z 509.9 (M+1) D. 2-[5-(2-Allyloxycarbonylamino-2-ethoxycarbonyl-ethyl)-isoxazol-3-yl]-pyrrolidine-1-carboxylic acid tert-butyl ester

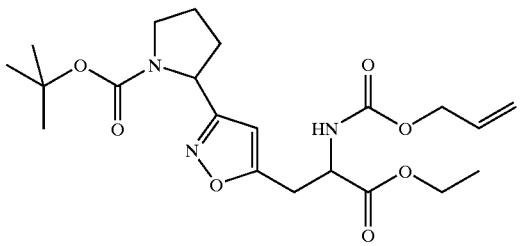

A mixture of 2-allyloxycarbonylamino-2-[3-(1-tert-butoxycarbonyl-pyrrolidin-2-yl)-isoxazol-5-ylmethyl]-malonic acid monoethyl ester and 2-allyloxycarbonylamino-2-[3-(1-tert-butoxycarbonyl-pyrrolidin-2-yl)-isoxazol-5-ylmethyl]-malonic acid diethyl ester (10.4 g, 21.5 mmol) was dissolved in dioxane (130 mL) and heated in an oil bath to 125° C. for 3 hours. The dioxane was then removed in vacuo. The residue was dissolved in ethyl acetate, washed with saturated sodium carbonate and brine, dried over magnesium sulfate and concentrated. The crude material was chromatographed on a Biotage Flash 40M column eluting with ethyl acetate/hexanes (1:4) to give the title compound as a clear oil (5.12 g, 56% 2 steps). MS (Cl) m/z 338.0 (M−99). 2-Allyloxycarbonylamino-2-[3-(1-tert-butoxycarbonyl-pyrrolidin-2-yl)-isoxazol-5-ylmethyl]-malonic acid diethyl ester was recovered (2.96 g, 27%). MS (Cl) m/z 509.9 (M+1), 409.9 (M−99)

E. 2-Allyloxycarbonylamino-2-[3-(1-tert-butoxycarbonyl-pyrrolidin-2-yl)-isoxazol-5-ylmethyl]-malonic acid monoethyl ester

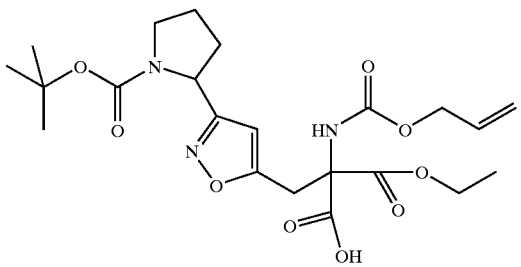

Sodium hydroxide, 1M, (21.5 mL, 21.5 mmol) was added in portions over 30 minutes to a dioxane (22 mL) solution of 2-allyloxycarbonylamino-2-[3-(1-tert-butoxycarbonyl-pyrrolidin-2-yl)-isoxazol-5-ylmethyl]-malonic acid diethyl ester (10.95 g, 21.5 mmol). After stirring overnight, the reaction had not gone to completion. An additional 0.2 equivalents of 1M sodium hydroxide (4.2 mL, 4.2 mmol) was added and stirring continued for 3 hours. The reaction was diluted with ethyl acetate (50 mL) and 1M sulfuric acid (23 mL) was added dropwise at 0° C. The aqueous portion was extracted twice with ethyl acetate. The combined organic portions were dried over magnesium sulfate and concentrated in vacuo to give a the title compound. The crude product was used directly in the next step without separation of the unreacted diester. MS (Cl) m/z 382.2 (M−99).

F. 2-Allyloxycarbonylamino-2-[3-(1-tert-butoxycarbonyl-pyrrolidin-2-yl)-isoxazol-5-ylmethyl]-malonic acid diethyl ester

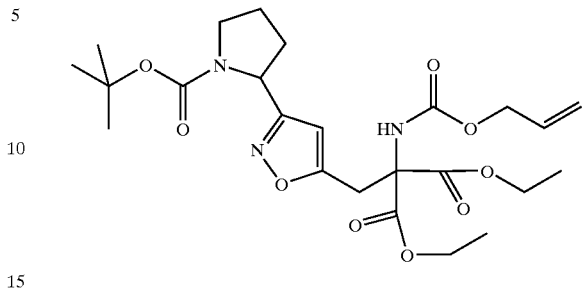

A dimethyl formamide (260 mL) solution of 2-(5-Bromomethyl-isoxazol-3-yl)-pyrrolidine-1-carboxylic acid tert-butyl ester (7.29 g, 56 mmol) and 2-allyloxycarbonyl-amino-malonic acid diethyl ester (8.25 g, 32 mmol) was cooled to 0° C. and cesium carbonate (25.41 g, 78 mmol) was added. The reaction was allowed to warm to room temperature and stirred for 3 hours. The reaction mixture was then poured into diethyl ether (2 L) and washed with water (5×200 mL) and brine. The organic portion was dried over magnesium sulfate and concentrated in vacuo. The crude residue was chromatographed on silica gel eluting with ethyl acetate:hexane (3:7) to afford the title compound as a clear colorless oil (10.95 g; 83%). MS (Cl) m/z 260.1 (M−99).

G. 2-Allyloxycarbonylamino-malonic acid diethyl ester

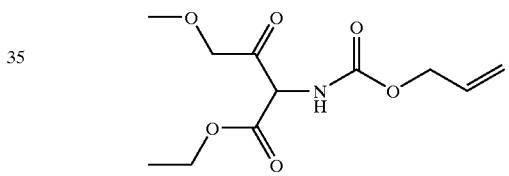

A methylene chloride (1.0 L) solution of diethylamino malonate hydrochloride (47.0 g, 226 mmol) was cooled to 0° C. and pyridine (45 mL, 564 mmol) was added. Previously insoluble solid dissolved upon addition of the pyridine. Allyl chloroformate (20 mL, 188 mmol) was slowly added dropwise to maintain the temperature of the reaction below 5° C. After the addition was complete, the reaction was stirred at 0° C. for 15 minutes. The reaction was washed with 1M hydrochloric acid (6×100 mL), dried over magnesium sulfate and concentrated in vacuo to give the title compound as a white solid (46.78 g, 80%). The crude product was used without further purification. MS (Cl) m/z 260.1 (M+1)

H. 2-(5-Bromomethyl-isoxazol-3-yl)-pyrrolidine-1-carboxylic acid tert-butyl ester

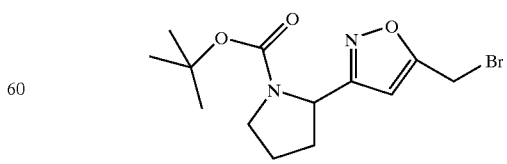

The title compound was prepared in the manner described for examples 7H and 7I, utilizing 2-(hydroxyimino-methyl)-pyrrolidine-1-carbamic acid tert-butyl ester in step 7I.

EXAMPLE 2

A. 2-Allyloxycarbonylamino-3-(3-{1-[(4-nitro-phenyl)-acetyl]-pyrrolidin-2-yl}-isoxazol-5-yl)propionic acid

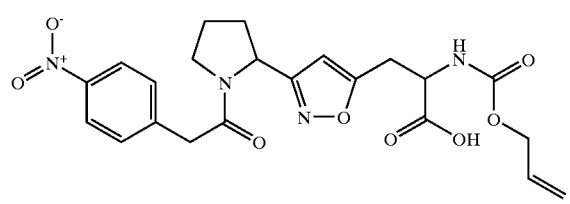

The hydrolysis of 2-allyloxycarbonylamino-3-(3-{1-[(4-nitro-phenyl)-acetyl]-pyrrolidin-2-yl}-isoxazol-5-yl)-propionic acid ethyl ester was carried out according to the same protocol as in Example 1A to afford the title compound. MS (Cl) m/z 472.6 (M+1), 471.7 (M−1).

B. 2-Allyloxycarbonylamino-3-(3-{1-[(4-nitro-phenyl)-acetyl]-pyrrolidin-2-yl}-isoxazol-5-yl)-propionic acid ethyl ester

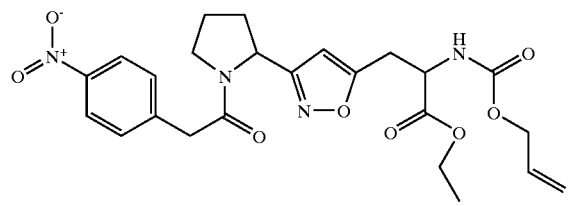

A dimethyl formamide (82 mL) solution of 4-nitrophenylacetic acid (1.61 g, 8.87 mmol) in dimethyl formamide (82 mL) was stirred with 4-hydroxybenzotriazole monohydrate (1.40 g, 10.4 mmol) for 10 minutes. 1-(3-Dimethylaminopropyl)-3-ethylcarbodiimde hydrochloride (1.86 g, 9.72 mmol) was added and the mixture was stirred until all 1-(3-dimethylaminopropyl)-3-ethylcarbodiimde hydrochloride had dissolved. To this solution, 2-allyloxycarbonylamino-3-(3-pyrrolidin-2-yl-isoxazol-5-yl)-propionic acid ethyl ester hydrochloride from Example 1C (3.16 g, 8.25 mmol) was added and the mixture stirred 30 minutes followed by addition of triethyl amine (1.26 mL, 9.04 mmol). After the reaction had stirred at room temperature over night it was poured into water and extracted with ethyl acetate three times. The combined extracts were washed with a saturated solution of sodium bicarbonate, water (2x) and brine. The organic portion was dried over magnesium sulfate and concentrated. The resulting residue was chromatographed on a Biotage Flash 40S column eluting with ethyl acetate/hexanes (5:1) to yield the title compound as a yellow oil (674 mg, 15%). MS (Cl) m/z 501.3 (M+1). Additionally, starting material 2-allyloxycarbonylamino-3-(3-pyrrolidin-2-yl-isoxazol-5-yl)-propionic acid ethyl ester was recovered (2.15 g, 75%). MS (Cl) m/z 338.1 (M+1)

EXAMPLE 3

A. 2-Allyloxycarbonylamino-3-[3-(1-{[4-(2,6-dichloro-benzoylamino)-phenyl]-acetyl}-pyrrolidin-2-yl)-isoxazol-5-yl]-propionic acid

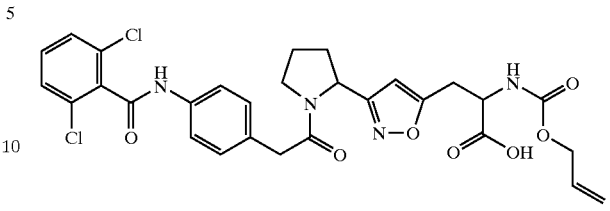

The hydrolysis of 2-allyloxycarbonylamino-3-[3-(1-{[4-(2,6-dichloro-benzoylamino)-phenyl]-acetyl}-pyrrolidin-2-yl)-isoxazol-5-yl]-propionic acid ethyl ester was carried out according to the same protocol as in example 1A to afford the title compound (77 mg, 75%). MS (Cl) m/z 616.7 (M+1), 612.5 (M−1).

B. 2-Allyloxycarbonylamino-3-[3-(1-{([4-(2,6-dichloro-benzoylamino)-phenyl]-acetyl}-pyrrolidin-2-yl)-isoxazol-5-yl]-propionic acid ethyl ester

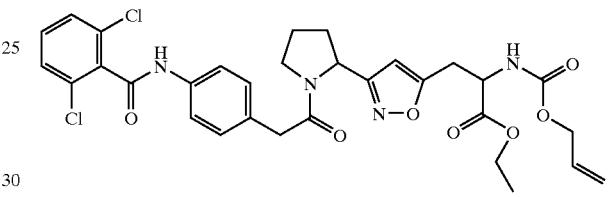

A dichloromethane (1 mL) solution 2-allyloxycarbonylamino-3-(3-{1-[(4-amino-phenyl)-acetyl]-pyrrolidin-2-yl}-isoxazol-5-yl)-propionic acid ethyl ester (80 mg, 0.170 mmol) was cooled to 0° C. and 2,6-dichlorobenzoylchloride (39 mg, 0.187 mmol) was added. The mixture was stirred for 15 minutes then pyridine (28 μL, 0.34 mmol) was added. The reaction was slowly warmed to room temperature and stirred overnight. The reaction was diluted with ethyl acetate and washed with water, 1M sodium hydroxide and brine. The organic portion was dried over magnesium sulfate and concentrated to give the title compound (84 mg, 78%). MS (Cl) m/z 635.3 (M+1), 632.5 (M−1)

C. 2-Allyloxycarbonylamino-3-(3-{1-[(4-amino-phenyl)-acetyl]-pyrrolidin-2-yl}-isoxazol-5-yl)propionic acid ethyl ester

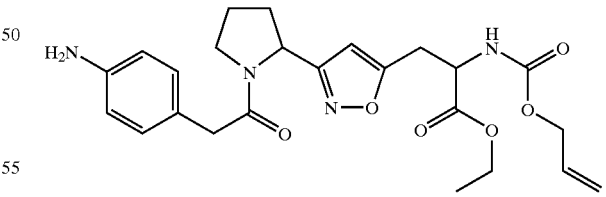

A solution of 2-allyloxycarbonylamino-3-(3-{1-[(4-nitro-phenyl)-acetyl]-pyrrolidin-2-yl}-isoxazol-5-yl)-propionic acid ethyl ester (2B) (565 mg, 1.13 mmol) and iron(0) powder (384 mg, 6.98 mmol) in ethanol/water (5 mL, 1:1) was heated to reflux. Hydrochloric acid, 1M, (0.29 mL, 0.29 mmol) was added drop wise and the reaction was heated at reflux for 45 minutes. It was then neutralized with 1M sodium hydroxide and filtered through celite. The filtrate was diluted with ethyl acetate and washed with water and brine. The organic portion was dried over magnesium sulfate and concentrated in vacuo. The crude residue was chromatographed on a Biotage Flash 40S column eluting with ethyl acetate/hexanes (6:1) to provide the title compound as a yellow oil (240 mg, 51%). MS (Cl) m/z 471.0 (M+1)

EXAMPLE 4

A. 2-Allyloxycarbonylamino-3-[3-(1-{[4-(3-o-tolyl-ureido)-phenyl]-acetyl}-pyrrolidin-2-yl)-isoxazol-5-yl]-propionic acid

The hydrolysis of 2-allyloxycarbonylamino-3-[3-(1-{[4-(3-o-tolyl-ureido)-phenyl]-acetyl}-pyrrolidin-2-yl)-isoxazol-5-yl]-propionic acid ethyl ester was carried out according to the same protocol as in example 1A to afford the title compound. MS (Cl) m/z 576.0 (M+1), 573.9 (M−1)

B. 2-Allyloxycarbonylamino-3-[3-(1-{[4-(3-o-tolyl-ureido)-phenyl]-acetyl}-pyrrolidin-2-yl)-isoxazol-5-yl]-propionic acid ethyl ester

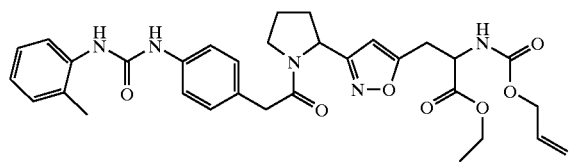

The title compound was prepared in the manner described in example 2B using [4-(3-o-tolyl-ureido)-phenyl]-acetic acid MS (Cl) m/z 604.0 (M+1).

EXAMPLE 5

A. 3-(3-{1-[(4-Acetylamino-phenyl)-acetyl]-pyrrolidin-2-yl}-isoxazol-5-yl)-2-allyloxycarbonylamino-propionic acid

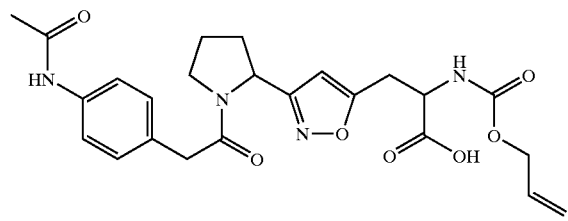

The hydrolysis of 3-(3-{1-[(4-acetylamino-phenyl)-acetyl]-pyrrolidin-2-yl}-isoxazol-5-yl)-2-allyloxycarbonyl-amino-propionic acid ethyl ester was carried out according to the same protocol as in example 1A to afford the title compound. MS (Cl) m/z 485.3 (M+1), 483.0 (M−1)

B. 3-(341-[(4-Acetylamino-phenyl)-acetyl]-pyrrolidin-2-yl)-isoxazol-5-yl)-2-allyloxycarbonylamino-propionic acid ethyl ester

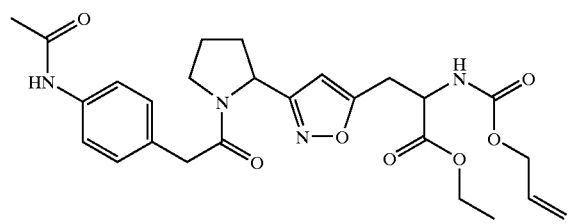

The title compound was prepared in the manner described in Example 3B using acetyl chloride in place of 2,6-dichlorobenzoylchloride. MS (Cl) m/z 513.0 (M+1).

EXAMPLE 6

A. 2-tert-Butoxycarbonylamino-3-[3-(1-{[4-(3-o-tolyl-ureido)-phenyl]-acetyl}-pyrrolidin-2-yl)-isoxazol-5-yl]-propionic acid

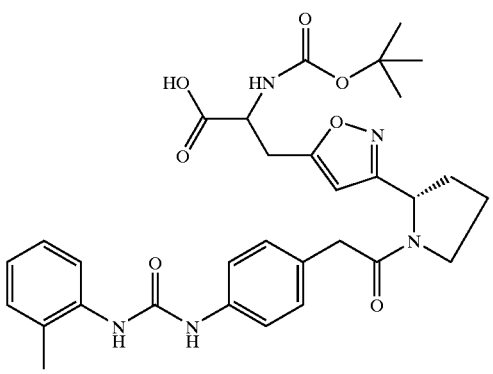

The hydrolysis of 2-tert-butoxycarbonylamino-3-[3-(1-{[4-(3-o-tolyl-ureido)-phenyl]-acetyl}-pyrrolidin-2-yl)-isoxazol-5-yl]-acid methyl ester was carried out according to the protocol in example 1A to afford the title compound. MS (Cl) m/z 590.2 (M−1), 492.2 (M−99)

B. 2-tert-Butoxycarbonylamino-3-[3-(1-{[4-(3-o-tolyl-ureido)-phenyl]-acetyl}-pyrrolidin-2-yl)-isoxazol-5-yl]-propionic acid methyl ester

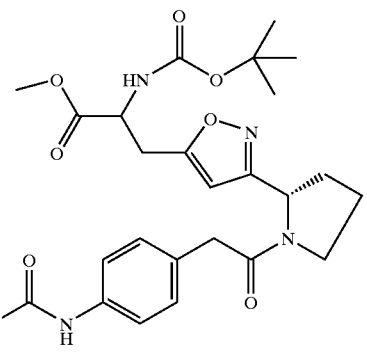

A solution of 1-(4-{2-[2-(hydroxyimino-methyl)-pyrrolidin-1-yl]-2-oxo-ethyl}-phenyl)-3-o-tolyl-urea (300 mg, 0.789 mmol), 2-tert-butoxycarbonylamino-pent-4-ynoic acid methyl ester (359 mg, 1.182 mmol, crude mixture) and triethyl amine (12.9 μL) in dichloromethane (2 mL) was stirred 5 minutes. A sodium hypochlorite solution (5.25%, 2 mL) was added. The reaction was stirred at room temperature overnight. The aqueous portion was extracted 4 times with dichloromethane. The combined organic portions were washed with brine, dried over magnesium sulfate and concentrated. Chromatography of the crude mixture on a Biotage Flash 40S column eluting with ethyl acetate/hexane 1:5 gave the title compound (66 mg, 14%). MS (Cl) m/z 604.5 (M−1), 505.9 (M−99)

C. 2-tert-Butoxycarbonylamino-pent-4-ynoic acid methyl ester

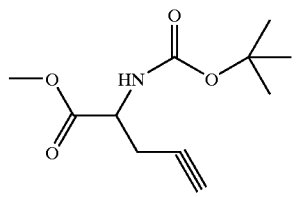

Potassium carbonate (1.687 g, 12.2 mmol) was added to an anhydrous methanol (91.5 mL) solution of 2-tert-butoxycarbonylamino-4-oxo-butyric acid benzyl ester (1.875 g, 6.10 mmol) and the reaction stirred 10 minutes. (1-Diazo-2-oxo-propyl)-phosphonic acid dimethyl ester (1.407 g, 7.32 mmol) was added and the reaction was stirred at room temp temperature 1 hour. The reaction was poured into diethyl ether and washed 4 times with 5% sodium bicarbonate, dried over magnesium sulfate and concentrated (1.05 g, crude product mixture). The crude product was used directly in the next step. $^1$H NMR (400 MHz, CDCl$_3$) δ 5.39–5.31 (m, 1H), 4.49–4.41 (m, 1H), 3.77 (s, 3H), 2.79–2.65 (m, 2H), 2.03 (s, 1H), 1.59 and 1.44 (2 singlets, rotamers, 3H).

D. 2-tert-Butoxycarbonylamino-4-oxo-butyric acid benzyl ester

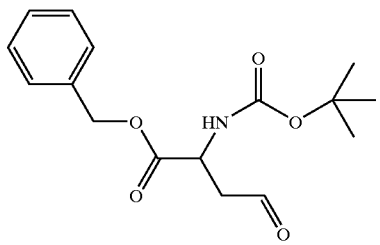

A dimethyl sulfoxide (10 mL) solution of 2-tert-butoxycarbonylamino-4-hydroxy-butyric acid benzyl ester (13.58 g, 43.9 mmol) and triethyl amine (18.35 mL, 131.7 mmol) was cooled to 0° C. Pyridine sulfur trioxide (21.0 g. 131.7 mmol) in dimethyl sulfoxide (80 mL) was added in a steady stream. The cooling bath was removed and the reaction stirred 1.5 hours. The reaction was poured into 130 mL ice water and extracted with diethyl ether (2×180 mL and 100 mL). The combined organic portion was washed sequentially with saturated sodium bicarbonate, water, brine and dried over magnesium sulfate. The solvent was removed in vacuo and the crude product was chromatographed on silica gel (900 mL) eluting with ethyl acetate/hexanes (1:4), to give the title compound as a clear, colorless oil (9.20 g, 70%). MS (Cl) m/z 208.0 (M−99).

EXAMPLE 7

A. 2-Acetylamino-4-(3-{1-[2-(4-benzyloxy-phenyl)-acetylamino]-3-methyl-butyl}-isoxazol-5-yl)-propionic acid

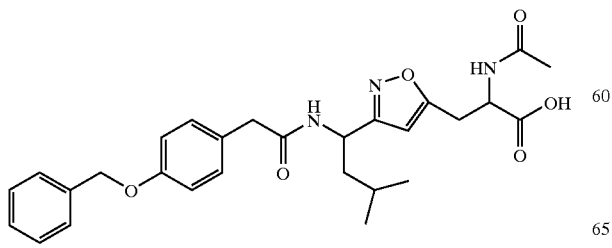

A 1:2 methanol/tetrahydrofuran (9 mL) solution of 2-acetylamino-4-(3-{1-[2-(4-benzyloxy-phenyl)-acetylamino]-3-methyl-butyl}-isoxazol-5-yl)-propionic acid ethyl ester (92 mg, 0.17 mmol) was combined with 2M aqueous lithium hydroxide (3 mL) at room temperature stirred for 3 hours. After the reaction was acidified to pH=1 with 1N hydrochloric acid, the aqueous portion was extracted with ethyl acetate (2×50 mL). The combined organic portions were dried over sodium sulfate, and concentrated to give 2-acetylamino-4-(3-{1-[2-(4-benzyloxy-phenyl)acetylamino]-3-methyl-butyl}-isoxazol-5-yl)-propionic acid as a white crystalline solid (83 mg, 95%). MS (Cl) m/z 508.1 (M+1), 506.1 (M−1).

B. 2-Acetylamino-4-(3-{1-[2-(4-benzyloxy-phenyl)-acetylamino]-3-methyl-butyl}-isoxazol-5-yl)-propionic acid ethyl ester

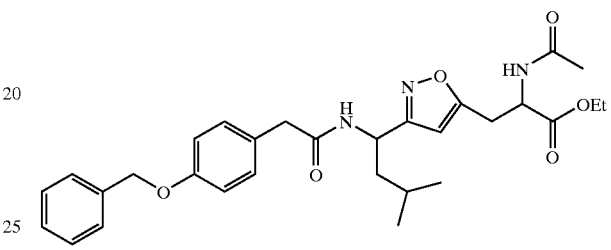

A solution of (4-benzyloxy-phenyl)-acetic acid (125 mg, 0.29 mmol, 1.00 equivalents) and 1-hydroxybenzotriazole hydrate (48 mg, 0.36 mmol, 1.23 equivalents) in dimethyl formamide (5 mL) was stirred at room temperature for 15 minutes. 1-(3-Dimethylaminopropyl)-3-ethylcarbodiimide (64 mg, 0.33 mmol, 1.15 equivalents) was added and the reaction was stirred for 15 minutes. 2-Acetylamino-3-[3-(1-amino-3-methyl-butyl)-isoxazol-5-yl]-propionic acid ethyl ester hydrochloride (100 mg, 0.29 mmol, 1.00 equivalents) was added and the reaction was stirred for 25 minutes Triethylamine (43 μl, 0.31 mmol, 1.07 equivalents) was added. The reaction was stirred at room temperature overnight then diluted with ethyl acetate (30 mL) and extracted with 1N hydrochloric acid (2×30 mL), saturated sodium bicarbonate (2×30 mL) and brine (30 mL). The organic portion was dried over sodium sulfate and the solvent was removed in vacuo. The residue was chromatographed on a 40S Biotage column (ethyl acetate) to give the title compound as a clear colorless oil (94 mg, 61%). MS (Cl) m/z 536.2 (M+1).

C. 2-Acetylamino-3-[3-(1-amino-3-methyl-butyl)-isoxazol-5-yl]-propionic acid ethyl ester hydrochloride

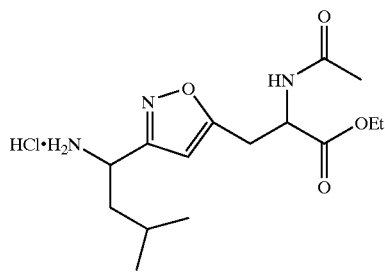

2-Acetylamino-3-[3-(1-tert-butoxycarbonylamino-3-methyl-butyl)-isoxazol-5-yl]-propionic acid ethyl ester (7F) (5.95 g, 14.5 mmol) was stirred in 4N hydrochloric acid in dioxane (25 mL) at room temperature overnight. The product was concentrated and dried under high vacuum to give the title compound as a white solid (5.38 g, 100%). MS (Cl) m/z 312.2 (M+1 for the free base).

D. (4-Benzyloxy-phenyl)-acetic acid

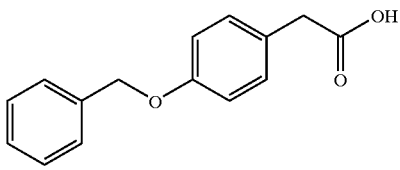

A 1:2 methanol/tetrahydrofuran (60 mL) solution of (4-benzyloxy-phenyl)-acetic acid methyl ester (1.35 g, 5.27 mmol) was combined with 2M aqueous lithium hydroxide (20 mL) at room temperature and the reaction was stirred overnight. The reaction was acidified to pH 1 with 1N hydrochloric acid and extracted with ethyl acetate (2×50 mL). The organic portions were dried over sodium sulfate and the solvent removed in vacuo to give the title compound as a white crystalline solid (1.25 g, 98%). $^1$H NMR (300 MHz, CDCl$_3$) δ 3.63 (s, 2H), 5.09 (s, 2H), 6.96–6.99 (d, 2H), 7.22–7.25 (d, 2H), 7.3–7.5 (m, 5H).

E. (4-Benzyloxy-phenyl)-acetic acid methyl ester

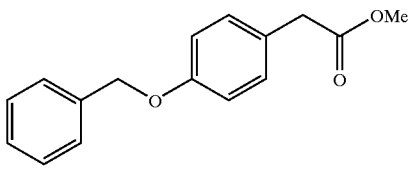

Cesium carbonate (5.35 g, 16.4 mmol, 3.00 equivalents) was added to a solution of methyl 4-hydroxyphenylacetate (1.00 g, 6.02 mmol, 1.10 equivalents) and benzyl bromide (0.65 mL, 5.47 mmol, 1.00 equivalents) in dichloromethane (40 mL) at 0° C. The mixture was allowed to warm to room temperature and stirred vigorously overnight. The reaction was extracted with 1N hydrochloric acid (2×100 mL) and brine (100 mL). The organic portion was dried over sodium sulfate and the solvent removed in vacuo. The resulting oily solid was chromatographed on a 40S Biotage column (20% ethyl acetate/Hexanes) to give the title ester as a clear colorless oil (1.35 g, 96%). $^1$H NMR (400 MHz, CDCl$_3$) δ 3.56 (s, 2H), 3.67 (s, 3H), 5.04 (s, 2H), 6.91–6.94 (d, 2H), 7.17–7.19 (d, 2H), 7.3–7.4 (m, 5H).

F. 2-Acetylamino-3-[3-(1-tert-butoxycarbonylamino-3-methyl-butyl)-isoxazol-5-yl]-propionic acid ethyl ester

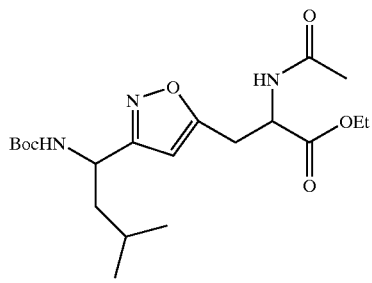

Sodium hydroxide, 1N, (20.5 mL, 20.5 mmol, 1.10 equivalents) was added to a dioxane solution of 2-acetylamino-2-[3-(1-tert-butoxycarbonylamino-3-methyl-butyl)-isoxazol-5-ylmethyl]-malonic acid diethyl ester (8.99 g, 18.6 mmol, 1.0 equivalents) at room temperature over 30 minutes and the reaction was stirred overnight. The reaction was diluted with ethyl acetate (200 mL) and acidified to pH=1–1.5 with 1N hydrochloric acid. The organic portion was washed with brine (200 mL) and dried over sodium sulfate. The solvent was removed in vacuo to give 8.58 g of a 1:1 mixture (by $^1$H NMR) of 2-Acetylamino-2-[3-(1-tert-butoxycarbonylamino-3-methyl-butyl)-isoxazol-5-ylmethyl-malonic acid monoethyl ester [MS (Cl) m/z 356.3 (M−99)] and the decarboxylated title compound [MS (Cl) m/z 412.3 (M+1), 312.2 (M−99), 410.3 (M−1)].

The mixture was refluxed in dioxane (150 mL) overnight and concentrated to yield an orange oil that was chromatographed using a Biotage column (40M, 50% ethyl acetate/hexanes) to give the title compound as a thick orange solid (6.72 g, 88%). MS (Cl) m/z 412.3 (M+1), 312.2 (M−99).

G. 2-Acetylamino-2-[3-(1-tert-butoxycarbonylamino-3-methyl-butyl)-isoxazol-5-ylmethyl]-malonic acid diethyl ester

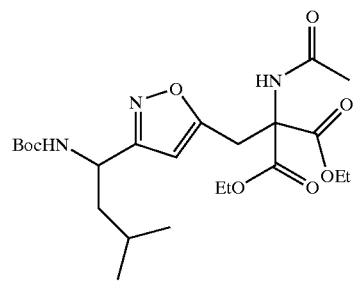

Cesium carbonate (18.28 g, 56.1 mmol, 3.0 equivalents) was added to a dimethyl formamide (300 mL) solution of [1-(5-bromomethyl-isoxazol-3-yl)-3-methyl-butyl]-carbamic acid tert-butyl ester (6.48 g, 18.7 mmol, 1.00 equivalents) and diethylacetamidomalonate (4.86 g, 22.4 mmol, 1.20 equivalents) at 0° C. The mixture was stirred at room temperature for 5 hours. The reaction was poured into diethyl ether (200 mL) and extracted with water (5×200 mL) and brine (200 mL). The organic portion was dried over sodium sulfate and the solvent was removed in vacuo to give the title compound as a viscous oil (8.99 g, 99.4%). MS (Cl) m/z 484.0 (M+1), 384.1 (M−99).

H. [1-(5-Bromomethyl-isoxazol-3-yl)-3-methyl-butyl]-carbamic acid t-butyl ester

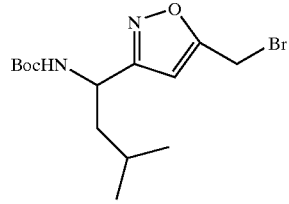

N-Chlorosuccinimide (5.80 g, 43.4 mmol, 1.00 equivalents), [1-(hydroxyimino-methyl)-3-methyl-butyl]-carbamic acid tert-butyl ester (10.00 g, 43.4 mmol, 1.00 equivalents) and pyridine (0.70 mL) were stirred in chloroform (70 mL) at room temperature for 1 hour. Propargyl bromide (4.83 mL, 54.3 mmol, 1.25 equivalents) was added and the reaction was heated to 45° C. Triethylamine (6.35 mL, 45.6 mmol, 1.05 equivalents) was added dropwise over 20 minutes at 45° C. The reaction was stirred for an additional 1 hour, then it was diluted with water (200 mL) and extracted with dichloromethane (2×200 mL). The combined organic extracts were washed with saturated sodium bicarbonate (2×200 mL) and brine (200 mL). The organic portion was dried over sodium sulfate. Evaporation of the solvent gave a brown residue that was chromatographed by flash chromatography on silica gel to give the title compound as a white solid (6.48 g, 43%). MS (Cl) m/z 247.0 (M−99)

I. 1-(Hydroxyimino-methyl)-3-methyl-butyl]-carbamic acid tert-butyl ester

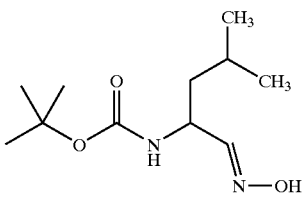

A mixture of (1-formyl-3-methyl-butyl)-carbamic acid tert-butyl ester, (2.13 g), hydroxylamine hydrochloride (0.71 g, 10.2 mmol) and NaOAc (2 g, 24.4 mmol) in MeOH (20 mL) and water (20 mL) was stirred vigorously. After 24 h the mixture was diluted with water (60 mL) and extracted with EtOAc (50 mL×3). The combined organics were washed with water and brine; dried over MgSO4; filtered and concentrated under reduced pressure. Purification by Flash 40 chromatography using a silica gel column and eluting with 15–25% EtOAc/hexane gave 1.5 g of the title compound as a white solid. MP 156–157° C.

EXAMPLE 8

A. 2-Allyloxycarbonylamino-3-[3-(1-benzoyl-pyrrolidin-2-yl)-isoxazol-5-yl]-propionic acid

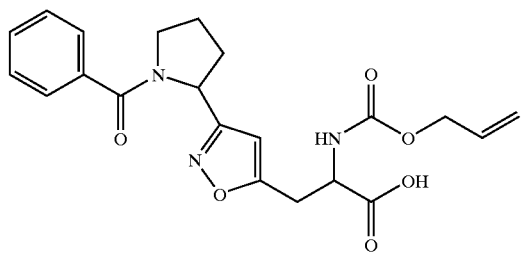

The hydrolysis of 8B was carried out according to the protocol in example 1A to afford the title compound. MS (Cl) m/z 414.2 (M+1), 412.2 (M−1).

B. 2-Allyloxycarbonylamino-3-[3-(1-benzoyl-pyrrolidin-2-yl)-isoxazol-5-yl]-propionic acid ethyl ester

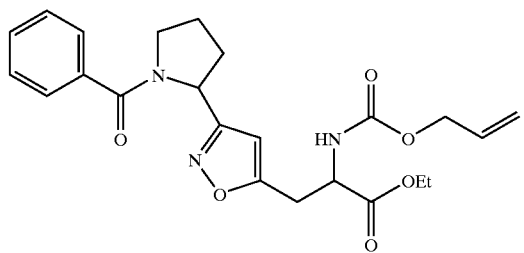

Benzoyl chloride (21 μl, 0.18 mmol, 1.0 equivalents) was added in one portion to a solution of 2-allyloxycarbonyl-amino-3-(3-pyrrolidin-2-yl-isoxazol-5-yl)-propionic acid ethyl ester hydrochloride (1C) (74 mg, 0.20 mmol, 1.1 equivalents) in pyridine (29 μl, 0.36 mmol, 2.0 equivalents) and dichloromethane (2 mL) at 0° C. The reaction was stirred at room temperature for 4 hours then diluted with ethyl acetate (30 mL). The reaction was extracted with 1N hydrochloric acid (30 mL) and brine (30 mL). The organic portion was dried over sodium sulfate and concentrated in vacuo to give the title compound (66 mg, 84%). MS (Cl) m/z 442.3 (M+1).

EXAMPLE 9

A. 2-Allyloxycarbonylamino-3-{3-[1-(biphenyl-4-carbonyl)-pyrrolidin-2-yl]-isoxazol-5-yl}-propionic acid

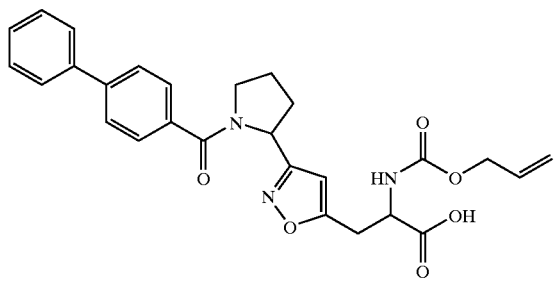

The hydrolysis of 9B was carried out using the protocol in example 1A to afford the title compound MS (Cl) m/z 490.0 (M+1), 487.8 (M−1).

B. 2-Allyloxycarbonylamino-3-{3-[1-(biphenyl-4-carbonyl)-pyrrolidin-2-yl]-isoxazol-5-yl}-propionic acid ethyl ester

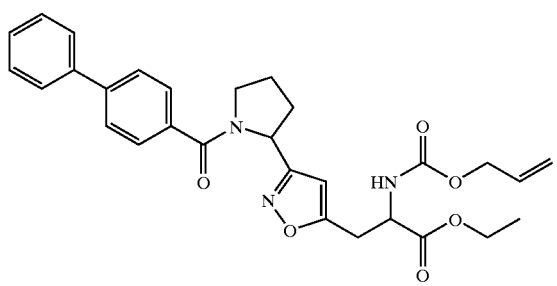

Prepared using the same method described in example 8B. MS (Cl) m/z 518.0 (M+1).

EXAMPLE 10

A. 2-Acetylamino-3-(3-{3-methyl-1-[2-(4-naphthalen-2-yl-phenyl)-acetylamino]-butyl}-isoxazol-5-yl)-propionic acid

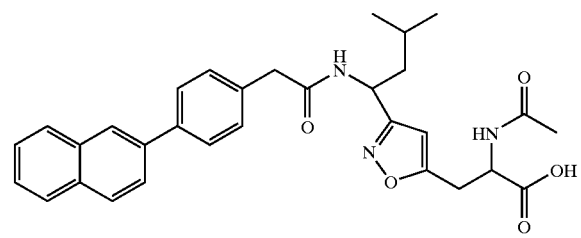

The hydrolysis of 10B was carried out using the protocol in example 1A to afford the title compound MS (Cl) m/z 528.0 (M+1), 525.8 (M−1).

B. 2-Acetylamino-3-(3-{3-methyl-1-[2-(4-naphthalen-2-yl-phenyl)-acetylamino]-butyl}-isoxazol-5-yl)-propionic acid

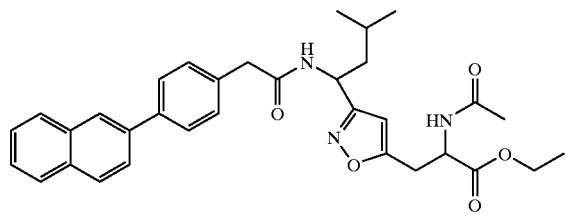

Prepared from (4-Naphthalen-2-yl-phenyl)-acetic acid in the manner described for example 7B.

C. (4-Naphthalen-2-yl-phenyl)-acetic acid

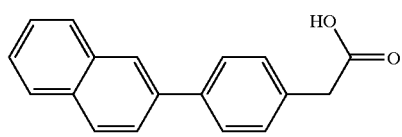

Lithium hydroxide, 2M, (3.0 mL) was added to a 2:1 tetrahydrofuran:methanol (9.0 mL) solution of (4-Naphthalen-2-yl-phenyl)-acetic acid methyl ester (270 mg, 0.977 mmol). The resulting mixture was stirred at room temperature for 1 hour. The reaction was acidified to pH=1 with 1M hydrochloric acid and extracted twice with ethyl acetate. The combined organic portions were washed with brine, dried over magnesium sulfate and concentrated in vacuo to give the title compound as a white solid (233 mg, 91%). $^1$H NMR (400 MHz, CDCl$_3$) δ 8.01–7.39 (m, 11H), 3.72 (s, 2H)

D. (4-Naphthalen-2-yl-phenyl)-acetic acid methyl ester

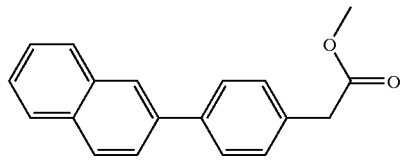

Tetrakis triphenyphosphine palladium (65 mg, 7.4 mol %) was added to a dimethoxy ethane (5.4 mL) solution of (4-Trifluoromethanesulfonyloxy-phenyl)-acetic acid methyl ester (447 mg, 1.5 mmol), 2-naphthaleneboronic acid (286 mg, 1.67 mmol) and cesium fluoride (505 mg, 3.33 mmol). The reaction was flushed with nitrogen and heated in an oil bath to 100° C. while stirring for 3 hours. The reaction was then diluted with ethyl acetate and extracted with water, 1M sodium hydroxide, water and brine. The organic portion was dried over magnesium sulfate and concentrated in vacuo. The resulting residue was chromatographed on a Biotage Flash 40S column eluting with 5% ethyl acetate in hexanes to give the title compound as a clear oil (273 mg, 66%). $^1$H NMR (400 MHz, CDCl$_3$) δ 8.01–7.38 (m, 11H), 3.72 (s, 3H), 3.69 (2H)

E. (4-Trifluoromethanesulfonyloxy-phenyl)-acetic acid methyl ester

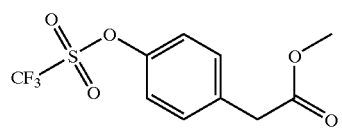

Trifluoromethane sulfonic anhydride (32.2 mmol) was added dropwise over 5 minutes to a −40° C. pyridine (70 mL) solution of (4-hydroxy-phenyl)-acetic acid methyl ester (5.35 g, 32.2 mmol). The reaction was stirred at −40° C. for 10 minutes and then at 0° C. for 2 hours. The reaction was diluted with diethyl ether and washed with water and 2N hydrochloric acid. The organic portion was dried over magnesium sulfate and concentrated in vacuo. The crude residue was chromatographed on a Biotage Flash 40M column eluting with ethyl acetate/hexanes (1:4) to provide the title compound as a clear, colorless oil, which crystallized upon standing 9.27 g, 97%). $^1$H NMR (400 MHz, CDCl$_3$) δ 7.37–7.34 (m, 2H), 7.24–7.21 (m, 2H), 3.70 (3H), 3.64 (2H).

EXAMPLE 11

A. 2,2-Dimethyl-3-[3-(3-methyl-1-{2-[4-(3-o-tolyl-ureido)-phenyl]-acetylamino}-butyl)-isoxazol-5-yl]-propionic acid

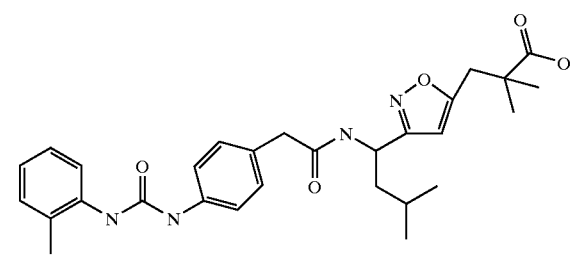

The hydrolysis of 11B was carried out using the protocol in example 1A to afford the title compound MS (Cl) m/z: 521.2 (M+1), 519.1 (M−1)

B. 2,2-Dimethyl-3-[3-(3-methyl-1-{2-[4-(3-o-tolyl-ureido)-phenyl]-acetylamino}-butyl)isoxazol-5-yl]-propionic acid methyl ester

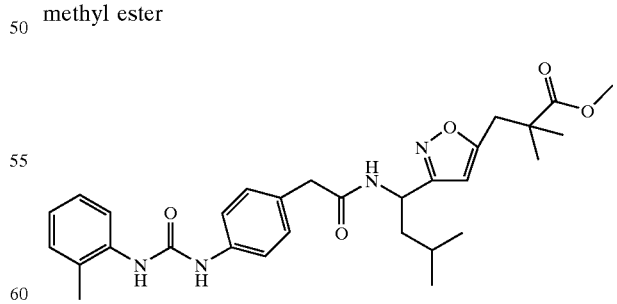

Prepared from 3-[3-(1-tert-butoxycarbonylamino-3-methyl-butyl)-isoxazol-5-yl]-2,2-dimethyl-propionic acid methyl ester in two steps by following the procedure outlined in examples 1C and 2B. MS (Cl) m/z: 535.1 (M+1), 535.1 (M−1)

C. 3-[3-(1-tert-Butoxycarbonylamino-3-methyl-butyl)-isoxazol-5-yl]-2,2-dimethyl-propionic acid methyl ester

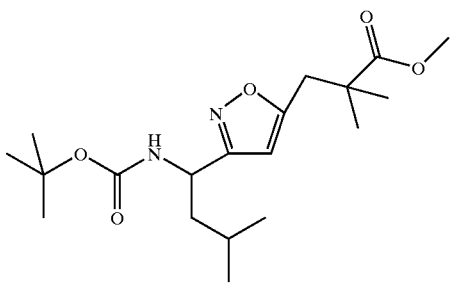

Prepared from [1-(hydroxyimino-methyl)-3-methyl-butyl]-carbamic acid tert-butyl ester (7I) and 2,2-dimethyl-pent-4-ynoic acid methyl ester according to the procedure outlined in example 6A. MS (Cl) m/z: 313.2 (M-tBu), 269.3 (M–99)

EXAMPLE 12

A. 3-[3-(3-Methyl-1-{2-[4-(3-o-tolyl-ureido)-phenyl]-acetylamino}-butyl)-isoxazol-5-yl]-2-phenyl-propionic acid

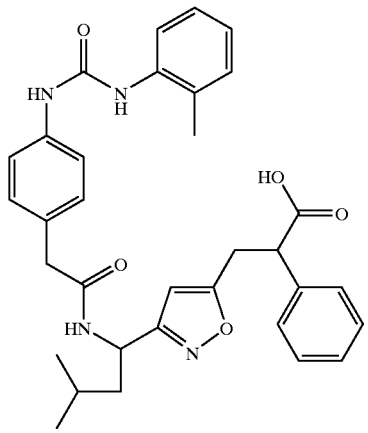

The hydrolysis of 12B was carried out using the protocol in example 1A to afford the title compound.

B. 3-[3-(3-Methyl-1-{2-[4-(3-o-tolyl-ureido)-phenyl]-acetylamino}-butyl)-isoxazol-5-yl]-2-phenyl-propionic acid methyl ester

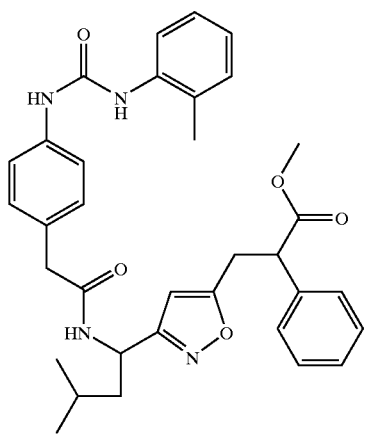

The title compound was prepared from 3-[3-(1-tert-butoxycarbonylamino-3-methyl-butyl)isoxazol-5-yl]-2-phenyl-propionic acid methyl ester in the manner described in example 11B.

C. 3-[3-(1-tert-Butoxycarbonylamino-3-methyl-butyl)-isoxazol-5-yl]-2-phenyl-propionic acid methyl ester

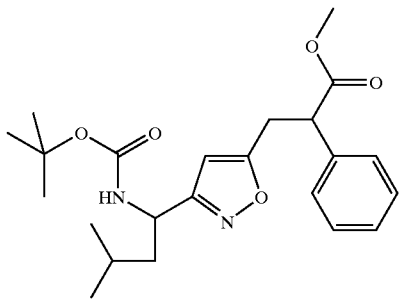

The title compound was prepared from 2-phenyl-pent-4-ynoic acid methyl ester in the manner described in example 6A.

D. 2-Phenyl-pent-4-ynoic acid methyl ester

Diisopropyl ethyl amine (5.9 mL, 42 mmol) was dissolved in tetrahydrofuran (30 mL). Butyllithium, 2.5 M in hexanes, (16.8 mL, 42 mmol) was added slowly at A solution of phenyl acetic acid (2.72 g, 20 mmol) in tetrahydrofuran (20 mL) was added slowly via a dropping funnel over 20 minutes. The reaction was stirred for 25 minutes. Propargyl bromide was added as an 80% weight solution in toluene (2.3 mL, 21.0 mmol). The reaction was stirred for 1.5 hours and 4N hydrochloric acid (15 mL) was added. The mixture was diluted with ethyl acetate (50 mL). The organic portion was concentrated in vacuo. The residue was dissolved in diethyl ether and extracted with water (3x) and 1N hydrochloric acid (3x). The organic portion was dried over magnesium sulfate and the solvent removed in vacuo. The resulting yellow solid (1.7 g) was dissolved in methanol (50 mL) and cooled to 0° C. Acetylchloride (2 mL) was added and the reaction was allowed to warm to room temperature. After the reaction stirred for 18 hours, the solvent was removed in vacuo. The residue was dissolved in diethyl ether. The solution was extracted with saturated sodium bicarbonate, water, and brine. The organic portion was dried over magnesium sulfate and the solvent removed in vacuo. The residue was chromatographed on silica gel with 10% ethyl acetate in hexanes to give the title compound as an oil (0.58 g, 15%)

EXAMPLE 13

A. 2-Acetylamino-3-[3-(1-{[4-(3-o-tolyl-ureido)-phenyl]-acetyl}-pyrrolidin-2-yl)-isoxazol-5-yl]-propionic acid

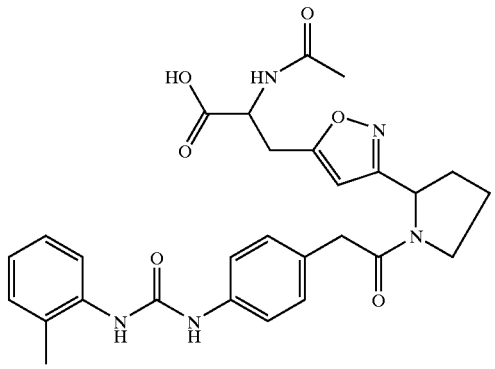

The hydrolysis of 13B was carried out using the protocol in example 1A to afford the title compound. MS (Cl) m/z 534.2 (M+1), 532.4 (M−1).

B. 2-Acetylamino-3-[3-({[4-(3-o-tolyl-ureido)-phenyl]-acetyl}-pyrrolidin-2-yl)-isoxazol-5-yl]-propionic acid ethyl ester

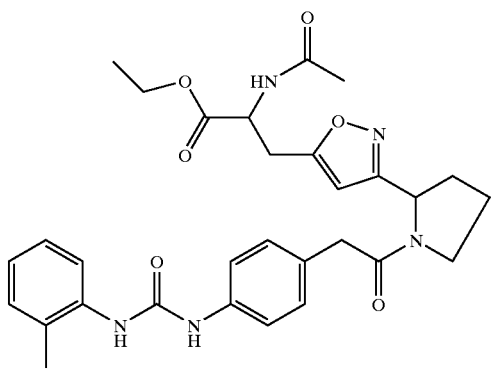

The title compound was prepared from 2-[5-(2-acetylamino-2-methoxycarbonyl-ethyl)-isoxazol-3-yl]-pyrrolidine-1-carboxylic acid tert-butyl ester as described in example 11B. MS (Cl) m/z 562.1 (M+1).

C. 2-[5-(2-Acetylamino-2-methoxycarbonyl-ethyl)-isoxazol-3-yl]-pyrrolidine-1-carboxylic acid tert-butyl ester

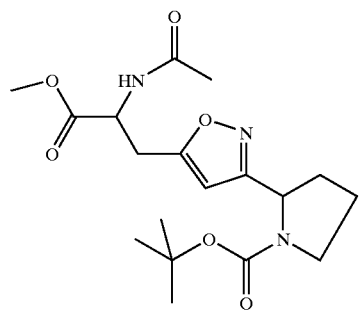

The title compound was prepared from the 2-(hydroxyimino-methyl)-pyrrolidine-1-carbamic acid tert-butyl ester and the 2-acetylamino-pent-4-ynoic acid methyl ester as described in example 6B. MS (Cl) m/z 296.0 (M−99)

EXAMPLE 14

A. 2-(2,6-Dichloro-benzoylamino)-3-[3-(1-{[4-(3-o-tolyl-ureido)-phenyl]-acetyl}-pyrrolidin-2-yl)-isoxazol-5-yl]-propionic acid

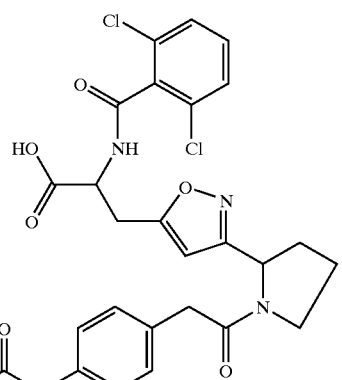
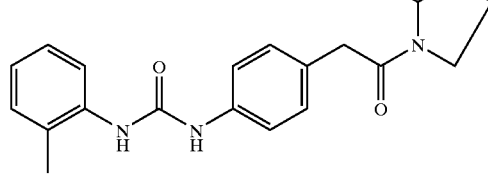

The hydrolysis of 14B was carried out using the protocol in example 1A to afford the title compound. MS (Cl) m/z 663.8 (M+1).

B. 2-(2,6-Dichloro-benzoylamino)-3-[3-(1-{[4-(3-o-tolyl-ureido)-phenyl]-acetyl}-pyrrolidin-2-yl)-isoxazol-5-yl]-propionic acid ethyl ester

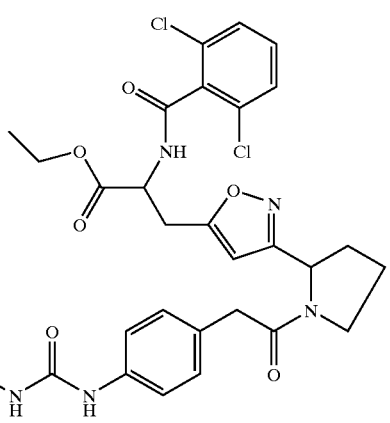
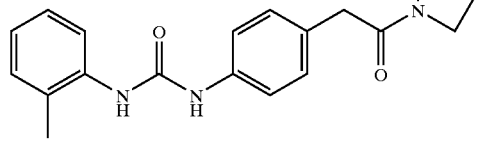

The title compound was prepared from 2-{5-[2-(2,6-dichloro-benzoylamino)-2-ethoxycarbonyl-ethyl]-isoxazol-3-yl}-pyrrolidine-1-carboxylic acid tert-butyl ester in a manner similar to that described in 11B. MS (Cl) m/z 691.8 (M+1), 689.7 (M−1).

C. 2-{5-[2-(2,6-Dichloro-benzoylamino)-2-ethoxycarbonyl-ethyl]-isoxazol-3-yl}-pyrrolidine-1-carboxylic acid tert-butyl ester

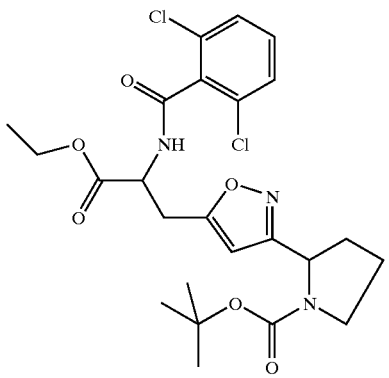

The title compound was prepared from 2-[5-(2-amino-2-ethoxycarbonyl-ethyl)-isoxazol-3-yl]-pyrrolidine-1-carboxylic acid tert-butyl ester hydrocloride and 2,6-dichlorobenzoylchloride in the manner described in example 3B. MS (Cl) m/z 525.9 (M+1), 425.9 (M−99).

D. 2-[5-(2-Amino-2-ethoxycarbonyl-ethyl)-isoxazol-3-yl]-pyrrolidine-1-carboxylic acid tert-butyl ester hydrocloride

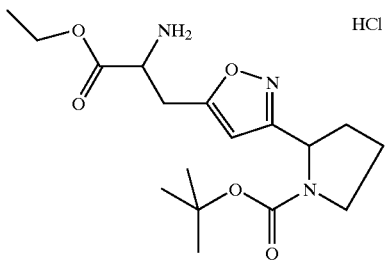

2-{5-[2-(Benzhydrylidene-amino)-2-ethoxycarbonyl-ethyl]-isoxazol-3-yl}-pyrrolidine-1-carboxy acid tert-butyl ester (700 mg, 1.35 mmol) was stirred in a mixture of ethyl acetate (20 mL) and 1N hydrochloric acid (100 mL) for 3 hours. The reaction was neutralized by the addition of saturated sodium bicarbonate. The aqueous portion was extracted with diethyl ether. The combined organics were dried over magnesium sulfate and the solvent removed in vacuo. The resulting oil (200 mg) was used directly in example 14C.

E. 2-{5-[2-(Benzhydrylidene-amino)-2-ethoxycarbonyl-ethyl]-isoxazol-3-yl}-pyrrolidine-1-carboxylic acid tert-butyl ester

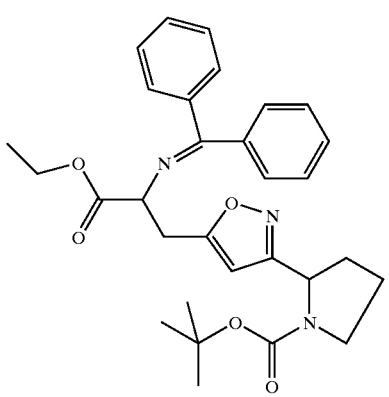

2-(5-Bromomethyl-isoxazol-3-yl)-pyrrolidine-1-carboxylic acid tert-butyl ester (1.0 g, 3 mmol) and N-(diphenylmethylene)glycine glycine ethyl ester (1.0 g, 3.74 mmol) were dissolved in toluene (10 mL). Aqueous potassium hydroxide, 18M, (0.25 mL, 4.5 mmol) and tetrabutylammonium bromide (97 mg, 0.30 mmol) were added. After the reaction was stirred at room temperature for 1 hour, 1N hydrochloric acid was added (4.5 mL). The organic phase was extracted with 1N hydrochloric acid, saturated sodium bicarbonate, and brine. The organic portion was dried over magnesium sulfate and the solvent removed in vacuo. The residue was chromatographed with 15% ethylacetate in hexanes on a Biotage 40S column to give the title compound (700 mg, 45%). MS (Cl) m/z 518.0 (M+1).

EXAMPLE 15

A. 2-Allyloxycarbonylamino-3-{3-[1-(toluene-4-sulfonyl)-pyrrolidin-2-yl]-isoxazol-5-yl}-propionic acid

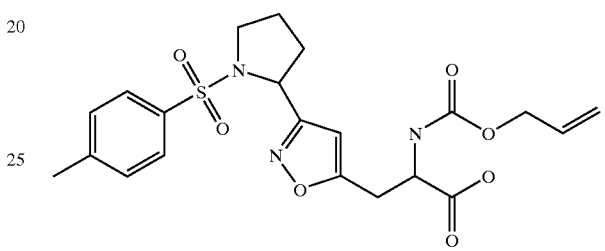

The hydrolysis of 15B was carried out using the protocol in example 1A to afford the title compound. MS (Cl) m/z 464.0 (M+1), 461.9 (M−1).

B. 2-Allyloxycarbonylamino-3-{3-[1-(toluene-4-sulfonyl)-pyrrolidin-2-yl]-isoxazol-5-yl}-propionic acid ethyl ester

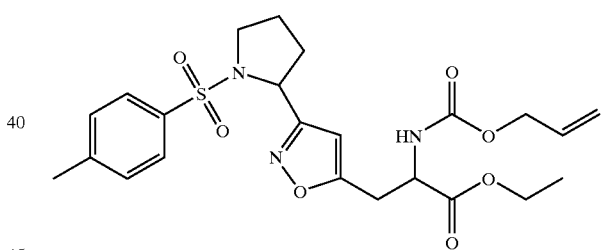

The title compound was prepared according to the method described in example 1B. MS (Cl) m/z 492.0 (M+1).

EXAMPLE 16

A. 2-Allyloxycarbonylamino-3-[3-(1-{[4-(2,6-dimethoxy-benzoylamino)-phenyl]-acetyl}-pyrrolidin-2-yl)-isoxazol-5-yl]-propionic acid

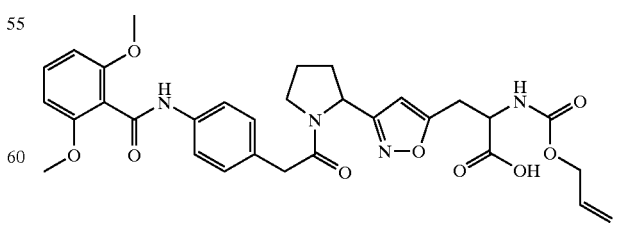

The hydrolysis of 16B was carried out using the protocol in example 1A to afford the title compound. MS (Cl) m/z 606.7 (M+1), 605.1 (M−1).

B. 2-Allyloxycarbonylamino-3-[3-(1-{[4-(2,6-dimethoxybenzoylamino)-phenyl]-acetyl}-pyrrolidin-2-yl)-isoxazol-5-yl]-propionic acid ethyl ester

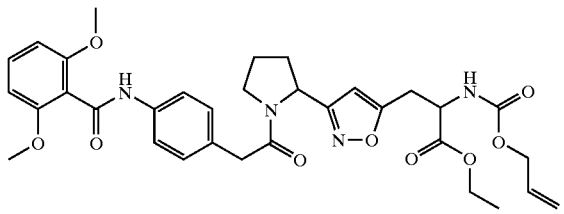

The title compound was prepared according to the procedure described in example 3B, using 2,6-dimethoxybenzoylchloride in place of 2,6-dichlorobenzoylchloride. MS (Cl) m/z 635.3 (M+1), 632.5 (M−1)

EXAMPLE 17

A. 2-Allyloxycarbonylamino-3-{3-[1-(3,4-dimethoxybenzenesulfonyl)-pyrrolidin-2-yl]-isoxazol-5-yl}-propionic acid

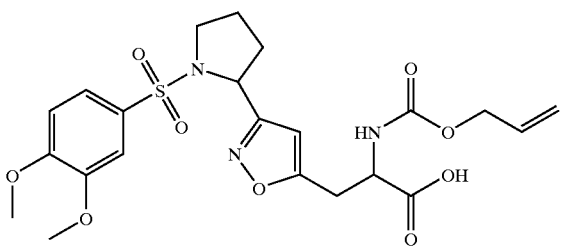

The hydrolysis of 17B was carried out using the protocol in example 1A to afford the title compound. MS (Cl) m/z 507.6 (M−1).

B. 2-Allyloxycarbonylamino-3-{3-[1-(3,4-dimethoxybenzenesulfonyl)-pyrrolidin-2-yl]-isoxazol-5-yl}-propionic acid ethyl ester

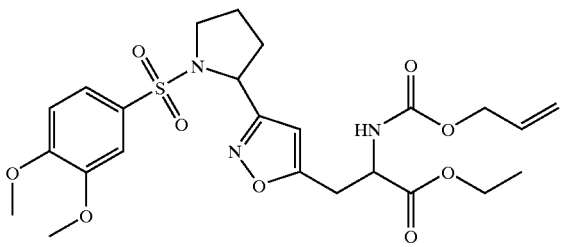

The title compound was prepared according to the method described in example 1B, using 3,4-dimethoxybenzenesulfonylchloride. MS (Cl) m/z 537.8 (M+1).

EXAMPLE 18

A. 2-Allyloxycarbonylamino-3-[3-(1-cyclopropanecarbonyl-pyrrolidin-2-yl)-isoxazol-5-yl]-propionic acid

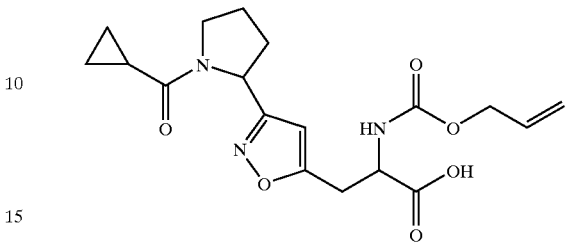

The hydrolysis of 18B was carried out using the protocol in example 1A to afford the title compound. MS (Cl) m/z 378.2 (M+1), 376.2 (M−1).

B. 2-Allyloxycarbonylamino-3-[3-(1-cyclopropanecarbonyl-pyrrolidin-2-yl)-isoxazol-5-yl]-propionic acid ethyl ester

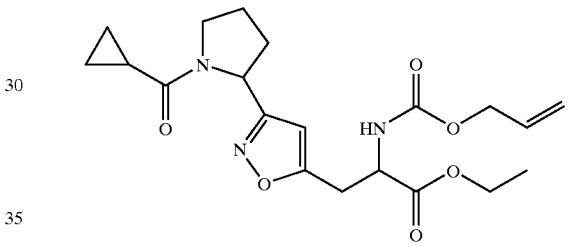

The title compound was prepared according to the method described in example 3B using the appropriate reagents. MS (Cl) m/z 406.1 (M+1).

EXAMPLE 19

A. 2-Acetylamino-3-[3-(3-methyl-1-{2-[4-(2-methylbenzyloxy)-phenyl]-acetylamino}-butyl)-isoxazol-5-yl]-propionic acid

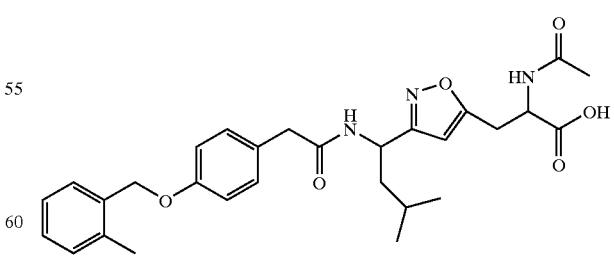

The hydrolysis of 19B was carried out using the protocol in example 1A to afford the title compound. MS (Cl) m/z 508.1 (M+1), 506.1 (M−1).

B. 2-Acetylamino-3-[3-(3-methyl-1-{2-[4-(2-methyl-benzyloxy)-phenyl]-acetylamino}-butyl)-isoxazol-5-yl]-propionic acid ethyl ester

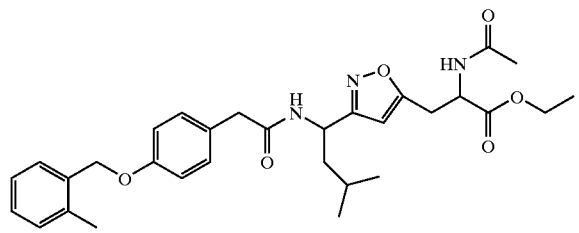

The title compound was prepared according to the method described in example 7B, using [4-(2-methyl-benzyloxy)-phenyl]-acetic acid. MS (Cl) m/z 550.2 (M+1).

B. [4-(2-Methyl-benzyloxy)-phenyl]-acetic acid

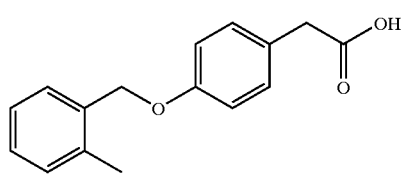

The title compound was prepared according to the method described in example 7D. $^1$H NMR (300 MHz, CDCl$_3$) δ 2.40 (s, 3H), 3.65 (s, 2H), 5.05 (s, 2H), 6.98–7.01 (d, 2H), 7.02–7.30 (m, 5H), 7.42–7.44 (d, 1H).

D. [4-(2-Methyl-benzyloxy)-phenyl]-acetic acid methyl ester

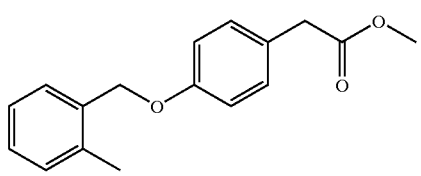

The title compound was prepared according to the method described in example 7E. $^1$H NMR (400 MHz, CDCl$_3$) δ 2.35 (s, 3H), 3.56 (s, 2H), 3.67 (s, 3H), 5.00 (s, 2H), 6.92–6.94 (d, 2H), 7.18–7.26 (m, 5H), 7.37–7.39 (d, 1H).

EXAMPLE 20

A. 2-Acetylamino-3-(3-{1-[2-(4'-ethyl-biphenyl-4-yl)-acetylamino]-3-methyl-butyl}-isoxazol-5-propionic acid

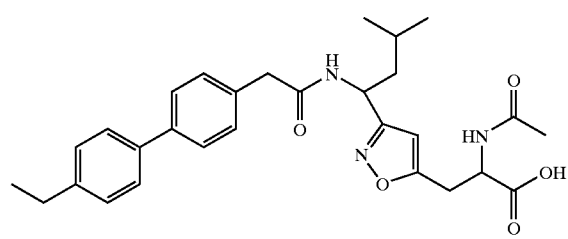

The hydrolysis of 20B was carried out using the protocol in example 1A to afford the title compound. MS (Cl) m/z 506.1 (M+1), 504.0 (M−1).

B. 2-Acetylamino-3-(3-{1-[2-(4'-ethyl-biphenyl-4-yl)-acetylamino]-3-methyl-butyl}-isoxazol-5-propionic acid ethyl ester

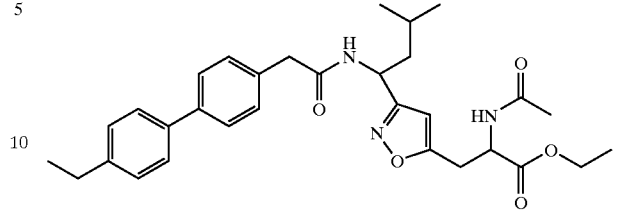

The title compound was prepared according to the method described in example 7B, using (4'-ethyl-biphenyl-4-yl)-acetic acid. MS (Cl) m/z 534.2 (M+1).

C. (4'-Ethyl-biphenyl-4-yl)-acetic acid

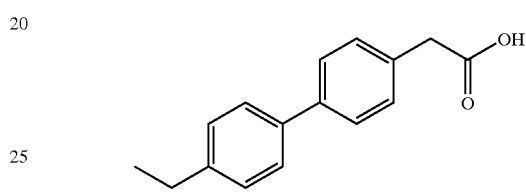

The title compound was prepared according to the method described in example 10B MS (Cl) m/z 239.0 (M−1).

D. (4'-Ethyl-biphenyl-4-yl)-acetic acid methyl ester

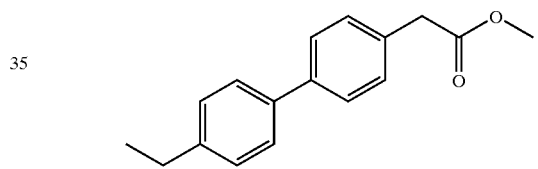

The title compound was prepared according to the method described in example 10C. $^1$H NMR (400 MHz, CDCl$_3$) δ 7.63 (d, J=8.1 Hz, 2H), 7.60 (d, J=8.1 Hz, 2H), 7.43 (d, J=8.1 Hz, 2H), 7.36 (d, J=8.1 Hz, 2H), 3.79 (s, 3H), 3.75 (s, 3H), 2.78 (q, J=7.5 Hz, 2H), 1.37 (t, J=7.5 Hz, 3H).

EXAMPLE 21

A. 2-Acetylamino-3-(3-{1-[(4-benzyloxy-phenyl)-acetyl]-pyrrolidin-2-yl}-isoxazol-5-yl)-propionic acid

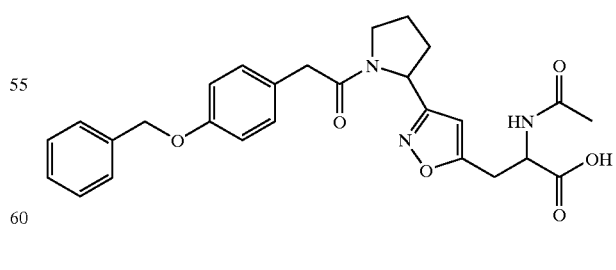

The title compound was prepared from 2-acetylamino-2-(3-{1-[(4-benzyloxy-phenyl)-acetyl]-pyrrolidin-2-yl}-isoxazol-5-ylmethyl)-malonic acid diethyl ester using the method of example 1D. MS (Cl) m/z 492.2 (M+1), 490.3 (M−1)

B. 2-Acetylamino-2-(3-{1-[(4-benzyloxy-phenyl)-acetyl]-pyrrolidin-2-yl}-isoxazol-5-ylmethyl)-malonic acid diethyl ester

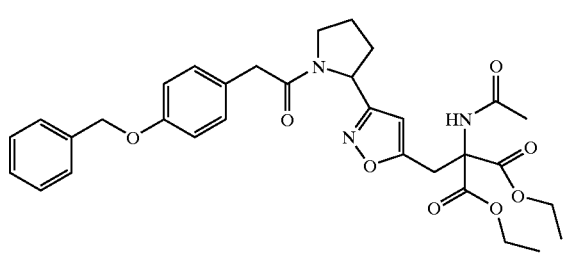

MS (Cl) m/z 602.0 (M+1)

EXAMPLE 22

A. 2-Acetylamino-3-[3-(1-{[4-(4-chloro-benzyloxy)-phenyl]-acetyl}-pyrrolidin-2-yl)-isoxazol-5-yl]-propionic acid

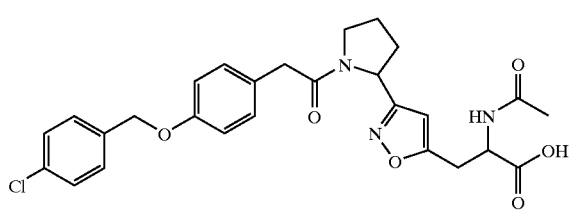

The title compound was prepared from 22B according to the method described in example 21A. MS (Cl) m/z 526.2 (M+1), 524.2 (M−1).

B. 2-Acetylamino-3-[3-(1-{[4-(4-chloro-benzyloxy)-phenyl]-acetyl}-pyrrolidin-2-yl)-isoxazol-5-ylmethyl)-malonic acid diethyl ester

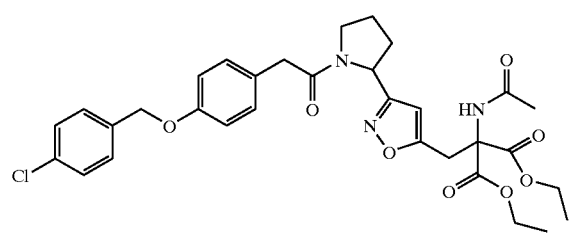

The title compound was prepared according to the method described in example 21B, using [4-(4-chloro-benzyloxy)-phenyl]-acetic acid. MS (Cl) m/z 626.0 (M+1).

C. [4-(4-Chloro-benzyloxy)-phenyl]-acetic acid

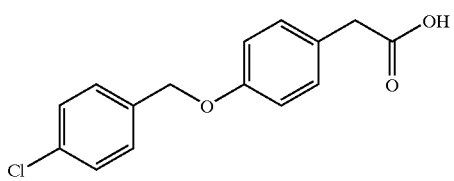

The title compound was prepared according to the method described in example 7D. $^1$H NMR (400 MHz, dimethyl sulfoxide) δ 3.44 (s, 2H), 5.05 (s, 2H), 6.88–6.92 (m, 2H), 7.11–7.14 (m, 2H), 7.42 (s, 4H), 12.20 (s, 1H). $^{13}$C NMR (100 MHz, dimethyl sulfoxide) 368.9, 115.2, 128.1, 129.1, 130.1 (2 overlapping peaks), 131.1, 133.0, 136.9, 157.5, 173.6.

D. [4-(4-Chloro-benzyloxy)-phenyl]-acetic acid methyl ester

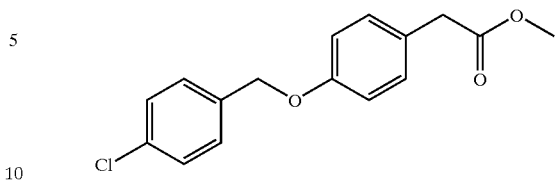

The title compound was prepared according to the method described in example 7E. $^1$H NMR (400 MHz, CDCl$_3$) δ 3.55 (s, 2H), 3.67 (s, 3H), 5.00 (s, 2H), 6.88–6.90 (d, 22H), 7.17–7.19 (d, 2H), 7.34 (s, 4H).

EXAMPLE 23

A. 2-Acetylamino-3-[3-(1-{[4-(3-phenyl-allyl)-phenyl]-acetyl}-pyrrolidin-2-yl)-isoxazol-5-yl]-propionic acid

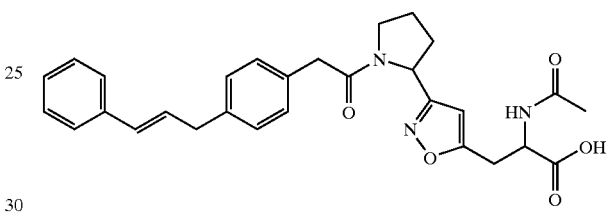

The title compound was prepared from 23B according to the method described in example 22A. MS (Cl) m/z 502.2 (M+1), 500.2 (M−1)

B. 2-Acetylamino-3-[3-(1-{[4-(3-phenyl-allyl)-phenyl]-acetyl}-pyrrolidin-2-yl)-isoxazol-5-ylmethyl)-malonic acid diethyl ester

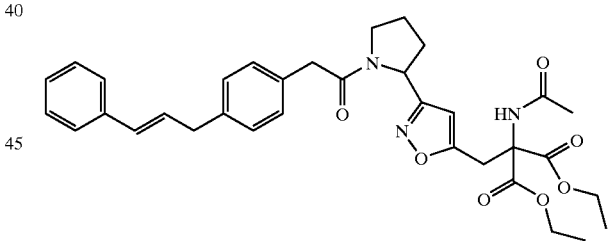

The title compound was prepared from [4-(3-phenyl-allyl)-phenyl]-acetic acid according to the method described in example 22B. MS (Cl) m/z 602.0 (M+1).

C. [4-(3-Phenyl-allyl)-phenyl]-acetic acid

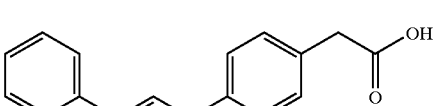

The title compound was prepared from [4-(3-phenyl-allyl)-phenyl]-acetic acid according to the method described in example 10B. $^1$H NMR (400 MHz, CDCl$_3$) δ 3.51 (d, 2H, J=7 Hz), 3.62 (s, 2H), 6.28–6.46 (m, 2H), 7.18–7.37 (m, 9H).

D. [4-(3-Phenyl-allyl)-phenyl]-acetic acid

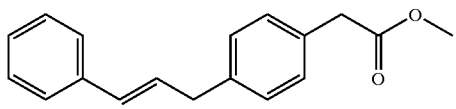

(4-Trifluoromethanesulfonyloxy-phenyl)-acetic acid methyl ester (500 mg, 1.68 mmol, 1.00 equivalents), palladium (II) chloride (15 mg, 5 mol %), bis-diphenylphosphinoethane (50 mg, 5 mol %), bis(pinacolato)diboron (469 mg, 1.85 mmol, 1.10 equivalents), and potassium acetate (495 mg, 5.04 mmol, 3.00 equivalents) were heated in dimethyl formamide (10 mL) at 80° C. for 3 hours. The black reaction mixture was cooled to room temperature. Palladium (II) chloride (15 mg, 5 mol %), bis-diphenylphosphinoethane (50 mg, 5 mol %), cinnamyl bromide (660 mg, 3.35 mmol, 2.00 equivalents), sodium carbonate (890 mg, 8.40 mmol, 5.00 equivalents), and water (4 mL) were added. The reaction mixture was heated to 80° C. overnight. The reaction was cooled to room temperature and diluted with ethyl acetate (50 mL). This mixture was extracted with saturated sodium bicarbonate (2×50 mL), water (2×50 mL) and brine (50 mL). The organic portion was dried over sodium sulfate. Evaporation of the solvent gave a black oily residue that was chromatographed on Biotage (5% ethyl acetate/hexanes) to give a 9:1 mixture of the title compound and acetic acid 3-phenyl-allyl ester (200 mg, 45%). $^1$H NMR (400 MHz, CDCl$_3$) δ 3.52 (dd, 2H, J=7, 1.2 Hz), 3.60 (s, 2H), 3.68 (s, 3H), 6.24–6.38 (m, 1H), 6.43–6.47 (d, 1H), 7.1–7.4 (m, 9H). This material was used in example 23C without further purification.

EXAMPLE 24

A. 2-(3-Methyl-1-{2-[4-(3-o-tolyl-ureido)-phenyl]-acetylamino}-butyl)-1H-benzoimidazole-4-carboxylic acid

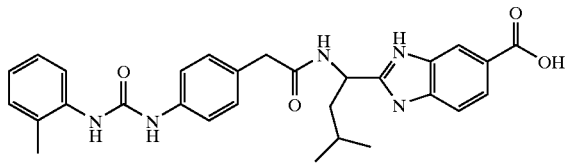

The title compound was prepared from 24B according to the method described in example 1A. MS (Cl) m/z 514.1 (M+1), 512.2 (M−1)

B. 2-(3-Methyl-1-{2-[4-(3-o-tolyl-ureido)-phenyl]-acetylamino}-butyl)-1H-benzoimidazole-4-carboxylic acid methyl ester

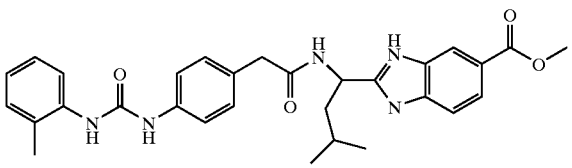

The title compound was prepared from 24C according to the method described in example 2B. MS (Cl) m/z 528.0 (M+1), 526.2 (M−1)

C. 2-(1-Amino-3-methyl-butyl)-1H-benzoimidazole-5-carboxylic acid methyl ester hydrochloride

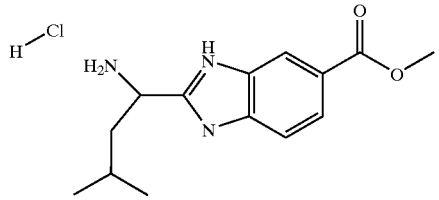

A solution of 4-Amino-3-(2-tert-butoxycarbonylamino-4-methyl-pentanoylamino)-benzoic acid methyl ester (690 mg, 1.82 mmol) in acetic acid (9 mL) was heated to 70° C. with stirring for 1.5 hours. The acetic acid was removed in vacuo and the crude mixture was dissolved up in 4M hydrochloric acid in dioxane (9 mL) and stirred at room temperature for 30 minutes. The reaction was concentrated in vacuo to give the title compound. MS (Cl) m/z 262.0 (M+1), 260.1 (M−1)

E. 4-Amino-3-(2-tert-butoxycarbonylamino-4-methyl-pentanoylamino)-benzoic acid methyl ester

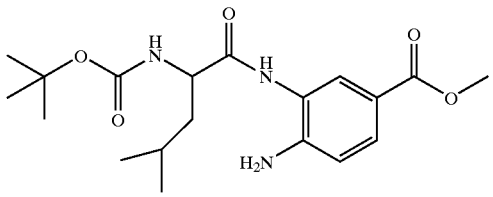

Hydroxybenzotriazole monohydrate (760 mg, 5.62 mmol) and 1-(3-dimethylaminopropyl)-3-ethylcarbodiimde hydrochloride (973 mg, 5.07 mmol) were added to a dimethyl formamide (30 mL) solution of N-tert-butoxycarbonyl-L-leucine (1.06 g, 4.57 mmol). The mixture was stirred until all 1-(3-dimethylaminopropyl)-3-ethylcarbodiimde hydrochloride had dissolved. Methyl 3,4-diaminobenzoate (759 mg, 4.57 mmol) in dimethyl formamide (10 mL) and triethyl amine (0.68 mL, 4.89 mmol) were added sequentially. The reaction was stirred at room temperature over night and poured into water. This mixture was extracted with ethyl acetate three times. The organic portion was extracted with a saturated solution of sodium bicarbonate, water (2×) and brine. The organic portion was dried over magnesium sulfate and the solvent removed in vacuo. The resulting residue was chromatographed on a Biotage Flash 40S column eluting with ethyl acetate/hexanes (2:3) which yielded the title compound (690 mg, 40%). MS (Cl) m/z 380.0 (M+1), 378.2 (M−1).

EXAMPLE 25

A. 2-(2,6-Dichloro-benzoylamino)-3-[3-(1-{2-[3-methoxy-4-(3-o-tolyl-ureido)-phenyl]-acetylamino}-3-methyl-butyl)-isoxazol-5-yl]-propionic acid

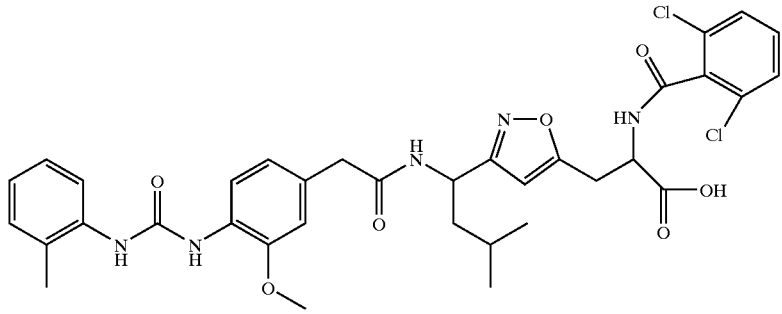

A mixture of 25B (56 mg, 0.13 mmol) in tert-butanol (1 mL) and 1N sodium hydroxide (0.27 mL) was stirred at reflux. After 30 minutes the mixture was concentrated under reduced pressure, and the resulting residue was dissolved in water and washed with ethyl acetate. The aqueous layer was acidified to pH 1 with 1N HCl and extracted into ethyl acetate. The combined organic layers were washed with water and brine, dried over sodium sulfate and concentrated under reduced pressure to give an off-white solid. MP 102–4° C.; MS (m/z) 710.3 and 713.3 (M+1).

B. 2-(2,6-Dichloro-benzoylamino)-3-[3-(1-{2-[3-methoxy-4-(3-o-tolyl-ureido)-phenyl]-acetylamino}-3-methyl-butyl)-isoxazol-5-yl]-propionic acid methyl ester

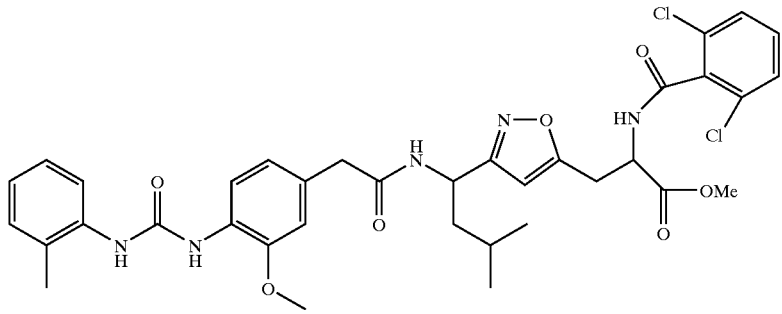

The title compound was prepared in the manner described in example 2B using 3-methoxy-4-(3-o-tolyl-ureido)-phenylacetic acid and 3-[3-(1-amino-3-methyl-butyl)-isoxazol-5-yl]-2-(2,6-dichloro-benzoylamino)-propionic acid methyl ester hydrochloride. 51% yield; white solid. MS (m/z) 724.2 and 726.2 (M+1).

C. 3-[3-(1-Amino-3-methyl-butyl)-isoxazol-5-yl]-2-(2,6-dichloro-benzoylamino)-propionic acid methyl ester hydrochloride

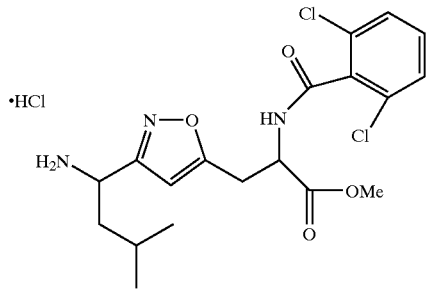

The title compound was prepared from 25D in the same manner as example 1C. MS (m/z) 428.3 and 430.3 (M+1).

D. 3-[3-(1-tert-Butoxycarbonylamino-3-methyl-butyl)-isoxazol-5-yl]-2-(2,6-dichloro-benzoylamino)-propionic acid methyl ester

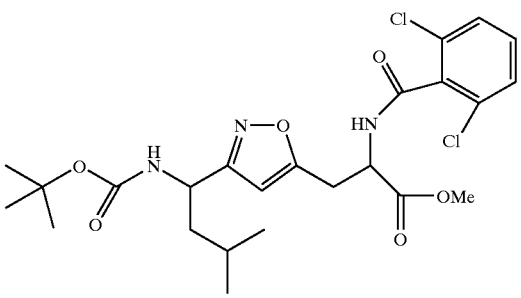

The title compound was prepared from 25E and 7I in the same manner as example 7H. MS (m/z) 526.2 and 528.0 (M−1).

E. 2-(2,6-Dichloro-benzoylamino)-pent-4-ynoic acid methyl ester

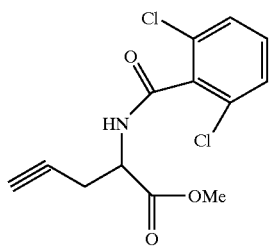

The title compound was prepared from 2-amino-pent-4-ynoic acid methyl ester and 2,5-dichlorobenzoyl chloride in the same manner as example 3B. MS (m/z) 300.2 and 302.2 (M+1).

EXAMPLE 26

A. 2-[3-(1-{2-[3-Methoxy-4-(3-o-tolyl-ureido)-phenyl]-acetylamino}-3-methyl-butyl)isoxazol-5-ylmethyl]-4-methyl-pentanoic acid

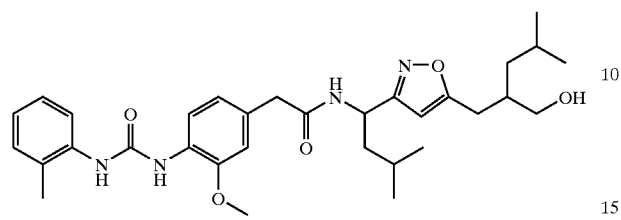

The title compound was prepared in the same manner as Example 25, steps A–D, using 4-methyl-2-propargyl pentanoic acid methyl ester in step D. MS (m/z) 577.3 (M−1).

EXAMPLE 27

A. 2-acetylamino-3-[3-(1-{2-[3-methoxy-4-(3-o-tolyl-ureido)-phenyl]-acetylamino}-3-methyl-butyl)-isoxazol-5-yl]-propionic acid

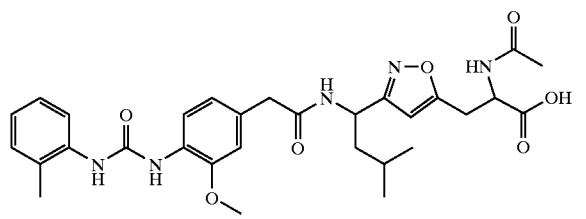

The title compound was prepared in the same manner as Example 7A and B, using 3-methoxy-4-(3-o-tolyl-ureido)-phenylacetic acid in part B. White solid; MP 123–5° C.; MS (m/z) 578.1 (M−1).

EXAMPLE 28

A. 2-Acetylamino-3-{3-[({[3-methoxy-4-(3-o-tolyl-ureido)-phenyl]-acetyl}-amino)-methyl]-phenyl}-propionic acid

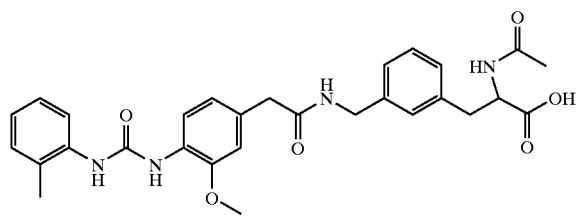

The title compound was prepared in the same manner as example 25, steps A and B, using 28B in step 25B. MS (m/z) 633 (M+1).

B. 2-Acetylamino-2-[(3-aminomethyl-phenyl)-methyl]-malonic acid diethyl ester

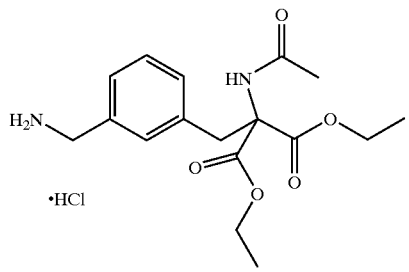

A mixture of 28C (1.15 g, 3.5 mmol), 10% Pd on carbon (0.15 g) and concentrated HCl (0.3 mL) in ethanol (50 mL) was placed on a Parr shaker apparatus under 45 p.s.i. hydrogen for 6 hours. The mixture was filtered through celite and concentrated under reduced pressure to give 1.2 g of the title compound as a white solid. MS (m/z) 337.3 (M+1).

C. 2-Acetylamino-2-[(3-cyanophenyl)-methyl]-malonic acid diethyl ester

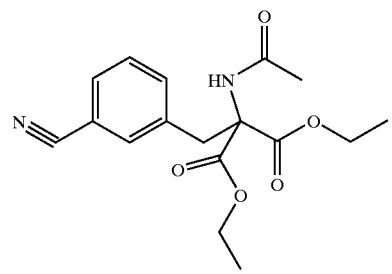

The title compound was prepared from alpha-bromo-meta-tolunitrile in the same manner as example 7G. MS (m/z) 333 (M+1).

EXAMPLE 29

Binding of Biotinylated CS-1 to Isolated VLA-4

The VLA-4/bCS-1 receptor ligand binding assay described herein tests the ability of a compound to specifically inhibit VLA-4 dependent binding.

A. Preparation of VLA-4 Coated Plates

VLA-4 coated plates were prepared the day before the assay was carried out. The VLA-4-expressing stock was isolated from Jurkat cells according to the protocol of Makarem et al., *J. Biol. Chem.*, 269, 4005–4011 (1994) and was diluted in 50 mM NaHCO$_3$ (pH 8.8) to a final concentration of 0.4 mg/ml. Aliquots of 100 ml of this stock solution were then added to each well of a 96 well Microfluor "B" U-bottom plate (Dynatech No. 0010107205) and incubated overnight at 4° C. The coating solution was removed by aspiration and the wells were quenched for 0.5 hour with PBS plus 1 mM MnCl containing 1% non-fat dry milk (200 ml/well, 37° C.). The dry milk was removed by aspiration immediately before addition of the biotinylated CS-1.

B. Binding of Biotinylated CS-1 to Isolated VLA-4

The biotinylated CS-1 peptide (bCS-1) was prepared. This peptide was diluted with PBS plus 1 mM MnCl containing 0.1% non-fat dry milk (PBSB) to a final concentration of 5 mg/ml. Aliquots of 200 ml are added to the wells of a 96 well polypropylene transfer plate containing compounds (32, 10, 3.2, 1, 0.32 and 0.1 mM), vehicle or antibodies (0.5 mg/ml) in PBSB containing 0.1% DMSO for 60 min (37° C.). The plate is washed three times with 200 ml/well of PBSB to remove unbound bCS-1. Following this, 100 ml of a 1:5000 dilution of streptavidin poly-HRP in PBSB was added to each well for 60 min (37° C.). Unbound streptavidin poly-HRP was removed by aspiration and the plate was washed three times with PBSB (200 ml/well). Following the final wash, 100 ml of TMB substrate was added to each well to react with the bound streptavidin poly-HRP and the OD of each well on the plate was determined on the Emax plate reader (650). The results were based on the mean of duplicate determinations.

EXAMPLE 30

VLA-4 Dependent THP1 Cell Binding to Baculovirus sVCAM

The THP1 baculovirus sVCAM cell binding assay tests the ability of a compound to inhibit VLA-4 dependent binding to sVCAM.

A. Preparation of sVCAM Coated Plates

The baculovirus sVCAM coated plates were prepared the day before the experiment was carried out. The baculovirus sVCAM stock from PanVera was diluted in 50 mM NaHCO$_3$ (pH 8.8) to a final concentration of 5 mg/ml. Aliquots of 50 ml of this stock solution were then added to each well of a 96 well Microfluor "B" U bottom plate (Dynatech No. 0010107205) and incubated overnight (4° C.). The coating solution was removed by aspiration and the wells were quenched for 1 hour with PBS containing 5% non-fat dry milk (150 ml/well, 4° C.). The dry milk is removed by shock dumping immediately before addition of the biotinylated CS-1.

B. Labeling and Binding of THP1 Cells

THP1 cells were obtained from the American Type Culture Collection (ATCC, Rockville, Md.) and grown in RPMI 1640 media containing 10% 1 mM MnCl$_2$ for 20 min (37° C.).

Following MnCl$_2$ activation, the cells were spun down (approximately 500 g for 5 min) and resuspended twice in serum free basal media (EBM, 37° C.). The cells in serum free media (2×10$^6$/ml) were then incubated with 5 mM Calcein AM for 30 min at 37° C. Following labeling, all cells are spun down (approximately 500 g for 5 min) and resuspended twice in RPMI 1640 containing 10% FBS to cleave any free calcein AM. The cells were then resuspended twice in DPBS (+1 mM CaCl$_2$ and 1 mM MgCl$_2$) containing 1 mg/ml BSA (DPBSB) and diluted to 667,000 cells/ml. Aliquots Of 200 ml were added to the wells of a 96 well polypropylene transfer plate containing test compounds (10, 5, 1 and 0.1 mM), vehicle or antibodies (0.5 mg/ml) in DPBSB containing 0.1% DMSO for 30 min (37° C.). The next 150 ml (100,000 cells) were removed from each well and transferred into appropriate wells of a quenched baculovirus sVCAM coated plate for 45 min (37° C.). Unbound cells were removed by aspiration and the plate was washed three times with DPBSB (100 ml/well). Following the final wash, 100 ml of DPBSB was added to each well and the plate was read on a Cytoflour II fluorescent plate reader. Three readings were taken per well at an excitation of 480 and emission of 530. The results were based on the mean of duplicate determinations. The average background fluorescence of blank wells was subtracted from each sample to give a corrected fluorescence intensity value for each sample.

What is claimed is:
1. A compound of Formula (1.0.0):

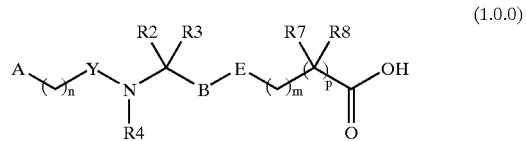

and pharmaceutically acceptable salts and other prodrug derivatives thereof, wherein:

A is $A^1$--NHC(=O)NH-$A^2$-, where $A^1$ and $A^2$ are each independently aryl where said aryl is substituted with 0 to 3 $R^9$;

B is:

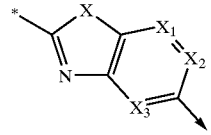

where the symbol "*" indicates the point of attachment of the moiety represented by partial Formula (1.1.22) to the moiety "$CR^2R^3$" in Formula (1.0.0); and the symbol indicates the point of attachment of the moiety represented by partial Formula (1.1.22) to the moiety "E" in Formula (1.0.0);

E is a single bond;

X is —O—; or —NR$^{10}$—;

$X^1$, $X^2$ and $X^3$ are each CH;

Y is —C(=O)—;

k is an integer independently selected from 0, 1 and 2;

m is 0;

n is an integer independently selected from 0, 1 and 2;

p is an integer independently selected from 0;

q is an integer independently selected from 0, 1 and 2;

r is an integer independently selected from 0, 1 and 2;

$R^2$ and $R^3$ are each independently selected from the group consisting of hydrogen; ($C_1$–$C_6$) alkyl substituted with 0 to 3 $R^{13}$; ($C_2$–$C_6$) alkenyl substituted with 0 to 3 $R^{13}$; ($C_1$–$C_6$) alkyl-OR$^5$ substituted with 0 to 3 $R^{13}$; ($C_1$–$C_6$) alkyl-SR$^5$ substituted with 0 to 3 $R^{13}$; ($C_1$–$C_6$) alkyl-SO$_2$R$^5$ substituted with 0 to 3 $R^{13}$;

$R^4$ is hydrogen; or ($C_1$–$C_6$) alkyl optionally substituted with $R^{13}$; or $R^4$ may be taken together with either $R^2$ or $R^3$ to form a carbocyclic or heterocyclic ring;

$R^5$ and $R^6$ are independently hydrogen; ($C_1$–$C_6$) alkyl; ($C_2$–$C_6$) alkenyl; ($C_2$–$C_6$) alkynyl; CF$_3$; aryl; cycloalkyl; heteroaryl; or heterocyclyl;

$R^7$ is ($C_1$–$C_6$) alkyl; $(CH_2)_kOR^5$; $(CH_2)_kNR^6C(=O)R^5$; $(CH_2)_kNR^6C(=O)OR^5$; $(CH_2)_kNR^6SO_2R^5$; $(CH_2)_kNR^6R^5$; F; CF$_3$; OCF$_3$; aryl, substituted with 0 to 3 $R^9$; heterocyclyl, substituted with 0 to 3 $R^9$; heteroaryl, substituted with 0 to 3 $R^9$; cycloalkyl, substituted with 0 to 3 $R^9$; or $R^7$ may be taken together with $R^8$ to form a cycloalkyl or heterocyclyl ring; or $R^7$ may be taken together with $R^{11}$ to form a cycloalkyl or heterocyclyl ring;

$R^8$ is hydrogen; F; ($C_1$–$C_6$) alkyl or ($C_1$–$C_6$) alkoxy;

$R^9$ is halogen; ($C_1$–$C_6$) alkyl; ($C_1$–$C_6$) alkoxy; ($C_3$–$C_6$) cycloalkyl; ($C_3$–$C_6$) cycloalkoxy cyano; $(CH_2)_kOH$;

$C(=O)R^5$; $(CH_2)_kC(O)NR^5R^6$; $(CH_2)_kNR^5R^6$; $(CH_2)_kNR^5SO_2R^6$; $CF_3$; $OCF_3$; $SO_2NR^5R^6$; $(CH_2)_mC(=O)OR^5$; when $R^9$ is attached to a saturated carbon atom $R^9$ may be =O or =S; when $R^9$ is attached to a sulphur atom $R^9$ may be =O;

$R^{10}$ is hydrogen; $C(=O)R^5$; $C(=O)OR^5$; $(C_1-C_6)$ alkyl; aryl; heterocyclyl; heteroaryl; cycloalkyl; or $SO_2R^5$;

$R^{11}$ and $R^{12}$ are independently hydrogen; $(C_1-C_6)$ alkyl; hydroxy; cyano; $(C_1-C_6)$ alkoxy; $NR^6C(=O)R^5$; $NR^6SO_2R^5$; $NR^6R^5$; $CF_3$; F; aryl; heterocyclyl; heteroaryl; cycloalkyl; cycloalkoxy; or $R^{11}$ may be taken together with $R^{12}$ to form a cycloalkyl or heterocyclyl ring; and $R^{13}$ is independently selected from the group consisting of halogen; $CF_3$; $(C_1-C_6)$ alkyl; aryl; heteroaryl; heterocyclyl; hydroxy; cyano; $(C_1-C_6)$ alkoxy; $(C_3-C_6)$ cycloalkyl; $(C_3-C_6)$ cycloalkoxy; $(C_2-C_6)$ alkynyl; $(C_2-C_6)$ alkenyl; $-NR^6R^5$; $-C(=O)NR^5R^6$; $SO_2R^5$; $C(=O)R^5$; $NR^5SO_2R^6$; $NR^5C(=O)R^6$; $C(=O)NR^5SO_2R^6$; $NR^5C(=O)OR^6$; and $SO_2NR^6R^5$.

2. A compound according to claim 1 wherein said aryl is phenyl independently substituted by 0 or 1 $R^9$ which is a member selected from the group consisting of F; Cl; $F_3C—$; methyl; methoxy; hydroxy; iso-propyl; cyclopropyloxy; and cyclopentyl.

3. A compound according to claim 2 wherein n is the integer 1 resulting in a methylene bridge.

4. A compound according to claim 3 wherein said component A and said methylene bridge attached thereto comprise a member selected from the group consisting of 3-methoxy-4-(N'-phenylurea)-phenylmethyl-; 4-(N'-phenylurea)-phenylmethyl-; 4-(N'-(2-methylphenyl)urea)-phenylmethyl-; 4-(N'-(2-methoxyphenyl)urea)-phenylmethyl-; 3-methoxy-4-(N'-(2-methylphenyl)urea)-phenylmethyl-; 4-(N'-(2-fluorophenyl)urea)-phenylmethyl-; 4-(N'-(2-chlorophenyl)urea)-phenylmethyl-; 4-(N'-(2-chlorophenyl)urea)-3-methoxyphenylmethyl-; and 4-(N'-(4-iso-propylphenyl)urea)-phenylmethyl-;.

5. A compound according to claim 2 wherein for the component of Formula (1.0.0) which is $—NR^4CR^2CR^3—$, $R^4$ is hydrogen, $R^2$ is hydrogen, and $R^3$ is hydrogen.

6. A compound according to claim 2 wherein for the component of Formula (1.0.0) which is $—NR^4CR^2CR^3—$, $R^4$ is hydrogen, $R^2$ is hydrogen, and $R^3$ is iso-butyl.

7. A compound according to claim 2 wherein for the component of Formula (1.0.0) which is $—NR^4CR^2CR^3—$, $R^2$ is hydrogen, $R^3$ is hydrogen.

8. A compound according to claim 2 wherein for the component of Formula (1.0.0) which is $—NR^4CR^2CR^3—$, $R^2$ is hydrogen, $R^3$ is hydrogen and $R^4$ is methyl.

9. A compound according to claim 2 wherein for the component of Formula (1.0.0) which is $—NR^4CR^2CR^3—$, $R^4$ is taken together with $R^2$ or $R^3$ to form pyrrolidinyl, whereby $R^4$ is methylene or ethylene, one of $R^2$ or $R^3$ is hydrogen, and the other of $R^2$ or $R^3$ is ethylene or methylene.

10. A compound according to claim 1 wherein in partial Formula (1.1.22), X is $—NR^{10}—$; and $R^{10}$ is $—H$.

11. A compound according to claim 1 wherein said compound is:
2-[({[3-Methoxy-4-(3-o-tolyl-ureido)-phenyl]-acetyl}-methyl-amino)-methyl]-benzooxazole-6-carboxylic acid.

12. A pharmaceutical composition comprising a compound of Formula (1.0.0) as defined in claim 1 together with a pharmaceutically acceptable carrier for said compound, wherein the amount of said compound present is effective for preventing, inhibiting, suppressing or reducing cell adhesion and consequent or associated pathogenic processes subsequently mediated by VLA-4.

13. A method of treating asthma, multiple sclerosis, rheumatoid arthritis, osteoarthritis, inflammatory bowel disease, psoriasis, host rejection following organ transplantation or atherosclerosis in a mammal by inhibiting cell adhesion mediated by VLA-4, comprising administering to said mammal in need of such treatment a therapeutically effective amount of a compound of Formula (1.0.0) as defined in claim 1 or a pharmaceutical composition as defined in claim 12.

14. 2-(3-Methyl-1-{2-[4-(3-o-tolyl-ureido)-phenyl]-acetylamino}-butyl)-1H-benzoimidazole-4-carboxylic acid.

* * * * *